United States Patent
Clausen et al.

(10) Patent No.: US 7,338,932 B2
(45) Date of Patent: Mar. 4, 2008

(54) METHODS OF MODULATING FUNCTIONS OF POLYPEPTIDE GALNAC-TRANSFERASES AND OF SCREENING TEST SUBSTANCES TO FIND AGENTS HEREFOR, PHARMACEUTICAL COMPOSITIONS COMPRISING SUCH AGENTS AND THE USE OF SUCH AGENTS FOR PREPARING MEDICAMENTS

(75) Inventors: Henrik Clausen, Hoite (DK); Eric Paul Bennett, Lyngby (DK); Helle Hassan, Frederiksberg (DK); Celso Albuquerque Reis, Vila Nova de Gaia (PT)

(73) Assignee: Glycozym APS, Horsholm (DK)

( * ) Notice: Subject to any disclaimer, the term of this patent is extended or adjusted under 35 U.S.C. 154(b) by 715 days.

(21) Appl. No.: 10/292,896

(22) Filed: Nov. 12, 2002

(65) Prior Publication Data

US 2003/0186850 A1    Oct. 2, 2003

Related U.S. Application Data

(63) Continuation-in-part of application No. PCT/DK01/00328, filed on May 10, 2001.

(60) Provisional application No. 60/425,204, filed on Nov. 8, 2002, provisional application No. 60/203,331, filed on May 11, 2000.

(51) Int. Cl.
  *A61K 38/16* (2006.01)
  *A61K 38/00* (2006.01)
  *C07H 1/00* (2006.01)
  *C07H 5/04* (2006.01)
  *C07H 19/00* (2006.01)

(52) U.S. Cl. .................... 514/8; 514/14; 536/1.11; 536/18.7; 536/22.1

(58) Field of Classification Search ............... 514/8, 514/14; 536/1.11, 18.7, 22.1, 22
See application file for complete search history.

(56) References Cited

U.S. PATENT DOCUMENTS 5,268,364 A    12/1993    Kojima et al.

FOREIGN PATENT DOCUMENTS

| WO | WO-99/12944 A2 | 3/1999 |
| WO | WO-99/64378 A2 | 12/1999 |
| WO | WO-01/85215 | 11/2001 |

OTHER PUBLICATIONS

Chung et al., "Acceptor Substrate-Based Selective Inhibition of Galactosyltransferases", Bioorganic & Medicinal Chemistry Letters, 8 (1998) 3359-3364.*
M. Tenno et al., Identification of two cysteine residues involved in the binding of UDP-GalNAc to UDP-CalNAc: polypeptide N-acetylgalactosaminyltransferase 1 (GalNAc-T1), European Journal of Biochemistry, Sep. 2002, vol. 269, No. 17, Abstract.
International Search Report, dated Feb. 15, 2002, which issued during the prosecution of International Application No. PCT/DK01/00328.
International Search Report, dated Jul. 26, 2004, which issued during the prosecution of International Application No. PCT/DK03/00763.
Abstract. Publication No. WO-95/26969 A1, New Derivative Inhibit Cell Adhesive Galactosyl Fucosyl Group Treat Inflammation Asthma Rheumatism Cancer.
Soudan, et al., "Capillary zone electrophoresis and MALDI-mass spectrometry for the monitoring of in vitro O-glycosylation of a threonine/serine-rich MUC5AC hexdecapeptide", Journal of Chromatography B, 1999, vol. 729, pp. 65-74.
Byrd, J.C., et al., "Inhibition of Mucin Synthesis by Benzyl-α-GalNAc in KATO III Gastric Cancer and Caco-2 Colon Cancer Cells", European Journal of Cancer, 1995, vol. 31A, No. 9, pp. 1498-1505.
Homa, Fred L., et al., "Isolation and Expression of a cDNA Clone Encoding a Bovine UDP-GalNAc: Polypeptide N-Acetylgalactosaminyltransferase", The Journal of Biological Chemistry, Jun. 15, 1993, vol. 268, No. 17, pp. 12609-12616.
Toba, Shinya, et al., "Brain-specific expression of a novel human UDP-GalNAc: polypeptide N-acetylgalactosaminyltransferase (GalNAc-T9)[1]", Biochimica et Biophysica Acta, 2000, vol. 1493, pp. 264-268.

White, Kenneth E., et al., "Molecular cloning of a novel human UDP-GalNAc:polypeptide N-acetylgalactosaminyltransferase, GalNAc-T8, and analysis as a candidate autosomal dominant hypophosphatemic rickets (ADHR) gene", Gene, 2000, vol. 246, pp. 347-356.

Bennett, Eric Paul, et al., "Cloning and Characterization of a Close Homologue of Human UDP-N-acetyl-α-D-galactosamine:Polypeptide N-Acetylgalactosaminyltransferase-T3, Designated GalNAc-T6", The Journal of Biological Chemistry, Sep. 3, 1999, vol. 274, No. 36, pp. 25362-25370.

Muller, Stefan, et al., "Recombinant MUC1 Probe Authentically Reflects Cell-specific O-Glycosylation Profiles of Endogenous Breast Cancer Mucin", The Journal of Biological Chemistry, Jul. 19, 2002, vol. 277, No. 29, pp. 26103-26112.

Gouyer, V., et al., "Inhibition of the Glycosylation and Alteration in the Intracellular Trafficking of Mucins and Other Glycoproteins by GalNAca-O-BN in Mucosal Cell Lines: An Effect Medicated Through the Intracellular Synthesis of Complex GalNAca-O-BN Oligosaccharides", Frontiers in Bioscience, Oct. 1, 2001, vol. 6, pp. d1235-d1244.

Tenno, Marl, et al., "The Lectin Domain of UDP-GalNAc:Polypeptide N-Acetylgalactosaminytransferase 1 is Involved in O-Gylcosylation of a Polypeptide with Multiple Acceptor Sites", The Journal of Biological Chemistry, Dec. 6, 2002, vol. 277, No. 49, pp. 47088-47096.

Hagen, Kelly G. Ten, et al., "Cloning and Characterization of Ninth Member of the UDP-GalNAc:Polypeptide N-Acetylgalactosaminyltransferase Family, ppGaNTase-T9", The Journal of Biological Chemistry, May 18, 2001, vol. 276, No. 20, pp. 17395-17404.

Schwientek, Tilo, et al., "Functional Conservation of Subfamilies of Putative UDP-N-acetylgalactosamine:Polypeptide N-Acetylgalactosaminyltransferases in Drosophila, *Caaenorhabditis elegans*, and Mammals", The Journal of Biological Chemistry, Jun. 21, 2002, vol. 277, No. 25, pp. 22623-22638.

Hassan, Helle, et al., "The Lectin Domain of UDP-N-acetyl-D-galactosamine:Polypeptide N-acetylgalactosaminyltransferase-T4 Directs Its Glycopeptide Specificities", The Journal of Biological Chemistry, Dec. 8, 2000, vol. 275, No. 49, pp. 38197-38205.

Gobom, Johan, et al., "Sample Purification and Preparation Technique Based on Nano-scale Reversed-Phase Columns for the Sensitive Analysis of Complex Peptide Mixtures by Matrix-assisted Laser Desorption/Ionization Mass Spectrometry", Journal of Mass Spectrometry, 1999, vol. 34, pp. 105-116.

Mirgorodskaya, Ekaterina, et al., "Partial Vapor-Phase Hydrolysis of Peptide Bonds: A Method for Mass Spectrometric Determination of O-Glycosylated Sites in Glycopeptides", Analytical Biochemistry, 1999, vol. 269, pp. 54-65.

Birken, Steven, et al., "Isolation and Amino Acid Sequence of COOH-terminal Fragments from the B Subunit of Human Choriogonadotropin", The Journal of Biological Chemistry, Aug. 10, 1977, vol. 252, No. 15, pp. 5386-5392.

Hill, Hoyle D., Jr., et al., "Ovine Submaxillary Mucin", The Journal of Biological Chemistry, Jun. 10, 1977, vol. 252, No. 11, pp. 3799-3804.

Hardy, Daniel M., et al., "A Sperm Membrane Protein that Binds in a Species-specific Manner to the Egg Extracellular Matrix is Homologous to von Willebrand Factor", The Journal of Biological Chemistry, Nov. 3, 1995, vol. 270, No. 44, pp. 26025-26028.

Matsuura, Hidemitsu, et al., "An a-N-Acetylgalactosaminylation at the Threonine Residue of a Defined Peptide Sequence Creates the Oncofectal Peptide Epitope in Human Fibronectin", The Journal of Biological Chemistry, Jun. 25, 1989, vol. 264, No. 18, pp. 10472-10476.

Bobek, Libuse A., et al., "Molecular Cloning, Sequence, and Specificity of Expression of the Gene Encoding the Low Molecular Weight Human Salivary Mucin (MUC7)", The Journal of Biological Chemistry, Sep. 25, 1993, vol. 268, No. 27, pp. 20563-20569.

Gum, James R., Jr., et al., "Molecular Cloning of Human Intestinal Mucin (MUC2) cDNA", The Journal of Biological Chemistry, Jan. 28, 1994, vo. 269, No. 4, pp. 2440-2446.

Albone, Earl F., et al., "Molecular Cloning of a Rat Submandibular Gland Apomucin", The Journal of Biological Chemistry, Jun. 17, 1994, vol. 269, No. 24, pp. 16845-16852.

Day, Philip J., et al., "Structure and Activity of an Active Site Substitution of Ricin A Chain", Biochemistry, 1996, vol. 35, pp. 11098-11103.

Wandall, Hans H., et al., "Substrate Specificities of Three Members of the Human UDP-N-Acetyl-α-D-galactosamine:Polypeptide N-Acetylgalactosaminyltransferase Family, GalNAc-T1, -T2, and -T3", The Journal of Biological Chemistry, Sep. 19, 1997, vol. 272, No. 38, pp. 23503-23514.

Sako, Dianne, et al., "A Sulfated Peptide Segment at the Amino Terminus of PSGL-1 is Critical for P-Selectin Binding", Cell, Oct. 20, 1995, vol. 83, pp. 323-331.

Reis, Celso A., et al., "Characterization of a Panel of Monoclonal Antibodies Using GalNAc Glycosylated Peptides and Recombinant MUC1", Tumor Biol., 1998, vol. 19, Supplement 1, pp. 127-133.

Colley, Karen J., "Golgi localization of glycosyltransferases: more questions than answers", Glycobiology, 1997, vol. 7, No. 1, pp. 1-13.

Dohi, Taeko, et al., "Detection of N-Acetylgalactosaminyltransferase mRNA Which Determines Expression of Sda Blood Group Carbohydrate Structure in Human Gastrointestinal Mucosa and Cancer", Int. J. Cancer, 1996, vol. 67, pp. 626-631.

Jentoft, Neil, "Why are proteins O-gylcosylated?", Tibs, Aug. 1990, vol. 15, pp. 291-94.

Rose, Mary C., "Mucins: structure, function, and role in pulmonary diseases", Invited Review, pp. L413-L429.

Mandel, Ulla, et al., "Simple Mucin-Type Carbohydrates in Oral Stratified Squamos and Salivary Gland Epithelia", The Journal of Investigative Dermatology, Oct. 1991, vol. 97, No. 4, pp. 713-721.

Taylor-Papadimitriou, Joyce, et al., "Exploiting altered glycosylation patterns in cancer: progress and challenges in diagnosis and therapy", Titech, Jun. 1994, vol. 12, pp. 227-233.

Girling, Anne, et al., "A Core Protein Epitope of the Polymorphic Epithelial Mucin Detected by the Monoclonal Antibody SM-3 is Selectively Exposed in a Range of Primary Carcinomas", Int. J. Cancer, 1989, vol. 43, pp. 1072-1076.

Scharfman, A., et al., "Interactions between human respiratory mucins and pathogens", Biochemical Society Transactions, 1995, vol. 23, pp. 836-839.

Breton, Christelle, et al., "Structure/function studies of glycosyltransferases", Carbohydrates and gylcoconjugates, pp. 536-571.

Trombetta, E. Sergio, et al., "Lectins as chaperones in glycoprotein folding", Carbohydrates and glycoconjugates, pp. 587-592.

Hazes, Bart, "The $(QxW)_3$ domain: A flexible lectin scaffold", Protein Science, 1996, vol. 5, pp. 1490-1501.

Muller, Stefan, et al., "Localization of O-Glycosylation Sites on Glycopeptide Fragments from Lactation-associated MUC1", The Journal of Biological Chemistry, Oct. 3, 1997 vol. 272, No. 4, pp. 24780-24793.

Ramakrishnan, Boopathy, et al., "Structure-based Design of B1, 4-Galactosyltransferase I (B4Gal-T1) with Equally Efficient N-Acetylgalactosaminyltransferase Activity", The Journal of Biological Chemistry, Jun. 7, 2002, vol. 277, No. 23, pp. 20833-20839.

Ramakrishnan, B., et al., "Crystal Structure of B1, 4-Galactosyltransferase Complex with UDP-Gal Reveals an Oligosaccharide Acceptor Binding Site", J. Mol. Biol., 2002, vol. 318, pp. 491-502.

Sasaki, Hiroshi, et al., "Carbohydrate Structure of Erythropoietin Expressed in Chinese Hamster Ovary Cells by a Human Erythropoietin cDNA", The Journal of Biological Chemistry, Sep. 5, 1987, vol. 262, No. 25, pp. 12059-12076.

Ryuko, Kanji, et al., "Characterization of a New MUC1 Monoclonal Antibody (VU-2-G7) Directed to the Glycosylated PDTR Sequence of MUC1", Tumor Biology, 2000, vol. 21, pp. 197-210.

Burdick, Michael D., "Oligosaccharies Expressed on MUC1 Produced by Pancreatic and Colon Tumor Cell Lines", The Journal of Biological Chemistry, Sep. 26, 1997, vol. 272, No. 39, pp. 24198-24202.

Mandel, Ulla, et al., "Expression of polypeptide GalNAc-transferases in stratified epithelia and squamous cell carcinomas: immunohistological evaluation using monoclonal antibodies to three members of the GalNAc-transferase family", Glycobiology, 1999, vol. 9, No. 1, pp. 43-52.

Jorgensen, Charlotte S., et al., "Polypeptide binding properties of the chaperone calreticulin", Eur. J. Biochem., 2000, vol. 267, pp. 2945-2954.

Sorensen, Tina, et al., "UDP-N-acetyl-α-D-galactosamine:polypeptide N-Acetylgalactosaminyltransferase: Identification and Separation of Two Distinct Transferase Activities", The Journal of Biological Chemistry, Oct. 13, 1995, vol. 270, No. 41, pp. 24166-24173.

Van den Steen, Philippe, et al., "Concepts and Principles of O-Linked Glycosylation", Critical Reviews in Biochemistry and Molecular Biology, 1998, vol. 33, No. 3, pp. 151-208.

Bennett, Eric Paul, et al., "cDNA Cloning and Expression of a Novel Human UDP-N-acetyl-α-D-galactosamine", The Journal of Biological Chemistry, 1996, vol. 271, No. 29, pp. 17006-17012.

White, Thayer, et al., "Purification and cDNA Cloning of a Human UDP-N-acetyl-α-D-galactosamine:polypeptide N-Acetylgalactosaminyltransferase", The Journal of Biological Chemistry, Oct. 13, 1995, vol. 270, No. 41, pp. 24156-24165.

Ulloa, Fausto, et al., "GalNAc-α-O-benzyl Inhibits Sialylation of de Novo Synthesized Apical but Not Basolateral Sialogylcoproteins and Blocks Lysosomal Enzyme Processing in a Post-trans-Golgi Network Compartment", The Journal of Biological Chemistry, Jun. 23, 2000, vol. 275, No. 25, pp. 18785-18793.

Yeaman, Charles, et al., "The O-glycosylated Stalk Domain is Required for Apical Sorting of Neurotrophin Receptors in Polarized MDCK Cells", The Journal of Cell Biology, Nov. 17, 1997, vol. 139, No. 4, pp. 929-940.

Alfalah, Marwan, et al., "O-linked glycans mediate apical sorting of human intestinal sucrase-isomaltase through association with lipid rafts", Current Biology, 1999, vol. 9, No. 11, pp. 593-596.

Huet, Guillemette, et al., "GalNAc-α-O-benzyl Inhibits NeuAca2-3 Glycosylation and Blocks the Intracellular Transport of Apical Glycoproteins and Mucus in Differentiated HT-29 Cells", The Journal of Cell Biology, 1998, vol. 141, pp. 1311-1322.

Kuan, Shih-Fan, et al., "Inhibition of Mucin Glycosylation by Aryl-N-acetyl-α-galactosaminides in Human Colon Cancer Cells", The Journal of Biological Chemistry, Nov. 15, 1989, vol. 264, No. 32, pp. 19271-19277.

Thomsson, Kristina A., et al., "Different O-glycosylation of respiratory mucin glycopeptides from a patient with cystic fibrosis", Glycoconjugate Journal, 1998, vol. 15, pp. 823-833.

Taylor-Papadimitriou, Joyce, et al., "Biology, biochemistry and immunology of carcinoma-associated mucins", Immunology Today, Mar. 1997, pp. 105-107.

Tabak, Lawrence A., "In Defense of the Oral Cavity: Structure, Biosynthesis, and Function of Salivary Mucins", Annu. Rev. Physiol., 1995, vol. 57, pp. 547-564.

Muller, Stefan, et al. "High Density O-Glycosylation of Tandem Repeat Peptide from Secretory MUC1 of T47D Breast Cancer Cells", The Journal of Biological Chemistry, Jun. 25, 1999, vol. 274, No. 26, pp. 18165-18172.

Hagen, Kelly G. Ten, et al., "Characterization of a UDP-GalNAc:Polypeptide N-Acetylgalactosaminyltransferase That Displays Glycopeptide N-Acetylgalactosaminyltransferase Activity", The Journal of Biological Chemistry, Sep. 24, 1999, vol. 274, No. 39, pp. 27867-27874.

Bennett, Eric Paul, et al., "Cloning of a Human UDP-N-Acetyl-α-D-Galactosamine:Polypeptide N-Acetylgalactosaminyltransferase That Complements Other GalNAc-Transferases in Complete O-Glycosylation of the MUC1 Tandem Repeat", The Journal of Biological Chemistry, Nov. 13, 1998, vol. 273, No. 46, pp. 30472-30481.

Bennett, Eric Paul, et al., "A novel human UDP-N-acetyl-D-galactosamine:polypeptide N-acetylgalactosaminyltransferase, GalNAc-T7, with specificity for partial GalNAc-glysocylated acceptor substrates", FEBS Letters, 1999, vol. 460, pp. 226-230.

Imberty, Anne, et al., "Fold recognition and molecular modeling of a lectin-like domain in UDP-GalNAc:polypeptide N-acetylgalactosaminyltransferases", Protein Engineering, 1997, vol. 10, No. 12, pp. 1353-1356.

Paulson, James C., et al., "Glycosyltransferases", The Journal of Biological Chemistry, Oct. 25, 1989, vol. 264, No. 30, pp. 17615-17618.

Hagen, Fred K., et al., "Structure-Function Analysis of the UDP-N-acetyl-D-galactosamine:Polypeptide N-acetylgalactosaminyltransferase", The Journal of Biological Chemistry, Mar. 5, 1999, vol. 274, No. 10, pp. 6797-6803.

Amado, Margarida, et al., "Identification and characterization of large galactosyltransferase gene families: galactosyltransferases for all functions", Biochimica et Biophysica Acta, 1999, vol. 1473, pp. 35-53.

Amado, Margarida, et al., "A Family of Human B3-Galactosyltransferases", The Journal of Biological Chemistry, May 22, 1998, vol. 273, No. 21, pp. 12770-12778.

Zanetta, Jean-Pierre, et al., "Massive in vitro synthesis of tagged oligosaccharides in 1-benzyl-2-acetamido-2-deoxy-α-D-galactopyranoside treated HT-29 cells", Glycobiology, 2000, vol. 10, No. 6, pp. 565-575.

Altschuler, Yoram, et al., "Clathrin-mediated Endocytosis of MUC1 is Modulated by its Glcyosylation State", Molecular Biology of the Cell, Mar. 2000, vol. 11, pp. 819-831.

Kingsley, David M., et al., "Three Types of Low Density Lipoprotein Receptor-deficient Mutant Have Pleiotropic Defects in the Synthesis of N-linked, O-linked, and Lipid-linked Carbohydrate Chains", The Journal of Cell Biology, May 1986, vol. 102, pp. 1576-1585.

\* cited by examiner

*Primary Examiner*—James O. Wilson
*Assistant Examiner*—Paul V. Ward
(74) *Attorney, Agent, or Firm*—Darby & Darby

(57) ABSTRACT

Attachment of O-glycans to proteins is controlled by a large family of homologous polypeptide GalNAc-transferases. Polypeptide GalNAc-transferases contain a C-terminal sequence with similarity to lectins. This invention discloses that the putative lectin domains of GalNAc-transferase isoforms, GalNAc-T4, -T7, -T2, and -T3, are functional and recognize carbohydrates, glycopeptides, and peptides and discloses the lectin domains of GalNAc-T1-T16. These lectin domains have different binding specificities and modulate the functions of GalNAc-transferase isoforms differently. Novel methods for identification of inhibitors or modulators of binding activities mediated by lectin domains of polypeptide GalNAc-transferases are disclosed. Direct binding activity of GalNAc-transferase lectins has been demonstrated for the first time and methods to measure lectin mediated binding of isolated lectins or enzymes with lectin domains are disclosed. The present invention specifically discloses a novel selective inhibitor of polypeptide GalNAc-transferase lectin domains, which provides a major advancement in that this inhibitor and related inhibitors sharing common characteristics of activity bind lectin domains without serving as acceptor substrate for glycosyltransferases involved in synthesis of O-glycans. This inhibitor is represented by the β-anomeric configuration of GalNAc-benzyl, GalNAcβ-benzyl. Methods for inhibiting intracellular transport, cell surface expression, and secretion of mucins and O-glycosylated glycoproteins without affecting O-glycosylation processing are disclosed using the novel selective inhibitor identified.

3 Claims, 18 Drawing Sheets

Fig. 4

MUC1 full coding and secreted constructs

A

B

_US 7,338,932 B2_

SEQUENCE LISTING

<160> NUMBER OF SEQ ID NOS: 130

<210> SEQ ID NO 1
<211> LENGTH: 20
<212> TYPE: PRT
<213> ORGANISM: Homo sapiens

<400> SEQUENCE: 1

His Gly Val Thr Ser Ala Pro Asp Thr Arg Pro Ala Pro Gly Ser Thr
1               5                   10                  15

```
Ala Pro Pro Ala
            20

<210> SEQ ID NO 2
<211> LENGTH: 24
<212> TYPE: PRT
<213> ORGANISM: Homo sapiens

<400> SEQUENCE: 2

Thr Ala Pro Pro Ala His Gly Val Thr Ser Ala Pro Asp Thr Arg Pro
1               5                   10                  15

Ala Pro Gly Ser Thr Ala Pro Pro
            20

<210> SEQ ID NO 3
<211> LENGTH: 276
<212> TYPE: PRT
<213> ORGANISM: Homo sapiens

<400> SEQUENCE: 3

Met Leu Ala Trp Arg Asp Gly Glu Leu Glu Ala Glu Thr Ser Ser Ser
1               5                   10                  15

Leu Phe Leu Leu Ala Met Gln Val Trp Met Cys Gly Gly Arg Met Glu
            20                  25                  30

Asp Ile Pro Cys Ser Arg Val Gly His Ile Tyr Arg Lys Tyr Val Pro
        35                  40                  45

Tyr Lys Val Pro Ala Gly Val Ser Leu Ala Arg Val Arg Thr Leu Lys
    50                  55                  60

Arg Val Ala Glu Val Trp Met Asp Glu Tyr Ala Glu Tyr Ile Tyr Gln
65                  70                  75                  80

Arg Arg Pro Glu Tyr Arg His Leu Ser Ala Gly Asp Val Ala Val Gln
                85                  90                  95

Lys Lys Leu Arg Ser Ser Leu Asn Cys Lys Ser Phe Lys Trp Phe Met
            100                 105                 110

Thr Lys Ile Ala Trp Asp Leu Pro Lys Phe Tyr Pro Pro Val Glu Pro
        115                 120                 125

Pro Ala Ala Ala Trp Gly Glu Ile Arg Asn Val Gly Thr Gly Leu Cys
    130                 135                 140

Ala Asp Thr Lys His Gly Ala Leu Gly Ser Pro Leu Arg Leu Glu Gly
145                 150                 155                 160

Cys Val Arg Gly Arg Gly Glu Ala Ala Trp Asn Asn Met Gln Val Phe
                165                 170                 175

Thr Phe Thr Trp Arg Glu Asp Ile Arg Pro Gly Asp Pro Gln His Thr
            180                 185                 190

Lys Lys Phe Cys Phe Asp Ala Ile Ser His Thr Ser Pro Val Thr Leu
        195                 200                 205

Tyr Asp Cys His Ser Met Lys Gly Asn Gln Leu Trp Lys Tyr Arg Lys
    210                 215                 220

Asp Lys Thr Leu Tyr His Pro Val Ser Gly Ser Cys Met Asp Cys Ser
225                 230                 235                 240

Glu Ser Asp His Arg Ile Phe Met Asn Thr Cys Asn Pro Ser Ser Leu
                245                 250                 255

Thr Gln Gln Trp Leu Phe Glu His Thr Asn Ser Thr Val Leu Glu Lys
            260                 265                 270

Phe Asn Arg Asn
            275
```

```
<210> SEQ ID NO 4
<211> LENGTH: 8
<212> TYPE: PRT
<213> ORGANISM: Homo sapiens

<400> SEQUENCE: 4

Trp Tyr Leu Glu Asn Val Tyr Pro
1               5

<210> SEQ ID NO 5
<211> LENGTH: 5
<212> TYPE: PRT
<213> ORGANISM: Homo sapiens

<400> SEQUENCE: 5

Gly Val Thr Ser Ala
1               5

<210> SEQ ID NO 6
<211> LENGTH: 4
<212> TYPE: PRT
<213> ORGANISM: Homo sapiens

<400> SEQUENCE: 6

Pro Asp Thr Arg
1

<210> SEQ ID NO 7
<211> LENGTH: 4
<212> TYPE: PRT
<213> ORGANISM: Homo sapiens

<400> SEQUENCE: 7

Val Thr Ser Ala
1

<210> SEQ ID NO 8
<211> LENGTH: 4
<212> TYPE: PRT
<213> ORGANISM: Homo sapiens

<400> SEQUENCE: 8

Gly Ser Thr Ala
1

<210> SEQ ID NO 9
<211> LENGTH: 25
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: where X is either T or V
<220> FEATURE:
<221> NAME/KEY: MISC_FEATURE
<222> LOCATION: (20)..(20)
<223> OTHER INFORMATION: where X is either S or V
<220> FEATURE:
<221> NAME/KEY: MISC_FEATURE
<222> LOCATION: (21)..(21)
<223> OTHER INFORMATION: where X is either T or V

<400> SEQUENCE: 9

Thr Ala Pro Pro Ala His Gly Val Xaa Ser Ala Pro Asp Thr Arg Pro
1               5                   10                  15
```

```
Ala Pro Gly Xaa Xaa Ala Pro Pro Ala
            20              25

<210> SEQ ID NO 10
<211> LENGTH: 20
<212> TYPE: PRT
<213> ORGANISM: Homo sapiens

<400> SEQUENCE: 10

Pro Thr Thr Thr Pro Ile Ser Thr Thr Thr Met Val Thr Pro Thr Pro
1               5                   10                  15

Thr Pro Thr Cys
            20

<210> SEQ ID NO 11
<211> LENGTH: 12
<212> TYPE: PRT
<213> ORGANISM: Homo sapiens

<400> SEQUENCE: 11

Ser Ala Pro Thr Thr Ser Thr Thr Ser Ala Pro Thr
1               5                   10

<210> SEQ ID NO 12
<211> LENGTH: 24
<212> TYPE: PRT
<213> ORGANISM: Homo sapiens

<400> SEQUENCE: 12

Cys Pro Pro Thr Pro Ser Ala Thr Thr Pro Ala Pro Pro Ser Ser Ser
1               5                   10                  15

Ala Pro Pro Glu Thr Thr Ala Ala
            20

<210> SEQ ID NO 13
<211> LENGTH: 13
<212> TYPE: PRT
<213> ORGANISM: Homo sapiens

<400> SEQUENCE: 13

Pro Thr Thr Asp Ser Thr Thr Pro Ala Pro Thr Thr Lys
1               5                   10

<210> SEQ ID NO 14
<211> LENGTH: 14
<212> TYPE: PRT
<213> ORGANISM: Homo sapiens

<400> SEQUENCE: 14

Val Thr His Pro Gly Tyr Pro Phe Val Thr His Pro Gly Tyr
1               5                   10

<210> SEQ ID NO 15
<211> LENGTH: 18
<212> TYPE: PRT
<213> ORGANISM: Homo sapiens

<400> SEQUENCE: 15

Pro Thr Glu Arg Thr Thr Thr Pro Thr Lys Arg Thr Thr Thr Pro Thr
1               5                   10                  15

Ile Arg

<210> SEQ ID NO 16
```

```
<211> LENGTH: 16
<212> TYPE: PRT
<213> ORGANISM: Ovine

<400> SEQUENCE: 16

Leu Ser Glu Ser Thr Thr Gln Leu Pro Gly Gly Gly Pro Gly Cys Ala
1               5                   10                  15

<210> SEQ ID NO 17
<211> LENGTH: 23
<212> TYPE: PRT
<213> ORGANISM: Homo sapiens

<400> SEQUENCE: 17

Pro Arg Phe Gln Asp Ser Ser Ser Ser Lys Ala Pro Pro Pro Leu Pro
1               5                   10                  15

Ser Pro Ser Arg Leu Pro Gly
            20

<210> SEQ ID NO 18
<211> LENGTH: 11
<212> TYPE: PRT
<213> ORGANISM: Artificial Sequence
<220> FEATURE:
<223> OTHER INFORMATION: synthetic peptide

<400> SEQUENCE: 18

Arg Pro Ala Pro Gly Ser Thr Ala Pro Pro Ala
1               5                   10

<210> SEQ ID NO 19
<211> LENGTH: 21
<212> TYPE: PRT
<213> ORGANISM: Artificial Sequence
<220> FEATURE:
<223> OTHER INFORMATION: synthetic peptide

<400> SEQUENCE: 19

Gln Ala Thr Glu Tyr Glu Tyr Leu Asp Tyr Asp Phe Leu Pro Glu Thr
1               5                   10                  15

Glu Pro Pro Glu Met
            20

<210> SEQ ID NO 20
<211> LENGTH: 33
<212> TYPE: DNA
<213> ORGANISM: Artificial Sequence
<220> FEATURE:
<223> OTHER INFORMATION: primer EBHC332

<400> SEQUENCE: 20
gtagagggat ctcgtctgaa tgtttacatt ata                              33

<210> SEQ ID NO 21
<211> LENGTH: 20
<212> TYPE: DNA
<213> ORGANISM: Artificial Sequence
<220> FEATURE:
<223> OTHER INFORMATION: primer T7

<400> SEQUENCE: 21
taatacgact cactataggg                                             20

<210> SEQ ID NO 22
<211> LENGTH: 20
```

```
<212> TYPE: DNA
<213> ORGANISM: Artificial Sequence
<220> FEATURE:
<223> OTHER INFORMATION: primers T7/EBHC201

<400> SEQUENCE: 22
aagcgggcac catatgctcg                                              20

<210> SEQ ID NO 23
<211> LENGTH: 29
<212> TYPE: DNA
<213> ORGANISM: Artificial Sequence
<220> FEATURE:
<223> OTHER INFORMATION: primer EBHC121H

<400> SEQUENCE: 23
gcgggatcca ggacttcctg ctggagatg                                    29

<210> SEQ ID NO 24
<211> LENGTH: 28
<212> TYPE: DNA
<213> ORGANISM: Artificial Sequence
<220> FEATURE:
<223> OTHER INFORMATION: primer EBHC107B

<400> SEQUENCE: 24
gcggatcctc agaatatttc tggaaggg                                     28

<210> SEQ ID NO 25
<211> LENGTH: 35
<212> TYPE: DNA
<213> ORGANISM: Artificial Sequence
<220> FEATURE:
<223> OTHER INFORMATION: primer EBHC75D

<400> SEQUENCE: 25
gcggaattct taaaagaaa gaccttcatc acagc                              35

<210> SEQ ID NO 26
<211> LENGTH: 28
<212> TYPE: DNA
<213> ORGANISM: Artificial Sequence
<220> FEATURE:
<223> OTHER INFORMATION: primer EBHC68

<400> SEQUENCE: 26
gcggaattcc tactgctgca ggttgagc                                     28

<210> SEQ ID NO 27
<211> LENGTH: 28
<212> TYPE: DNA
<213> ORGANISM: Artificial Sequence
<220> FEATURE:
<223> OTHER INFORMATION: primer EBHC219H

<400> SEQUENCE: 27
gcgggatcca acgatggaaa ggaacatg                                     28

<210> SEQ ID NO 28
<211> LENGTH: 31
<212> TYPE: DNA
<213> ORGANISM: Artificial Sequence
<220> FEATURE:
<223> OTHER INFORMATION: EBHC215

<400> SEQUENCE: 28
```

```
agcggatcca ggaacactta atcattttgg c                               31

<210> SEQ ID NO 29
<211> LENGTH: 31
<212> TYPE: DNA
<213> ORGANISM: Artificial Sequence
<220> FEATURE:
<223> OTHER INFORMATION: primer EBHC318

<400> SEQUENCE: 29
gcgggatcct tttcatgcct ccgcaggagc c                               31

<210> SEQ ID NO 30
<211> LENGTH: 30
<212> TYPE: DNA
<213> ORGANISM: Artificial Sequence
<220> FEATURE:
<223> OTHER INFORMATION: primer EBHC307

<400> SEQUENCE: 30
gcgggatccg acgaaagtgc tgttgtgctc                                 30

<210> SEQ ID NO 31
<211> LENGTH: 32
<212> TYPE: DNA
<213> ORGANISM: Artificial Sequence
<220> FEATURE:
<223> OTHER INFORMATION: primer EBHC909

<400> SEQUENCE: 31
gcgggatcct gctttaactg gagggctaga gc                              32

<210> SEQ ID NO 32
<211> LENGTH: 30
<212> TYPE: DNA
<213> ORGANISM: Artificial Sequence
<220> FEATURE:
<223> OTHER INFORMATION: primer EBHC907

<400> SEQUENCE: 32
gcgggatcca tcagttacac ttcaggcttc                                 30

<210> SEQ ID NO 33
<211> LENGTH: 34
<212> TYPE: DNA
<213> ORGANISM: Artificial Sequence
<220> FEATURE:
<223> OTHER INFORMATION: primer EBHC514H

<400> SEQUENCE: 33
gcgggatccc ctggacctca tgctggaggc catg                            34

<210> SEQ ID NO 34
<211> LENGTH: 32
<212> TYPE: DNA
<213> ORGANISM: Artificial Sequence
<220> FEATURE:
<223> OTHER INFORMATION: primer EBHC511N

<400> SEQUENCE: 34
agcggatcct ggggatgatc tgggtcctag ac                              32

<210> SEQ ID NO 35
<211> LENGTH: 32
<212> TYPE: DNA
<213> ORGANISM: Artificial Sequence
```

```
<220> FEATURE:
<223> OTHER INFORMATION: primer EBHC1122H

<400> SEQUENCE: 35
gcgaagcttc aggatgaggg aagacagaga tg                                32

<210> SEQ ID NO 36
<211> LENGTH: 35
<212> TYPE: DNA
<213> ORGANISM: Artificial Sequence
<220> FEATURE:
<223> OTHER INFORMATION: primer EBHC1116H

<400> SEQUENCE: 36
gcgaagcttc tctctaaaca ctatggatct tattc                             35

<210> SEQ ID NO 37
<211> LENGTH: 33
<212> TYPE: DNA
<213> ORGANISM: Artificial Sequence
<220> FEATURE:
<223> OTHER INFORMATION: primer EBHC1820

<400> SEQUENCE: 37
gcgggatcct ctgaaagaaa gtatgaaatt agc                               33

<210> SEQ ID NO 38
<211> LENGTH: 30
<212> TYPE: DNA
<213> ORGANISM: Artificial Sequence
<220> FEATURE:
<223> OTHER INFORMATION: primer EBHC1821

<400> SEQUENCE: 38
gcgggatcct cactggctgt tggtctgacc                                   30

<210> SEQ ID NO 39
<211> LENGTH: 34
<212> TYPE: DNA
<213> ORGANISM: Artificial Sequence
<220> FEATURE:
<223> OTHER INFORMATION: primer EBHC1320

<400> SEQUENCE: 39
gcgggatccc tgccgcctgc agggccgctc ccag                              34

<210> SEQ ID NO 40
<211> LENGTH: 32
<212> TYPE: DNA
<213> ORGANISM: Artificial Sequence
<220> FEATURE:
<223> OTHER INFORMATION: primer EBHC1321

<400> SEQUENCE: 40
gcgggatcct cagtgccgtc ggtgtttgat cc                                32

<210> SEQ ID NO 41
<211> LENGTH: 31
<212> TYPE: DNA
<213> ORGANISM: Artificial Sequence
<220> FEATURE:
<223> OTHER INFORMATION: primer EBHC2520

<400> SEQUENCE: 41
gcgggatccc cgcgagcggc agcccgacgg c                                 31
```

<210> SEQ ID NO 42
<211> LENGTH: 30
<212> TYPE: DNA
<213> ORGANISM: Artificial Sequence
<220> FEATURE:
<223> OTHER INFORMATION: primer EBHC2521

<400> SEQUENCE: 42
gcgggatcct cagttcctat tgaattttc                              30

<210> SEQ ID NO 43
<211> LENGTH: 31
<212> TYPE: DNA
<213> ORGANISM: Artificial Sequence
<220> FEATURE:
<223> OTHER INFORMATION: primer EBHC629

<400> SEQUENCE: 43
gcgaattcgt gaagtgactc agccacttaa g                           31

<210> SEQ ID NO 44
<211> LENGTH: 28
<212> TYPE: DNA
<213> ORGANISM: Artificial Sequence
<220> FEATURE:
<223> OTHER INFORMATION: primer EBHC614

<400> SEQUENCE: 44
gcgaattcgt ctctgtcaga cacgtgtc                               28

<210> SEQ ID NO 45
<211> LENGTH: 32
<212> TYPE: DNA
<213> ORGANISM: Artificial Sequence
<220> FEATURE:
<223> OTHER INFORMATION: primer EBHC1051

<400> SEQUENCE: 45
gcgggatccg gctcggtgct gcgggcgcag cg                          32

<210> SEQ ID NO 46
<211> LENGTH: 35
<212> TYPE: DNA
<213> ORGANISM: Artificial Sequence
<220> FEATURE:
<223> OTHER INFORMATION: primer EBHC1032

<400> SEQUENCE: 46
gcgggatcct cataacatgc gctctttgaa gaacc                       35

<210> SEQ ID NO 47
<211> LENGTH: 34
<212> TYPE: DNA
<213> ORGANISM: Artificial Sequence
<220> FEATURE:
<223> OTHER INFORMATION: primer EBHC2000

<400> SEQUENCE: 47
gcgggatccg atgttgcacv vtccccacca cacc                        34

<210> SEQ ID NO 48
<211> LENGTH: 31
<212> TYPE: DNA
<213> ORGANISM: Artificial Sequence
<220> FEATURE:
<223> OTHER INFORMATION: primer EBHC2002

-continued

```
<400> SEQUENCE: 48
gcgggatcct catcgttcat ccacagcatt g                              31

<210> SEQ ID NO 49
<211> LENGTH: 32
<212> TYPE: DNA
<213> ORGANISM: Artificial Sequence
<220> FEATURE:
<223> OTHER INFORMATION: primer EBHC1720

<400> SEQUENCE: 49
gcgggatcct ctgctgcctg cattgagggc tg                             32

<210> SEQ ID NO 50
<211> LENGTH: 32
<212> TYPE: DNA
<213> ORGANISM: Artificial Sequence
<220> FEATURE:
<223> OTHER INFORMATION: primer EBHC1721

<400> SEQUENCE: 50
gcgggatcct catgtgccca aggtcatgtt cc                             32

<210> SEQ ID NO 51
<211> LENGTH: 31
<212> TYPE: DNA
<213> ORGANISM: Artificial Sequence
<220> FEATURE:
<223> OTHER INFORMATION: primer EBHC412

<400> SEQUENCE: 51
gcgggatccc aagaggaagt tggaggtgcc g                              31

<210> SEQ ID NO 52
<211> LENGTH: 31
<212> TYPE: DNA
<213> ORGANISM: Artificial Sequence
<220> FEATURE:
<223> OTHER INFORMATION: primer EBHC438

<400> SEQUENCE: 52
gcgggatccc aggggtcctc aagagctcac c                              31

<210> SEQ ID NO 53
<211> LENGTH: 33
<212> TYPE: DNA
<213> ORGANISM: Artificial Sequence
<220> FEATURE:
<223> OTHER INFORMATION: primer EBHC1913

<400> SEQUENCE: 53
gcgggatccc tactacttat ggcaggacaa ccg                            33

<210> SEQ ID NO 54
<211> LENGTH: 30
<212> TYPE: DNA
<213> ORGANISM: Artificial Sequence
<220> FEATURE:
<223> OTHER INFORMATION: primer EBHC1912

<400> SEQUENCE: 54
gcgtcatgtg tgtggcaaca gctgccactg                                30

<210> SEQ ID NO 55
```

```
<211> LENGTH: 157
<212> TYPE: DNA
<213> ORGANISM: Artificial Sequence
<220> FEATURE:
<223> OTHER INFORMATION: synthetic nucleic acid

<400> SEQUENCE: 55
gcggccgctc tagaactagt ggatccagca gccatcatca tcatcatcac agcagcggcc      60
tggtgccgcg cggcagccat atggctagca tgactggtgg acagcaaatg ggtcgcggaa     120
ttccgatatc aagcttatcg ataccgtcga cctcgag                              157

<210> SEQ ID NO 56
<211> LENGTH: 123
<212> TYPE: DNA
<213> ORGANISM: Artificial Sequence
<220> FEATURE:
<223> OTHER INFORMATION: synthetic nucleic acid

<400> SEQUENCE: 56
gaattcgcgg ccgcagcagc catcatcatc atcatcacag cagcggcctg gtgccgcgcg      60
gcagccatat ggctagcatg actggtggac agcaaatgga tccactagtt ctagagcggc     120
cgc                                                                   123

<210> SEQ ID NO 57
<211> LENGTH: 1746
<212> TYPE: DNA
<213> ORGANISM: Homo sapiens

<400> SEQUENCE: 57
atgtgggggc gcacggcgcg gcggcgctgc ccgcgggaac tgcggcgcgg ccggaggcg       60 ctgttggtgc tcctggcgct actggcgttg gccgggctgg gctcggtgct gcgggcgcag     120
cgtggggccg gggccggggc tgccgagccg ggaccccgc gcaccccgcg ccccgggcgg      180
cgcgagccgg tcatgccgcg gccgccggtg ccggcgaacg cgctgggcgc gcggggcgag     240
gcggtgcggc tgcagctgca gggcgaggag ctgcggctgc aggaggagag cgtgcggctg     300
caccagatta acatctacct cagcgaccgc atctcactgc accgccgcct gcccgagcgc     360
tggaacccgc tgtgcaaaga gaagaaatat gattatgata atttgcccag acatctgtt      420 atcatagcat tttataatga agcctggtca actctccttc ggacagttta cagtgtcctt     480
gagacatccc cggatatcct gctagaagaa gtgatccttg tagatgacta cagtgataga    540
gagcacctga aggagcgctt ggccaatgag ctttcggac tgcccaaggt gcgcctgatc      600
cgcgccaaca agagagaggg cctggtgcga gcccggctgc tggggcgtc tgcggcgagg     660 ggcgatgttc tgaccttcct ggactgtcac tgtaatgcc acgaagggtg gctggagccg     720
ctgctgcaga ggatccatga agaggagtcg gcagtggtgt gcccggtgat tgatgtgatc    780
gactggaaca ccttcgaata cctggggaac tccggggagc cccagatcgg cggtttcgac    840
tggaggctgg tgttcacgtg gcacacagtt cctgagaggg agaggatacg gatgcaatcc    900
cccgtcgatg tcatcaggtc tccaacaatg gctggtggc tgtttgctgt gagtaagaaa    960
tattttgaat atctggggtc ttatgataca ggaatggaag tttggggagg agaaaacctc   1020
gaattttcct ttaggatctg gcagtgtggt ggggttctgg aaacacaccc atgttccccat   1080 gttggccatg ttttccccaa gcaagctccc tactcccgca caaggctct ggccaacagt    1140 gttcgtgcag ctgaagtatg gatggatgaa tttaaagagc tctactacca tcgcaacccc   1200
cgtgcccgct tggaaccttt tgggatgtg acagagagga agcagctccg ggacaagctc    1260
```

```
cagtgtaaag acttcaagtg gttcttggag actgtgtatc cagaactgca tgtgcctgag    1320
gacaggcctg gcttcttcgg gatgctccag aacaaaggac taacagacta ctgctttgac    1380
tataaccctc ccgatgaaaa ccagattgtg ggacaccagg tcattctgta cctctgtcat    1440
gggatgggcc agaatcagtt tttcgagtac acgtcccaga agaaatacg ctataacacc    1500 caccagcctg agggctgcat tgctgtggaa gcaggaatgg ataccttat catgcatctc    1560 tgcgaagaaa ctgccccaga gaatcagaag ttcatcttgc aggaggatgg atctttattt    1620
cacgaacagt ccaagaaatg tgtccaggct gcgaggaagg agtcgagtga cagtttcgtt    1680
ccactcttac gagactgcac caactcggat catcagaaat ggttcttcaa agagcgcatg    1740
ttatga                                                               1746
```

<210> SEQ ID NO 58
<211> LENGTH: 581
<212> TYPE: PRT
<213> ORGANISM: Homo sapiens

<400> SEQUENCE: 58

```
Met Trp Gly Arg Thr Ala Arg Arg Cys Pro Arg Glu Leu Arg Arg
1               5                   10                  15

Gly Arg Glu Ala Leu Leu Val Leu Leu Ala Leu Leu Ala Leu Ala Gly
            20                  25                  30

Leu Gly Ser Val Leu Arg Ala Gln Arg Gly Ala Gly Ala Gly Ala Ala
        35                  40                  45

Glu Pro Gly Pro Pro Arg Thr Pro Arg Pro Gly Arg Arg Glu Pro Val
    50                  55                  60

Met Pro Arg Pro Pro Val Pro Ala Asn Ala Leu Gly Ala Arg Gly Glu
65                  70                  75                  80

Ala Val Arg Leu Gln Leu Gln Gly Glu Glu Leu Arg Leu Gln Glu Glu
                85                  90                  95

Ser Val Arg Leu His Gln Ile Asn Ile Tyr Leu Ser Asp Arg Ile Ser
            100                 105                 110

Leu His Arg Arg Leu Pro Glu Arg Trp Asn Pro Leu Cys Lys Glu Lys
        115                 120                 125

Lys Tyr Asp Tyr Asp Asn Leu Pro Arg Thr Ser Val Ile Ile Ala Phe
    130                 135                 140

Tyr Asn Glu Ala Trp Ser Thr Leu Leu Arg Thr Val Tyr Ser Val Leu
145                 150                 155                 160

Glu Thr Ser Pro Asp Ile Leu Leu Glu Glu Val Ile Leu Val Asp Asp
                165                 170                 175

Tyr Ser Asp Arg Glu His Leu Lys Glu Arg Leu Ala Asn Glu Leu Ser
            180                 185                 190

Gly Leu Pro Lys Val Arg Leu Ile Arg Ala Asn Lys Lys Gly Leu
        195                 200                 205

Val Arg Ala Arg Leu Leu Gly Ala Ser Ala Ala Arg Gly Asp Val Leu
    210                 215                 220

Thr Phe Leu Asp Cys His Cys Glu Cys His Glu Gly Trp Leu Glu Pro
225                 230                 235                 240

Leu Leu Gln Arg Ile His Glu Glu Ser Ala Val Val Cys Pro Val
                245                 250                 255

Ile Asp Val Ile Asp Trp Asn Thr Phe Glu Tyr Leu Gly Asn Ser Gly
            260                 265                 270

Glu Pro Gln Ile Gly Gly Phe Asp Trp Arg Leu Val Phe Thr Trp His
```

```
                    275                 280                 285
Thr Val Pro Glu Arg Glu Arg Ile Arg Met Gln Ser Pro Val Asp Val
    290                 295                 300

Ile Arg Ser Pro Thr Met Ala Gly Gly Leu Phe Ala Val Ser Lys Lys
305                 310                 315                 320

Tyr Phe Glu Tyr Leu Gly Ser Tyr Asp Thr Gly Met Glu Val Trp Gly
                325                 330                 335

Gly Glu Asn Leu Glu Phe Ser Phe Arg Ile Trp Gln Cys Gly Gly Val
                340                 345                 350

Leu Glu Thr His Pro Cys Ser His Val Gly His Phe Ser Pro Ser Lys
                355                 360                 365

Leu Pro Thr Pro Arg Asn Lys Ala Leu Ala Asn Ser Val Arg Ala Ala
    370                 375                 380

Glu Val Trp Met Asp Glu Phe Lys Glu Leu Tyr Tyr His Arg Asn Pro
385                 390                 395                 400

Arg Ala Arg Leu Glu Pro Phe Gly Asp Val Thr Glu Arg Lys Gln Leu
                405                 410                 415

Arg Asp Lys Leu Gln Cys Lys Asp Phe Lys Trp Phe Leu Glu Thr Val
                420                 425                 430

Tyr Pro Glu Leu His Val Pro Glu Asp Arg Pro Gly Phe Phe Gly Met
                435                 440                 445

Leu Gln Asn Lys Gly Leu Thr Asp Tyr Cys Phe Asp Tyr Asn Pro Pro
    450                 455                 460

Asp Glu Asn Gln Ile Val Gly His Gln Val Ile Leu Tyr Leu Cys His
465                 470                 475                 480

Gly Met Gly Gln Asn Gln Phe Phe Glu Tyr Thr Ser Gln Lys Glu Ile
                485                 490                 495

Arg Tyr Asn Thr His Gln Pro Glu Gly Cys Ile Ala Val Glu Ala Gly
                500                 505                 510

Met Asp Thr Leu Ile Met His Leu Cys Glu Glu Thr Ala Pro Glu Asn
                515                 520                 525

Gln Lys Phe Ile Leu Gln Glu Asp Gly Ser Leu Phe His Glu Gln Ser
    530                 535                 540

Lys Lys Cys Val Gln Ala Ala Arg Lys Glu Ser Ser Asp Ser Phe Val
545                 550                 555                 560

Pro Leu Leu Arg Asp Cys Thr Asn Ser Asp His Gln Lys Trp Phe Phe
                565                 570                 575

Lys Glu Arg Met Leu
                580

<210> SEQ ID NO 59
<211> LENGTH: 1920
<212> TYPE: DNA
<213> ORGANISM: Homo sapiens

<400> SEQUENCE: 59
atgctcctaa ggaagcgata caggcacaga ccatgcagac tccagttcct cctgctgctc      60
ctgatgctgg gatgcgtcct gatgatggtg gcgatgttgc accctcccca ccacaccctg     120
caccagactg tcacagccca agccagcaag cacagccctg aagccaggta ccgcctggac     180
tttggggaat cccaggattg gtactggaa gctgaggatg agggtgaaga gtacagccct     240
ctggagggcc tgccacccct tatctcactg cgggaggatc agctgctggt ggccgtggcc     300
ttaccccagg ccagaaggaa ccagagccag ggcaggagag tgggagcta ccgcctcatc     360
```

```
aagcagccaa ggaggcagga taaggaagcc ccaaagaggg actgggggc tgatgaggac    420
ggggaggtgt ctgaagaaga ggagttgacc ccgttcagcc tggacccacg tggcctccag    480
gaggcactca gtgcccgcat ccccctccag agggctctgc ccgaggtgcg gcacccactg    540
tgtctgcagc agcaccctca ggacagcctg cccacagcca gcgtcatcct ctgtttccat    600
gatgaggcct ggtccactct cctgcggact gtacacagca tcctcgacac agtgccagg    660
gccttcctga aggagatcat cctcgtggac gacctcagcc agcaaggaca actcaagtct    720
gctctcagcg aatatgtggc caggctggag ggggtgaagt tactcaggag caacaagagg    780
ctgggtgcca tcagggcccg gatgctgggg gccaccgaga ccaccgggga tgtgctcgtc    840
ttcatggatg cccactgcga gtgccaccca ggctggctgg agcccctcct cagcagaata    900
gctggtgaca ggagccgagt ggtatctccg gtgatagatg tgattgactg gaagactttc    960
cagtattacc cctcaaagga cctgcagcgt ggggtgttgg actggaagct ggatttccac   1020
tgggaacctt tgccagagca tgtgaggaag gccctccagt cccccataag ccccatcagg   1080
agccctgtgg tgcccggaga ggtggtggcc atggacagac attacttcca aaacactgga   1140
gcgtatgact ctcttatgtc gctgcgaggt ggtgaaaacc tcgaactgtc tttcaaggcc   1200
tggctctgtg gtggctctgt tgaaatcctt ccctgctctc gggtaggaca catctaccaa   1260
aatcaggatt cccattcccc cctcgaccag gaggccaccc tgaggaacag ggttcgcatt   1320
gctgagacct ggctggggtc attcaaagaa accttctaca agcatagccc agaggccttc   1380
tccttgagca aggctgagaa gccagactgc atggaacgct gcagctgca aaggagactg    1440
ggttgtcgga cattccactg gtttctggct aatgtctacc ctgagctgta cccatctgaa   1500
cccaggccca gttctctgg aaagctccac aacactggac ttgggctctg tgcagactgc    1560
caggcagaag gggacatcct gggctgtccc atggtgttgg ctccttgcag tgacagccgg   1620
cagcaacagt acctgcagca caccagcagg aaggagattc actttggcag cccacagcac   1680
ctgtgctttg ctgtcaggca ggagcaggtg attcttcaga actgcacgga ggaaggcctg   1740
gccatccacc agcagcactg ggacttccag gagaatggga tgattgtcca cattctttct   1800
gggaaatgca tggaagctgt ggtgcaagaa aacaataaag atttgtacct gcgtccgtgt   1860
gatggaaaag cccgccagca gtggcgtttt gaccagatca atgctgtgga tgaacgatga   1920
```

<210> SEQ ID NO 60
<211> LENGTH: 639
<212> TYPE: PRT
<213> ORGANISM: Homo sapiens

<400> SEQUENCE: 60

Met Leu Leu Arg Lys Arg Tyr Arg His Arg Pro Cys Arg Leu Gln Phe
1               5                   10                  15

Leu Leu Leu Leu Leu Met Leu Gly Cys Val Leu Met Met Val Ala Met
            20                  25                  30

Leu His Pro Pro His His Thr Leu His Gln Thr Val Thr Ala Gln Ala
        35                  40                  45

Ser Lys His Ser Pro Glu Ala Arg Tyr Arg Leu Asp Phe Gly Glu Ser
    50                  55                  60

Gln Asp Trp Val Leu Glu Ala Glu Asp Glu Gly Glu Glu Tyr Ser Pro
65                  70                  75                  80

Leu Glu Gly Leu Pro Pro Phe Ile Ser Leu Arg Glu Asp Gln Leu Leu
                85                  90                  95

Val Ala Val Ala Leu Pro Gln Ala Arg Arg Asn Gln Ser Gln Gly Arg

```
                100                 105                 110
Arg Gly Gly Ser Tyr Arg Leu Ile Lys Gln Pro Arg Gln Asp Lys
            115                 120                 125
Glu Ala Pro Lys Arg Asp Trp Gly Ala Asp Glu Asp Gly Glu Val Ser
130                 135                 140
Glu Glu Glu Glu Leu Thr Pro Phe Ser Leu Asp Pro Arg Gly Leu Gln
145                 150                 155                 160
Glu Ala Leu Ser Ala Arg Ile Pro Leu Gln Arg Ala Leu Pro Glu Val
                165                 170                 175
Arg His Pro Leu Cys Leu Gln Gln His Pro Gln Asp Ser Leu Pro Thr
                180                 185                 190
Ala Ser Val Ile Leu Cys Phe His Asp Glu Ala Trp Ser Thr Leu Leu
                195                 200                 205
Arg Thr Val His Ser Ile Leu Asp Thr Val Pro Arg Ala Phe Leu Lys
                210                 215                 220
Glu Ile Ile Leu Val Asp Asp Leu Ser Gln Gln Gly Gln Leu Lys Ser
225                 230                 235                 240
Ala Leu Ser Glu Tyr Val Ala Arg Leu Glu Gly Val Lys Leu Leu Arg
                245                 250                 255
Ser Asn Lys Arg Leu Gly Ala Ile Arg Ala Arg Met Leu Gly Ala Thr
                260                 265                 270
Arg Ala Thr Gly Asp Val Leu Val Phe Met Asp Ala His Cys Glu Cys
            275                 280                 285
His Pro Gly Trp Leu Glu Pro Leu Leu Ser Arg Ile Ala Gly Asp Arg
            290                 295                 300
Ser Arg Val Val Ser Pro Val Ile Asp Val Ile Asp Trp Lys Thr Phe
305                 310                 315                 320
Gln Tyr Tyr Pro Ser Lys Asp Leu Gln Arg Gly Val Leu Asp Trp Lys
                325                 330                 335
Leu Asp Phe His Trp Glu Pro Leu Pro Glu His Val Arg Lys Ala Leu
                340                 345                 350
Gln Ser Pro Ile Ser Pro Ile Arg Ser Pro Val Val Pro Gly Glu Val
                355                 360                 365
Val Ala Met Asp Arg His Tyr Phe Gln Asn Thr Gly Ala Tyr Asp Ser
                370                 375                 380
Leu Met Ser Leu Arg Gly Gly Glu Asn Leu Glu Leu Ser Phe Lys Ala
385                 390                 395                 400
Trp Leu Cys Gly Gly Ser Val Glu Ile Leu Pro Cys Ser Arg Val Gly
                405                 410                 415
His Ile Tyr Gln Asn Gln Asp Ser His Ser Pro Leu Asp Gln Glu Ala
                420                 425                 430
Thr Leu Arg Asn Arg Val Arg Ile Ala Glu Thr Trp Leu Gly Ser Phe
                435                 440                 445
Lys Glu Thr Phe Tyr Lys His Ser Pro Glu Ala Phe Ser Leu Ser Lys
            450                 455                 460
Ala Glu Lys Pro Asp Cys Met Glu Arg Leu Gln Leu Gln Arg Arg Leu
465                 470                 475                 480
Gly Cys Arg Thr Phe His Trp Phe Leu Ala Asn Val Tyr Pro Glu Leu
                485                 490                 495
Tyr Pro Ser Glu Pro Arg Pro Ser Phe Ser Gly Lys Leu His Asn Thr
            500                 505                 510
Gly Leu Gly Leu Cys Ala Asp Cys Gln Ala Glu Gly Asp Ile Leu Gly
            515                 520                 525
```

Cys Pro Met Val Leu Ala Pro Cys Ser Asp Ser Arg Gln Gln Tyr
          530                 535                 540

Leu Gln His Thr Ser Arg Lys Glu Ile His Phe Gly Ser Pro Gln His
545                 550                 555                 560

Leu Cys Phe Ala Val Arg Gln Glu Gln Val Ile Leu Gln Asn Cys Thr
                565                 570                 575

Glu Glu Gly Leu Ala Ile His Gln His Trp Asp Phe Gln Glu Asn
            580                 585                 590

Gly Met Ile Val His Ile Leu Ser Gly Lys Cys Met Glu Ala Val Val
            595                 600                 605

Gln Glu Asn Asn Lys Asp Leu Tyr Leu Arg Pro Cys Asp Gly Lys Ala
    610                 615                 620

Arg Gln Gln Trp Arg Phe Asp Gln Ile Asn Ala Val Asp Glu Arg
625                 630                 635

<210> SEQ ID NO 61
<211> LENGTH: 1671
<212> TYPE: DNA
<213> ORGANISM: Homo sapiens

<400> SEQUENCE: 61

```
atgaggagat tgtctactg caaggtggtt ctagccactt cgctgatgtg ggttcttgtt      60
gatgtcttct tactgctgta cttcagtgaa tgtaacaaat gtgatgacaa aaggagaga     120 tctctgctgc ctgcattgag ggctgttatt tcaagaaacc aagaagggcc aggagaaatg    180
ggaaaagctg tgttgattcc taaagatgac caggagaaaa tgaaagagct gtttaaaatc    240
aatcagttta accttatggc cagtgatttg attgccctta atagaagtct gccagatgta    300
agattagaag gatgtaagac aaaagtctac cctgatgaac ttccaaacac aagtgtagtc    360
attgtgtttc ataatgaagc ttggagcact ctccttagaa ctgtttacag tgtgataaat    420
cgttccccac actatctact ctcagaggtc atcttggtag atgatgccag tgaaagagat    480
tttctcaagt tgacattaga gaattacgtg aaaaatttag aagtgccagt aaaaattatt    540
aggatggaag aacgctctgg gttaatacgt gcccgtcttc gaggagcagc tgcttcaaaa    600
gggcaggtca taactttttct tgatgcacac tgtgaatgca cgttaggatg gctggagcct    660 tgctggcaa gaataaagga agacaggaaa acggttgtct gccctatcat tgatgtgatt    720
agtgatgata ctttttgaata tatgctgggg tcagacatga cttatggggg ttttaactgg    780
aaactgaatt tccgctggta tcctgttccc aaagagaaa tggacaggag gaaaggagac    840
agaacattac tgtcaggac ccctactatg gctggtggcc tattttctat tgacagaaac    900
tactttgaag agatagggaac ttacgatgca ggaatggata tctggggtgg agagaatctt    960
gaaatgtctt ttaggatttg gcaatgtgga ggctccttgg agattgttac ttgctcccat   1020
gttggtcatg tttttcggaa ggcaactcca tacactttc ctggtggcac tggtcatgtc   1080
atcaacaaga caacaggag actggcagaa gtttggatgg atgaatttaa agatttcttc   1140
tacatcatat ccccaggtgt tgtcaaagtg gattatggaa atgtgtcagt cagaaaaaca   1200
ctaagagaaa atctgaagtg taagcccttt tcttggtacc tagaaaacat ctatccggac   1260
tcccagatcc caagacgtta ttactcactt ggtgagataa gaatgttga aaccaatcag   1320 tgtttagaca acatgggccg caaggaaaat gaaaaagtgg gtatattcaa ctgtcatggt   1380
atgggaggaa atcaggtatt tcttacact gctgacaaag aaatccgaac cgatgacttg   1440
tgcttggatg tttctagact caatggacct gtaatcatgt taaaatgcca ccatatgaga   1500
```

-continued

```
ggaaatcagt tatgggaata tgatgctgag agactcacgt tgcgacatgt taacagtaac    1560
caatgtctcg atgaaccttc tgaagaagac aaaatggtgc ctacaatgca ggactgtagt    1620
ggaagcagat cccaacagtg gctgctaagg aacatgacct tgggcacatg a             1671
```

<210> SEQ ID NO 62
<211> LENGTH: 556
<212> TYPE: PRT
<213> ORGANISM: Homo sapiens

<400> SEQUENCE: 62

```
Met Arg Arg Phe Val Tyr Cys Lys Val Val Leu Ala Thr Ser Leu Met
1               5                   10                  15

Trp Val Leu Val Asp Val Phe Leu Leu Tyr Phe Ser Glu Cys Asn
            20                  25                  30

Lys Cys Asp Asp Lys Lys Glu Arg Ser Leu Leu Pro Ala Leu Arg Ala
        35                  40                  45

Val Ile Ser Arg Asn Gln Glu Gly Pro Gly Glu Met Gly Lys Ala Val
    50                  55                  60

Leu Ile Pro Lys Asp Asp Gln Glu Lys Met Lys Glu Leu Phe Lys Ile
65                  70                  75                  80

Asn Gln Phe Asn Leu Met Ala Ser Asp Leu Ile Ala Leu Asn Arg Ser
                85                  90                  95

Leu Pro Asp Val Arg Leu Glu Gly Cys Lys Thr Lys Val Tyr Pro Asp
            100                 105                 110

Glu Leu Pro Asn Thr Ser Val Ile Val Phe His Asn Glu Ala Trp
        115                 120                 125

Ser Thr Leu Leu Arg Thr Val Tyr Ser Val Ile Asn Arg Ser Pro His
    130                 135                 140

Tyr Leu Leu Ser Glu Val Ile Leu Val Asp Asp Ala Ser Glu Arg Asp
145                 150                 155                 160

Phe Leu Lys Leu Thr Leu Glu Asn Tyr Val Lys Asn Leu Glu Val Pro
                165                 170                 175

Val Lys Ile Ile Arg Met Glu Glu Arg Ser Gly Leu Ile Arg Ala Arg
            180                 185                 190

Leu Arg Gly Ala Ala Ala Ser Lys Gly Gln Val Ile Thr Phe Leu Asp
        195                 200                 205

Ala His Cys Glu Cys Thr Leu Gly Trp Leu Glu Pro Leu Leu Ala Arg
    210                 215                 220

Ile Lys Glu Asp Arg Lys Thr Val Val Cys Pro Ile Ile Asp Val Ile
225                 230                 235                 240

Ser Asp Asp Thr Phe Glu Tyr Met Ala Gly Ser Asp Met Thr Tyr Gly
                245                 250                 255

Gly Phe Asn Trp Lys Leu Asn Phe Arg Trp Tyr Pro Val Pro Gln Arg
            260                 265                 270

Glu Met Asp Arg Arg Lys Gly Asp Arg Thr Leu Pro Val Arg Thr Pro
        275                 280                 285

Thr Met Ala Gly Gly Leu Phe Ser Ile Asp Arg Asn Tyr Phe Glu Glu
    290                 295                 300

Ile Gly Thr Tyr Asp Ala Gly Met Asp Ile Trp Gly Gly Glu Asn Leu
305                 310                 315                 320

Glu Met Ser Phe Arg Ile Trp Gln Cys Gly Gly Ser Leu Glu Ile Val
                325                 330                 335

Thr Cys Ser His Val Gly His Val Phe Arg Lys Ala Thr Pro Tyr Thr
```

```
                340             345             350
Phe Pro Gly Gly Thr Gly His Val Ile Asn Lys Asn Asn Arg Arg Leu
            355                 360                 365

Ala Glu Val Trp Met Asp Glu Phe Lys Asp Phe Phe Tyr Ile Ile Ser
        370                 375                 380

Pro Gly Val Val Lys Val Asp Tyr Gly Asp Val Ser Val Arg Lys Thr
385                 390                 395                 400

Leu Arg Glu Asn Leu Lys Cys Lys Pro Phe Ser Trp Tyr Leu Glu Asn
                405                 410                 415

Ile Tyr Pro Asp Ser Gln Ile Pro Arg Arg Tyr Tyr Ser Leu Gly Glu
            420                 425                 430

Ile Arg Asn Val Glu Thr Asn Gln Cys Leu Asp Asn Met Gly Arg Lys
        435                 440                 445

Glu Asn Glu Lys Val Gly Ile Phe Asn Cys His Gly Met Gly Gly Asn
    450                 455                 460

Gln Val Phe Ser Tyr Thr Ala Asp Lys Glu Ile Arg Thr Asp Asp Leu
465                 470                 475                 480

Cys Leu Asp Val Ser Arg Leu Asn Gly Pro Val Ile Met Leu Lys Cys
                485                 490                 495

His His Met Arg Gly Asn Gln Leu Trp Glu Tyr Asp Ala Glu Arg Leu
            500                 505                 510

Thr Leu Arg His Val Asn Ser Asn Gln Cys Leu Asp Glu Pro Ser Glu
        515                 520                 525

Glu Asp Lys Met Val Pro Thr Met Gln Asp Cys Ser Gly Ser Arg Ser
    530                 535                 540

Gln Gln Trp Leu Leu Arg Asn Met Thr Leu Gly Thr
545                 550                 555
```

<210> SEQ ID NO 63
<211> LENGTH: 1911
<212> TYPE: DNA
<213> ORGANISM: Homo sapiens

<400> SEQUENCE: 63

```
atgcggcgcc tgactcgtcg gctggttctg ccagtcttcg gggtgctctg gatcacggtg      60
ctgctgttct ctgggtaac caagaggaag ttggaggtgc cgacgggacc tgaagtgcag     120
accccctaagc cttcggacgc tgactgggac gacctgtggg accagtttga tgagcggcgg     180
tatctgaatg ccaaaaagtg gcgcgttggt gacgacccct ataagctgta tgctttcaac     240
cagcgggaga gtgagcggat ctccagcaat cgggccatcc ggacactcg ccatctgaga     300
tgcacactgc tggtgtattg cacggacctt ccacccacta gcatcatcat caccttccac     360
aacgaagccc gctccacgct gctcaggacc atccgcagtg tattaaaccg caccccctacg     420
catctgatcc gggaaatcat attagtggat gacttcagca atgaccctga tgactgtaaa     480
cagctcatca aattgcccaa ggtgaaatgc ttgcgcaata tgaacggca aggtctggtc     540
cggtcccgga ttcggggcgc tgacatcgcc cagggcacca ctctgacttt cctcgacagc     600
cactgtgagg tgaacaggga ctggctccag cctctgttgc acagggtcaa agaagactac     660
acgcgggtgg tgtgccctgt gatcgatatc attaacctgg acaccttcac ctacatcgag     720
tctgcctcgg agctcagagg ggggtttgac tggagcctcc acttccagtg ggagcagctc     780
tccccagagc agaagctcgg cgcctggacc cacggaagc ccatcaggac tcctatcata     840
gctggagggc tcttcgtgat cgacaaagct tggtttgatt acctggggaa atatgatatg     900
```

-continued

```
gacatggaca tctggggtgg ggagaacttt gaaatctcct tccgagtgtg gatgtgcggg       960
ggcagcctag agatcgtccc ctgcagccga gtggggcacg tcttccggaa gaagcacccc      1020
tacgttttcc ctgatggaaa tgccaacacg tatataaaga acaccaagcg gacagctgaa      1080
gtgtggatgg atgaatacaa gcaatactat tacgctgccc ggccattcgc cctggagagg      1140
cccttcggga tgttgagag cagattggac ctgaggaaga atctgcgctg ccagagcttc       1200
aagtggtacc tggagaatat ctaccctgaa ctcagcatcc caaggagtc ctccatccag       1260 aagggcaata tccgacagag acagaagtgc ctggaatctc aaaggcagaa caaccaagaa      1320
accccaaacc taaagttgag ccctgtgcc aaggtcaaag cgaagatgc aaagtcccag        1380 gtatgggcct tcacatacac ccagcagatc ctccaggagg agctgtgcct gtcagtcatc      1440
accttgttcc ctggcgcccc agtggttctt gtcctttgca agaatggaga tgaccgacag      1500
caatggacca aaactggttc ccacatcgag cacatagcat cccacctctg cctcgataca      1560
gatatgttcg gtgatggcac cgagaacggc aaggaaatcg tcgtcaaccc atgtgagtcc      1620
tcactcatga gccagcactg ggacatggtg agctcttgag gacccctgcc agaagcagca     1680
agggccatgg ggtggtgctt ccctggacca gaacagactg gaaactgggc agcaagcagc     1740
ctgcaaccac ctcagacatc ctggactggg aagtggaggc agagccccc aggacaggag      1800 caactgtctc agggaggaca gaggaaaaca tcaagcca atgggctca agacaaatc         1860 ccacatgttc tcaaggccgt taagttccag tcctggccag tcattccctg a              1911
```

<210> SEQ ID NO 64
<211> LENGTH: 552
<212> TYPE: PRT
<213> ORGANISM: Homo sapiens

<400> SEQUENCE: 64

```
Met Arg Arg Leu Thr Arg Arg Leu Val Leu Pro Val Phe Gly Val Leu
1               5                   10                  15

Trp Ile Thr Val Leu Leu Phe Phe Trp Val Thr Lys Arg Lys Leu Glu
                20                  25                  30

Val Pro Thr Gly Pro Glu Val Gln Thr Pro Lys Pro Ser Asp Ala Asp
            35                  40                  45

Trp Asp Asp Leu Trp Asp Gln Phe Asp Glu Arg Arg Tyr Leu Asn Ala
        50                  55                  60

Lys Lys Trp Arg Val Gly Asp Asp Pro Tyr Lys Leu Tyr Ala Phe Asn
65                  70                  75                  80

Gln Arg Glu Ser Glu Arg Ile Ser Ser Asn Arg Ala Ile Pro Asp Thr
                85                  90                  95

Arg His Leu Arg Cys Thr Leu Leu Val Tyr Cys Thr Asp Leu Pro Pro
            100                 105                 110

Thr Ser Ile Ile Ile Thr Phe His Asn Glu Ala Arg Ser Thr Leu Leu
        115                 120                 125

Arg Thr Ile Arg Ser Val Leu Asn Arg Thr Pro Thr His Leu Ile Arg
    130                 135                 140

Glu Ile Ile Leu Val Asp Asp Phe Ser Asn Asp Pro Asp Asp Cys Lys
145                 150                 155                 160

Gln Leu Ile Lys Leu Pro Lys Val Lys Cys Leu Arg Asn Asn Glu Arg
                165                 170                 175

Gln Gly Leu Val Arg Ser Arg Ile Arg Gly Ala Asp Ile Ala Gln Gly
            180                 185                 190

Thr Thr Leu Thr Phe Leu Asp Ser His Cys Glu Val Asn Arg Asp Trp
```

```
              195                 200                 205
Leu Gln Pro Leu Leu His Arg Val Lys Glu Asp Tyr Thr Arg Val Val
210                 215                 220

Cys Pro Val Ile Asp Ile Ile Asn Leu Asp Thr Phe Thr Tyr Ile Glu
225                 230                 235                 240

Ser Ala Ser Glu Leu Arg Gly Gly Phe Asp Trp Ser Leu His Phe Gln
            245                 250                 255

Trp Gln Leu Ser Pro Glu Gln Lys Leu Gly Ala Trp Thr Pro Arg
            260                 265                 270

Lys Pro Ile Arg Thr Pro Ile Ile Ala Gly Gly Leu Phe Val Ile Asp
                275                 280                 285

Lys Ala Trp Phe Asp Tyr Leu Gly Lys Tyr Asp Met Asp Met Asp Ile
290                 295                 300

Trp Gly Gly Glu Asn Phe Glu Ile Ser Phe Arg Val Trp Met Cys Gly
305                 310                 315                 320

Gly Ser Leu Glu Ile Val Pro Cys Ser Arg Val Gly His Val Phe Arg
                325                 330                 335

Lys Lys His Pro Tyr Val Phe Pro Asp Gly Asn Ala Asn Thr Tyr Ile
                340                 345                 350

Lys Asn Thr Lys Arg Thr Ala Glu Val Trp Met Asp Glu Tyr Lys Gln
                355                 360                 365

Tyr Tyr Tyr Ala Ala Arg Pro Phe Ala Leu Glu Arg Pro Phe Gly Asn
            370                 375                 380

Val Glu Ser Arg Leu Asp Leu Arg Lys Asn Leu Arg Cys Gln Ser Phe
385                 390                 395                 400

Lys Trp Tyr Leu Glu Asn Ile Tyr Pro Glu Leu Ser Ile Pro Lys Glu
                405                 410                 415

Ser Ser Ile Gln Lys Gly Asn Ile Arg Gln Arg Gln Lys Cys Leu Glu
                420                 425                 430

Ser Gln Arg Gln Asn Asn Gln Glu Thr Pro Asn Leu Lys Leu Ser Pro
            435                 440                 445

Cys Ala Lys Val Lys Gly Glu Asp Ala Lys Ser Gln Val Trp Ala Phe
450                 455                 460

Thr Tyr Thr Gln Gln Ile Leu Gln Glu Glu Leu Cys Leu Ser Val Ile
465                 470                 475                 480

Thr Leu Phe Pro Gly Ala Pro Val Leu Val Leu Cys Lys Asn Gly
                485                 490                 495

Asp Asp Arg Gln Gln Trp Thr Lys Thr Gly Ser His Ile Glu His Ile
                500                 505                 510

Ala Ser His Leu Cys Leu Asp Thr Asp Met Phe Gly Asp Gly Thr Glu
            515                 520                 525

Asn Gly Lys Glu Ile Val Val Asn Pro Cys Glu Ser Ser Leu Met Ser
530                 535                 540

Gln His Trp Asp Met Val Ser Ser
545                 550

<210> SEQ ID NO 65
<211> LENGTH: 1677
<212> TYPE: DNA
<213> ORGANISM: Homo sapiens

<400> SEQUENCE: 65
atgaggaaga tccgcgccaa tgccatcgcc atcctgaccg tagcctggat cctgggcact      60
ttctactact tatggcagga caaccgagcc cacgcagcat cctccggcgg ccggggcgcg     120
```

```
cagagggcag gcaggaggtc ggagcagctc cgcgaggacc gcaccatccc gctcattgtg      180
acaggaactc cctcgaaagg ctttgatgag aaggcctacc tgtcggccaa gcagctgaag      240
gctggagagg acccctacag acagcacgcc ttcaaccagc tggagagtga caagctgagc      300
ccagaccggc ccatccggga cacccgccat acagctgcc catctgtgtc ctactcctcg       360
gacctgccag ccaccagcgt catcatcacc ttccacaatg aggcccgttc caccctgctg      420
cgcacagtga agagtgtcct gaaccgaact cctgccaact tgatccagga gatcatttta     480
gtggatgact tcagctcaga tccggaagac tgtctactcc tgaccaggat ccccaaggtc      540
aagtgcctgc gcaatgatcg gcgggaaggg ctgatccggt cccgagtgcg tggggcggac     600
gtggctgcag ctaccgttct cacctttctg gatagccact cgaagtgaa caccgagtgg      660 ctgccgccca tgctgcagcg ggtgaaggag gaccacaccc gcgtggtgag tcccatcatt     720
gatgtcatca gtctggataa ttttgcctac cttgcagcat ctgctgacct tcgtggaggg    780
ttcgactgga gcctgcattt caagtgggag cagatccctc ttgagcagaa gatgacccgg     840
acagacccca ccaggcccat aaggacgcct gtcatagctg gaggaatctt cgtgatcgac    900
aagtcctggt ttaaccactt gggaaagtat gatgcccaga tggacatctg gggggagag    960 aattttgagc tctccttcag ggtgtggatg tgtggtggca gtctggagat cgtcccctgc   1020
agccgggtgg ccatgtctt caggaaacgg caccctaca acttccctga gggtaatgcc    1080
ctcacctaca tcaggaatac taagcgcact gcagaagtgt ggatggatga atacaagcaa    1140
tactactatg aggcccggcc ctcggccatc gggaaggcct tcggcagtgt ggctacgcgg   1200
atagagcaga ggaagaagat gaactgcaag tccttccgct ggtacctgga aacgtctac    1260 ccagagctca cggtcccccgt gaaggaagca ctccccggca tcattaagca gggggtgaac    1320
tgcttagaat ctcagggcca gaacacagct ggtgacttcc tgcttggaat ggggatctgc   1380
agagggtctg ccaagaaccc gcagcccgcc caggcatggc tgttcagtga ccacctcatc    1440
cagcagcagg ggaagtgcct ggctgccacc tccaccttaa tgtcctcccc tggatcccca   1500
gtcatactgc agatgtgcaa ccctagagaa ggcaagcaga atggaggag aaaaggatct   1560 ttcatccagc attcagtcag tggcctctgc ctggagacaa agcctgccca gctggtgacc    1620
agcaagtgtc aggctgacgc ccaggcccag cagtggcagc tgttgccaca cacatga       1677
```

<210> SEQ ID NO 66
<211> LENGTH: 558
<212> TYPE: PRT
<213> ORGANISM: Homo sapiens

<400> SEQUENCE: 66

```
Met Arg Lys Ile Arg Ala Asn Ala Ile Ala Ile Leu Thr Val Ala Trp
1               5                   10                  15

Ile Leu Gly Thr Phe Tyr Tyr Leu Trp Gln Asp Asn Arg Ala His Ala
            20                  25                  30

Ala Ser Ser Gly Gly Arg Gly Ala Gln Arg Ala Gly Arg Arg Ser Glu
        35                  40                  45

Gln Leu Arg Glu Asp Arg Thr Ile Pro Leu Ile Val Thr Gly Thr Pro
    50                  55                  60

Ser Lys Gly Phe Asp Glu Lys Ala Tyr Leu Ser Ala Lys Gln Leu Lys
65                  70                  75                  80

Ala Gly Glu Asp Pro Tyr Arg Gln His Ala Phe Asn Gln Leu Glu Ser
                85                  90                  95
```

-continued

```
Asp Lys Leu Ser Pro Asp Arg Pro Ile Arg Asp Thr Arg His Tyr Ser
        100                 105                 110
Cys Pro Ser Val Ser Tyr Ser Ser Asp Leu Pro Ala Thr Ser Val Ile
        115                 120                 125
Ile Thr Phe His Asn Glu Ala Arg Ser Thr Leu Leu Arg Thr Val Lys
        130                 135                 140
Ser Val Leu Asn Arg Thr Pro Ala Asn Leu Ile Gln Glu Ile Ile Leu
145                 150                 155                 160
Val Asp Asp Phe Ser Ser Asp Pro Glu Asp Cys Leu Leu Leu Thr Arg
                165                 170                 175
Ile Pro Lys Val Lys Cys Leu Arg Asn Asp Arg Arg Glu Gly Leu Ile
                180                 185                 190
Arg Ser Arg Val Arg Gly Ala Asp Val Ala Ala Ala Thr Val Leu Thr
                195                 200                 205
Phe Leu Asp Ser His Cys Glu Val Asn Thr Glu Trp Leu Pro Pro Met
        210                 215                 220
Leu Gln Arg Val Lys Glu Asp His Thr Arg Val Val Ser Pro Ile Ile
225                 230                 235                 240
Asp Val Ile Ser Leu Asp Asn Phe Ala Tyr Leu Ala Ala Ser Ala Asp
                245                 250                 255
Leu Arg Gly Gly Phe Asp Trp Ser Leu His Phe Lys Trp Glu Gln Ile
                260                 265                 270
Pro Leu Glu Gln Lys Met Thr Arg Thr Asp Pro Thr Arg Pro Ile Arg
        275                 280                 285
Thr Pro Val Ile Ala Gly Gly Ile Phe Val Ile Asp Lys Ser Trp Phe
        290                 295                 300
Asn His Leu Gly Lys Tyr Asp Ala Gln Met Asp Ile Trp Gly Gly Glu
305                 310                 315                 320
Asn Phe Glu Leu Ser Phe Arg Val Trp Met Cys Gly Gly Ser Leu Glu
                325                 330                 335
Ile Val Pro Cys Ser Arg Val Gly His Val Phe Arg Lys His Pro
                340                 345                 350
Tyr Asn Phe Pro Glu Gly Asn Ala Leu Thr Tyr Ile Arg Asn Thr Lys
        355                 360                 365
Arg Thr Ala Glu Val Trp Met Asp Glu Tyr Lys Gln Tyr Tyr Tyr Glu
        370                 375                 380
Ala Arg Pro Ser Ala Ile Gly Lys Ala Phe Gly Ser Val Ala Thr Arg
385                 390                 395                 400
Ile Glu Gln Arg Lys Met Asn Cys Lys Ser Phe Arg Trp Tyr Leu
                405                 410                 415
Glu Asn Val Tyr Pro Glu Leu Thr Val Pro Val Lys Glu Ala Leu Pro
                420                 425                 430
Gly Ile Ile Lys Gln Gly Val Asn Cys Leu Glu Ser Gln Gly Gln Asn
        435                 440                 445
Thr Ala Gly Asp Phe Leu Leu Gly Met Gly Ile Cys Arg Gly Ser Ala
        450                 455                 460
Lys Asn Pro Gln Pro Ala Gln Ala Trp Leu Phe Ser Asp His Leu Ile
465                 470                 475                 480
Gln Gln Gln Gly Lys Cys Leu Ala Ala Thr Ser Thr Leu Met Ser Ser
                485                 490                 495
Pro Gly Ser Pro Val Ile Leu Gln Met Cys Asn Pro Arg Glu Gly Lys
                500                 505                 510
Gln Lys Trp Arg Arg Lys Gly Ser Phe Ile Gln His Ser Val Ser Gly
```

```
                    515                 520                 525
          Leu Cys Leu Glu Thr Lys Pro Ala Gln Leu Val Thr Ser Lys Cys Gln
             530                 535                 540

Ala Asp Ala Gln Ala Gln Gln Trp Gln Leu Leu Pro His Thr
          545                 550                 555
```

<210> SEQ ID NO 67
<211> LENGTH: 33
<212> TYPE: DNA
<213> ORGANISM: Artificial Sequence
<220> FEATURE:
<223> OTHER INFORMATION: primer T1LECFOR

<400> SEQUENCE: 67
caaaggaagc ttatggagat atatcgtcaa gag                                      33

<210> SEQ ID NO 68
<211> LENGTH: 43
<212> TYPE: DNA
<213> ORGANISM: Artificial Sequence
<220> FEATURE:
<223> OTHER INFORMATION: primer T1LECREV

<400> SEQUENCE: 68
gcaagctcga ggcggccgct cagaatattt ctggaagggt gac                           43

<210> SEQ ID NO 69
<211> LENGTH: 37
<212> TYPE: DNA
<213> ORGANISM: Artificial Sequence
<220> FEATURE:
<223> OTHER INFORMATION: primer T2LECFOR

<400> SEQUENCE: 69
caaggaagct tcttatggaa atattcagag cagattg                                  37

<210> SEQ ID NO 70
<211> LENGTH: 38
<212> TYPE: DNA
<213> ORGANISM: Artificial Sequence
<220> FEATURE:
<223> OTHER INFORMATION: primer T2LECREV

<400> SEQUENCE: 70
gcaagctcga ggcggccgcc tactgctgca ggttgagc                                 38

<210> SEQ ID NO 71
<211> LENGTH: 37
<212> TYPE: DNA
<213> ORGANISM: Artificial Sequence
<220> FEATURE:
<223> OTHER INFORMATION: primer T3LECFOR

<400> SEQUENCE: 71
caaggaagct tcatttggtg atctttcaaa aagattt                                  37

<210> SEQ ID NO 72
<211> LENGTH: 40
<212> TYPE: DNA
<213> ORGANISM: Artificial Sequence
<220> FEATURE:
<223> OTHER INFORMATION: primer T3LECREV

<400> SEQUENCE: 72
gcaagctcga ggcggccgca ggaacactta atcattttgg                               40

<210> SEQ ID NO 73
<211> LENGTH: 28
<212> TYPE: DNA
<213> ORGANISM: Artificial Sequence
<220> FEATURE:
<223> OTHER INFORMATION: primer T4LECFOR

<400> SEQUENCE: 73
agaaaagaag cttatggtga tatttctg                                28

<210> SEQ ID NO 74
<211> LENGTH: 28
<212> TYPE: DNA
<213> ORGANISM: Artificial Sequence
<220> FEATURE:
<223> OTHER INFORMATION: primer T4LECREV

<400> SEQUENCE: 74
agcggatccg acgaagtgct gttgtgct                                28

<210> SEQ ID NO 75
<211> LENGTH: 35
<212> TYPE: DNA
<213> ORGANISM: Artificial Sequence
<220> FEATURE:
<223> OTHER INFORMATION: primer T5LECFOR

<400> SEQUENCE: 75
caaggaagct ttagatgttg gcaacctcac ccagc                        35

<210> SEQ ID NO 76
<211> LENGTH: 44
<212> TYPE: DNA
<213> ORGANISM: Artificial Sequence
<220> FEATURE:
<223> OTHER INFORMATION: primer T5LECREV

<400> SEQUENCE: 76
gcaagctcga ggcggccgca agcatcagtt acacttcagg cttc              44

<210> SEQ ID NO 77
<211> LENGTH: 33
<212> TYPE: DNA
<213> ORGANISM: Artificial Sequence
<220> FEATURE:
<223> OTHER INFORMATION: primer T6LECFOR

<400> SEQUENCE: 77
caaggaagct tccttcggtg acatttcgga acg                          33

<210> SEQ ID NO 78
<211> LENGTH: 39
<212> TYPE: DNA
<213> ORGANISM: Artificial Sequence
<220> FEATURE:
<223> OTHER INFORMATION: primer T6LECREV

<400> SEQUENCE: 78
gcaagctcga ggcggccgct gggtcctaga caaagagcc                    39

<210> SEQ ID NO 79
<211> LENGTH: 33
<212> TYPE: DNA
<213> ORGANISM: Artificial Sequence
<220> FEATURE:

<223> OTHER INFORMATION: primer T7LECFOR

<400> SEQUENCE: 79
agaaaagaag cttatgggga tatatcggag ctg                33

<210> SEQ ID NO 80
<211> LENGTH: 44
<212> TYPE: DNA
<213> ORGANISM: Artificial Sequence
<220> FEATURE:
<223> OTHER INFORMATION: primer T7LECREV

<400> SEQUENCE: 80
gcaagctcga ggcggccgct ctctaaacac tatggatgtt attc                44

<210> SEQ ID NO 81
<211> LENGTH: 34
<212> TYPE: DNA
<213> ORGANISM: Artificial Sequence
<220> FEATURE:
<223> OTHER INFORMATION: primer T8LECFOR

<400> SEQUENCE: 81
caaggaagct tttggagacg tttcttccag aatg                34

<210> SEQ ID NO 82
<211> LENGTH: 42
<212> TYPE: DNA
<213> ORGANISM: Artificial Sequence
<220> FEATURE:
<223> OTHER INFORMATION: primer T8LECREV

<400> SEQUENCE: 82
gcaagctcga ggcggccgct cactggctgt tggtctgacc cc                42

<210> SEQ ID NO 83
<211> LENGTH: 34
<212> TYPE: DNA
<213> ORGANISM: Artificial Sequence
<220> FEATURE:
<223> OTHER INFORMATION: primer T9LECFOR

<400> SEQUENCE: 83
caaggaagct ttcggggacg tgtctgagag gctg                34

<210> SEQ ID NO 84
<211> LENGTH: 42
<212> TYPE: DNA
<213> ORGANISM: Artificial Sequence
<220> FEATURE:
<223> OTHER INFORMATION: primer T9LECREV

<400> SEQUENCE: 84
gcaagctcga ggcggccgct cagtgccgtg cgtgtttgat cc                42

<210> SEQ ID NO 85
<211> LENGTH: 34
<212> TYPE: DNA
<213> ORGANISM: Artificial Sequence
<220> FEATURE:
<223> OTHER INFORMATION: primer T10LECFOR

<400> SEQUENCE: 85
caaggaagct tccgctgggg atgtcgcagt ccag                34

<210> SEQ ID NO 86
<211> LENGTH: 41
<212> TYPE: DNA
<213> ORGANISM: Artificial Sequence
<220> FEATURE:
<223> OTHER INFORMATION: primer T10LECREV

<400> SEQUENCE: 86
gcaagctcga ggcggccgct cagttcctat tgaattttc c					41

<210> SEQ ID NO 87
<211> LENGTH: 32
<212> TYPE: DNA
<213> ORGANISM: Artificial Sequence
<220> FEATURE:
<223> OTHER INFORMATION: primer T11LECFOR

<400> SEQUENCE: 87
caaggaagct tgcaatatca gtgagcgtgt gg					32

<210> SEQ ID NO 88
<211> LENGTH: 40
<212> TYPE: DNA
<213> ORGANISM: Artificial Sequence
<220> FEATURE:
<223> OTHER INFORMATION: primer T11LECREV

<400> SEQUENCE: 88
gcaagctcga ggcggccgcc caccttaacc ttccaaatgc					40

<210> SEQ ID NO 89
<211> LENGTH: 31
<212> TYPE: DNA
<213> ORGANISM: Artificial Sequence
<220> FEATURE:
<223> OTHER INFORMATION: primer T12LECFOR

<400> SEQUENCE: 89
caaggaagct tgggatgtga cagagaggaa g					31

<210> SEQ ID NO 90
<211> LENGTH: 45
<212> TYPE: DNA
<213> ORGANISM: Artificial Sequence
<220> FEATURE:
<223> OTHER INFORMATION: primer T12LECREV

<400> SEQUENCE: 90
gcaagctcga ggcggccgct cataacatgc gctctttgaa gaacc					45

<210> SEQ ID NO 91
<211> LENGTH: 32
<212> TYPE: DNA
<213> ORGANISM: Artificial Sequence
<220> FEATURE:
<223> OTHER INFORMATION: primer T13LECFOR

<400> SEQUENCE: 91
caaggaagct tctgagaagc cagactgcat gg					32

<210> SEQ ID NO 92
<211> LENGTH: 41
<212> TYPE: DNA
<213> ORGANISM: Artificial Sequence
<220> FEATURE:
<223> OTHER INFORMATION: primer T13LECREV

<400> SEQUENCE: 92
gcaagctcga ggcggccgct catcgttcat ccacagcatt g                    41

<210> SEQ ID NO 93
<211> LENGTH: 36
<212> TYPE: DNA
<213> ORGANISM: Artificial Sequence
<220> FEATURE:
<223> OTHER INFORMATION: primer T14LECFOR

<400> SEQUENCE: 93
caaggaagct tatggagatg tgtcagtcag aaaaac                          36

<210> SEQ ID NO 94
<211> LENGTH: 42
<212> TYPE: DNA
<213> ORGANISM: Artificial Sequence
<220> FEATURE:
<223> OTHER INFORMATION: primer T14LECREV

<400> SEQUENCE: 94
gcaagctcga ggcggccgct catgtgccca aggtcatgtt cc                   42

<210> SEQ ID NO 95
<211> LENGTH: 34
<212> TYPE: DNA
<213> ORGANISM: Artificial Sequence
<220> FEATURE:
<223> OTHER INFORMATION: primer T15LECFOR

<400> SEQUENCE: 95
caaggaagct ttcgggaatg ttgagagcag attg                            34

<210> SEQ ID NO 96
<211> LENGTH: 43
<212> TYPE: DNA
<213> ORGANISM: Artificial Sequence
<220> FEATURE:
<223> OTHER INFORMATION: primer T15LECREV

<400> SEQUENCE: 96
gcaagctcga ggcggccgct caagaactca ccatgtccca gtg                  43

<210> SEQ ID NO 97
<211> LENGTH: 40
<212> TYPE: DNA
<213> ORGANISM: Artificial Sequence
<220> FEATURE:
<223> OTHER INFORMATION: primer T16LECFOR

<400> SEQUENCE: 97
caaggaagct tgcagtgtgg ctacgcggat agagcagagg                      40

<210> SEQ ID NO 98
<211> LENGTH: 42
<212> TYPE: DNA
<213> ORGANISM: Artificial Sequence
<220> FEATURE:
<223> OTHER INFORMATION: primer T16LECREV

<400> SEQUENCE: 98
gcaagctcga ggcggccgct catgtgtgtg gcaacagctg cc                   42

<210> SEQ ID NO 99
<211> LENGTH: 513

<210> SEQ ID NO 99
<211> LENGTH: 513
<212> TYPE: DNA
<213> ORGANISM: Homo sapiens

<400> SEQUENCE: 99

```
aaagaagctt atggagatat atcgtcaaga gttggtctaa gacacaaact acaatgcaaa      60
ccttttcct ggtacctaga gaatatatat cctgattctc aaattccacg tcactatttc     120
tcattgggag agatacgaaa tgtggaaacg aatcagtgtc tagataacat ggctagaaaa     180
gagaatgaaa aagttggaat ttttaattgc catggtatgg ggggtaatca ggttttctct     240
tatactgcca acaagaaat tagaacagat gacctttgct tggatgtttc caaacttaat     300
ggcccagtta caatgctcaa atgccaccac ctaaaaggca accaactctg ggagtatgac     360
ccagtgaaat taaccctgca gcatgtgaac agtaatcagt gcctggataa agccacagaa     420
gaggatagcc aggtgcccag cattagagac tgcaatggaa gtcggtccca gcagtggctt     480
cttcgaaacg tcaccttcc agaaatattc tga                                   513
```

<210> SEQ ID NO 100
<211> LENGTH: 167
<212> TYPE: PRT
<213> ORGANISM: Homo sapiens

<400> SEQUENCE: 100

```
Tyr Gly Asp Ile Ser Ser Arg Val Gly Leu Arg His Lys Leu Gln Cys
1               5                   10                  15

Lys Pro Phe Ser Trp Tyr Leu Glu Asn Ile Tyr Pro Asp Ser Gln Ile
            20                  25                  30

Pro Arg His Tyr Phe Ser Leu Gly Glu Ile Arg Asn Val Glu Thr Asn
        35                  40                  45

Gln Cys Leu Asp Asn Met Ala Arg Lys Glu Asn Glu Lys Val Gly Ile
    50                  55                  60

Phe Asn Cys His Gly Met Gly Gly Asn Gln Val Phe Ser Tyr Thr Ala
65                  70                  75                  80

Asn Lys Glu Ile Arg Thr Asp Asp Leu Cys Leu Asp Val Ser Lys Leu
                85                  90                  95

Asn Gly Pro Val Thr Met Leu Lys Cys His His Leu Lys Gly Asn Gln
            100                 105                 110

Leu Trp Glu Tyr Asp Pro Val Lys Leu Thr Leu Gln His Val Asn Ser
        115                 120                 125

Asn Gln Cys Leu Asp Lys Ala Thr Glu Glu Asp Ser Gln Val Pro Ser
    130                 135                 140

Ile Arg Asp Cys Asn Gly Ser Arg Ser Gln Gln Trp Leu Leu Arg Asn
145                 150                 155                 160

Val Thr Leu Pro Glu Ile Phe
                165
```

<210> SEQ ID NO 101
<211> LENGTH: 417
<212> TYPE: DNA
<213> ORGANISM: Homo sapiens

<400> SEQUENCE: 101

```
tatccagagt taagggttcc agaccatcag gatatagctt tggggccttg cagcaggga      60
actaactgcc tcgacacttt gggacacttt gctgatggtg tggttggagt ttatgaatgt     120
cacaatgctg ggggaaacca ggaatgggcc ttgacgaagg agaagtcggt gaagcacatg     180
gatttgtgcc ttactgtggt ggaccgggca ccgggctctc ttataaagct gcagggctgc     240
```

```
cgagaaaatg acagcagaca gaaatgggaa cagatcgagg gcaactccaa gctgaggcac    300
gtgggcagca acctgtgcct ggacagtcgc acggccaaga gcgggggcct aagcgtggag    360
gtgtgtggcc cggcccttc gcagcagtgg aagttcacgc tcaacctgca gcagtag       417
```

<210> SEQ ID NO 102
<211> LENGTH: 138
<212> TYPE: PRT
<213> ORGANISM: Homo sapiens

<400> SEQUENCE: 102

```
Tyr Pro Glu Leu Arg Val Pro Asp His Gln Asp Ile Ala Phe Gly Ala
1               5                   10                  15

Leu Gln Gln Gly Thr Asn Cys Leu Asp Thr Leu Gly His Phe Ala Asp
            20                  25                  30

Gly Val Val Gly Val Tyr Glu Cys His Asn Ala Gly Gly Asn Gln Glu
        35                  40                  45

Trp Ala Leu Thr Lys Glu Lys Ser Val Lys His Met Asp Leu Cys Leu
    50                  55                  60

Thr Val Val Asp Arg Ala Pro Gly Ser Leu Ile Lys Leu Gln Gly Cys
65                  70                  75                  80

Arg Glu Asn Asp Ser Arg Gln Lys Trp Glu Gln Ile Glu Gly Asn Ser
                85                  90                  95

Lys Leu Arg His Val Gly Ser Asn Leu Cys Leu Asp Ser Arg Thr Ala
            100                 105                 110

Lys Ser Gly Gly Leu Ser Val Glu Val Cys Gly Pro Ala Leu Ser Gln
        115                 120                 125

Gln Trp Lys Phe Thr Leu Asn Leu Gln Gln
    130                 135
```

<210> SEQ ID NO 103
<211> LENGTH: 507
<212> TYPE: DNA
<213> ORGANISM: Homo sapiens

<400> SEQUENCE: 103

```
tcatttggtg atcttcaaa aagatttgaa ataaaacacc gtcttcggtg taaaaatttt    60
acatggtatc tgaacaacat ttatccagag gtgtatgtgc cagaccttaa tcctgttata   120
tctggataca ttaaaagcgt tggtcagcct ctatgtctgg atgttggaga aaacaatcaa   180
ggaggcaaac cattaattat gtatacatgt catggacttg ggggaaacca gtactttgaa   240
tactctgctc aacatgaaat tcggcacaac atccagaagg aattatgtct tcatgctgct   300
caaggtctcg ttcagctgaa ggcatgtacc tacaaaggtc acaagacagt tgtcactgga   360
gagcagatat gggagatcca gaaggatcaa cttctataca atccattctt aaaaatgtgc   420
ctttcagcaa atggagagca tccaagttta gtgtcatgca cccatcaga tccactccaa   480 aaatggatac ttagccaaaa tgattaa                                       507
```

<210> SEQ ID NO 104
<211> LENGTH: 167
<212> TYPE: PRT
<213> ORGANISM: Homo sapiens

<400> SEQUENCE: 104

```
Phe Gly Asp Leu Ser Lys Arg Phe Glu Ile Lys His Arg Leu Arg Cys
1               5                   10                  15
```

-continued

```
Lys Asn Phe Thr Trp Tyr Leu Asn Asn Ile Tyr Pro Glu Val Tyr Val
             20                  25                  30

Pro Asp Leu Asn Pro Val Ile Ser Gly Tyr Ile Lys Ser Val Gly Gln
         35                  40                  45

Pro Leu Cys Leu Asp Val Gly Glu Asn Gln Gly Gly Lys Pro Leu
     50                  55                  60

Ile Met Tyr Thr Cys His Gly Leu Gly Gly Asn Gln Tyr Phe Glu Tyr
 65                  70                  75                  80

Ser Ala Gln His Glu Ile Arg His Asn Ile Gln Lys Glu Leu Cys Leu
                 85                  90                  95

His Ala Ala Gln Gly Leu Val Gln Leu Lys Ala Cys Thr Tyr Lys Gly
            100                 105                 110

His Lys Thr Val Val Thr Gly Glu Gln Ile Trp Glu Ile Gln Lys Asp
        115                 120                 125

Gln Leu Leu Tyr Asn Pro Phe Leu Lys Met Cys Leu Ser Ala Asn Gly
    130                 135                 140

Glu His Pro Ser Leu Val Ser Cys Asn Pro Ser Asp Pro Leu Gln Lys
145                 150                 155                 160

Trp Ile Leu Ser Gln Asn Asp
                165
```

<210> SEQ ID NO 105
<211> LENGTH: 423
<212> TYPE: DNA
<213> ORGANISM: Homo sapiens

<400> SEQUENCE: 105

```
gaggatagac caggctggca tggggctatt cgcagtagag ggatctcgtc tgaatgttta      60
gattataatt ctcctgacaa caaccccaca ggtgctaacc tttcactgtt tggatgccat    120
ggtcaaggag gcaatcaatt ctttgaatat acttcaaaca agaaataag gtttaattct      180
gtgacagagt tatgtgcaga ggtacctgag caaaaaaatt atgtgggaat gcaaaattgt    240
cccaaagatg ggttccctgt accagcaaac attatttggc attttaaaga agatggaact    300
attttttcacc cacactcagg actgtgtctt agtgcttatc ggacaccgga gggccgacct   360
gatgtacaaa tgagaacttg tgatgctcta gataaaaatc aaatttggag ttttgagaaa    420
tag                                                                    423
```

<210> SEQ ID NO 106
<211> LENGTH: 174
<212> TYPE: PRT
<213> ORGANISM: Homo sapiens

<400> SEQUENCE: 106

```
Ala Tyr Gly Asp Ile Ser Glu Arg Lys Leu Leu Arg Glu Arg Leu Arg
 1               5                  10                  15

Cys Lys Ser Phe Asp Trp Tyr Leu Lys Asn Val Phe Pro Asn Leu His
             20                  25                  30

Val Pro Glu Asp Arg Pro Gly Trp His Gly Ala Ile Arg Ser Arg Gly
         35                  40                  45

Ile Ser Ser Glu Cys Leu Asp Tyr Asn Ser Pro Asp Asn Pro Thr
     50                  55                  60

Gly Ala Asn Leu Ser Leu Phe Gly Cys His Gly Gln Gly Gly Asn Gln
 65                  70                  75                  80

Phe Phe Glu Tyr Thr Ser Asn Lys Glu Ile Arg Phe Asn Ser Val Thr
                 85                  90                  95
```

Glu Leu Cys Ala Glu Val Pro Glu Gln Lys Asn Tyr Val Gly Met Gln
            100                 105                 110

Asn Cys Pro Lys Asp Gly Phe Pro Val Pro Ala Asn Ile Ile Trp His
            115                 120                 125

Phe Lys Glu Asp Gly Thr Ile Phe His Pro His Ser Gly Leu Cys Leu
            130                 135                 140

Ser Ala Tyr Arg Thr Pro Glu Gly Arg Pro Asp Val Gln Met Arg Thr
145                 150                 155                 160

Cys Asp Ala Leu Asp Lys Asn Gln Ile Trp Ser Phe Glu Lys
                165                 170

<210> SEQ ID NO 107
<211> LENGTH: 510
<212> TYPE: DNA
<213> ORGANISM: Homo sapiens

<400> SEQUENCE: 107
ttagatgttg gcaacctcac ccagcaaagg gagctgcgaa agaaactgaa gtgcaaaagt      60
ttcaaatggt acttggagaa tgtctttcct gacttaaggg ctcccattgt gagagctagt     120
ggtgtgctta ttaatgtggc tttgggtaaa tgcatttcca ttgaaaacac tacagtcatt     180
ctggaagact gcgatgggag caaagagctt caacaattta attacacctg gttaagactt     240
attaaatgtg gagaatggtg tatagccccc atccctgata aggagccgt aaggctgcac      300 ccttgtgata acagaaacaa agggctaaaa tggctgcata atcaacatc agtctttcat      360 ccagaactgg tgaatcacat tgtttttgaa aacaatcagc aattattatg cttggaagga     420 aattttctc aaaagatcct gaaagtagct gcctgtgacc cagtgaagcc atatcaaaag      480
tggaaatttg aaaaatatta tgaagcctga                                      510

<210> SEQ ID NO 108
<211> LENGTH: 168
<212> TYPE: PRT
<213> ORGANISM: Homo sapiens

<400> SEQUENCE: 108

Asp Val Gly Asn Leu Thr Gln Gln Arg Glu Leu Arg Lys Lys Leu Lys
1               5                   10                  15

Cys Lys Ser Phe Lys Trp Tyr Leu Glu Asn Val Phe Pro Asp Leu Arg
            20                  25                  30

Ala Pro Ile Val Arg Ala Ser Gly Val Leu Ile Asn Val Ala Leu Gly
            35                  40                  45

Lys Cys Ile Ser Ile Glu Asn Thr Thr Val Ile Leu Glu Asp Cys Asp
        50                  55                  60

Gly Ser Lys Glu Leu Gln Gln Phe Asn Tyr Thr Trp Leu Arg Leu Ile
65                  70                  75                  80

Lys Cys Gly Glu Trp Cys Ile Ala Pro Ile Pro Asp Lys Gly Ala Val
                85                  90                  95

Arg Leu His Pro Cys Asp Asn Arg Asn Lys Gly Leu Lys Trp Leu His
            100                 105                 110

Lys Ser Thr Ser Val Phe His Pro Glu Leu Val Asn His Ile Val Phe
            115                 120                 125

Glu Asn Asn Gln Gln Leu Leu Cys Leu Glu Gly Asn Phe Ser Gln Lys
            130                 135                 140

Ile Leu Lys Val Ala Ala Cys Asp Pro Val Lys Pro Tyr Gln Lys Trp
145                 150                 155                 160

```
<210> SEQ ID NO 109
<211> LENGTH: 498
<212> TYPE: DNA
<213> ORGANISM: Homo sapiens

<400> SEQUENCE: 109
tccttcggtg acatttcgga acgactgcag ctgagggaac aactgcactg tcacaacttt      60
tcctggtacc tgcacaatgt ctacccagag atgtttgttc ctgacctgac gcccaccttc     120
tatggtgcca tcaagaacct cggcaccaac caatgcctgg atgtgggtga aacaaccgc     180 ggggggaagc ccctcatcat gtactcctgc acggccttg gcggcaacca gtactttgag     240
tacacaactc agagggacct tcgccacaac atcgcaaagc agctgtgtct acatgtcagc     300
aagggtgctc tgggccttgg agctgtcac ttcactggca agaatagcca ggtccccaag     360
gacgaggaat gggaattggc ccaggatcag ctcatcagga actcaggatc tggtacctgc     420
ctgacatccc aggacaaaaa gccagccatg gccccctgca atcccagtga ccccatcag     480 ttgtggctct tgtctag                                                    498

<210> SEQ ID NO 110
<211> LENGTH: 165
<212> TYPE: PRT
<213> ORGANISM: Homo sapiens

<400> SEQUENCE: 110

Ser Phe Gly Asp Ile Ser Glu Arg Leu Gln Leu Arg Glu Gln Leu His
1               5                   10                  15

Cys His Asn Phe Ser Trp Tyr Leu His Asn Val Tyr Pro Glu Met Phe
                20                  25                  30

Val Pro Asp Leu Thr Pro Thr Phe Tyr Gly Ala Ile Lys Asn Leu Gly
            35                  40                  45

Thr Asn Gln Cys Leu Asp Val Gly Glu Asn Asn Arg Gly Gly Lys Pro
        50                  55                  60

Leu Ile Met Tyr Ser Cys His Gly Leu Gly Gly Asn Gln Tyr Phe Glu
65                  70                  75                  80

Tyr Thr Thr Gln Arg Asp Leu Arg His Asn Ile Ala Lys Gln Leu Cys
                85                  90                  95

Leu His Val Ser Lys Gly Ala Leu Gly Leu Gly Ser Cys His Phe Thr
            100                 105                 110

Gly Lys Asn Ser Gln Val Pro Lys Asp Glu Glu Trp Glu Leu Ala Gln
        115                 120                 125

Asp Gln Leu Ile Arg Asn Ser Gly Ser Gly Thr Cys Leu Thr Ser Gln
    130                 135                 140

Asp Lys Lys Pro Ala Met Ala Pro Cys Asn Pro Ser Asp Pro His Gln
145                 150                 155                 160

Leu Trp Leu Phe Val
                165

<210> SEQ ID NO 111
<211> LENGTH: 501
<212> TYPE: DNA
<213> ORGANISM: Homo sapiens

<400> SEQUENCE: 111
```

```
tatggggata tatcggagct gaaaaaattt cgagaagatc acaactgcca aagttttaag    60
tggttcatgg aagaaatagc ttatgatatc acctcacact accctttgcc acccaaaaat   120
gttgactggg gagaaatcag aggcttcgaa actgcttact gcattgatag catgggaaaa   180
acaaatggag gctttgttga actaggaccc tgccacagga tgggagggaa tcagctttc    240 agaatcaatg aagcaaatca actcatgcag tatgaccagt gtttgacaaa gggagctgat   300
ggatcaaaag ttatgattac acactgtaat ctaaatgaat taaggaatg gcagtacttc    360 aagaacctgc acagatttac tcatattcct tcaggaaagt gtttagatcg ctcagaggtc   420
ctgcatcaag tattcatctc caattgtgac tccagtaaaa cgactcaaaa atgggaaatg   480
aataacatcc atagtgttta g                                             501
```

```
<210> SEQ ID NO 112
<211> LENGTH: 166
<212> TYPE: PRT
<213> ORGANISM: Homo sapiens

<400> SEQUENCE: 112

Tyr Gly Asp Ile Ser Glu Leu Lys Lys Phe Arg Glu Asp His Asn Cys
1               5                   10                  15

Gln Ser Phe Lys Trp Phe Met Glu Glu Ile Ala Tyr Asp Ile Thr Ser
            20                  25                  30

His Tyr Pro Leu Pro Pro Lys Asn Val Asp Trp Gly Glu Ile Arg Gly
        35                  40                  45

Phe Glu Thr Ala Tyr Cys Ile Asp Ser Met Gly Lys Thr Asn Gly Gly
    50                  55                  60

Phe Val Glu Leu Gly Pro Cys His Arg Met Gly Gly Asn Gln Leu Phe
65                  70                  75                  80

Arg Ile Asn Glu Ala Asn Gln Leu Met Gln Tyr Asp Gln Cys Leu Thr
                85                  90                  95

Lys Gly Ala Asp Gly Ser Lys Val Met Ile Thr His Cys Asn Leu Asn
            100                 105                 110

Glu Phe Lys Glu Trp Gln Tyr Phe Lys Asn Leu His Arg Phe Thr His
        115                 120                 125

Ile Pro Ser Gly Lys Cys Leu Asp Arg Ser Glu Val Leu His Gln Val
    130                 135                 140

Phe Ile Ser Asn Cys Asp Ser Ser Lys Thr Thr Gln Lys Trp Glu Met
145                 150                 155                 160

Asn Asn Ile His Ser Val
                165
```

```
<210> SEQ ID NO 113
<211> LENGTH: 534
<212> TYPE: DNA
<213> ORGANISM: Homo sapiens

<400> SEQUENCE: 113
gacgtttctt ccagaatggc actccgggaa aaactgaaat gtaaaacttt tgactggtac    60
ctgaaaaatg tttatccact cttgaagcca ctccacacca tcgtgggcta tggaagaatg   120
aaaaacctat tggatgaaaa tgtctgcttg gatcagggac ccgttccagg caacaccccc   180
atcatgtatt actgccatga attcagctca cagaatgtct actatcacct aactggggag   240
ctctatgtgg acaactgat tgcagaggcc agtgctagtg atcgctgcct gacagaccct   300
ggcaaggcgg agaagcccac cttagaacca tgctccaagg cagctaagaa tagactgcat   360
```

```
atatattggg attttaaacc gggaggagct gtcataaaca gagataccaa gcggtgtctg     420
gagatgaaga aggatctttt gggtagccac gtgcttgtgc tccagacctg tagcacgcaa     480
gtgtgggaaa tccagcacac tgtcagagac tggggtcaga ccaacagcca gtga           534
```

<210> SEQ ID NO 114
<211> LENGTH: 179
<212> TYPE: PRT
<213> ORGANISM: Homo sapiens

<400> SEQUENCE: 114

Phe Gly Asp Val Ser Ser Arg Met Ala Leu Arg Glu Lys Leu Lys Cys
1               5                   10                  15

Lys Thr Phe Asp Trp Tyr Leu Lys Asn Val Tyr Pro Leu Leu Lys Pro
            20                  25                  30

Leu His Thr Ile Val Gly Tyr Gly Arg Met Lys Asn Leu Leu Asp Glu
        35                  40                  45

Asn Val Cys Leu Asp Gln Gly Pro Val Pro Gly Asn Thr Pro Ile Met
    50                  55                  60

Tyr Tyr Cys His Glu Phe Ser Ser Gln Asn Val Tyr Tyr His Leu Thr
65                  70                  75                  80

Gly Glu Leu Tyr Val Gly Gln Leu Ile Ala Glu Ala Ser Ala Ser Asp
                85                  90                  95

Arg Cys Leu Thr Asp Pro Gly Lys Ala Glu Lys Pro Thr Leu Glu Pro
            100                 105                 110

Cys Ser Lys Ala Ala Lys Asn Arg Leu His Ile Tyr Trp Asp Phe Lys
        115                 120                 125

Pro Gly Gly Ala Val Ile Asn Arg Asp Thr Lys Arg Cys Leu Glu Met
    130                 135                 140

Lys Lys Asp Leu Leu Gly Ser His Val Leu Val Leu Gln Thr Cys Ser
145                 150                 155                 160

Thr Gln Val Trp Glu Ile Gln His Thr Val Arg Asp Trp Gly Gln Thr
                165                 170                 175

Asn Ser Gln

<210> SEQ ID NO 115
<211> LENGTH: 534
<212> TYPE: DNA
<213> ORGANISM: Homo sapiens

<400> SEQUENCE: 115

```
ttcggggacg tgtctgagag gctggccctg cgtcagaggc tgaagtgtcg cagcttcaag     60
tggtacctgg agaacgtgta cccggagatg agggtctaca caacacccct cacgtacgga    120
gaggtgagaa acagcaaagc cagtgcctac tgtctggacc agggagcgga ggacggcgac    180
cgggcgatcc tctaccccctg ccacgggatg tcctcccagc tggtgcgta cagcgctgac    240 ggcctgctgc agctggggcc tctgggctcc acagccttct gcctgactc caagtgtctg    300 gtggatgacg gcacgggccg catgcccacc ctgaagaggt gtgaggatgt ggcgcggcca    360
acacagcggc tgtgggactt cacccagagt ggccccattg tgagccgggc cacgggccgc    420
tgcctggagg tggagatgtc caaagatgcc aactttgggc tccggctggt ggtacagagg    480
tgctcggggc agaagtggat gatcagaaac tggatcaaac acgcacggca ctga           534
```

<210> SEQ ID NO 116
<211> LENGTH: 177
<212> TYPE: PRT

<213> ORGANISM: Homo sapiens

<400> SEQUENCE: 116

Phe Gly Asp Val Ser Glu Arg Leu Ala Leu Arg Gln Arg Leu Lys Cys
1               5                   10                  15

Arg Ser Phe Lys Trp Tyr Leu Glu Asn Val Tyr Pro Glu Met Arg Val
            20                  25                  30

Tyr Asn Asn Thr Leu Thr Tyr Gly Glu Val Arg Asn Ser Lys Ala Ser
        35                  40                  45

Ala Tyr Cys Leu Asp Gln Gly Ala Glu Asp Gly Asp Arg Ala Ile Leu
    50                  55                  60

Tyr Pro Cys His Gly Met Ser Ser Gln Leu Val Arg Tyr Ser Ala Asp
65                  70                  75                  80

Gly Leu Leu Gln Leu Gly Pro Leu Gly Ser Thr Ala Phe Leu Pro Asp
                85                  90                  95

Ser Lys Cys Leu Val Asp Asp Gly Thr Gly Arg Met Pro Thr Leu Lys
            100                 105                 110

Arg Cys Glu Asp Val Ala Arg Pro Thr Gln Arg Leu Trp Asp Phe Thr
        115                 120                 125

Gln Ser Gly Pro Ile Val Ser Arg Ala Thr Gly Arg Cys Leu Glu Val
    130                 135                 140

Glu Met Ser Lys Asp Ala Asn Phe Gly Leu Arg Leu Val Val Gln Arg
145                 150                 155                 160

Cys Ser Gly Gln Lys Trp Met Ile Arg Asn Trp Ile Lys His Ala Arg
                165                 170                 175

His

<210> SEQ ID NO 117
<211> LENGTH: 564
<212> TYPE: DNA
<213> ORGANISM: Homo sapiens

<400> SEQUENCE: 117
gctggggatg tcgcagtcca gaaaaagctc cgcagctccc ttaactgcaa gagtttcaag      60
tggtttatga cgaagatagc ctgggacctg cccaaattct acccaccegt ggagccccecg    120 gctgcagctt gggggagat ccgaaatgtg gcacagggc tgtgtgcaga cacaaagcac       180
ggggccttgg gctccccact aaggctagag ggctgcgtcc gaggccgtgg ggaggctgcc     240
tggaacaaca tgcaggtatt caccttcacc tggagagagg acatccggcc tggagacccc     300
cagcacacca agaagttctg ctttgatgcc atttcccaca ccagccctgt cacgctgtac     360
gactgccaca gcatgaaggg caaccagctg tggaaatacc gcaaagacaa gaccctgtac     420
caccctgtca gtggcagctg catggactgc agtgaaagtg accataggat cttcatgaac     480
acctgcaacc catcctctct cacccagcag tggctgtttg aacacaccaa ctcaacagtc     540
ttggaaaaat tcaataggaa ctga                                            564

<210> SEQ ID NO 118
<211> LENGTH: 187
<212> TYPE: PRT
<213> ORGANISM: Homo sapiens

<400> SEQUENCE: 118

Ala Gly Asp Val Ala Val Gln Lys Lys Leu Arg Ser Ser Leu Asn Cys
1               5                   10                  15

Lys Ser Phe Lys Trp Phe Met Thr Lys Ile Ala Trp Asp Leu Pro Lys

```
                20                  25                  30
Phe Tyr Pro Pro Val Glu Pro Ala Ala Trp Gly Glu Ile Arg
        35                  40                  45
Asn Val Gly Thr Gly Leu Cys Ala Asp Thr Lys His Gly Ala Leu Gly
        50                      55                  60
Ser Pro Leu Arg Leu Glu Gly Cys Val Arg Gly Arg Gly Glu Ala Ala
65                      70                  75                  80
Trp Asn Asn Met Gln Val Phe Thr Phe Thr Trp Arg Glu Asp Ile Arg
                    85                  90                  95
Pro Gly Asp Pro Gln His Thr Lys Lys Phe Cys Phe Asp Ala Ile Ser
                100                 105                 110
His Thr Ser Pro Val Thr Leu Tyr Asp Cys His Ser Met Lys Gly Asn
            115                 120                 125
Gln Leu Trp Lys Tyr Arg Lys Asp Lys Thr Leu Tyr His Pro Val Ser
        130                 135                 140
Gly Ser Cys Met Asp Cys Ser Glu Ser Asp His Arg Ile Phe Met Asn
145                 150                 155                 160
Thr Cys Asn Pro Ser Ser Leu Thr Gln Gln Trp Leu Phe Glu His Thr
                165                 170                 175
Asn Ser Thr Val Leu Glu Lys Phe Asn Arg Asn
            180                 185

<210> SEQ ID NO 119
<211> LENGTH: 549
<212> TYPE: DNA
<213> ORGANISM: Homo sapiens

<400> SEQUENCE: 119
tgcaatatca gtgagcgtgt ggaactgaga aagaagttgg gctgtaaatc atttaaatgg     60
tatttggata atgtataccc agagatgcag atatctgggt cccacgccaa accccaacaa    120 cccattttg tcaatagagg gccaaaacga cccaaagtcc ttcaacgtgg aaggctctat    180
cacctccaga ccaacaaatg cctggtggcc cagggccgcc caagtcagaa gggaggtctc    240
gtggtgctta aggcctgtga ctacagtgac ccaaatcaga tctggatcta taatgaagag    300
catgaattgg ttttaaatag tctcctttgt ctagatatgt cagagactcg ctcatcagac    360
ccgccacggc tcatgaaatg ccacgggtca ggaggatccc agcagtggac ctttgggaaa    420 acaatcggc tataccaggt gtcggttgga cagtgcctga gagcagtgga tcccctgggt    480
cagaagggct ctgtcgccat ggcgatctgc gatggctcct cttcacagca gtggcatttg    540
gaaggttaa                                                           549

<210> SEQ ID NO 120
<211> LENGTH: 181
<212> TYPE: PRT
<213> ORGANISM: Homo sapiens

<400> SEQUENCE: 120

Asn Ile Ser Glu Arg Val Glu Leu Arg Lys Lys Leu Gly Cys Lys Ser
1               5                   10                  15
Phe Lys Trp Tyr Leu Asp Asn Val Tyr Pro Glu Met Gln Ile Ser Gly
                20                  25                  30
Ser His Ala Lys Pro Gln Gln Pro Ile Phe Val Asn Arg Gly Pro Lys
            35                  40                  45
Arg Pro Lys Val Leu Gln Arg Gly Arg Leu Tyr His Leu Gln Thr Asn
        50                  55                  60
```

```
Lys Cys Leu Val Ala Gln Gly Arg Pro Ser Gln Lys Gly Gly Leu Val
 65                  70                  75                  80

Val Leu Lys Ala Cys Asp Tyr Ser Asp Pro Asn Gln Ile Trp Ile Tyr
                 85                  90                  95

Asn Glu Glu His Glu Leu Val Leu Asn Ser Leu Leu Cys Leu Asp Met
             100                 105                 110

Ser Glu Thr Arg Ser Ser Asp Pro Pro Arg Leu Met Lys Cys His Gly
         115                 120                 125

Ser Gly Gly Ser Gln Gln Trp Thr Phe Gly Lys Asn Asn Arg Leu Tyr
130                 135                 140

Gln Val Ser Val Gly Gln Cys Leu Arg Ala Val Asp Pro Leu Gly Gln
145                 150                 155                 160

Lys Gly Ser Val Ala Met Ala Ile Cys Asp Gly Ser Ser Ser Gln Gln
                165                 170                 175

Trp His Leu Glu Gly
            180

<210> SEQ ID NO 121
<211> LENGTH: 525
<212> TYPE: DNA
<213> ORGANISM: Homo sapiens

<400> SEQUENCE: 121
tgggatgtga cagagaggaa gcagctccgg gacaagctcc agtgtaaaga cttcaagtgg      60
ttcttggaga ctgtgtatcc agaactgcat gtgcctgagg acaggcctgg cttcttcggg     120
atgctccaga caaaggact aacagactac tgctttgact ataaccctcc cgatgaaaac      180
cagattgtgg acaccaggt cattctgtac ctctgtcatg ggatgggcca gaatcagttt     240
ttcgagtaca cgtcccagaa agaaatacgc tataacaccc accagcctga gggctgcatt     300
gctgtggaag caggaatgga tacccttatc atgcatctct gcaagaaaac tgccccagag     360
aatcagaagt tcatcttgca ggaggatgga tctttatttc acgaacagtc caagaaatgt     420
gtccaggctg cgaggaagga gtcgagtgac agtttcgttc cactcttacg agactgcacc     480
aactcggatc atcagaaatg gttcttcaaa gagcgcatgt tatga                    525

<210> SEQ ID NO 122
<211> LENGTH: 173
<212> TYPE: PRT
<213> ORGANISM: Homo sapiens

<400> SEQUENCE: 122

Asp Val Thr Glu Arg Lys Gln Leu Arg Asp Lys Leu Gln Cys Lys Asp
  1               5                  10                  15

Phe Lys Trp Phe Leu Glu Thr Val Tyr Pro Glu Leu His Val Pro Glu
                 20                  25                  30

Asp Arg Pro Gly Phe Phe Gly Met Leu Gln Asn Lys Gly Leu Thr Asp
             35                  40                  45

Tyr Cys Phe Asp Tyr Asn Pro Pro Asp Glu Asn Gln Ile Val Gly His
         50                  55                  60

Gln Val Ile Leu Tyr Leu Cys His Gly Met Gly Gln Asn Gln Phe Phe
 65                  70                  75                  80

Glu Tyr Thr Ser Gln Lys Glu Ile Arg Tyr Asn Thr His Gln Pro Glu
                 85                  90                  95

Gly Cys Ile Ala Val Glu Ala Gly Met Asp Thr Leu Ile Met His Leu
            100                 105                 110
```

```
Cys Glu Glu Thr Ala Pro Glu Asn Gln Lys Phe Ile Leu Gln Glu Asp
            115                 120                 125

Gly Ser Leu Phe His Glu Gln Ser Lys Lys Cys Val Gln Ala Ala Arg
        130                 135                 140

Lys Glu Ser Ser Asp Ser Phe Val Pro Leu Leu Arg Asp Cys Thr Asn
145                 150                 155                 160

Ser Asp His Gln Lys Trp Phe Phe Lys Glu Arg Met Leu
                165                 170

<210> SEQ ID NO 123
<211> LENGTH: 528
<212> TYPE: DNA
<213> ORGANISM: Homo sapiens

<400> SEQUENCE: 123
tctgagaagc cagactgcat ggaacgcttg cagctgcaaa ggagactggg ttgtcggaca        60
ttccactggt ttctggctaa tgtctaccct gagctgtacc catctgaacc caggcccagt       120
ttctctggaa agctccacaa cactggactt gggctctgtg cagactgcca ggcagaaggg       180
gacatcctgg gctgtcccat ggtgttggct ccttgcagtg acagccggca gcaacagtac       240
ctgcagcaca ccagcaggaa ggagattcac tttggcagcc cacagcacct gtgctttgct       300
gtcaggcagg agcaggtgat tcttcagaac tgcacggagg aaggcctggc catccaccag       360
cagcactggg acttccagga gaatgggatg attgtccaca ttctttctgg gaaatgcatg       420
gaagctgtgg tgcaagaaaa caataaagat ttgtacctgc gtccgtgtga tggaaaagcc       480
cgccagcagt ggcgttttga ccagatcaat gctgtggatg aacgatga                    528

<210> SEQ ID NO 124
<211> LENGTH: 174
<212> TYPE: PRT
<213> ORGANISM: Homo sapiens

<400> SEQUENCE: 124

Glu Lys Pro Asp Cys Met Glu Arg Leu Gln Leu Gln Arg Arg Leu Gly
1               5                   10                  15

Cys Arg Thr Phe His Trp Phe Leu Ala Asn Val Tyr Pro Glu Leu Tyr
            20                  25                  30

Pro Ser Glu Pro Arg Pro Ser Phe Ser Gly Lys Leu His Asn Thr Gly
        35                  40                  45

Leu Gly Leu Cys Ala Asp Cys Gln Ala Glu Gly Asp Ile Leu Gly Cys
    50                  55                  60

Pro Met Val Leu Ala Pro Cys Ser Asp Ser Arg Gln Gln Gln Tyr Leu
65                  70                  75                  80

Gln His Thr Ser Arg Lys Glu Ile His Phe Gly Ser Pro Gln His Leu
                85                  90                  95

Cys Phe Ala Val Arg Gln Glu Gln Val Ile Leu Gln Asn Cys Thr Glu
            100                 105                 110

Glu Gly Leu Ala Ile His Gln His Trp Asp Phe Gln Glu Asn Gly
        115                 120                 125

Met Ile Val His Ile Leu Ser Gly Lys Cys Met Glu Ala Val Val Gln
    130                 135                 140

Glu Asn Asn Lys Asp Leu Tyr Leu Arg Pro Cys Asp Gly Lys Ala Arg
145                 150                 155                 160

Gln Gln Trp Arg Phe Asp Gln Ile Asn Ala Val Asp Glu Arg
                165                 170
```

<210> SEQ ID NO 125
<211> LENGTH: 498
<212> TYPE: DNA
<213> ORGANISM: Homo sapiens

<400> SEQUENCE: 125

```
tatggagatg tgtcagtcag aaaaacacta agagaaaatc tgaagtgtaa gcccttttct      60
tggtacctag aaaacatcta tccggactcc cagatcccaa gacgttatta ctcacttggt     120
gagataagaa atgttgaaac caatcagtgt ttagacaaca tgggccgcaa ggaaaatgaa     180
aaagtgggta tattcaactg tcatggtatg ggaggaaatc aggtattttc ttacactgct     240
gacaaagaaa tccgaaccga tgacttgtgc ttggatgttt ctagactcaa tggacctgta     300
atcatgttaa atgccacca tgagagga aatcagttat gggaatatga tgctgagaga      360
ctcacgttgc gacatgttaa cagtaaccaa tgtctcgatg aaccttctga agaagacaaa     420
atggtgccta caatgcagga ctgtagtgga agcagatccc aacagtggct gctaaggaac     480
atgaccttgg gcacatga                                                   498
```

<210> SEQ ID NO 126
<211> LENGTH: 165
<212> TYPE: PRT
<213> ORGANISM: Homo sapiens

<400> SEQUENCE: 126

```
Tyr Gly Asp Val Ser Val Arg Lys Thr Leu Arg Glu Asn Leu Lys Cys
1               5                   10                  15

Lys Pro Phe Ser Trp Tyr Leu Glu Asn Ile Tyr Pro Asp Ser Gln Ile
            20                  25                  30

Pro Arg Arg Tyr Tyr Ser Leu Gly Glu Ile Arg Asn Val Glu Thr Asn
        35                  40                  45

Gln Cys Leu Asp Asn Met Gly Arg Lys Glu Asn Glu Lys Val Gly Ile
    50                  55                  60

Phe Asn Cys His Gly Met Gly Gly Asn Gln Val Phe Ser Tyr Thr Ala
65                  70                  75                  80

Asp Lys Glu Ile Arg Thr Asp Asp Leu Cys Leu Asp Val Ser Arg Leu
                85                  90                  95

Asn Gly Pro Val Ile Met Leu Lys Cys His His Met Arg Gly Asn Gln
            100                 105                 110

Leu Trp Glu Tyr Asp Ala Glu Arg Leu Thr Leu Arg His Val Asn Ser
        115                 120                 125

Asn Gln Cys Leu Asp Glu Pro Ser Glu Glu Asp Lys Met Val Pro Thr
    130                 135                 140

Met Gln Asp Cys Ser Gly Ser Arg Ser Gln Gln Trp Leu Leu Arg Asn
145                 150                 155                 160

Met Thr Leu Gly Thr
                165
```

<210> SEQ ID NO 127
<211> LENGTH: 516
<212> TYPE: DNA
<213> ORGANISM: Homo sapiens

<400> SEQUENCE: 127

```
tcgggaatgt tgagagcaga ttggacctga ggaagaatct cgctgccag agcttcaagt       60
ggtacctgga gaatatctac cctgaactca gcatcccaa ggagtcctcc atccagaagg      120
```

```
gcaatatccg acagagacag aagtgcctgg aatctcaaag gcagaacaac caagaaaccc      180
caaacctaaa gttgagcccc tgtgccaagg tcaaggcgaa agatgcaaag tcccaggtat      240
gggccttcac atacacccag aagatcctcc aggaggagct gtgcctgtca gtcatcacct      300
tgttccctgg cgccccagtg gttcttgtcc tttgcaagaa tggagatgac cgacagcaat      360
ggaccaaaac tggttcccac atcgagcaca tagcatccca cctctgcctc gatacagata      420
tgttcggtga tggcaccgag aacggcaagg aaatcggcgt caacccatgt gagtcctcac      480
tcatgagcca gcactgggac atggtgagtt cttgag                               516
```

```
<210> SEQ ID NO 128
<211> LENGTH: 171
<212> TYPE: PRT
<213> ORGANISM: Homo sapiens

<400> SEQUENCE: 128

Phe Gly Asn Val Glu Ser Arg Leu Asp Leu Arg Lys Asn Leu Arg Cys
 1               5                  10                  15

Gln Ser Phe Lys Trp Tyr Leu Glu Asn Ile Tyr Pro Glu Leu Ser Ile
            20                  25                  30

Pro Lys Glu Ser Ser Ile Gln Lys Gly Asn Ile Arg Gln Arg Gln Lys
        35                  40                  45

Cys Leu Glu Ser Gln Arg Gln Asn Asn Gln Glu Thr Pro Asn Leu Lys
    50                  55                  60

Leu Ser Pro Cys Ala Lys Val Lys Gly Glu Asp Ala Lys Ser Gln Val
65                  70                  75                  80

Trp Ala Phe Thr Tyr Thr Gln Lys Ile Leu Gln Glu Glu Leu Cys Leu
                85                  90                  95

Ser Val Ile Thr Leu Phe Pro Gly Ala Pro Val Val Leu Val Leu Cys
            100                 105                 110

Lys Asn Gly Asp Asp Arg Gln Gln Trp Thr Lys Thr Gly Ser His Ile
        115                 120                 125

Glu His Ile Ala Ser His Leu Cys Leu Asp Thr Asp Met Phe Gly Asp
    130                 135                 140

Gly Thr Glu Asn Gly Lys Glu Ile Gly Val Asn Pro Cys Glu Ser Ser
145                 150                 155                 160

Leu Met Ser Gln His Trp Asp Met Val Ser Ser
                165                 170
```

```
<210> SEQ ID NO 129
<211> LENGTH: 492
<212> TYPE: DNA
<213> ORGANISM: Homo sapiens

<400> SEQUENCE: 129
agtgtggcta cgcggataga gcagaggaag aagatgaact gcaagtcctt ccgctggtac       60
ctggagaacg tctacccaga gctcacggtc cccgtgaagg aagcactccc cggcatcatt      120
aagcaggggg tgaactgctt agaatctcag ggccagaaca cagctggtga cttcctgctt      180
ggaatgggga tctgcagagg gtctgccaag aacccgcagc cgcccaggc atggctgttc       240 agtgaccacc tcatccagca gcaggggaag tgcctggctg ccacctccac cttaatgtcc      300
tcccctggat ccccagtcat actgcagatg tgcaaccctaa gaagggcaa gcagaaatgg      360 aggagaaaag gatctttcat ccagcattca gtcagtggcc tctgcctgga gacaaagcct      420
gcccagctgg tgaccagcaa gtgtcaggct gacgcccagg cccagcagtg gcagctgttg      480
```

```
ccacacacat ga                                                              492
```

<210> SEQ ID NO 130
<211> LENGTH: 163
<212> TYPE: PRT
<213> ORGANISM: Homo sapiens

<400> SEQUENCE: 130

```
Ser Val Ala Thr Arg Ile Glu Gln Arg Lys Lys Met Asn Cys Lys Ser
1               5                   10                  15

Phe Arg Trp Tyr Leu Glu Asn Val Tyr Pro Glu Leu Thr Val Pro Val
            20                  25                  30

Lys Glu Ala Leu Pro Gly Ile Ile Lys Gln Gly Val Asn Cys Leu Glu
        35                  40                  45

Ser Gln Gly Gln Asn Thr Ala Gly Asp Phe Leu Leu Gly Met Gly Ile
    50                  55                  60

Cys Arg Gly Ser Ala Lys Asn Pro Gln Pro Ala Gln Ala Trp Leu Phe
65                  70                  75                  80

Ser Asp His Leu Ile Gln Gln Gln Gly Lys Cys Leu Ala Ala Thr Ser
                85                  90                  95

Thr Leu Met Ser Ser Pro Gly Ser Pro Val Ile Leu Gln Met Cys Asn
            100                 105                 110

Pro Arg Glu Gly Lys Gln Lys Trp Arg Arg Lys Gly Ser Phe Ile Gln
        115                 120                 125

His Ser Val Ser Gly Leu Cys Leu Glu Thr Lys Pro Ala Gln Leu Val
    130                 135                 140

Thr Ser Lys Cys Gln Ala Asp Ala Gln Ala Gln Gln Trp Gln Leu Leu
145                 150                 155                 160

Pro His Thr
```

METHODS OF MODULATING FUNCTIONS OF POLYPEPTIDE GALNAC-TRANSFERASES AND OF SCREENING TEST SUBSTANCES TO FIND AGENTS HEREFOR, PHARMACEUTICAL COMPOSITIONS COMPRISING SUCH AGENTS AND THE USE OF SUCH AGENTS FOR PREPARING MEDICAMENTS

This application claims priority under 35 U.S.C. § 119(e) to U.S. Provisional Application Ser. No. 60/425,204 TO BE ASSIGNED filed Nov. 8, 2002 and entitled "Methods to Identify Agents Modulating Functions of Polypeptide GalNAc-transferases, Pharmaceutical Compositions Comprising Such Agents and the Use of Such Agents for Preparing Medicaments" by Henrik Clausen and Eric Paul Bennett. This application is also a continuation-in-part of International Patent Application No. PCT/DK01/00328 filed May 10, 2001, which published on Nov. 15, 2001 as International Publication No. WO 01/85215. PCT/DK01/00328 claims priority of U.S. Provisional Patent Application No. 60/203,331 filed on May 11, 2000, which is now abandoned. Each of these priority applications is incorporated herein by reference and in their entirety.

TECHNICAL FIELD

The present invention relates generally to the biosynthesis, sorting and secretion of mucins, O-glycosylated glycoproteins, and glycoproteins. In particular, this invention concerns a method of modulating functions of a homologous family of UDP-N-acetyl-α-D-galactosamine: polypeptide N-acetylgalactosaminyltransferases (GalNAc-transferases), which add N-acetylgalactosamine (GalNAc) to the hydroxy group of serine and threonine amino acid residues in peptides and proteins.

Further, this invention concerns a method of screening one or more test substances for the ability to modulate polypeptide GalNAc-transferase enzymatic activity in a cell-free or cell-based assay, in order to find agents which are effective in binding to one or more lectin domains of polypeptide GalNAc-transferases, for example, selective inhibitors of the binding properties of the above mentioned lectin domains and selective inhibitors of the effects that these lectin domains exert on intracellular transport, transport to cell surface, and secretion of mucins, glycoproteins, and proteins.

Even further, this invention provides a preferable inhibitor, GalNAcβ-benzyl, which is a novel inhibitor and representative of a novel group of inhibitors which display the common characteristic of selectively inhibiting lectins of polypeptide GalNAc-transferases in direct binding assays and not serve as substrates for other glycosyltransferases involved in O-glycan biosyntheses, while exhibiting inhibitory activity of secretion and intracellular transport of mucins and glycoproteins in cells. GalNAcβ-benzyl and related inhibitors with the same biological functions represent preferable selective inhibitor compared to GalNAcα-benzyl because these do not serve as substrates for glycosyltransferases extending O-glycans and do not provide a general inhibition of the O-glycosylation process in cells.

Also, the present invention concerns pharmaceutical compositions comprising an agent which is effective in modulating functions of one or more polypeptide GalNAc-transferases, as well as the use of an agent which is effective in inhibiting one or more lectin domains of polypeptide GalNAc-transferases and modulating functions mediated by said lectin domains for preparing medicaments for the treatment of various disorders.

BACKGROUND OF THE INVENTION

Mucin-type O-glycosylation, one of the most abundant forms of protein glycosylation, is found on secreted and cell surface associated glycoproteins of all eukaryotic cells except yeast. Mucin-type O-glycans contribute to a number of important molecular functions, including: direct effects on protein conformation, solubility, and stability; specific receptor functions that regulate cell trafficking and cell-cell interactions; and microbial clearance. Mucin-type O-glycans are synthesised in the Golgi through the sequential addition of saccharide residues, first to hydroxyl groups on serines and threonines of a protein core and subsequently to hydroxyl groups on the growing saccharide chains that extend from the protein core. There is great diversity in the structures created by O-glycosylation (hundreds of potential structures), which are produced by the catalytic activity of hundreds of glycosyltransferase enzymes that are resident in the Golgi complex. Diversity exists at the level of the glycan structure and in positions of attachment of O-glycans to protein backbones. Despite the high degree of potential diversity, it is clear that O-glycosylation is a highly regulated process that shows a high degree of conservation among multicellular organisms.

The factors that regulate the attachment of O-glycans to particular protein sites and their extension into specific structures are poorly understood. Longstanding hypotheses in this area propose that mucin-type O-glycosylation occurs in a stochastic manner where structure of acceptor proteins combined with topology and kinetic properties of resident Golgi glycosyltransferases determine the order and degree of glycosylation (1). This concept does not fully explain the high degree of regulation and specialisation that governs the O-glycosylation process. In particular it is difficult to envision how large mucin molecules with high densities of O-glycans are glycosylated in the Golgi by stochastic mechanisms that also create other sparsely glycosylated proteins.

The first step in mucin-type O-glycosylation is catalysed by one or more members of a large family of UDP-GalNAc: polypeptide N-acetylgalactosaminyltransferases (GalNAc-transferases) (EC 2.4.1.41), which transfer GalNAc to serine and threonine acceptor sites[42]. To date twelve members of the mammalian GalNAc-transferase family have been identified and characterized, and several additional putative members of this gene family have been predicted from analysis of genome databases. The GalNAc-transferase isoforms have different kinetic properties and show differential expression patterns temporally and spatially, suggesting that they have distinct biological functions[42]. Sequence analysis of GalNAc-transferases have led to the hypothesis that these enzymes contain two distinct subunits: a central catalytic unit, and a C-terminal unit with sequence similarity to the plant lectin ricin, designated the "lectin domain" (3-6). Previous experiments involving site-specific mutagenesis of selected conserved residues confirmed that mutations in the catalytic domain eliminated catalytic activity. In contrast, mutations in the "lectin domain" had no significant effects on catalytic activity of the GalNAc-transferase isoform, GalNAc-T1 (3). Thus, the C-terminal "lectin domain" was believed not to be functional and not to play roles for the enzymatic functions of GalNAc-transferases (3).

Recent evidence demonstrates that some GalNAc-transferases exhibit unique activities with partially GalNAc-glycosylated glycopeptides. The catalytic actions of at least three GalNAc-transferase isoforms, GalNAc-T4, -T7, and -T10, selectively act on glycopeptides corresponding to mucin tandem repeat domains where only some of the clustered potential glycosylation sites have been GalNAc glycosylated by other GalNAc-transferases[7-9, 44]. GalNAc-T4 and -T7 recognize different GalNAc-glycosylated peptides and catalyse transfer of GalNAc to acceptor substrate sites in addition to those that were previously utilized. One of the functions of such GalNAc-transferase activities is predicted to represent a control step of the density of O-glycan occupancy in mucins and mucin-like glycoproteins with high density of O-glycosylation. It was hypothesized that such sequential actions of multiple GalNAc-transferase isoforms may be required to complete O-glycan attachments to some mucin peptide sequences allowing for detailed control of density.

One example of this is the glycosylation of the cancer-associated mucin MUC1. MUC1 contains a tandem repeat O-glycosylated region of 20 residues (HGVTSAPDTRPAPGSTAPPA) (SEQ ID NO: 1) with five potential O-glycosylation sites. GalNAc-T1, -T2, and -T3 can initiate glycosylation of the MUC1 tandem repeat and incorporate at only three sites (HGVTSAPDTRPAPGSTAPPA (SEQ ID NO: 1), GalNAc attachment sites underlined). GalNAc-T4 is unique in that it is the only GalNAc-transferase isoform identified so far that can complete the O-glycan attachment to all five acceptor sites in the 20 amino acid tandem repeat sequence of the breast cancer associated mucin, MUC1. GalNAc-T4 transfers GalNAc to at least two sites not used by other GalNAc-transferase isoforms on the GalNAc4TAP24 glycopeptide (TAPPAHGVTSAPDTRPAPGSTAPP (SEQ ID NO: 2), GalNAc attachment sites underlined) (8). An activity such as that exhibited by GalNAc-T4 appears to be required for production of the glycoform of MUC1 expressed by cancer cells where all potential sites are glycosylated (10). Normal MUC1 from lactating mammary glands has approximately 2.6 O-glycans per repeat (11) and MUC1 derived from the cancer cell line T47D has 4.8 O-glycans per repeat (10). The cancer-associated form of MUC1 is therefore associated with higher density of O-glycan occupancy and this is accomplished by a GalNAc-transferase activity identical to or similar to that of GalNAc-T4.

The specific mechanism by which GalNAc-T4, -T7, and -T10 recognize and function with GalNAc-glycosylated glycopeptides is not known. However, it was originally demonstrated that the GalNAc-glycopeptide specificity exerted by GalNAc-T4 is directed or at least dependent on its lectin domain. A single amino acid substitution in the T4 lectin domain predicted to inactivate its function abolished the GalNAc-glycopeptide specificity of T4 without adversely affecting the basic catalytic mechanism of the transferase[42]. This suggests that the lectin domain interacts with GalNAc-glycopeptides and confers a novel catalytic function to the enzyme protein. Despite extensive attempts it has in the past not been possible to demonstrate actual binding of the transferase and lectin to sugars and glycopeptides, but it was possible to demonstrate selective inhibition of the GalNAc-glycopeptide activity of GalNAc-T4 using 230 mM concentration of GalNAc[42]. Millimolar concentrations of GalNAcα-benzyl can inhibit the lectin mediated GalNAc-glycopeptide substrate specificity of GalNAc-T4 as well as -T7. Polypeptide GalNAc-transferases, which have not displayed apparent GalNAc-glycopeptide specificities, also appear to be modulated by their lectin domains.

Recently, it was found that mutations in the GalNAc-T1 lectin domain, similarly to those previously analysed in GalNAc-T4[42], modified the activity of the enzyme in a similar fashion as GalNAc-T4. Thus, while wild type GalNAc-T1 added multiple consequtive GalNAc residues to a peptide substrate with multiple acceptor sites, mutated GalNAc-T1 failed to add more than one GalNAc residue to the same substrate[45]. The mechanism is however not understood.

Glycosylation confers physico-chemical properties including protease resistance, solubility, and stability to proteins (12-14). Glycosylation furthermore confers changes in immunological responses to proteins and glycoproteins. O-glycosylation on mucins and mucin-like glycoproteins protect these molecules found in the extracellular space and body fluids from degradation. Control of O-glycosylation with respect to sites and number (density) of O-glycan attachments to proteins as well as control of the O-glycan structures made at specific sites or in general on glycoproteins, is of interest for several purposes. Diseased cells e.g. cancer cells often dramatically change their O-glycosylation and the altered glycans and glycoproteins may constitute targets for therapeutic and diagnostic measures (15; 16). Mucins functioning in body fluids may have different properties depending on density and structure of O-glycans attached in protection against disease, including infections by micro-organisms. Furthermore, mucins with different glycosylation may change physico-chemical properties including stability and solubility properties that may influence turnover and removal of mucous. A number of lung diseases, e.g. cystic fibrosis, asthma, chronic bronchitis, smokers lungs, are associated with symptomatic mucous accumulation (17-19), and it is likely that the nature and structure of mucins play a role in the pathogenesis of such diseases.

Partial inhibitors of O-glycosylation in cells have been reported. Aryl-N-acetyl-α-galactosaminides such as benzyl-, phenyl-, and p-nitrophenyl-GalNAc were originally found to inhibit the second step in O-glycosylation, the O-glycan processing step, by inhibiting synthesis of core 1 (Galβ1-3GalNAcα1-R) and more complex structures 20. Benzyl-αGalNAc was also found to inhibit sialylation. It is generally believed that the downstream effects of benzyl-αGalNAc treatment are mediated by substrate competition of biosynthetic glycosylation products of benzyl-αGalNAc. Thus, e.g. the immediate glycosylation product of benzyl-αGalNAc is Galβ1-3GalNAcα-benzyl and this serves as an efficient substrate for the core 1 α2-3sialyltransferase ST3Gal-I[21,22]. GalNAcα-benzyl has been the most widely used inhibitor of O-glycosylation, but it has only been used in cell culture as effective treatment concentrations lead to intracellular build-up of vesicles with GalNAcα-benzyl products and treated cells change morphology and growth characteristics[46].

Treatment of cells with benzyl-αGalNAc inhibit O-glycan processing and affect apical sorting of some O-glycosylated proteins[23-25]. The mechanism for this is generally believed to be through inhibition of sialylation[46]. Inhibition of mucin secretion has also been observed in culture cells, more specifically HT29 MTX cells, but this effect is not generally found in mucin secreting cells[46].

True inhibitors of O-glycosylation, i.e. inhibitors of the initial O-glycan attachment process governed by polypeptide GalNAc-transferases have not been identified.

Inhibitors of the initiating step in O-glycosylation could completely or selectively block attachment of O-glycans to O-glycosylation sites in proteins. Compounds inhibiting the catalytic function of a selected subset of the polypeptide GalNAc-transferase family may be predicted to only lead to partial inhibition of O-glycosylation capacity of cells. Proteins with no or little O-glycosylation may have entirely different biological properties than their normal glycosylated counterparts. Complete inhibition of O-glycosylation is not desirable because of the many diverse functions of O-glycans, and it is expected to result in cell death. Selective inhibition of O-glycosylation on the other hand is desirable in many cases such as cancer cells producing glycoproteins and mucins with more dense O-glycosylation than normal cells. For example breast cancer cells appear to hyperglycosylate the cancer-associated cell surface mucin MUC1 compared to glycosylation in normal cells (10). The overexpression of MUC1 and hyperglycosylation found in cancer cells are likely to be important for the pathobiology of cancers. Methods of inhibiting the hyperglycosylation of mucins in cancer cells is desirable.

It is apparent from the above that inhibitors in the prior art interfere with O-glycan processing, i.e. the glycosylation process that extend GalNAc residues directly attached to proteins at serine and threonine residues. Existing inhibitors of O-glycosylation are not suitable for therapeutic treatment in mammals including man as they profoundly affect O-glycosylation processing as well as lead to undesired morphological and growth effects on culture cells.

Consequently, there exists a need in the art for methods of inhibiting the functions of polypeptide GalNAc-transferases. Preferable in selectively inhibiting O-glycosylation attachments in glycoproteins and mucins. There also exists a need in the art for therapeutic compounds that display selectively and limited inhibition of O-glycosylation without generally affecting the process of O-glycosylation. The present invention meets these needs, and further presents other related advantages.

SUMMARY OF THE INVENTION

Mucin-type O-glycosylation, one of the most abundant forms of protein glycosylation, is found on secreted and cell surface associated glycoproteins of all eukaryotic cells except yeast. Mucin-type O-glycans contribute to a number of important molecular functions, including: direct effects on protein conformation, solubility, and stability; specific receptor functions that regulate cell trafficking and cell-cell interactions; and microbial clearance. Mucin-type O-glycans are synthesised in the Golgi through the sequential addition of saccharide residues, first to hydroxyl groups on serines and threonines of a protein core and subsequently to hydroxyl groups on the growing saccharide chains that extend from the protein core. There is great diversity in the structures created by O-glycosylation (hundreds of potential structures), which are produced by the catalytic activity of hundreds of glycosyltransferase enzymes that are resident in the Golgi complex. Diversity exists at the level of the glycan structure and in positions of attachment of O-glycans to protein backbones. Despite the high degree of potential diversity, it is clear that O-glycosylation is a highly regulated process that shows a high degree of conservation among multicellular organisms.

The factors that regulate the attachment of O-glycans to particular protein sites and their extension into specific structures are poorly understood. Longstanding hypotheses in this area propose that mucin-type O-glycosylation occurs in a stochastic manner where structure of acceptor proteins combined with topology and kinetic properties of resident Golgi glycosyltransferases determine the order and degree of glycosylation (1). This concept does not fully explain the high degree of regulation and specialisation that governs the O-glycosylation process. In particular it is difficult to envision how large mucin molecules with high densities of O-glycans are glycosylated in the Golgi by stochastic mechanisms that also create other sparsely glycosylated proteins.

The first step in mucin-type O-glycosylation is catalysed by one or more members of a large family of UDP-GalNAc: polypeptide N-acetylgalactosaminyltransferases (GalNAc-transferases) (EC 2.4.1.41), which transfer GalNAc to serine and threonine acceptor sites[42]. To date twelve members of the mammalian GalNAc-transferase family have been identified and characterized, and several additional putative members of this gene family have been predicted from analysis of genome databases. The GalNAc-transferase isoforms have different kinetic properties and show differential expression patterns temporally and spatially, suggesting that they have distinct biological functions[42]. Sequence analysis of GalNAc-transferases have led to the hypothesis that these enzymes contain two distinct subunits: a central catalytic unit, and a C-terminal unit with sequence similarity to the plant lectin ricin, designated the "lectin domain" (3-6). Previous experiments involving site-specific mutagenesis of selected conserved residues confirmed that mutations in the catalytic domain eliminated catalytic activity. In contrast, mutations in the "lectin domain" had no significant effects on catalytic activity of the GalNAc-transferase isoform, GalNAc-T1 (3). Thus, the C-terminal "lectin domain" was believed not to be functional and not to play roles for the enzymatic functions of GalNAc-transferases (3).

Recent evidence demonstrates that some GalNAc-transferases exhibit unique activities with partially GalNAc-glycosylated glycopeptides. The catalytic actions of at least three GalNAc-transferase isoforms, GalNAc-T4, -T7, and -T10, selectively act on glycopeptides corresponding to mucin tandem repeat domains where only some of the clustered potential glycosylation sites have been GalNAc glycosylated by other GalNAc-transferases[7-9, 44]. GalNAc-T4 and -T7 recognize different GalNAc-glycosylated peptides and catalyse transfer of GalNAc to acceptor substrate sites in addition to those that were previously utilized. One of the functions of such GalNAc-transferase activities is predicted to represent a control step of the density of O-glycan occupancy in mucins and mucin-like glycoproteins with high density of O-glycosylation. It was hypothesized that such sequential actions of multiple GalNAc-transferase isoforms may be required to complete O-glycan attachments to some mucin peptide sequences allowing for detailed control of density.

One example of this is the glycosylation of the cancer-associated mucin MUC1. MUC1 contains a tandem repeat O-glycosylated region of 20 residues (HGVTSAPDTRPA-PGSTAPPA) (SEQ ID NO: 1) with five potential O-glycosylation sites. GalNAc-T1, -T2, and -T3 can initiate glycosylation of the MUC1 tandem repeat and incorporate at only three sites (HGVTSAPDTRPAPGSTAPPA (SEQ ID NO: 1). GalNAc attachment sites underlined). GalNAc-T4 is unique in that it is the only GalNAc-transferase isoform identified so far that can complete the O-glycan attachment to all five acceptor sites in the 20 amino acid tandem repeat sequence of the breast cancer associated mucin, MUC1. GalNAc-T4 transfers GalNAc to at least two sites not used by other GalNAc-transferase isoforms on the GalNAc4TAP24 glycopeptide (TAPPAHGV TSAPDTRPAPGSTAPP (SEQ ID NO: 2), GalNAc attachment sites underlined) (8). An activity such as that exhibited by GalNAc-T4 appears to be required for production of the glycoform of MUC1 expressed by cancer cells where all potential sites are glycosylated (10). Normal MUC1 from lactating mammary glands has approximately 2.6 O-glycans per repeat (11) and MUC1 derived from the cancer cell line T47D has 4.8 O-glycans per repeat (10). The cancer-associated form of MUC1 is therefore associated with higher density of O-glycan occupancy and this is accomplished by a GalNAc-transferase activity identical to or similar to that of GalNAc-T4.

The specific mechanism by which GalNAc-T4, -T7, and -T10 recognize and function with GalNAc-glycosylated glycopeptides is not known. However, it was originally demonstrated that the GalNAc-glycopeptide specificity exerted by GalNAc-T4 is directed or at least dependent on its lectin domain. A single amino acid substitution in the T4 lectin domain predicted to inactivate its function abolished the GalNAc-glycopeptide specificity of T4 without adversely affecting the basic catalytic mechanism of the transferase[42]. This suggests that the lectin domain interacts with GalNAc-glycopeptides and confers a novel catalytic function to the enzyme protein. Despite extensive attempts it has in the past not been possible to demonstrate actual binding of the transferase and lectin to sugars and glycopeptides, but it was possible to demonstrate selective inhibition of the GalNAc-glycopeptide activity of GalNAc-T4 using 230 mM concentration of GalNAc[42]. Millimolar concentrations of GalNAcα-benzyl can inhibit the lectin mediated GalNAc-glycopeptide substrate specificity of GalNAc-T4 as well as -T7. Polypeptide GalNAc-transferases, which have not displayed apparent GalNAc-glycopeptide specificities, also appear to be modulated by their lectin domains. Recently, it was found that mutations in the GalNAc-T1 lectin domain, similarly to those previously analysed in GalNAc-T4[42], modified the activity of the enzyme in a similar fashion as GalNAc-T4. Thus, while wild type GalNAc-T1 added multiple consequtive GalNAc residues to a peptide substrate with multiple acceptor sites, mutated GalNAc-T1 failed to add more than one GalNAc residue to the same substrate[45]. The mechanism is however not understood.

Glycosylation confers physico-chemical properties including protease resistance, solubility, and stability to proteins (12-14). Glycosylation furthermore confers changes in immunological responses to proteins and glycoproteins. O-glycosylation on mucins and mucin-like glycoproteins protect these molecules found in the extracellular space and body fluids from degradation. Control of O-glycosylation with respect to sites and number (density) of O-glycan attachments to proteins as well as control of the O-glycan structures made at specific sites or in general on glycoproteins, is of interest for several purposes. Diseased cells e.g. cancer cells often dramatically change their O-glycosylation and the altered glycans and glycoproteins may constitute targets for therapeutic and diagnostic measures (15; 16). Mucins functioning in body fluids may have different properties depending on density and structure of O-glycans attached in protection against disease, including infections by micro-organisms. Furthermore, mucins with different glycosylation may change physico-chemical properties including stability and solubility properties that may influence turnover and removal of mucous. A number of lung diseases, e.g. cystic fibrosis, asthma, chronic bronchitis, smokers lungs, are associated with symptomatic mucous accumulation (17-19), and it is likely that the nature and structure of mucins play a role in the pathogenesis of such diseases.

Partial inhibitors of O-glycosylation in cells have been reported. Aryl-N-acetyl-α-galactosaminides such as benzyl-, phenyl-, and p-nitrophenyl-GalNAc were originally found to inhibit the second step in O-glycosylation, the O-glycan processing step, by inhibiting synthesis of core 1 (Galβ1-3GalNAcα1-R) and more complex structures[20]. Benzyl-αGalNAc was also found to inhibit sialylation. It is generally believed that the downstream effects of benzyl-αGalNAc treatment are mediated by substrate competition of biosynthetic glycosylation products of benzyl-αGalNAc. Thus, e.g. the immediate glycosylation product of benzyl-αGalNAc is Galβ1-3GalNAcα-benzyl and this serves as an efficient substrate for the core 1α2-3sialyltransferase ST3Gal-I[21,22]. GalNAcα-benzyl has been the most widely used inhibitor of O-glycosylation, but it has only been used in cell culture as effective treatment concentrations lead to intracellular build-up of vesicles with GalNAcα-benzyl products and treated cells change morphology and growth characteristics[46].

Treatment of cells with benzyl-αGalNAc inhibit O-glycan processing and affect apical sorting of some O-glycosylated proteins[23-25]. The mechanism for this is generally believed to be through inhibition of sialylation[46]. Inhibition of mucin secretion has also been observed in culture cells, more specifically HT29 MTX cells, but this effect is not generally found in mucin secreting cells[46].

True inhibitors of O-glycosylation, i.e. inhibitors of the initial O-glycan attachment process governed by polypeptide GalNAc-transferases have not been identified.

Inhibitors of the initiating step in O-glycosylation could completely or selectively block attachment of O-glycans to O-glycosylation sites in proteins. Compounds inhibiting the catalytic function of a selected subset of the polypeptide GalNAc-transferase family may be predicted to only lead to partial inhibition of O-glycosylation capacity of cells. Proteins with no or little O-glycosylation may have entirely different biological properties than their normal glycosylated counterparts. Complete inhibition of O-glycosylation is not desirable because of the many diverse functions of O-glycans, and it is expected to result in cell death. Selective inhibition of O-glycosylation on the other hand is desirable in many cases such as cancer cells producing glycoproteins and mucins with more dense O-glycosylation than normal cells. For example breast cancer cells appear to hyperglycosylate the cancer-associated cell surface mucin MUC1 compared to glycosylation in normal cells (10). The overexpression of MUC1 and hyperglycosylation found in cancer cells are likely to be important for the pathobiology of cancers. Methods of inhibiting the hyperglycosylation of mucins in cancer cells is desirable.

It is apparent from the above that inhibitors in the prior art interfere with O-glycan processing, i.e. the glycosylation process that extend GalNAc residues directly attached to proteins at serine and threonine residues. Existing inhibitors of O-glycosylation are not suitable for therapeutic treatment in mammals including man as they profoundly affect O-glycosylation processing as well as lead to undesired morphological and growth effects on culture cells.

Consequently, there exists a need in the art for methods of inhibiting the functions of polypeptide GalNAc-transferases. Preferable in selectively inhibiting O-glycosylation attachments in glycoproteins and mucins. There also exists a need in the art for therapeutic compounds that display selectively and limited inhibition of O-glycosylation without generally affecting the process of O-glycosylation. The present invention meets these needs, and further presents other related advantages.

(i) contacting a polypeptide GalNAc-transferase, or a cell that recombinantly expresses a polypeptide GalNAc-transferase, with one or more test substances under assay conditions suitable for the detection of said enzymatic activity; and (ii) measuring whether said enzymatic activity is thereby modulated by one or more of the test substances. Brief Description of the Drawings.

(iii) The present invention provides a novel method for large scale screening of test substances for the ability to inhibit lectin-mediated activity of polypeptide Gal-NAc-transferases in a cell-free assay, which comprises: contacting an isolated polypeptide GalNAc-transferase, an isolated lectin domain from a polypeptide GalNAc-transferase, or a fragment of a polypeptide GalNAc-transferase capable of diplaying lectin-mediated binding on its substrate, with one or more test substances under assay conditions suitable for the detection of said binding ability; and (iv) measuring whether said lectin-mediated activity is thereby inhibited or modulated by one or more of the substances.

DETAILED DESCRIPTION OF AN EXEMPLARY EMBODIMENT OF THE INVENTION

The present invention also provides a method of screening one or more test substances for the ability to inhibit or modulate intracellular transport and/or cell surface expression of mucins, O-glycosylated glycoproteins, glycoproteins and proteins in a cell-based assay, which comprises:

(i) contacting a cell that expresses mucins, O-glycosylated glycoproteins, glycoproteins and proteins, with one or more test substances under assay conditions suitable for the detection of inhibition or modulation of said expression; and (ii) measuring whether intracellular transport and cell surface expression of said mucins, O-glycosylated glycoproteins, glycoproteins and proteins are thereby inhibited or modulated by one or more of the substances.

The present invention also provides a method of screening one or more test substances for the ability to inhibit or modulate secretions of mucins, O-glycosylated glycoproteins, glycoproteins and proteins in a cell-based assay, which comprises:

(i) contacting a cell that secretes mucins, O-glycosylated glycoproteins, glycoproteins with one or more test substances under assay conditions suitable for the detection of inhibition or modulation of said secretion; and (ii) measuring whether secretion of said mucins, O-glycosylated glycoproteins, glycoproteins and proteins are thereby inhibited or modulated by one or more of the substances.

Substances identified as agents which are effective in inhibiting one or more lectin domains of polypeptide Gal-NAc-transferases may e.g. be selected from the group consisting of naturally or non-naturally occurring carbohydrates, peptides, glycopeptides, glycoconjugates and portions and fragments thereof. They may also be found among nucleic acids as well as small organic or inorganic molecules. They include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)2, and Fab expression library fragments, and epitope-binding fragments thereof)], and polypeptides. A substance to be used as an agent according to the invention may be an endogenous physiological compound or it may be a natural or synthetic compound.

Agents in accordance with the present invention are useful for changing the density and sites of O-glycan occupancy in mucins and O-linked glycoproteins. Further uses are in changing Golgi-transport and intracellular sorting events conferred by the lectin domains of GalNAc-transferases. For example, inhibitors of lectin domains of Gal-NAc-transferases may be useful in manipulating disease-associated O-glycosylation to augment immunity and to prepare vaccines. Further use may be found in manipulating mucin secretion and O-glycan density in diseases associated with mucous accumulation to decrease secretion and enhance clearance of mucins. Further use may entail modulating O-glycosylation of recombinant glycoproteins by inhibition of polypeptide GalNAc-transferases in host expression cells. These and other aspects of the present invention will become evident upon reference to the following detailed description and drawings.

Accordingly, the present invention also provides a pharmaceutical composition comprising an agent which is effective in modulating functions of one or more polypeptide GalNAc-transferases, and a pharmaceutically acceptable carrier. More specifically, said agent may be an agent which is effective in inhibiting one or more lectin domains of polypeptide GalNAc-transferases and modulating functions mediated by said lectin domains and, in particular, said agent may be selected from the group consisting of carbohydrates, peptides, glycopeptides, glycoconjugates and portions and fragments thereof.

Further, the present invention covers the use of an agent which is effective in inhibiting one or more lectin domains of polypeptide GalNAc-transferases and modulating functions mediated by said lectin domains for preparing a medicament for the treatment of tumors and cancers; a medicament for the treatment of lung diseases associated with mucous accumulation such as asthma, chronic bronchitis, smoker's lung, and cystic fibrosis; a medicament for the treatment of diseases of exocrine glands associated with increased or decreased mucin secretion such as Sjøgren's syndrome and dry mouth; and a medicament for the treatment of disorders associated with dysregulation of selectin-mediated leukocyte trafficking such as autoimmunity, arthritis, leukemias, lymphomas, immunosuppression, sepsis, wound healing, acute and chronic inflammation.

Panel B is an illustration of the reactions with TAP25V21 monitored by capillary electrophoresis, where GalNAc-T1 and -T4 were mixed. Numbers above peaks refer to numbers of moles of GalNAc incorporated into the peptide.

Figure 2:
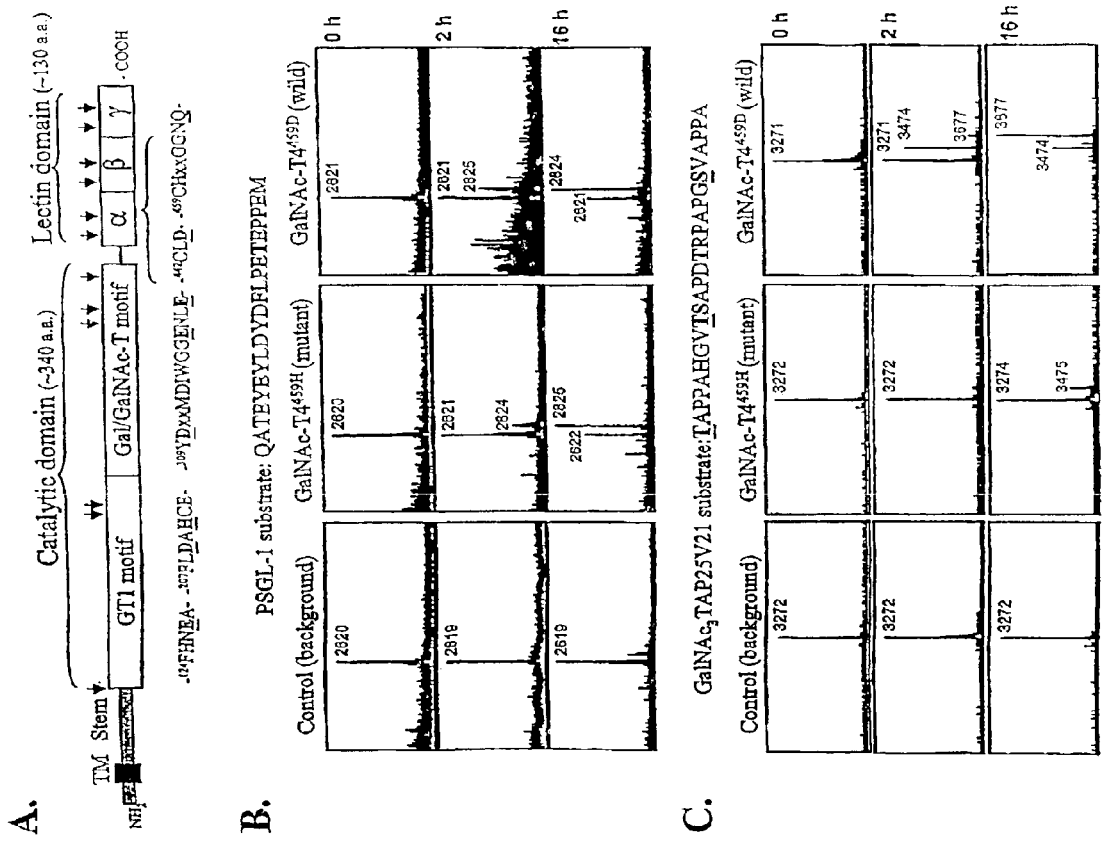

FIG. 2 illustrates that the lectin domain of GalNAc-T4 selectively directs its MUC1 glycopeptide specificity. Panel A is a schematic depiction of the domain structure of polypeptide GalNAc-transferases modified from Hagen et al. (3). Arrows indicate conserved cysteine residues and the major conserved sequence motifs are shown with numbering according to the sequence of GalNAc-T1. Bold underlined residues in the catalytic domain indicate some residues required for catalysis, whereas the two marked residues in the lectin domain are not essential for catalytic activity of GalNAc-T1 (3). A D459H mutation in the lectin domain of GalNAc-T4 corresponds to the illustrated D444H in GalNAc-T1. Panel B is a time-course MALDI-TOF (matrix-assisted-laser-desorption-ionization time-of-flight) analysis of the glycosylation independent activities of wild-type GalNAc-T4$^{459D}$ and the lectin mutant GalNAc-T4$^{459H}$ using the unique substrate for this enzyme isoform derived from PSGL-1 [Thr in bold is the acceptor site (8)]. The control represents co-purified endogenous activity found with irrelevant expression constructs. Wild-type and mutant GalNAc-T4 exhibit identical glycosylation independent activities. Panel C is a time-course MALDI-TOF analysis using the unique glycosylation dependent substrate GalNAc$_3$TAP25V21 (GalNAc attachment sites bold and underlined, and the two available acceptor sites for GalNAc-T4 in bold). The mutant GalNAc-T4 is virtually inactive with the glycopeptide substrate.

Figure 3:
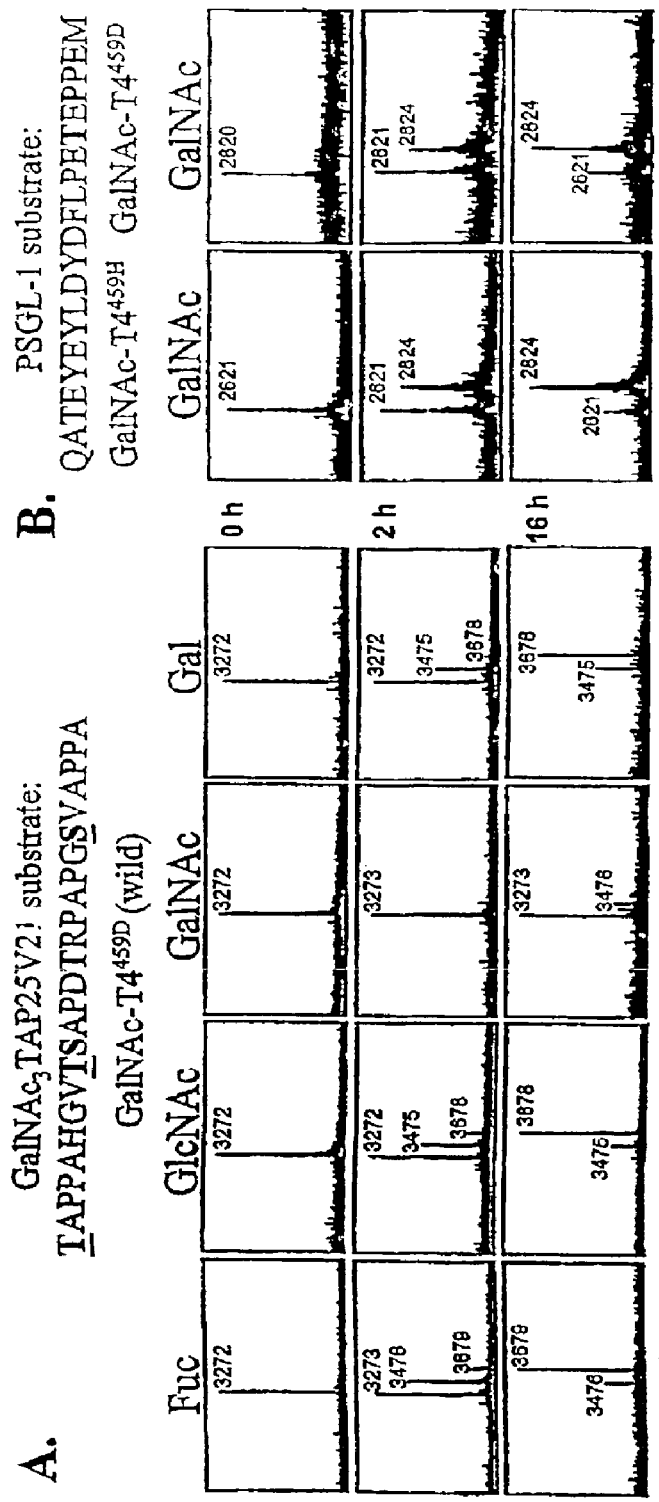

FIG. 3 illustrates that the lectin domain of GalNAc-T4 functions as a lectin and has selective specificity for GalNAc. Panel A: Inhibition of the glycosylation dependent function of GalNAc-T4 by free sugars. Time-course MALDI-TOF analysis of GalNAc-T4$^{459D}$ in the presence of 0.23 M free sugars, indicate selective inhibition of activity in the presence of GalNAc. Panel B: Time-course MALDI-TOF analysis of the glycosylation independent functions of wild-type and mutant GalNAc-T4, show that GalNAc has no effect on the general catalytic function of the enzyme.

Figure 4:
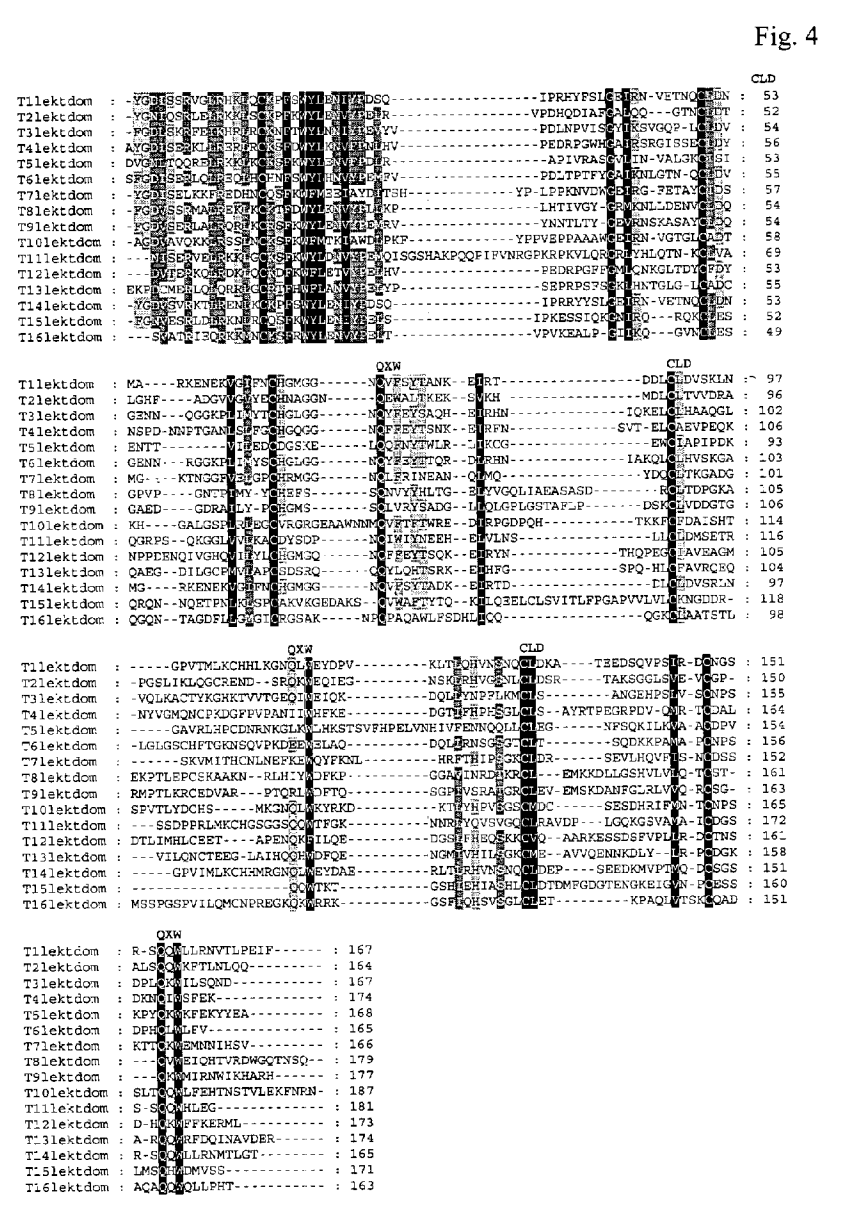

FIG. 4 is a multiple sequence alignment (ClustalW) of lectin domains derived from 16 human polypeptide GalNAc-transferases. Potitions of conserved motifs CLD and QxW in the α, β, and γ repeats are indicated. The numbering indicated in the margins reflects numbering of the analysed sequence region of each GalNAc-transferase. Conserved residues are indicated by black box'ing.

FIGS. 5A and B are schematic representations of human soluble secreted MUC1 expression constructs used for stable transfectants of CHO cells. Panel A: IgG2A His-tag was inserted into Bsu36I/XbaI site of MUC1FL, generating a His-tagged MUC1 construct containing the endogenous MUC1 secretion signal peptide. Panel B: Muc1FL Sau3AI insert was inserted into the BamHI site of pcDNA-inf., generating a non-tagged MUC1 construct containing the γ-interferon secretion signal peptide.

Figure 6:
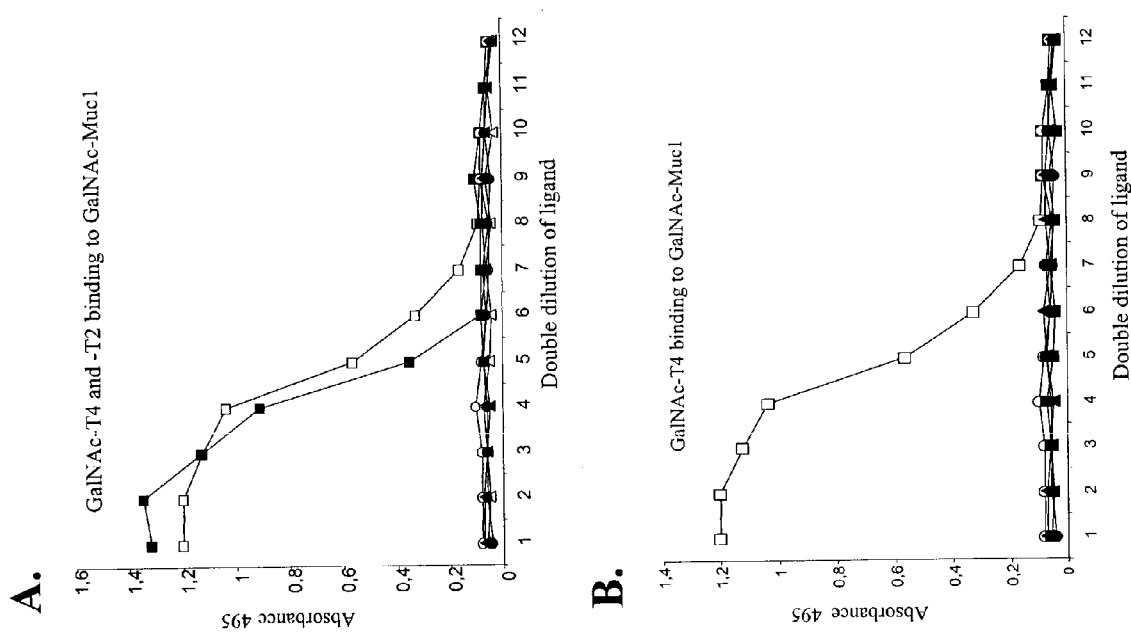

FIG. 6 is a plot of absorbance v. ligand dilution showing GalNAc-transferase binding to GalNAc-MUC1 glycopeptide. A direct binding assay (ELISA) mediated by the lectin domain was developed and validated with soluble secreted GalNAc-T4 and -T2 enzyme proteins. ELISA plates were coated with peptides or glycopeptides at 1 μg/ml, blocked with BSA, and incubated with biotinylated enzymes. After washing, bound enzyme proteins were detected with HRP-Streptavidin as described in detail in Example 8. Secreted soluble constructs of GalNAc-transferases which are enzymatically active may bind to (glyco)peptide substrates through their catalytic units as originally described for GalNAc-T2[26]. However, GalNAc-transferase binding to substrates by the catalytic domain requires UDP and divalent cat-ions (binding destroyed by EDTA treatment), in accordance with previous experience[26]. Panel A: GalNAc-T4 wild type enzyme proteins (□) and GalNAc-T2 (■) selectively bind GalNAc-MUC1 glycopeptides, with no significant binding observed to the unglycosylated peptide (GalNAc-T4 wt (▲) and GalNAcT2 (▲)). Panel B: Furthermore, the GalNAc-T4 lectin mutant did not bind to either glycosylated Muc1 (GalNAc-Muc1) (●) or non glycosylated Muc1 (Muc1) (○), whereas GalNAc-T4 wild type binds GalNAc-Muc1 (□) but not nonglcosylated Muc1 (■). Binding was not affected by 10 mM EDTA. Soluble secreted GalNAc-T4 mutant, GalNAc-T4$^{459H}$ [42], in which the lectin domain has been selectively inactivated by a single amino acid substitution, showed no binding demonstrating that the binding observed with the wild type enzyme is mediated through the lectin domain.

Figure 7:
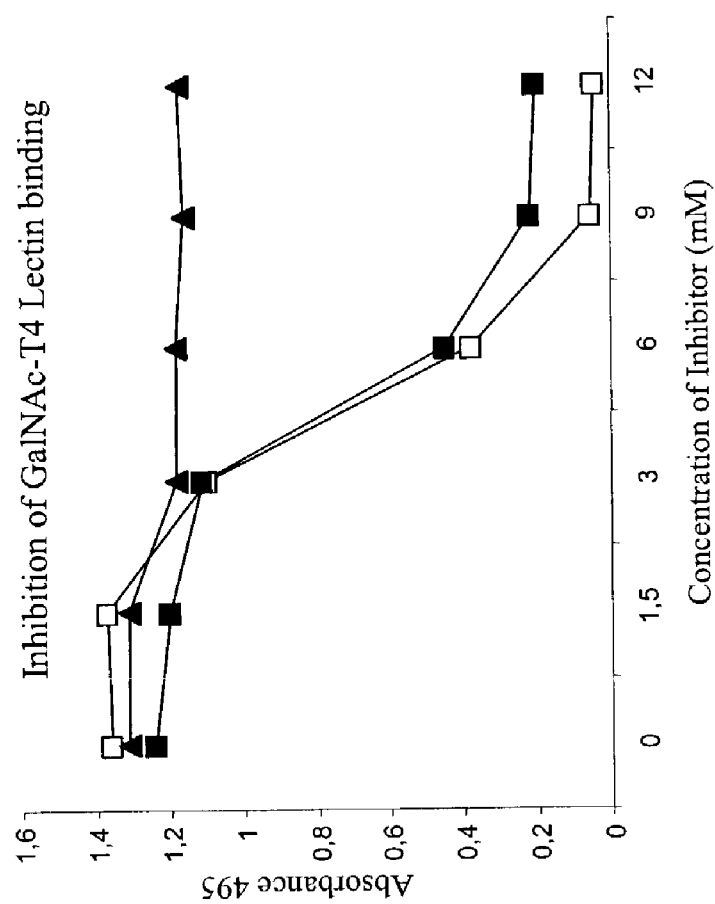

FIG. 7 is a plot (absorbance at 495 v. concentration of inhibitor) showing inhibition of GalNAc-T4 lectin binding. Direct binding assays were performed with preincubation of GalNAc-T4 with inhibitors followed by incubation of GalNAc-T4 in ELISA plates activated with GalNAc-Muc1 as described in detail in Example8. GalNAcα-benzyl (■) as well as GalNAcβ-benzyl (□) inhibit at 3-6 mM, whereas the control GlcNAcα-benzyl (▲) showed no inhibition. This demonstrates that the GalNAc-transferase lectin domains show no specificity for the anomeric configuration of GalNAc, and identifies a novel inhibitor, GalNAcβ-benzyl, of GalNAc-transferase lectins.

Figure 8:
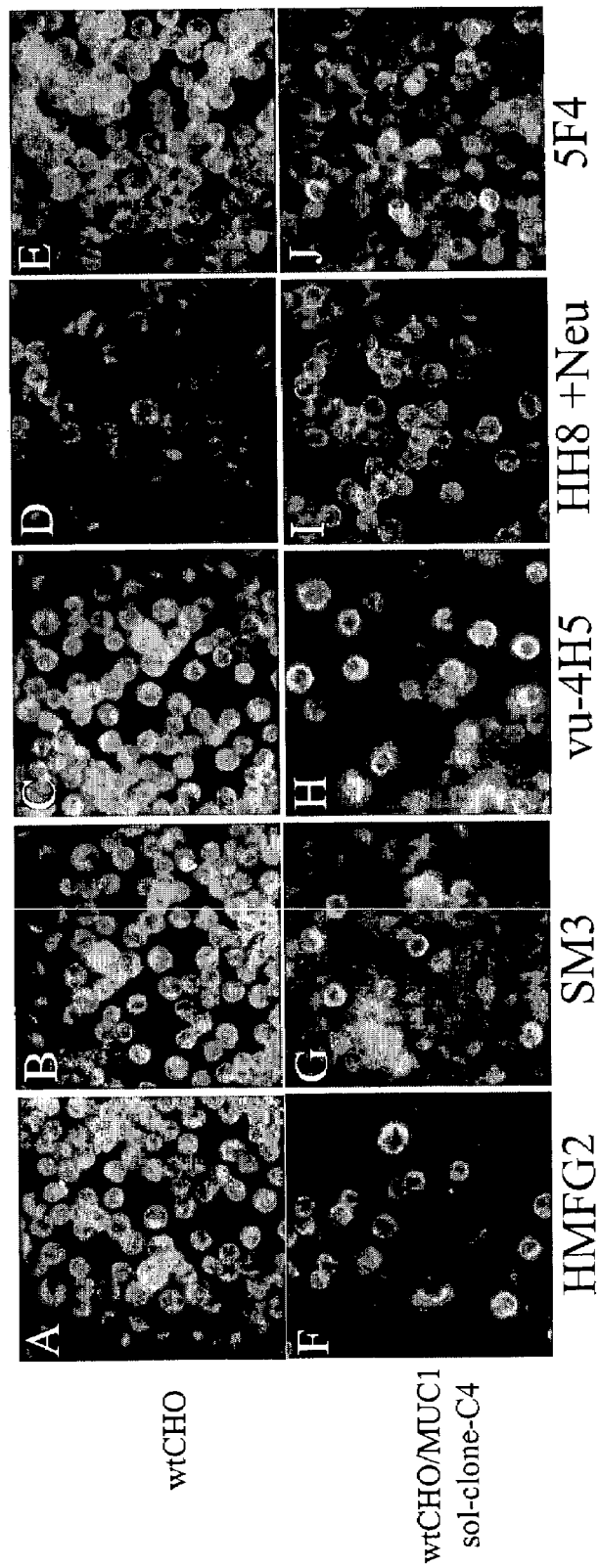

FIGS. 8 A-J are a series of photomicrographs showing immunostaining of wild type CHO and transfected wild type CHO cells with a secreted MUC1 construct. CHOldlD/MUCsol-cloneD5 was established from this population. MUC1 expression in the cytoplasm of 10-20% cells is visualized by HMFG2, SM3, and vu-4H5 antibodies. Anti-T antibody HH8 reacted only after neuraminidase pretreatment and the anti-Tn antibody reacted similarly before and after neuraminidase treatment. This suggests that cells grown in GalNAc alone produce mainly the Tn glycoform of MUC 1, while cells grown in Gal and GalNAc produce mainly the sialylated T (core 1) glycoforms.

Figure 9:
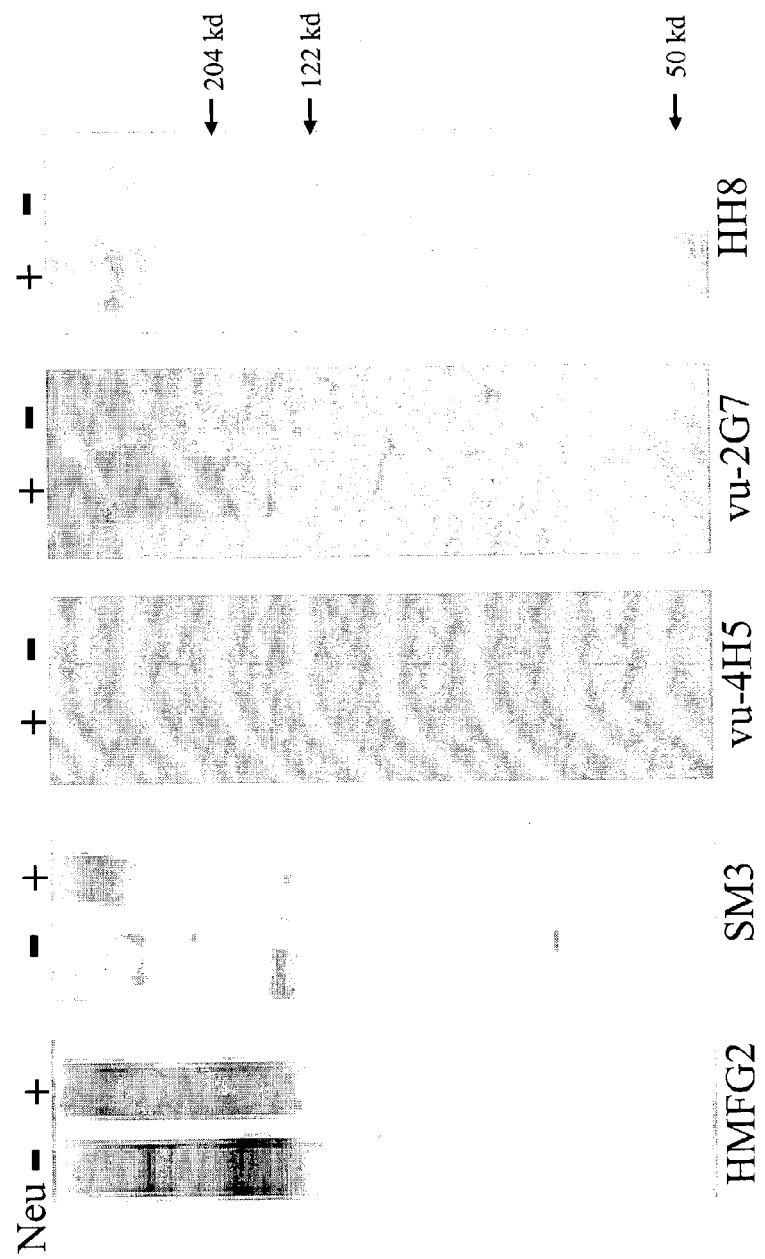

FIG. 9 is a series of SDS-PAGE Western analysis of MUC1 secreted from wild type CHO cells stably transfected cells with a secreted MUC1 construct (CHOldlD/MUCsol-cloneD5). Neu+ indicates pretreatment of samples with neuraminidase as described in Examples. Cells were grown in culture medium after 24 or 48 hours analysed directly or after neuraminidase treatment.

Figure 10:
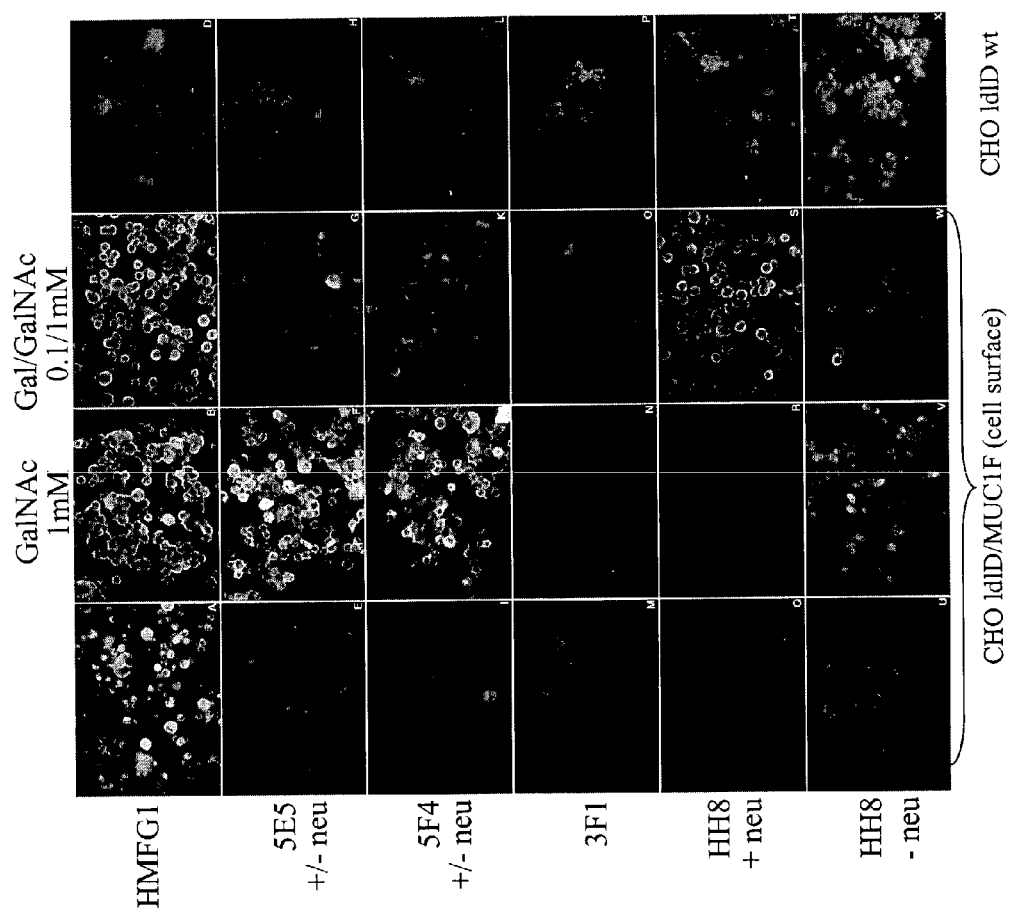

FIG. 10 A-X (left to right from top to bottom) is a series of photomicrographs showing immunostaining of CHO ldlD cells stably transfected cells with a full coding cell surface secreted MUC1 construct. CHOldlD/MUC1F-clone2 cells were grown in Optimem medium without and with 1 mM GalNAc, and 1 mM GalNAc plus 0.1 mM Gal for 24-48 hours. Cells were trypsinized, washed, air-dried on cover slides, and immunostained as described in Examples with antibodies to MUC1 and T and Tn carbohydrates. Reactivity was evaluated before and after neuraminidase treatment of dried acetone fixed cells. +/−neu indicates that the staining was identical with or without neuraminidase pretreatment.

FIGS. 11A and B are SDS-PAGE Western analysis of MUC1 secreted from CHO ldlD cells stably transfected cells with a secreted MUC1 construct. CHOldlD/MUCsolcloneD5 cells were grown in the presence or absence of sugars indicated, and samples of the culture medium analysed directly after 24-48 hours. Positive control (GalNAc-peptide) is a 60-mer MUC1 tandem repeat GalNAc-glycopeptide glycosylated with human polypeptide GalNAc-transferase GalNAc-T2. Lane labeled control includes medium from CHO ldlD cells. Anti-MUC1 monoclonal antibodies 5E5 and HMFG2 were used.

FIGS. 12A and B are SDS-PAGE Western analysis of MUC1 secreted from CHO ldlD cells stably transfected cells with a secreted MUC1 construct. Same experiment as FIG. 11 using anti-MUC1 monoclonal antibodies VU-4H5 and VU-2G7.

FIGS. 13A-D are a series of photomicrographs (left to right from top to bottom of) anti-MUC1 antibody immunofluorescense staining of CHO ldlD cells stably transfected with a full coding cell surface MUC1 (CHOldlD/MUC1F-clone2). Cell grown in the presence of GalNAc were treated with the O-glycosylation inhibitor GalNAcα-benzyl or control GlcNAcα-benzyl. Cells were grown in plates and stained without permeabilization as described in Example 10.

Figure 14:
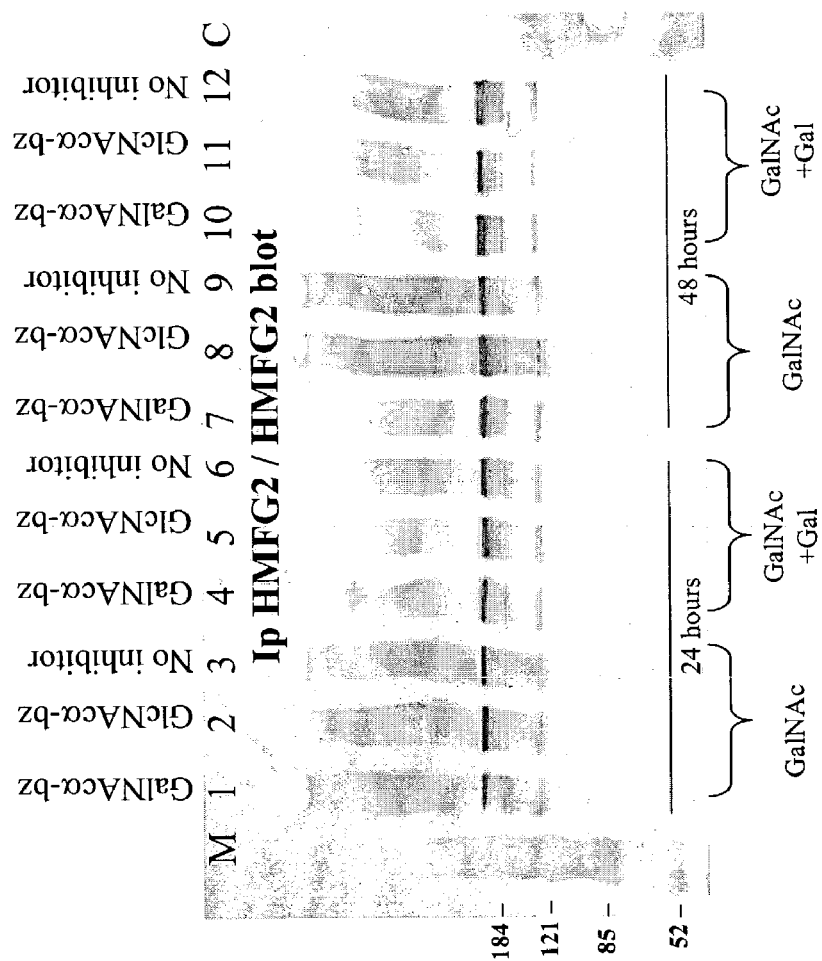

FIG. 14 is an SDS-PAGE Western analysis of GalNAcα-benzyl inhibition of MUC1 expression in CHO ldlD cells stably transfected with a full coding MUC1 construct. Cells were grown for 24 hours (lanes 1-6) or 48 hours (lanes 7-12) in the presence of 1 mM GalNAc (lanes 1-3 and 7-9) or 1 mM GalNAc and 0.1 mM Gal (lanes 4-6 and 10-12) to limit core O-glycosylation to GalNAcα1-O-Ser/Thr and Galβ1-3GalNAcα1-O-Ser/Thr, respectively. Cells were further treated with 2 mM GalNAcα-benzyl (lanes 1, 4, 7, 10), 2 mM GlcNAcα-benzyl (lanes 2, 5, 8, 11) or no inhibitor (lanes 3, 6, 9, 12). Cells were washed and lysed at 24 or 48 hours and the lysates subjected to immunoprecipitation with monoclonal antibody HMFG2, which broadly recognize MUC1 glycoforms. Immunoprecipitates were analysed by SDS-PAGE and western blot using HMFG2 antibody to detect MUC1 expression. Lane M indicates molecular markers with assigned mw. Lane C includes a control MUC1 180-mer tandem repeat peptide which has been GalNAc-glycosylated with 3 moles GalNAc per repeat using GalNAc-T2. The sharp bands migrating at 100-200 kd are immunoglobulins indicated by IgG. At 24 hours the MUC1 glycoforms expressed by cells grown in GalNAc or Gal and GalNAc migrated similarly, indicating that synthesis of sialylated core 1 O-glycans were time limited (lanes 1-6). At 48 hours, MUC1 glycoforms migrating as higher molecular weight species were expressed by cells grown in Gal and GalNAc (lanes 11-12). Treatment with GalNAcα-benzyl had no significant effect at 24 hours (lanes 1 and 4), but after 48 hours a significant reduction in MUC1 expression was found in cells grown in GalNAc as well as in Gal and GalNAc (lanes 7 and 10). In the latter case a significant shift in migration further confirmed that GalNAcα-benzyl also serves as an inhibitor of O-glycan extension and reduces O-glycosylation to GalNAcα1-O-Ser/Thr. GlcNAcα-benzyl served as a control and had no effect on MUC1 expression and O-glycosylation compared to untreated cells (lanes 8 and 11).

Figure 15:
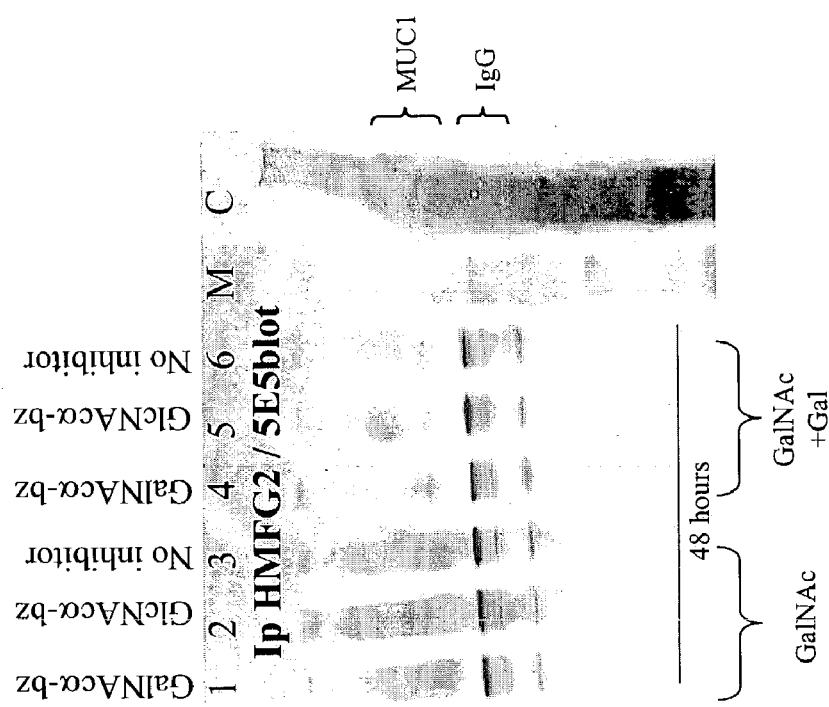
Figure 16:
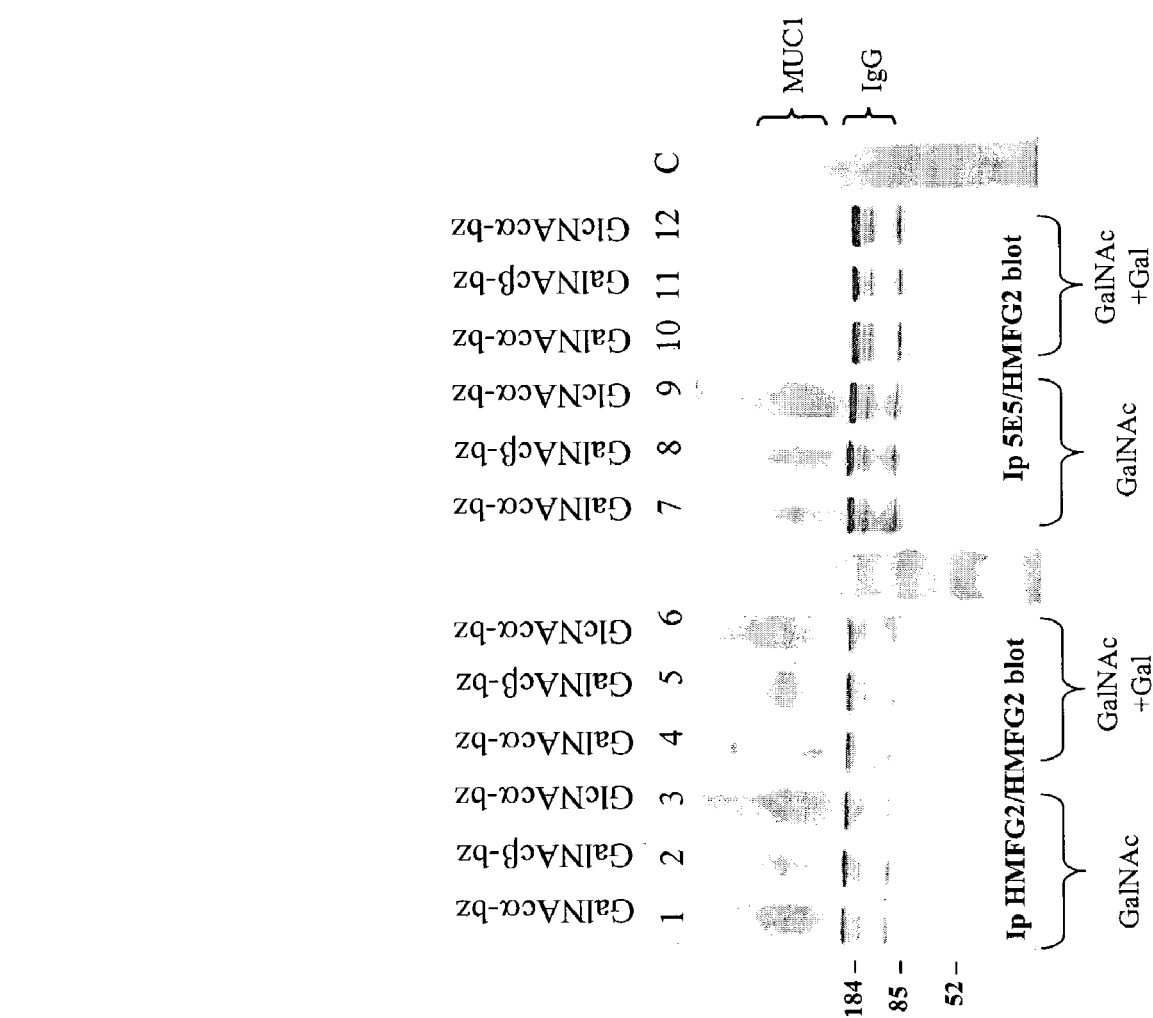

FIG. 15 is a SDS-PAGE Western analysis resulting from the same experiment as in FIG. 14, but using a novel monoclonal antibody, 5E5, to visualize MUC1 expression. Cells were grown for 48 hours in the presence of 1 mM GalNAc (lanes 1-3) or 1 mM GalNAc and 0.1 mM Gal (lanes 4-6) to limit core O-glycosylation to GalNAcα1-O-Ser/Thr and Galβ1-3GalNAcα1-O-Ser/Thr, respectively. Cells were further treated with 2 mM GalNAcα-benzyl (lanes 1, 4), 2 mM GlcNAcα-benzyl (lanes 2, 5) or no inhibitor (lanes 3, 6). Cells were washed and lysed at 48 hours and the lysates subjected to immunoprecipitation with monoclonal antibody HMFG2, which broadly recognize MUC1 glycoforms. Immunoprecipitates were analysed by SDS-PAGE and western blot using 5E5 antibody, which selectively recognize GalNAc-glycosylated MUC1 expression and show no reactivity with unglycosylated MUC1 peptides. Lanes M and C as described in legend to FIG. 14. Treatment with GalNAcα-benzyl produced a significant reduction in MUC1 expression in cells grown in GalNAc as well as in Gal and GalNAc (lanes 1 and 4). In cells grown in Gal and GalNAc (lanes 4-6) only weak expression of MUC1 was detected, but treatment of cells with GalNAcα-benzyl still produced a marked shift in migration to lower molecular weight migrating species FIG. 16 is an SDS-PAGE Western analysis showing the identification of a novel inhibitor, GalNAcβ-benzyl, which exhibits the same effect on mucin transport as GalNAcα-benzyl, but does not affect O-glycan extension and O-glycosylation in general. CHO ldlD cells stably transfected with a full coding MUC1 construct were grown for 36 hours in the presence of 1 mM GalNAc (lanes 1-3 and 7-9) or 1 mM GalNAc and 0.1 mM Gal (lanes 4-6 and 10-12) to limit core O-glycosylation to GalNAcα1-O-Ser/Thr and Galβ1-3GalNAcα1-O-Ser/Thr, respectively. Cells were further treated with 2 mM GalNAcα-benzyl (lanes 1, 4, 7, 10), 2 mM GalNAcβ-benzyl (lanes 2, 5, 8, 11) or 2 mM GlcNAcα-benzyl (lanes 3, 6, 9, 12). Cells were washed and lysed at 36 hours and the lysates subjected to immunoprecipitation with monoclonal antibodies HMFG2 (lanes 1-6) or 5E5 (lanes 7-12). Immunoprecipitates were analysed by SDS-PAGE and western blot using HMFG2 antibody. Lanes M and C as described in legend to FIG. 9. Treatment with GalNAcβ-benzyl produced the same or better reduction in MUC1 expression as treatment with GalNAcα-benzyl in cells grown in GalNAc as well as in Gal and GalNAc (lanes 2, 5, 8). In cells grown in Gal and GalNAc (lanes 4-6) MUC1 expression was reduced with GalNAcβ-benzyl treatment (lane 5), but in contrast to cells treated with GalNAcα-benzyl (lane 4), GalNAcβ-benzyl produced no change in the migration of MUC1 demonstrating that this inhibitor does not affect O-glycosylation. The lack of immunoprecipitation of MUC1 by 5E5 in cells grown in Gal and GalNAc (lanes 10-12) indicates that MUC1 is glycosylated with more complex structures than GalNAcα1-O-Ser/Thr as recognized by this antibody.

Figure 17:
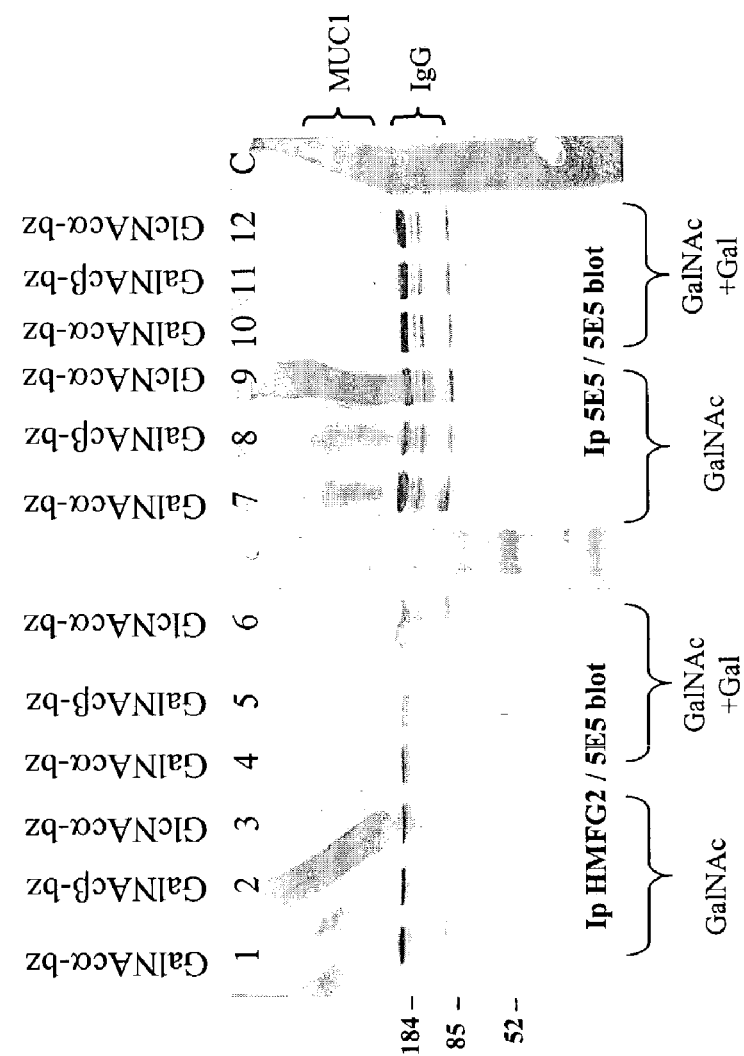

FIG. 17 is an SDS-PAGE Western analysis resulting from the same experiment as FIG. 16, except that expression is visualized by the monoclonal antibody 5E5. Cells were grown for 36 hours in the presence of 1 mM GalNAc (lanes 1-3 and 7-9) or 1 mM GalNAc and 0.1 mM Gal (lanes 4-6 and 10-12) to limit core O-glycosylation to GalNAcα1-O-Ser/Thr and Galβ1-3-GalNAcα1-O-Ser/Thr, respectively. Cells were further treated with 2 mM GlcNAcα-benzyl (lanes 1, 4, 7, 10), 2 mM GalNAcβ-bezcyl (lanes 2, 5, 8, 11) or 2 mM galNAcα-benzyl (lanes 3, 6, 9, 12). Cells were washed and lysed at 36 hours and the lysates subjected to immunoprecipitation with monoclonal antibodies HMFG2 (lanes 1-6) or 5E5 (lanes 7-12). Immunoprecipitates were analysed by SDS-PAGE and western blot using 5E5 antibody. Lanes M and C as described in legend to FIG. 14. Treatment with GalNAcβ-benzyl produced the same or better reduction in MUC1 expression as treatment with GalNAcα-benzyl in cells grown in GalNAc (lanes 2 and 8).

The lack of immunostaining of MUC1 by 5E5 in cells grown in Gal and GalNAc indicates that MUC1 is glycosylated with more complex structures than GalNAcα1-O-Ser/Thr as recognized by this antibody.

FIGS. 18A-O (left to right from top to bottom) is a series of photomicrographs showing that the main O-glycan phenotype of CHO ldlD cells grown in Gal and GalNAc is sialylated T and that the 5E5 antibody does not react with MUC1, with T or silaylated T glycoforms of MUC1.

DETAILED DESCRIPTION OF THE INVENTION

All patent applications, patents, and literature references cited in this specification are hereby incorporated by reference in their entirety. In the case of conflict, the present description, including definitions, is intended to control.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "about" or "approximately" means within 50% of a given value, preferably within 20%, more preferably within 10%, more preferably still within 5%, and most preferably within 1% of a given value. Alternatively, the term "about" or "approximately" means that a value can fall within a scientifically acceptable error range for that type of value, which will depend on how qualitative a measurement can be given the available tools. "About" or "approximately" may define a distribution around a mean value, rather than a single value.

Molecular Biology Definitions. In accordance with the present invention, there may be employed conventional molecular biology, microbiology and recombinant DNA techniques within the skill of the art. Such techniques are explained fully in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

"Complementary DNA or cDNA" as used herein refers to a DNA molecule or sequence that has been enzymatically synthesised from the sequences present in an mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns are inserted adjacent to, or within, exogenous DNA sequences.

A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridising sequences. Hybridization stringency has been defined in numerous publication known to the skilled in the art (Meinkoth and Wahl, Anal. Biochem. 138,267-284, 1984; Maniatis et al., Molecular cloning: a laboratory manual. Cold Spring Harbor Laboratory Press, 1989; J. Q. Zhang, Eur. J. Biochem. 239,835-841:1996; M. Friedman-Einat, General and Comparative Endocrinology 115,354-363:1999: M. Szabo, J. Bacteriology, 1544-1553: 1995; S. Sau, J. Bacteriology, 21182126, 1996). Nucleic acids are "hybridizable" to each other when at least one strand can anneal to another nucleic acid under defined stringency conditions. High stringency hybridization is defined as 42° C. over night hybridization under standard conditions (Maniatis et al., Molecular cloning: a laboratory manual. Cold Spring Harbor Laboratory Press, 1989), followed by 5 washes with 2×SSC, 0.1% SDS at 42° C., once with 0.5×SSC, 0.1% SDS at 55° C. and once with 0.1×SSC, 0.1% SDS at 55° C. (1×SSC is 0.15M NaCl, 0.015M Na citrate). Northern and Southern nucleic acid blotting hybridization techniques, especially for the purpose of investigating hybridization specificity, is well known to those skilled in the field of the invention.

An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

A "probe" refers to a nucleic acid that forms a hybrid structure with a sequence in a target region due to complementarily of at least one sequence in the probe with a sequence in the target region.

A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position.

Function-conservative variants of polypeptide GalNAc-transferases are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties. This includes but is not limited to, replacement of an amino acid with one having similar structural or physical properties, including polar or non-polar character, size, shape and charge (see, e.g., Table A).

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule (e.g., an mRNA or a cDNA) transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein (i.e., a signal sequence) that is cleaved from, and therefore may not be part of, the final protein. A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

A "mutation" means any process or mechanism resulting in a mutant protein, enzyme, polypeptide, polynucleotide, gene, or cell. This includes any mutation in which a protein, enzyme, polynucleotide, or gene sequence is altered, and any detectable change in a cell arising from such a mutation. The altered protein, enzyme, polypeptide or polynucleotide is a "mutant", also called a "variant." Typically, a mutation occurs in a polynucleotide or gene sequence, by point mutations (substitutions), deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. Table A outlines which amino acids correspond to which codon(s).

Thus, due to the degeneracy of the genetic code, any three-nucleotide codon that encodes a GalNAc-transferase or a GalNac-transferace lectin domain polypeptides described herein is within the scope of the invention.

The terms "mutant" and "variant" may also be used to indicate a modified or altered gene, DNA or RNA sequence, enzyme, cell, etc., i.e., any kind of mutant. Such changes also include changes in the promoter, ribosome binding site, etc.

As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In addition, modifications, which do not normally alter the primary sequence of the GalNAc-transferase lectin domain polypeptides, include in vivo or in vitro chemical derivatization of polypeptides, e.g., acetylation, methylation, or carboxylation. Also included as variant polypeptides of this invention are these polypeptides modified by glycosylation, e.g., those made by modifying the glycosylation patterns of a polypeptide during its synthesis and processing or in further processing steps; or by exposing the polypeptide to enzymes which affect glycosylation, such as mammalian glycosylating or deglycosylating enzymes. Also embraced as variant polypeptides are the above-identified mutagenized sequences, which have phosphorylated amino acid residues, e.g., phosphotyrosine, phosphoserine, or phosphothreonine.

TABLE A

Amino Acids, Corresponding Codons, and Functionality/Property

| Amino Acid | SLC | DNA codons | Side Chain Property |
|---|---|---|---|
| Isoleucine | I | ATT, ATC, ATA | Hydrophobic |
| Leucine | L | CTT, CTC, CTA, CTG, TTA, TTG | Hydrophobic |
| Valine | V | GTT, GTC, GTA, GTG | Hydrophobic |
| Phenylalanine | F | TTT, TTC | Aromatic side chain |
| Methionine | M | ATG | Sulphur group |
| Cysteine | C | TGT, TGC | Sulphur group |
| Alanine | A | GCT, GCC, GCA, GCG | Hydrophobic |
| Glycine | G | GGT, GGC, GGA, GGG | Hydrophobic |
| Proline | P | CCT, CCC, CCA, CCG | Secondary amine |
| Threonine | T | ACT, ACC, ACA, ACG | Aliphatic hydroxyl |
| Serine | S | TCT, TCC, TCA, TCG, AGT, AGC | Aliphatic hydroxyl |
| Tyrosine | T | TAT, TAC | Aromatic side chain |
| Tryptophan | W | TGG | Aromatic side chain |
| Glutamine | Q | CAA, CAG | Amide group |
| Asparagine | N | AAT, AAC | Amide group |
| Histidine | H | CAT, CAC | Basic side chain |
| Glutamic acid | E | GAA, GAG | Acidic side chain |
| Aspartic Acid | D | GAT, GAC | Acidic side chain |
| Lysine | K | AAA, AAG | Basic side chain |

TABLE A-continued

Amino Acids, Corresponding Codons, and Functionality/Property

| Amino Acid | SLC | DNA codons | Side Chain Property |
|---|---|---|---|
| Arginine | R | CGT, CGC, CGA, CGG, AGA, AGG | Basic side chain |
| Stop codons | Stop | TAA, TAG, TGA | — |

As referred to herein, "sequence similarity" means the extent to which nucleotide or protein sequences are related. The extent of similarity between two sequences can be based on percent sequence identity and/or conservation. Amino acids other than those indicated as conserved may differ in a protein or enzyme so that the percent protein or amino acid sequence similarity between any two proteins of similar function may vary and can be, for example, at least 70%, preferably 75%, more preferably 80%, even more preferably 85%, and most preferably at least 90%, as determined according to an alignment scheme.

"Sequence identity" herein means the extent to which two nucleotide or amino acid sequences are invariant.

"Sequence alignment" means the process of lining up two or more sequences to achieve maximal levels of sequence identity (and, in the case of amino acid sequences, conservation), e.g., for the purpose of assessing the degree of sequence similarity. Numerous methods for aligning sequences and assessing similarity and/or identity are known in the art such as, for example, the ClustalW method, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

A "donor substrate" is a molecule recognised by, e.g., a polypeptide GalNAc-transferees and that contributes a N-acetylgalactosamine moiety for the transferase reaction. For polypeptide GalNAc-transferases, a donor substrate is UDP-N-acetylgalactosamine or with some GalNAc-transferase isoforms UDP-galactose. An "acceptor substrate" is a molecule, preferably a peptide, protein, glycopeptide, and glycoprotein, that is recognised by, e.g., a polypeptide GalNAc-transferase and that is the target for the modification catalysed by the transferase, i.e., receives the carbohydrate moiety. For polypeptide GalNAc-transferases, acceptor substrates include without limitation peptides, proteins, glycopeptides, and glycoproteins.

The term "agonist" refers to a molecule that increases the amount of, or prolongs the duration of, the activity of the polypeptide. The term "enhancer" refers to a molecule that similarly increases the amount of, or prolongs the duration of, the activity of the polypeptide. The term "antagonist" refers to a molecule, which decreases the biological or immunological activity of the polypeptide. The term "inhibitor" similarly refers to a molecule, which decreases the biological or immunological activity of the polypeptide. Agonists, antagonists, and inhibitors may include proteins, nucleic acids, carbohydrates, or any other molecules that associate with a polypeptide GalNAc-transferase.

The term "agent" includes small molecules, peptide mimetics and polypeptides. "Mimetics" of GalNAc-transferase lectin-domain inhibitors are molecules that functionally mimic the structure or function of a GalNAc-transferase lectin-domain inhibitor. Molecular mimetics include, but are not limited to: small organic compounds; nucleic acids and nucleic acid derivatives; saccharides or oligosaccharides; peptide mimetics including peptides, proteins, and derivatives thereof, such as peptides containing non-peptide organic moieties, synthetic peptides which may or may not contain amino acids and/or peptide bonds, but retain the structural and functional features of a peptide ligand; pyrrolidines; peptoids and oligopeptoids which are molecules comprising N-substituted glycine, such as those described by Simon et al. (1992) Proc. Natl. Acad. Sci. USA 89:9367.

The human N-acetylgalactosaminyltransferase T1 gene (GALNT1) has been described previously[26]. The sequence of the GALNT1 mRNA and the sequence of the GalNAc-T1 polypeptide have been submitted to GenBank/EBI Data Bank and assigned accession numbers X85018 and CAA59380, respectively.

The human N-acetylgalactosaminyltransferase T2 gene (GALNT2) has been described previously[26]. The sequence of the GALNT2 mRNA and the sequence of the GalNAc-T2 polypeptide have been submitted to GenBank/EBI Data Bank and assigned accession numbers X85019 and CAA59381, respectively.

The human N-acetylgalactosaminyltransferase T3 gene (GALNT3) has been described previously[27]. The sequence of the GALNT3 mRNA and the sequence of the GalNAc-T3 polypeptide have been submitted to GenBank/EBI Data Bank and assigned accession numbers X92689 and CAA63371, respectively.

The human N-acetylgalactosaminyltransferase T4 gene (GALNT4) has been described previously[8]. The sequence of the GALNT4 mRNA and the sequence of the GalNAc-T4 polypeptide have been submitted to GenBank/EBI Data Bank and assigned accession numbers Y08564 and CAA69875, respectively.

The human N-acetylgalactosaminyltransferase T5 gene (GALNT5) has been described previously[7]. The sequence of the GALNT5 mRNA and the sequence of the GalNAc-T5 polypeptide have been submitted to GenBank/EBI Data Bank and assigned accession numbers AJ245539 and CAB65104, respectively.

The human N-acetylgalactosaminyltransferase T6 gene (GALNT6) has been described previously[48]. The sequence of the GALNT6 mRNA and the sequence of the GalNAc-T6 polypeptide have been submitted to GenBank/EBI Data Bank and assigned accession numbers AJ133523 and CAB55325, respectively. The human N-acetylgalactosaminyltransferase T7 gene (GALNT7) has been described previously[8]. The sequence of the GALNT7 mRNA and the sequence of the GalNAc-T7 polypeptide have been submitted to GenBank/EBI Data Bank and assigned accession numbers AJ002744 and CAB60270, respectively.

The human N-acetylgalactosaminyltransferase T8 gene (GALNT8) has been described previously[49]. The sequence of the GALNT8 mRNA and the sequence of the GalNAc-T8 polypeptide have been submitted to GenBank/EBI Data Bank and assigned accession numbers AJ271385 and CAB89199, respectively.

The human N-acetylgalactosaminyltransferase T9 gene (GALNT9) has been described previously[50]. The sequence of the GALNT9 mRNA and the sequence of the GalNAc-T8 polypeptide have been submitted to GenBank/EBI Data Bank and assigned accession numbers AB040672 and BAB13699, respectively.

The human N-acetylgalactosaminyltransferase T10 nucleic acid sequence (GALNT10) and the sequence of the encoded GalNAc-T10 polypeptide have been submitted to GenBank/EBI Data Bank. The nucleic acid accession number is AJ505950. The amino acid sequence is as follows:

(SEQ ID NO: 3)
MLAWRDGELEAETSSSLFLLAMQVWMCGGRMEDIPCSRVGHIYR

KYVPYKVPAGVSLARVRTLKRVAEVWMDEYAEYIYQRRPEYRHLSAGDVA
VQKKLRSS.

LNCKSFKWFMTKIAWDLPKFYPPVEPPAAAWGEIRNVGTGLCADTKHGAL
GSPLRLEG.

CVRGRGEAAWNNMQVFTFTWREDIRPGDPQHTKKFCFDAISHTSPVTLYD
CHSMKGNQ.

LWKYRKDKTLYHPVSGSCMDCSESDHRIFMNTCNPSSLTQQWLFEHTNST
VLEKFNRN.

The human N-acetylgalactosaminyltransferase T11 gene (GALNT11) has been described previously[43]. The sequence of the GALNT11 mRNA and the sequence of the GalNAc-T11 polypeptide have been submitted to GenBank/EBI Data Bank and assigned accession numbers Y12434 and CAC79625, respectively.

The human N-acetylgalactosaminyltransferase T12 nucleic acid sequence (GALNT12) and the sequence of the GalNAc-T12 polypeptide have been submitted to GenBank/EBI Data Bank. The nucleic acid accession number is AJ132365. This sequence is disclosed herewith.

The human N-acetylgalactosaminyltransferase T13 nucleic acid sequence (GALNT13) and the sequence of the GalNAc-T13 polypeptide have been submitted to GenBank/EBI Data Bank. The nucleic acid accession number is AR153422.

The references cited above for describing human GalNAc-T1-13 are incorporated herein by reference in their entirety and to the same extent as if each reference was individually incorporated by reference.

Expression to produce enzymatically-active polypeptide GalNAc-transferases can be carried out in any number of conventional expression systems familiar to those skilled in the art. In one embodiment, GalNAc-transferases are expressed in a secreted soluble form, which can be recovered from the culture medium. Such secreted enzymes lack the N-terminal cytoplasmic tail and transmembrane retention sequence, and have N-terminal sequence starting in the predicted stem region (depicted domain structures of polypeptide GalNAc-transferases shown in FIG. 2A). The boundaries of the stem is N-terminally defined by the hydrophobic signal sequence, while the C-terminal boundary is less clearly defined but limited to the conserved catalytic unit of the enzymes as defined by multiple sequence alignments. For some isoforms including GalNAc-T2 the N-terminal sequence have been determined in naturally occurring soluble proteins derived from proteolytic cleavage[26]. In another embodiment, host cells (e.g. CHO cells) are engineered to express full coding GalNAc-transferases and glycosylate substrates in vivo in host cells.

Expression to produce functional lectin domains of polypeptide GalNAc-transferases without the catalytic unit (or activity) can be carried out in any number of conventional expression systems familiar to those skilled in the art. In one embodiment, GalNAc-transferase lectins are expressed in a secreted soluble form, which can be recovered from the culture medium. Such secreted soluble forms lack the N-terminal cytoplasmic tail, transmembrane retention sequence, stem region and the catalytic unit. The boundaries of the catalytic units and lectin domains are defined by multiple sequence alignments and experimentation of lectin binding activity (multiple sequence alignment analysis of the C-terminal sequences polypeptide GalNAc-transferases including the most C-terminal boundaries of the catalytic domains and the entire lectin domains shown in FIG. 4). The boundaries cannot be clearly defined but the most C-terminal well-conserved sequence motif of the catalytic units (WYLENVYP) (SEQ ID NO: 4) can be excluded from the lectin domains. Parts of or the entire catalytic domains may be included to produce functional lectin domains, and inclusion of inactivating mutations in the catalytic units (e.g. mutations in the DxH motif important for donor substrate binding, or residues important for acceptor substrate binding3) may be used to avoid additional binding activity mediated through the catalytic units. In another embodiment, host cells (e.g. CHO cells) are engineered to express full coding polypeptide GalNAc-transferases with or without mutations in their catalytic units and binding mediated through lectin domains are determined in vivo in host cells.

Figure 5:
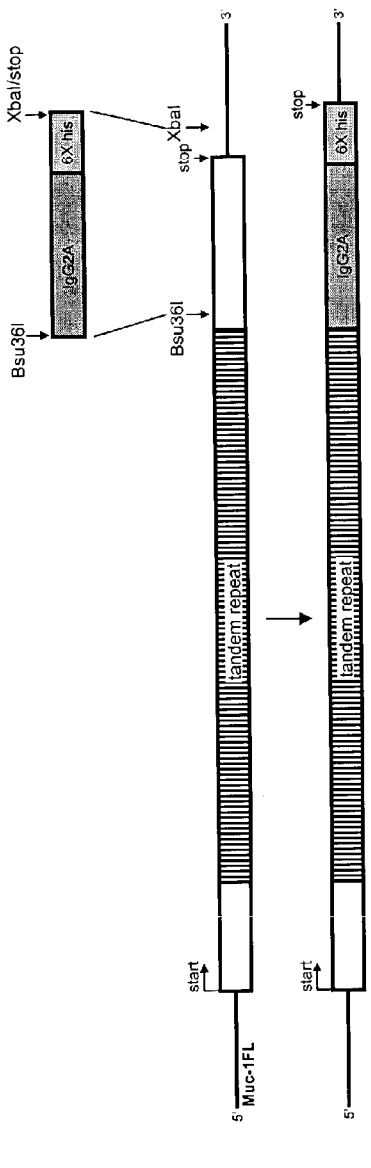
Figure 5:
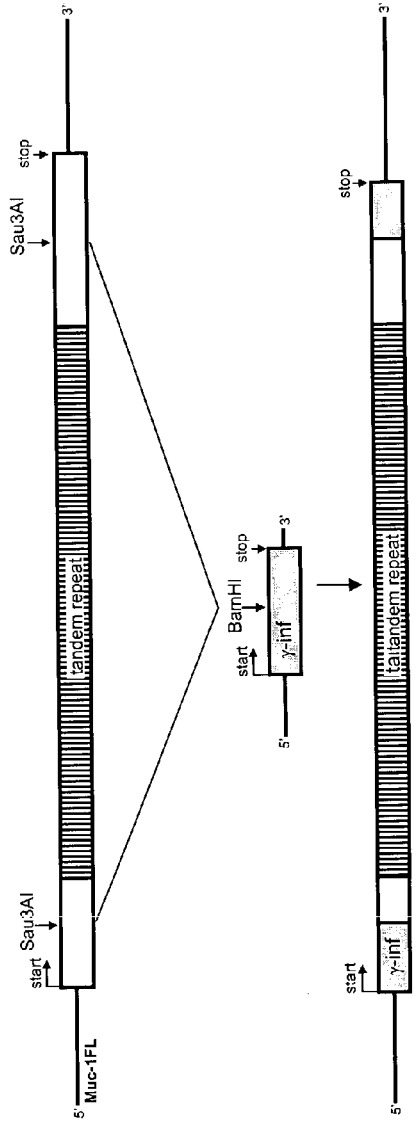

Cells stably or transiently transfected with full coding or secreted expression constructs of mucins, mucin-like glycoproteins, O-glycosylated proteins, or proteins can be carried out by any number of conventional methods familiar to those skilled in the art. In one embodiment, the mucin MUC1 is expressed in a soluble form, which can be recovered from the culture medium (FIG. 5 illustrates MUC1 expression constructs used in this invention; the DNA sequence is available from GenBank accession number M61170). In another embodiment, host cells (e.g. CHO or CHO ldlD cells) are engineered to express MUC1 on the cell surface. In a preferred embodiment of the invention the cells are mammalian and more preferably, the cells are human.

Human cell lines expressing cell surface mucins or secreting mucins can be selected, cultured and treated by any number of conventional methods familiar to those skilled in the art. In one embodiment, mucins are expressed in a secreted soluble form without transmembrane retention sequence, which can be recovered from the culture medium. In another embodiment, host cells (e.g. CHO ldlD cells) are engineered to express full coding mucins on the cell surface.

2. General Aspects of the Invention

In accordance with the screening method of the invention, enzymatically active GalNAc-transferases are contacted with an acceptor substrate and an N-acetylgalactosamine donor substrate, preferably UDP-N-acetylgalactosamine, under conditions for transfer of N-acetylgalactosamine from the donor substrate to the acceptor substrate, in the presence of one or more test substances. Glycosylated acceptor substrate is then obtained in a varying degree.

Preferred acceptor substrates are proteins, peptides, glycoproteins, and glycopeptides. Particularly preferred acceptor substrates for GalNAc-T4 are GalNAc-glycosylated glycopeptides from MUC1, MUC2, and MUC5AC tandem repeats or multimers of those molecules. Particularly preferred acceptor substrates for GalNAc-T7 are GalNAc-glycosylated glycopeptides from MUC2 and rat submaxillary gland mucin tandem repeats or multimers of those molecules. Particularly preferred acceptor substrates for GalNAc-T2 are peptides from MUC1, MUC2, MUC5AC and MUC7 tandem repeats or multimers of those molecules. Particularly preferred acceptor substrates for GalNAc-T3 are peptides from MUC1, MUC2, MUC5AC and MUC7 tandem repeats or multimers of those molecules.

Transfer assays for carrying out glycosylation are familiar to those in the art, and are described in the literature cited above and in the examples provided below.

As noted, human GalNAc-T4 demonstrates unique acceptor substrate specificity. GalNAc-T4 has been found to transfer GalNAc to two sites in the MUC1 tandem repeat sequence: Ser in GVTSA (SEQ ID NO: 5) and Thr in PDTR (SEQ ID NO: 6) using a 24-mer glycopeptide with GalNAc residues attached at sites utilized by GalNAc-T1, -T2 and T3 (TAPPAHGVTSAPDTRPAPGSTAPPA, (SEQ ID NO: 2) wherein the GalNAc sites are underlined) (8). In an important aspect of the invention, the action of GalNAc-T4 is dependent on prior GalNAc attachments at least at one site of the five acceptor sites in the MUC1 tandem repeat. In another important aspect of the invention this activity is dependent on the lectin domain of GalNAc-T4. In yet another important embodiment of the invention this activity can be blocked by GalNAc and GalNAc containing compounds such as benzyl-GalNAc.

As noted, human GalNAc-T7 demonstrates unique acceptor substrate specificity. GalNAc-T7 has only been found to transfer to acceptor substrates which have previously been partially GalNAc-glycosylated (7; 9). A preferred acceptor substrate is derived from MUC2, MUC5AC and rat submaxillary gland mucin tandem repeats. In an important embodiment of the invention the activity of GalNAc-T7 can be blocked by GalNAc and GalNAc containing compounds such as benzyl-GalNAc, and Gal and Gal containing compounds such as benzyl-Gal and Galβ1-3GalNAcα1-benzyl.

Human GalNAc-T2 demonstrates unique UDP-Gal donor substrate specificity with MUC2 peptide substrate (28). In an important embodiment of the invention the activity of GalNAc-T2 with UDP-Gal can be blocked by GalNAc and GalNAc containing compounds such as benzyl-GalNAc.

Human GalNAc-T3 demonstrates unique UDP-Gal donor substrate specificity with rat submaxillary gland mucin peptide substrate. In an important embodiment of the invention the activity of GalNAc-T3 with UDP-Gal can be blocked by GalNAc and GalNAc containing compounds such as benzyl-GalNAc.

The lectin domains of some GalNAc-transferases, notably GalNAc-T4 and -T7, are shown herewith to be important for the GalNAc-glycopeptide substrate specificities exhibited by these GalNAc-transferase isoforms. The mechanism by which the lectin domains exert this effect on the enzyme activities is unknown. However, because GalNAc and GalNAcα-benzyl were found to selectively inhibit these activities it was hypothesized that the lectin domains functioned by recognizing the sugar or glycopeptide in a lectin-like interaction[42]. Considerable efforts have been applied to demonstrate actual binding without success in the past (Bennett et al. unpublished, personal communications).

In the present invention a direct binding assay was developed using secreted soluble GalNAc-T4 and -T2, and chemoenzymatically produced multimeric MUC1 tandem repeat GalNAc-glycopeptides (FIG. 6). Short MUC1 glycopeptides of traditional length of 15-20 amino acids have failed to provide significant binding in the same assay system, and one improvement leading to the success was the application of extended multimeric MUC1 GalNAc-glycopeptides. Binding was also found to an enzymatically GalNAc-glycosylated fusion protein expressed in E. coli and containing 30 amino acids of the MUC2 tandem repeat. Another improvement was the use of biotinylation of the enzymes, which provided an improved signal compared to previous attempts with identifying retained or bound enzyme by measuring activity. The specific activities of GalNAc-transferases as measured in in vitro assays are relatively low, and in past attempts to use binding and elution of enzyme acitivity presumably the detection level was not sufficient to detect binding. The developed assay was validated to demonstrate binding through the lectin domains by several ways: i) binding was selective for GalNAc-glycosylated glycopeptides with no significant binding to unglycosylated peptides; ii) a single amino acid substitution in the lectin domains of GalNAc-T4 (and -T2), known to selectively destroy GalNAc-glycopeptide specificity of these enzymes without affecting the catalytic unit[42] abolished binding; iii) binding was not affected by EDTA treatment which is known to destroy catalytic activity of GalNAc-transferases[26, 28, 51, 52]; iv) binding was selectively inhibited by the monosacharide GalNAc and not by other sugars. In order to minimize the size and functional complexity of GalNAc-transferase lectins to be used as probes for binding studies, we used multiple sequence alignment analysis to predict and design suitable expression constructs for isolated lectin domains (FIG. 4). In the present invention a direct binding assay was developed using isolated lectin domains of GalNAc-T4 and -T2 with minimal size (FIG. 7). Analysis of the fine specificity of the binding by inhibition studies showed that GalNAc-T2 and -T4 lectins exhibit restricted specificity for GalNAc structures, and surprisingly that the anomeric configuration of the GalNAc residue is not important. Thus, both GalNAcα- and GalNAcβ-benzyl inhibited binding to the same degree. The lectin Helix Pomatia (HP) was used as a control plant lectin with known binding specificity for GalNAcα-structures. HP lectin showed a very different highly preferred binding specificity for GalNAcα-structures.

Studies with GalNAcα-benzyl have shown that this compound is effectively taken up by cells and used in the Golgi compartments[46]. It is also well known in the art that sugar-aryl compounds are taken up by the cell and used in the Golgi compartments. Thus, the surprising finding that GalNAc-transferase lectins can be inhibited by βGalNAc (GalNAcβ-benzyl), provides a new tool to study the function of polypeptide GalNAc-transferases in vivo; GalNAcβ-benzyl, because it, too, will enter the cell and be used in the Golgi compartments.

Availability of a binding assay is a useful tool to identify and characterize inhibitors of GalNAc-transferase lectins. In accordance with the binding assay method of the invention GalNAc-transferases are contacted with a glycopeptide, glycoprotein, fusionprotein, or other appropriate structure or polymer containing the sugar hapten structure recognized by the GalNAc-transferase lectins, preferably N-acetylgalactosamine, and the GalNAc-transferase protein or lectin bound is quantitatively measured. The GalNAc-transferases may be in the form of a secreted soluble construct as applied in this invention, and any extended or truncated construct of a GalNAc-transferase as well as hybrid fusion protein that maintains the binding properties of the lectin. The ligand may be in the form of a chemoenzymatically produced MUC1 GalNAc-glycopeptide as applied in this invention, and any glycopeptide, glycoprotein, fusionprotein of any size or sequence, or other appropriate structure or polymer containing the sugar hapten structure recognized by the GalNAc-transferase lectins. Synthesis and chemoenzymatic synthesis of glycopeptides are familiar to those in the art, and are described in the literature cited above and in the Examples provided below. The ligand sugar may be GalNAc, N-acetylgalactosamine, or any other sugar in any linkage and sequence recognized by a GalNAc-transferase lectin. The binding assay may be an enzyme-linked solid phase immunoadsorption assay (ELISA) as applied in the invention, and any variant assay hereof where binding to ligand can be detected including without limitation radio-immunoassay (RIA), surface plasmon resonance (SPR), chemoluminescense, nuclear magnetic resonance spectroscopy ($^1$H-NMR), and other methods know in the art. Binding may be detected by horse-radish-peroxidase HRP-Avidin biotin as applied in this invention, and any other detection system including without limitation enzyme reactions, fluorescence, radioactivity, spectroscopy, spectrometry and other methods. The GalNAc-transferases may be labelled by biotinylation as applied in this invention, and any other labelling including without limitation antibody tags, enzymes, fluorochromes, radioisotopes and other methods know in the art, as well as detected by antibodies, phage antibody fragments or other binding proteins. The assay may used to characterize binding specificities of GalNAc-transferase lectins, screen and identify inhibitors of GalNAc-transferase lectins, and screen and identify competitive binders such as different GalNAc-transferase lectins and other lectins and proteins with binding properties for carbohydrates.

An in vivo model system for secretion of mucins was developed. A truncated secreted expression construct of the human cell surface mucin MUC1 containing 32 tandem repeats (FIG. 5), was stably transfected into CHO wild type and CHO ldlD cells[53]. FIG. 8 illustrates intracellur expression of soluble MUC1 in wild type CHO transfectant clone, wtCHO/MUC1sol-clone-C4, visualized by multiple monoclonal anti-MUC1 antibodies. Analysis of glycosylation was performed with a panel of antibodies with well-defined specificities for carbohydrate structures, and reactivity was mainly found with anti-T after pre-treatment with neuraminidase to remove sialic acids. Weak staining with anti-Tn was also found in some cells. FIG. 9 illustrates western blot analysis of secreted MUC1 from the same cells. High molecular weight MUC1 migrating with apparent mw higher than 300 Kd is labelled by HMFG2, SM3, and VU-2G7, while all antibodies including VU-4H5 label a low molecular weight MUC1 migrating with apparent mw of 130 Kd and presumed to represent virtually unglycosylated MUC1. Pretreatment with neuraminidase decreased migration of the high molecular weight MUC1 bands, and anti-T antibody reactivity emerged. Stable MUC1 transfectants in CHO ldlD showed similar patterns of reactivity when grown in Gal and GalNAc.

An in vivo model system for cell surface expression of mucins was developed. A full coding expression construct of the human cell surface mucin MUC1 containing 32 tandem repeats (FIG. 5), was stably transfected into CHO wild type and CHO ldlD cells. CHO ldlD cells were originally established by Krieger et al.[53] and found to have a defect in UDP-Gal/GalNAc epimerase that renders the cells incapable of producing UDP-Gal and UDP-GalNAc. Lack of UDP-Gal limits the synthesis of all types of glycoconjugates including glycosphingolipids, N-linked and O-linked glycoproteins. The synthesis of O-linked glycoproteins will be arrested at GalNAcα1-O-Ser/Thr with or without addition of α2,6 linked sialic acid. In the absence UDP-GalNAc mainly O-linked mucin-type glycoconjugates are affected, and essentially no glycosylation occur, as the first sugar attached is GalNAc. The defect in CHO ldlD cells can be selectively restored by addition of 1 mM GalNAc and or 0.1 mM Gal to the growth medium[53]. Addition of both sugars essentially restores normal glycosylation, whereas addition of GalNAc alone limits O-glycosylation to GalNAcα1-O-Ser/Thr with or without addition of α2,6 linked sialic acid, and also affects galactosylation of N-linked glycosylation and glycolipid biosynthesis. Altschuler et al.[54] have previously shown that cell surface expression of MUC1 in CHO ldlD cells requires addition of GalNAc.

Cell surface expression of MUC1 was established in stably transfected CHO wildtype and CHO ldlD cells. MUC1 was detected at the surface of non-permeabilized cells using monoclonal anti-MUC1 antibodies (FIG. 10). In accordance with Alschuler et al.[54] MUC1 surface expression in CHO ldlD cells was only found in cells grown in GalNAc or Gal and GalNAc, whereas cells grown without sugars or only in Gal failed to express MUC1 at the surface. In agreement with the conclusion drawn by Altchuler et al.[54] surface expression of MUC1 was dependent only on the first step in O-glycosylation, the addition of GalNAc.

MUC1 produced in CHO ldlD cells grown without GalNAc is not accumulated in Golgi, but degraded in lysosomes[54]. This indicates that measuring total MUC1 in cell lysates rather than exclusively at the cell surface may be used as a measure of MUC1 expression. The experiments shown in FIGS. 11-13 use immunoprecipitation of total cell lysates with anti-MUC1 antibody followed by western blot analysis with the same or different anti-MUC1 antibody to quantify and characterize MUC1 expression in cells. MUC1 produced in cell grown without GalNAc or only in the presence of Gal migrate close to the predicted mass of the protein core. With the addition of GalNAc to the medium high molecular weight forms of MUC1 are found, and these react with all antibodies except VU-2G7. The antibody 5E5 only reacts with Tn glycoforms and lack of reactivity with MUC1 from cells grown in Gal and GalNAc indicate that the majority of MUC1 produced is glycosylated with sialyl-T structures.

GalNAcα-benzyl is a well-known inhibitor of O-glycosylation extension[46]. Treatment of cells with 1-2 mM GalNAcα-benzyl partially blocks core 1 O-glycosylation including α2,3 sialylation. Treatment of cells with GalNAcα-benzyl is also known to affect surface expression of mucins and O-glycosylated glycoproteins, as well as in some cases secretion of mucins. A number of mammalian cell lines have been treated with 1-2 mM GalNAcα-benzyl in the past and the resulting effects on O-glycosylation as well as mucin secretion have varied with cell type (for a detailed review see[55])

Figure 13:
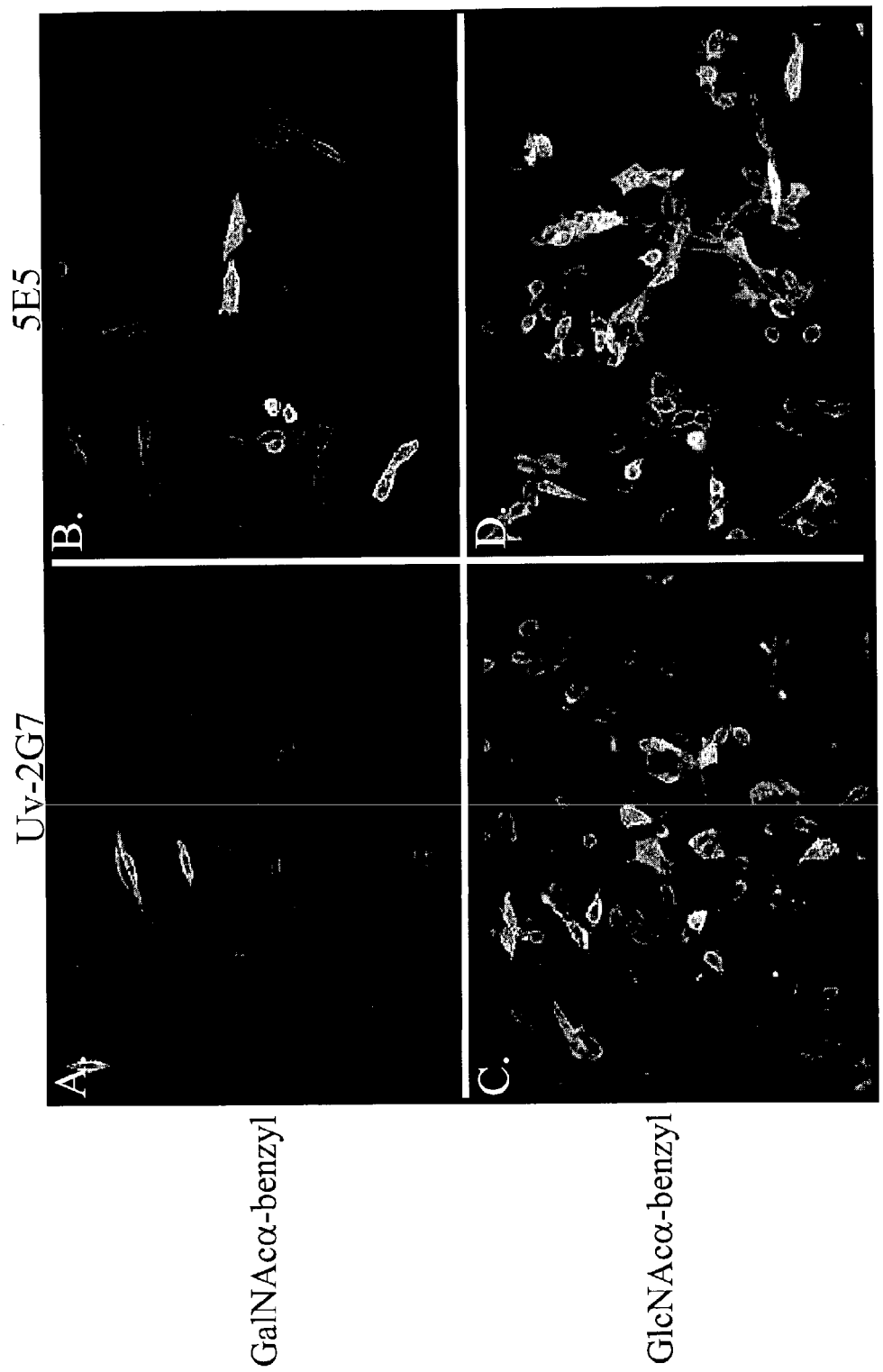

The effect of GalNAcα-benzyl on mucin transport and secretion has been concluded to be due to blockage of O-glycosylation extension[55]. FIGS. 13-15 illustrate that CHO ldlD cells grown in Gal and GalNAc (or wild type CHO cells), and treated with 2 mM GalNAcα-benzyl in agreement with this, exhibits reduced expression of MUC1 as well as altered O-glycosylation as judged by an altered SDS-PAGE migration pattern. Wildtype CHO cells as well as CHO ldlD cells grown in Gal and GalNAc produce O-glycans of the mono- and disialylated core 1 structures (NeuAcα2-3Galβ1-3[NeuAcα2-6]+/−GalNAcα-O-Ser/

Thr). Treatment with GalNAcα-benzyl results in some exposure of unsialylated core 1 as evaluated by staining with anti-T monoclonal antibody HH8, whereas only very little Tn is exposed as evaluated with anti-Tn monoclonal antibody 5F4. The altered SDS-PAGE migration of MUC1 produced in CHO ldlD cells grown in Gal and GalNAc (or wild type CHO cells, not shown) shown in FIGS. 14-15 (lanes 4 and 10 when indicated) reflects mainly loss of sialic acids.

If the effect of GalNAcα-benzyl treatment on mucin transport and secretion is due to inhibition of sialylation, then treatment of CHO ldlD cells grown only in GalNAc and hence producing only GalNAcα1-O-Ser/Thr O-glycosylation (neglible STn is produced as evidenced by lack of staining with anti-STn monoclonal antibodies 3F1 and TKH2, while cells stain very strongly with anti-Tn monoclonal antibodies 5F4 and 1E3), should have no effect on expression of MUC1 in these cells. Surprisingly as shown in FIGS. 14-15 (lanes 1 and 7 when indicated), GalNAcα-benzyl treatment does inhibit MUC1 expression in CHO ldlD cells with O-glycosylation controlled and limited to Tn glycoforms. This result shows for the first time that mucin transport and secretion may be directly affected by treatment with GalNAcα-benzyl and not through a mechanism involving inhibtion of sialylation or the O-glycosylation extension pathways. Combined with the findings of Altchuler et al.[54], these results indicate that mucin transport and secretion requires some degree of GalNAc O-glycosylation, whereas O-glycan extension including sialylation seems to be of less importance for this process.

An appropriate control for GalNAcα-benzyl treatment has not previously been studied. Selection of a benzyl monosaccharide that is not involved in and does not affect glycosylation pathways in cells is problematic. We chose to use GlcNAca-benzyl as such a control as this structure is not used in glycosylation pathways of mammalian glycoproteins and glycosphingolipids. As shown in FIGS. 14-15 (lanes 2,5, 8, and 11, when indicated) treatment of CHO ldlD cells with 2 mM GlcNAcα-benzyl had no effect on MUC1 expression and glycosylation. GlcNAcα-benzyl thus serves as a control for treatment of cells with benzyl sugars, and this is important because benzyl sugars and their biosynthetic products appear to aggregate in cells and cause morphological changes with prolonged treatment[46].

Since transport of mucin in cells was selectively inhibited by GalNAcα-benzyl (and not GlcNAcα-benzyl), even in cells limited to GalNAcα1-O-Ser/Thr O-glycosylation, we hypothesized that polypeptide GalNAc-transferases and in particular their lectin domains could be involved in ensuring mucin transport and preventing direction to lysosomes. One hypothesis would suggest that inhibition of the GalNAc-glycopeptide acceptor substrate specificity of GalNAc-transferases leads to mucin glycoforms with lower density of O-glycan occupancy (shown in vitro for e.g. MUC1 tandem repeats[42]), and that this decrease in O-glycan density results in increased targeting to lysosomal degradation and hence decrease in expression. Another hypothesis would suggest that the lectin domains of GalNAc-transferases in general have the capacity to bind GalNAc and hence provide a lectin mediated chaperone-like function, which is required for Golgi transport of O-glycosylated proteins. Lectin chaperones are well known to function ER transport as well as in lysosomal targeting[56], but the existence of such lectin chaperones for cell surface expression and secretion have not been demonstrated in the Golgi or trans-Golgi network.

As described above we found in the present invention that GalNAc-transferase lectins in a binding assay to GalNAc-glycopeptides surprisingly showed similar inhibition with GalNAcα-benzyl and GalNAcβ-benzyl. This indicates that these lectins in contrast to many lectins including Helix Pomatia fail to distinguish the anomeric configuration of the monosaccharide hapten recognized. βGalNAc is a rare linkage in mammalian glycoproteins and is found only in N-linked glycoproteins in man associated with the hormone specific glycosylation pattern where it generally is sulphated. Although, βGalNAc is found in both ganglioseries (GalNAcβ1-4Galβ1-4Glcβ1-Cer) and globoseries (GalNAcβ1-3Galα1-4Galβ1-4Glcβ1-Cer) it is expected that treatment of cells with 2 mM GalNAcβ-benzyl will not interfere significantly with glycosylation. This is based on the findings that the β1,3galactosyltransferases (β3Gal-T4 and β3Gal-T5, respectively) involved in extending βGalNAc in these two glycolipid structures show no or very poor activity with GalNAcβ-benzyl[57,58]. The only βGalNAc containing structure in O-linked glycosylation is found in the blood group related Sda structure (GalNAcβ1-4(Neuα2-3)Galβ1-3GalNAcα1-O-Ser/Thr) which has very restricted expression[59].

We therefore tested if GalNAcβ-benzyl treatment of cells showed the same effects as GalNAcα-benzyl treatment. As shown in FIGS. 16-17 (lane 5) GalNAcβ-benzyl treatment does not interfere with O-glycosylation in contrast to GalNAcα-benzyl (lane 4), as no difference in SDS-PAGE migration is observed. However, GalNAcα-benzyl, as well as GalNAcβ-benzyl treatment of cells, produces similar significant reduction in expression of MUC1 FIGS. 16-17. This shows surprisingly and for the first time that GalNAcβ-benzyl represents a selective inhibitor of mucin transport and secretion. GalNAcβ-benzyl is a novel preferred inhibitor of transport, surface expression and secretion of O-glycosylated proteins and mucins, because it does not interfere with the O-glycosylation extension process. GalNAcβ-benzyl is not expected to accumulate biosynthetic oligosaccharide products similar to those found with GalNAcα-benzyl treatment[46]. The finding that GalNAcβ-benzyl exerts these effects on mucin expression combined with the finding that it inhibits polypeptide GalNAc-transferases strongly indicate that the mechanism by which GalNAcα- and GalNAcβ-benzyl inhibits mucin expression is through inhibition of GalNAc-transferase lectins. This supports the second hypothesis articulated above. Polypeptide GalNAc-transferase lectins thus represent prime targets for intervention with mucin secretion and cell surface expression, and GalNAcβ-benzyl represents a novel selective prototype inhibitor for such intervention.

Preferred compounds for inhibition of GalNAc-transferase lectins are inactive as acceptor substrates for glycosyltransferases. In particular, the following glycosyltransferase activities: core 1 UDP-Gal:GalNAc-peptide β1,3galactosyltransferases, CMP-NeuAc:GalNAc-peptide α2,6sialyltransferases, and UDP-GlcNAc:β1,3N-acetylglucosaminyltransferases involved in O-glycosylation, are inactive with the preferred inhibitory compounds. Examples of such inhibitory compounds are GalNAcα1-O-benzyl with substitution of hydroxyl groups at C3 and/or C6 with methyl or acetyl groups to block acceptor sites.

The methods described herein are designed to identify substances and compounds that bind to and or modulate the biological activity of a polypeptide GalNAc-transferase or GalNAc-transferase lectin, including substances that interfere with or enhance the activity of a polypeptide GalNAc-transferase lectin. GalNAc-transferase lectins may be used in the form of a truncated lectin domain as shown in Example 8, as a secreted GalNAc-transferase enzyme as shown in Example 8, or as a truncated protein or fusion protein with or without catalytic activity but with retained lectin domain and carbohydrate binding activity.

Agents that modulate a polypeptide GalNAc-transferase or GalNAc-transferase lectin can be identified based on their ability to associate with such a transferase or lectin. Therefore, the invention also provides a method of identifying agents that associate with a polypeptide GalNAc-transferase or GalNAc-transferase lectin. Agents identified using the method of the invention may be isolated, cloned and sequenced using conventional techniques. An agent that associates with a polypeptide GalNAc-transferase or GalNAc-transferase lectin may be an agonist or antagonist of the biological or immunological activity of the transferase or lectin.

Agents that can associate with a polypeptide GalNAc-transferase or GalNAc-transferase lectin may be identified by reacting such GalNAc-transferase or GalNAc-transferase lectin with a test substance, which potentially associates with a polypeptide GalNAc-transferase or lectin under conditions which permit the association, and removing and/or detecting the associated GalNAc-transferase or lectin and substance. The substance-GalNAc-transferase or substance-lectin complex, free substance, or non-complexed polypeptide may be assayed. Conditions, which permit the formation of substance-GalNAc-transferase or substance-lectin complexes, may be selected having regard to factors such as the nature and amounts of the substance and the polypeptide.

The substance-transferase or substance-lectin complex, free substance or non-complexed transferase or lectin may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, a labelled antibody against the transferase or the substance or a labelled lectin or a labelled substance may be utilized. The antibodies, lectins, or test substances may be labelled with a detectable substance as described above.

A polypeptide GalNAc-transferase or GalNAc-transferase lectin, or a test substance used in the method of the invention may be insolubilized. For example, a lectin, transferase, or a test substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized lectin, transferase or substance may be prepared by reacting the material with a suitable insoluble carrier using known chemical or physical methods, for example, cyanogen bromide coupling.

The invention also contemplates a method for evaluating an agent for its ability to modulate the biological activity of a polypeptide GalNAc-transferase or GalNAc-transferase lectin by assaying for an agonist or antagonist (i.e. enhancer or inhibitor) of the association of the transferase or lectin with a substance that interacts with the polypeptide (e.g. carbohydrate binding site or parts thereof). The basic method for evaluating whether an agent is an agonist or antagonist of the association of a polypeptide GalNAc-transferase or lectin and a substance that associates with the transferase or lectin is to prepare a reaction mixture containing the transferase lectin and the substance under conditions which permit the formation of substance-transferase or substance-lectin complexes, in the presence of a test agent. The test agent may be initially added to the mixture, or may be added subsequent to the addition of the transfearse or lectin and substance. Control reaction mixtures without the test agent or with a placebo are also prepared. The formation of complexes is detected and the formation of complexes in the control reaction, but not in the reaction mixture, indicates that the test agent interferes with the interaction of the transferase/lectin and substance. The reactions may be carried out in the liquid phase or the transferase/lectin, substance, or test agent may be immobilized as described herein.

It will be understood that the agonists and antagonists, i.e. enhancers and inhibitors, that can be assayed using the methods of the invention may act on one or more of the interaction sites on the transferase or lectin or substance including agonist binding sites, competitive antagonist binding sites, non-competitive antagonist binding sites or allosteric sites. It will also be understood that competitive assays, in addition to direct assays, can be used to screen for and identify the agents of the present invention.

The invention also makes it possible to screen for antagonists that inhibit the effects of an agonist of the interaction of a polypeptide GalNAc-transferase or GalNAc-transferase lectin with a substance capable of associating with the lectin. Thus, the invention may be used to assay for an agent that competes for the same interacting site of a polypeptide GalNAc-transferase lectin.

Test compounds are screened from, for example, large libraries of synthetic or natural compounds. Numerous means are currently used for random and directed synthesis of saccharide, peptide, and nucleic acid based compounds. Examples of available libraries are synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.).

Agents which are effective in modulating a polypeptide GalNAc-transferase lectin can be identified, based on their ability to interfere with or enhance the lectin mediated binding capacity of the GalNAc-transferase protein or fragment hereof containing the lectin region. Therefore, the invention provides a method for evaluating a test substance for its ability to modulate the binding capacity of a polypeptide GalNAc-transferase lectin comprising (a) reacting a binding substrate with a GalNAc-transferase or lectin polypeptide or fragment hereof in the presence of a test substance;
(b) measuring the amount of binding substrate bound to the GalNAc-transferase polypeptide or fragment hereof, and
(c) carrying out steps (a) and (b) in the absence of the test substance to determine if the substance interferes with or enhances the binding by the polypeptide GalNAc-transferase.

Suitable binding substrates for use in the methods of the invention are polypeptides, glycopolypeptides, or glycoproteins, which are either synthetic or naturally occurring structures. The GalNAc-transferase lectin polypeptide may be obtained from natural sources or produced using recombinant methods as described and referenced herein.

The binding or modifying substrates or acceptor or donor substrates may be labelled with a detectable substance as described herein, and the interaction of the polypeptide of the invention with the binding or modifying substrates will give rise to a detectable change. The detectable change may be colorimetric, photometric, radiometric, potentiometric, etc. The GalNAc-transferase lectin polypeptide is reacted with the binding or modifying substrates at a pH and temperature effective for the polypeptide to bind the substrates, and where preferably one of the components is labeled, to produce a detectable change. It is preferred to use a buffer with the substrates to maintain the pH within the pH range effective for the polypeptides. The buffer and substrates may be used as an assay composition. Other compounds such as EDTA and detergents may be added to the assay composition.

The reagents suitable for applying the methods of the invention to evaluate agents that modulate a polypeptide GalNAc-transferase or GalNAc-transferase lectin may be packaged into convenient kits providing the necessary materials packaged into suitable containers. The kits may also include suitable supports useful in performing the methods of the invention.

Agents that modulate polypeptide GalNAc-transferase(s) or GalNAc-transferase lectin(s) can also be identified by treating immortalized cells which express the transferase(s) with a test substance, and comparing the intracellular transport, degradation, surface expression, or secretion of O-glycosylated proteins, mucins, and glycoproteins performed of the cells with those of the cells in the absence of the test substance and/or with immortalized cells which do not express the transferase(s). Examples of immortalized cells that can be used include human cell lines, Chinese hamster ovary (CHO) cells and mutant cells CHO ldlD$^{53}$, which express polypeptide GalNAc-transferase(s) or lectin(s) and produce cell membrane bound or secereted forms of the human mucin MUC1. In the absence of an inhibitor the cells will produce and transport MUC1 to the cell surface or secrete MUC1 into the growth medium. Substances that reduce the cell surface expression or the quantity of MUC1 in the medium may be considered an inhibitor.

The agents identified by the methods described herein, may be used for modulating the biological activity of a polypeptide GalNAc-transferase or a GalNAc-transferase lectin, and they may be used as prototype drugs in the treatment of conditions mediated by a polypeptide GalNAc-transferase or GalNAc-transferase lectin and in designing further substances effective to treat such conditions. In particular, they may be used to alter density of O-glycosylation on glycoproteins and mucins produced by cells, the intracellular transport and surface expression of glycoproteins and mucins, the secretion of glycoproteins and mucins, and other functions governed by the polypeptide GalNAc-transferases and their lectins in transport and secretion of glycoproteins and mucins.

Therefore, the present invention has potential application in the treatment of various disorders associated with aberrant O-glycosylation and/or mucin production in mammals, preferably humans. Such disorders include the following: tumors and cancers, lungs diseases associated with mucous accumulation such as asthma, chronic bronchitis, smoker's lung, cystic fibrosis, diseases of exocrine glands associated with increased or decreased mucin secretion such as Sjøgrens syndrome, dry mouth etc. Other disorders include dysregulation of selectin-mediated leukocyte trafficking and would include but not be limited to disorders involving autoimmunity, arthritis leukaemia's, lymphomas, immunosuppression, sepsis, wound healing, acute and chronic in action, cell mediated immunity, and the like.

The agents identified by the methods described herein, have potential application in treatment of tumors including inhibition of tumor metastasis and growth and/or regression of same. Tumor metastasis may be inhibited by inhibiting the adhesion of circulating cancer cells. The agents of the invention have particular potential application may be especially useful in the treatment of various forms of neoplasia such as leukaemias, lymphomas, melanomas, adenomas, sarcomas, and carcinomas of solid tissues in patients. In particular the composition may be used for treating malignant melanoma, pancreatic cancer, cervico-uterine cancer, cancer of the liver, kidney, stomach, lung, rectum, breast, bowel, gastric, thyroid, neck, cervix, salivary gland, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The substances etc. are particularly useful in the prevention and treatment of tumors of lining mucosa and glands and the metastases derived from these tumors.

Accordingly, the various agents may be formulated into pharmaceutical compositions for administration to subjects in a biologically compatible form suitable for administration in vivo. By biologically compatible form suitable for administration in vivo is meant a form of the agent to be administered in which any toxic effects are outweighed by the therapeutic effects. The agents may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of an agent may vary according to factors such as the disease state, age, sex, and weight of the individual, and the ability of pharmaceutical composition or polypeptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The active agent may be administered in a convenient manner such as by injection (subcutaneous, intravenous, etc.), oral administration, inhalation, transdermal application, or rectal administration. Depending on the route of administration, the active agent may be coated in a material to protect the agent from the action of enzymes, acids and other natural conditions that may inactivate it.

The compositions described herein can be prepared by methods known per se for the preparation of pharmaceutically acceptable compositions which can be administered to subjects, such that an effective quantity of the active agent is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the agents in association with one or more pharmaceutically acceptable vehicles or diluents, and contained in buffered solutions with a suitable pH and iso-osmotic with the physiological fluids.

The phrase "pharmaceutically acceptable" refers to molecular entities and compositions that are physiologically tolerable and do not typically produce an allergic or similar untoward reaction (for example, gastric upset, dizziness and the like) when administered to an individual. Preferably, and particularly where a immunogenic composition is used in humans, the term "pharmaceutically acceptable" denotes approved by a regulatory agency (for example, the U.S. Food and Drug Agency) or listed in a generally recognized pharmacopeia for use in animals (for example, the U.S. Pharmacopeia).

Toxicity and therapeutic efficacy of compounds can be determined by standard pharmaceutical procedures, for example in cell culture assays or using experimental animals to determine the LD50 and the ED50. The parameters LD50 and ED50 are well known in the art, and refer to the doses of a compound that are lethal to 50% of a population and therapeutically effective in 50% of a population, respectively. The dose ratio between toxic and therapeutic effects is referred to as the therapeutic index and may be expressed as the ratio:LD50/ED50. Compounds that exhibit large therapeutic indices are preferred. While compounds that exhibit toxic side effects may be used. However, in such instances it is particularly preferable to use delivery systems that specifically target such compounds to the site of affected tissue so as to minimize potential damage to other cells, tissues or organs and to reduce side effects.

Data obtained from cell culture assay or animal studies may be used to formulate a range of dosages for use in humans. The dosage of compounds used in therapeutic methods of the present invention preferably lie within a range of circulating concentrations that includes the ED50 concentration but with little or no toxicity (e.g., below the LD50 concentration). The particular dosage used in any application may vary within this range, depending upon factors such as the particular dosage form employed, the route of administration utilized, the conditions of the individual (e.g., patient), and so forth.

Non-human animals include, without limitation, laboratory animals such as mice, rats, rabbits, hamsters, guinea pigs, etc.; domestic animals such as dogs and cats; farm animals such as sheep, goats, pigs, horses, and cows; and non-human primates.

A therapeutically effective dose may be initially estimated from cell culture assays and formulated in animal models to achieve a circulating concentration range that includes the IC50. The IC50 concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by the routes described above.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

After pharmaceutical compositions have been prepared, they can be placed in an appropriate container and labelled for treatment of an indicated condition. For administration of an inhibitor of a polypeptide GalNAc-transferase, such labelling would include amount, frequency, and method of administration.

The use of inhibitors of the lectin domain mediated activities of the above mentioned polypeptide GalNAc-transferase isoforms and other isoforms allows for unique selective inhibition of these functions in vitro and in vivo in cells and organisms. This is desirable in manipulating the density of O-glycans, e.g. changing high density O-glycosylated tumour-associated MUC1 to low density normal MUC1 in cells. Further this is desirable in inhibiting any adhesive role the lectin domains may play in Golgi transport and intracellular sorting.

Preferred agents for inhibition of GalNAc-transferase lectins are inactive as acceptor substrates for glycosyltransferases. In particular, the following glycosyltransferase activities are inactive with the preferred inhibitory compounds: core 1 UDP-Gal:GalNAc-peptide β1,3-galactosyltransferases, CMP-NeuAc:GalNAc-peptide α2,6-sialyltransferases, and UDP-GlcNAc:β1,3N-acetylglucosaminyltransferases involved in O-glycosylation. Examples of such inhibitory compounds are GalNAcα1-O-benzoyl with substitution of hydroxyl groups at C3 and/or C6 by methyl or acetyl groups to block acceptor sites.

Agents which are effective in modulating a polypeptide GalNAc-transferase can be identified based on their ability to interfere with or enhance the activity of the transferase. Therefore, the invention provides a method for evaluating a test substance for its ability to modulate the activity of a polypeptide GalNAc-transferase comprising
(a) reacting an acceptor substrate and a donor substrate for a GalNAc-transferase polypeptide in the presence of a test substance;
(b) measuring the amount of donor substrate transferred to acceptor substrate, and
(c) carrying out steps (a) and (b) in the absence of the test substance to determine if the substance interferes with or enhances transfer of the sugar donor to the acceptor by the polypeptide GalNAc-transferase.

Suitable acceptor substrates for use in the methods of the invention are polypeptides, glycopolypeptides, or glycoproteins which are either synthetic or naturally occurring structures. Acceptors will generally comprise the hydroxyamino acids serine and/or threonine. The donor substrate may be a nucleotide sugar, dolichol-phosphate-sugar or dolichol-pyrophosphate-oligosaccharide, for example, uridine diphospho-N-acetylgalactosamine (UDP-GalNAc), uridine diphospho-galactose (UDP-Gal), or derivatives or analogs thereof. The GalNAc-transferase polypeptide may be obtained from natural sources or produced using recombinant methods as described and referenced herein.

These and other embodiments of the present invention are described in more detail below. The following examples are intended to further illustrate the invention without limiting its scope.

EXAMPLES

Example 1

Figure 1:
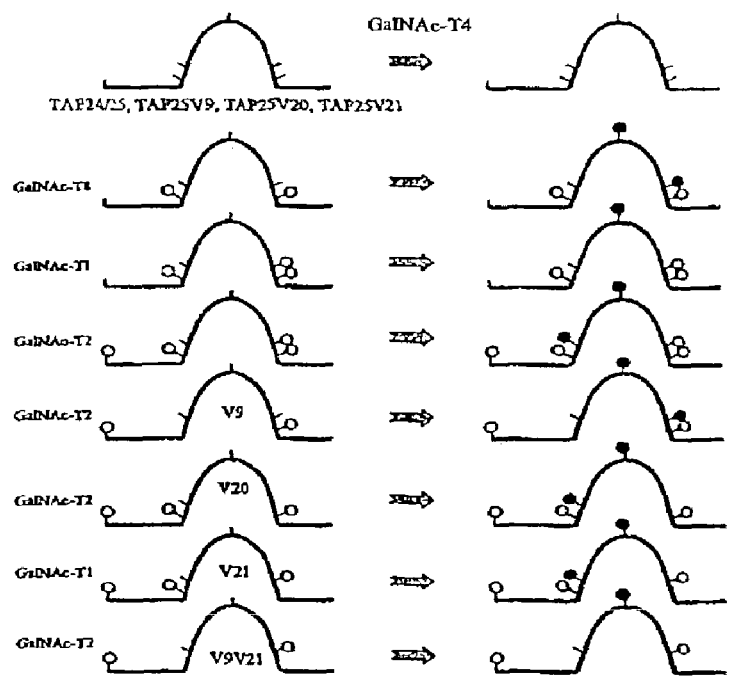
FIG. 1 illustrates that the MUC1 glycopeptide specificity of polypeptide GalNAc-T4 is not directed by a specific glycoform. Panel A is a schematic depiction of product development assays monitored by capillary electrophoresis (CE) and/or MALDI-TOF mass spectrometry. Left side illustrates MUC1 tandem repeat peptide glycoforms (open circles indicate attachments of GalNAc) prepared by in vitro glycosylation with indicated GalNAc-transferase isoforms. Right side illustrates products (closed circles indicate Gal-NAc residues added) developed in 6 hours by GalNAc-T4.Glycopeptides were characterized by mass spectrometry.
Figure 1:
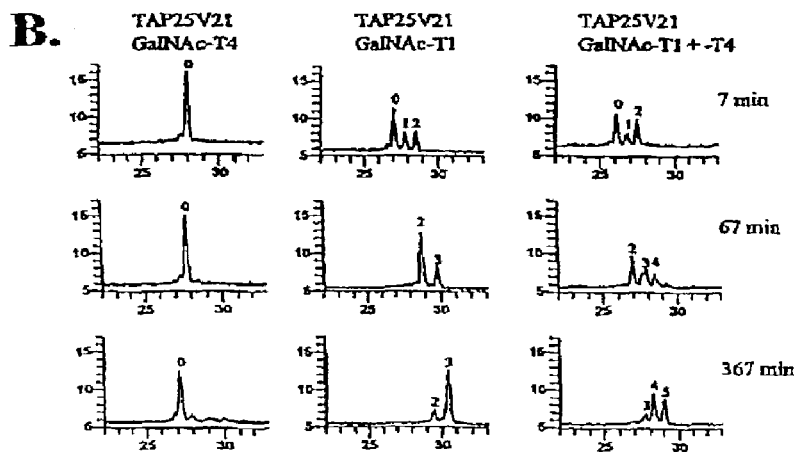

The MUC1 Glycopeptide Specificity of GalNAc-T4 is not Directed by a Specific Glycoform The GalNAc-T4 isoform displays enzyme activity which, in addition to showing activity with some peptide substrates, exhibits unique activity with glycopeptides where prior glycosylation is a prerequisite for activity (8). GalNAc-T4 is unique in that it is the only GalNAc-transferase isoform identified so far that can complete the O-glycan attachment to all five acceptor sites in the 20 amino acid tandem repeat sequence (HGVTSAPDTRPAPGSTAPPA) (SEQ ID NO: 1) of the breast cancer associated mucin, MUC1. GalNAc-T4 transfers GalNAc to at least two sites not used by other GalNAc-transferase isoforms on the GalNAc$_4$TAP24 glycopeptide (TAPPAHGVTSAPDTRPAPGSTAPP (SEQ ID NO: 2), GalNAc attachment sites underlined) (8). An activity such as that exhibited by GalNAc-T4 appears to be required for production of the glycoform of MUC1 expressed by cancer cells where all potential sites are glycosylated (10). In order to analyse activity of GalNAc-T4 with MUC1 derived GalNAc-peptides in detail different glycoforms of 24/25-mer peptides (TAP24/25) by using different GalNAc-transferase isoforms to catalyse glycosylation of selected sites in combination with valine substitutions of acceptor sites were prepared. Surprisingly, analysis of the substrate specificity of GalNAc-T4 with different glycoforms of MUC1 revealed that GalNAc-T4 did not show a requirement for any single site of GalNAc attachment (FIG. 1). By the contrary, there was only a requirement for at least one of the three sites to be glycosylated. Thus, substitution of any one of the sites glycosylated in the GalNAc$_4$TAP24/25 glycopeptide by valine did not affect activation of GalNAc-T4 activity for glycopeptides. Catalytic activity with certain sites was affected by site specific modifications, in particular glycosylation of S in -VTSA- (SEQ ID NO: 7) or -GSTA-(SEQ ID NO: 8) was influenced by glycosylation at adjacent and distant sites. This result suggested that a unique and novel triggering event of GalNAc-T4 activity existed in the presence of the glycosylated MUC1 substrate. This activity could not be ascribed to simple conformational changes in the acceptor substrate induced by the glycosylation. This surprising finding led us to hypothesise that a triggering event that was independent of the general catalytic activity of the enzyme led to acquisition of specificity for GalNAc-glycopeptides.

Example 2

The Lectin Domain of GalNAc-T4 Selectively Directs its MUC1 Glycopeptide Specificity One potential candidate for such a triggering event of glycopeptide activity was the lectin domain, which was previously shown by mutational analysis to have no significant affect on the activity of the GalNAc-T1 isoform (3). Since GalNAc-T4 exhibits both glycosylation independent and glycosylation dependent activities, it offers a model system to analyse the different specificities as separate functions. Hagen et al. (3) originally demonstrated that critical substitutions in the lectin domain of GalNAc-T1 have little affect on catalytic activity (reduction by 10-50%) with peptide substrates, while substitutions in the catalytic domain destroyed activity (FIG. 2, Panel A). It was predicted that mutation of an aspartate residue adjacent to a conserved CLD motif in the lectin domain to histidine (D444H in GalNAc-T1 corresponding to D459H in GalNAc-T4) would destroy lectin function based on analysis of ricin (29), but mutation of this residue (D444H) in GalNAc-T1 only appeared to reduce activity by approximately 50%. To test if the lectin domain influenced glycopeptide specificity of GalNAc-T4, recombinant secreted forms of GalNAc-T4$^{459D}$ and -T4$^{459H}$ were prepared. GalNAc-T4$^{459D}$ and -T4$^{459H}$ exhibited essentially the same specific activity with several unglycosylated peptides, in agreement with the results obtained for GalNAc-T1 (3) (illustrated for a PSGL-1 substrate in FIG. 2, Panel B). In contrast, the glycopeptide specificity of mutant GalNAc-T4$^{459H}$ was selectively affected by the introduced mutations. Glycopeptides derived from tandem repeats of MUC1, MUC2 and MUC5AC (7) were virtually inactive as substrates, as is illustrated in FIG. 2 (Panel C), which depicts assays with a GalNAc$_3$TAP25V21 glycopeptide. Essentially identical results were observed with unsubstituted TAP24 and GalNAc₄TAP24 glycopeptide. These results surprisingly demonstrates that the lectin domain is required for the glycopeptide specificity of enzyme activity, but not for activity with naked peptide substrates. This shows that the lectin domain triggers the catalytic domain of GalNAc-T4 to act on GalNAc-glycopeptide substrates by an as yet unknown mechanism. Furthermore, it demonstrates that the basic catalytic function and the triggering event are independent properties associated with distinct domains of GalNAc-transferases.

Example 3

The Lectin Domain of GalNAc-T4 Functions as a Lectin and has Selective Specificity for GalNAc In order to determine if actual carbohydrate binding contributed to the function of the lectin domain, we analysed whether triggering of glycopeptide specificity could be blocked by specific carbohydrates in solution. We could not detect direct binding of GalNAc-T2 and -T4 to free GalNAc using conventional binding assays presumably due to low affinity. More sensitive analyses will be required to demonstrate binding. However, as shown in FIG. 3 (Panel A) the glycosylation dependent specificity of GalNAc-T4 was almost completely inhibited by incubation with 0.23 M free GalNAc, whereas other sugars, Gal, GlcNAc, or Fuc, failed to show significant inhibition. Assays with 50 mM sugars gave the same pattern, but with less (approximately 50%) inhibition by GalNAc (not shown). Furthermore, similar inhibition was found with 10 mM α-D-GalNAc-1-benzyl, whereas αGlcNAc-benzyl did not inhibit catalytic activity. None of the sugars had significant affects on the glycosylation independent activities of GalNAc-T4$^{459D}$ or -T4$^{459H}$, when assayed with naked peptides (FIG. 3, Panel B). This demonstrates that the lectin domain of GalNAc-T4 must bind to GalNAc and contributes to the ability of GalNAc T4 to catalyse glycosylation of glycopeptides. It further demonstrates examples of inhibitors that selectively block the GalNAc-peptide substrate specificity of GalNAc-T4. The finding that neither Gal nor Galβ1-3GalNAcα1-benzyl produced significant inhibition compared to GalNAc suggests that the second step of O-glycosylation (extension of the oligosaccharide side chains), which is catalysed by the β3galactosyltransferase forming the core 1 structure Galβ1-3GalNAcα1-O-Ser/Thr, may block the functional activity of the lectin domain of GalNAc-T4. Thus, once the O-glycan processing step involving elongation to the core 1 structure is accomplished, GalNAc-T4 would not be capable of catalysing glycosylation of glycopeptides. This suggests that O-glycan elongation/branching and O-glycan density may be regulated by competition among GalNAc-transferases (lectin domain) and the glycosyltransferases involved in O-glycan extension, especially the core 1 synthase β3Galtransferase.

Example 4

The Lectin Domain of GalNAc-T7 Functions as a Lectin and has Selective Specificity for GalNAc and Galβ1-3GalNAc GalNAc-T7 exhibits exclusive glycopeptide specificity and no unsubstituted acceptor peptide substrates have been identified thus far (7). GalNAc-T7 has a different glycopeptide substrate specificity than GalNAc-T4 and does not function with MUC1 derived glycopeptides. The best substrate identified to date is derived from the tandem repeat region of rat submaxillary gland mucin (30). The activity of GalNAc-T7 with GalNAc2-3EA2 was significantly inhibited by benzyl-αGalNAc, benzyl-βGal, and the Galβ1-3GalNAcα1-benzyl disaccharide core 1 structure at 5 mM concentrations (Table I).

TABLE I

Inhibition of GalNAc-T7 activity with GalNAc2-3EA2 substrate
Activity (nmol/min/ml) in the presence of inhibitors (5 mM)

| None | bz-αMan | bz-βGal | bz-αGalNAc | Galβ1-3GalNAcα1-bz |
|---|---|---|---|---|
| 6.8 | 6.7 | 4.7 | 5.4 | 4.5 |

Example 5

The Lectin Domain of GalNAc-T2 is Functional and has Selective Specificity for GalNAc and the MUC2 and MUC5AC Tandem Repeat Peptides GalNAc-T2 exhibits galactosyltransferase activity in the presence of the Muc2 acceptor substrate (28). Furthermore, testing a panel of peptide substrates it was found that GalNAc-T2 also utilized Muc7 and to lesser degree the EA2 peptide in the presence of UDP-Gal (GalNAc-T2 activity with UDP-Gal: Muc2, 90 nmol/min/ml; Muc7, 13 nmol/min/ml; EA2, 1.5 nmol/min/ml). The galactosyltransferase activity with Muc2 substrate was selectively inhibited by GalNAc and not other sugars.

TABLE II

Inhibition of GalNAc-T2 activities with Muc2 acceptor substrate

| Donor Substrate | Activity (nmol/min/ml) in the presence of inhibitors (230 mM) | | | | |
|---|---|---|---|---|---|
| | None | GalNAc | GlcNAc | Gal | Fuc |
| UDP-GalNAc | 340 | 300 | 310 | 300 | 370 |
| UDP-Gal | 90 | 24 | 68 | 89 | 89 |

Since the galactosyltransferase activity exhibited by GalNAc-T2 exhibits an entirely different acceptor substrate pattern than the N-acetylgalactosaminyltransferase activity, it is concluded that the lectin domain exhibits peptide binding specificity in addition to GalNAc. Hence, the mechanism of activation resemble that of the glycopeptide specificity of GalNAc-T4 only the trigger is a peptide sequence motif comprised in the Muc2 and Muc7 peptide sequences. Inhibitors to the lectin domain of GalNAc-T2 will block its ability to bind nascent unglycosylated MUC2 mucin polypeptides and hence affect a potential chaperone effect of GalNAc-T2 in Golgi.

Example 6

The Lectin Domain of GalNAc-T3 is Functional and has Selective Specificity for GalNAc and the MUC5AC and Rat Submaxillary Tandem Repeat Peptides GalNAc-T3 was found also to exhibit galactosyltransferase activity but only in the presence of the EA2 acceptor substrate (GalNAc-T2 activity with UDP-Gal: Muc2, 0 nmol/min/ml; Muc7, 0.1 nmol/min/ml; EA2, 6.8 nmol/min/ml). The galactosyltransferase activity with Muc2 substrate was selectively inhibited by GalNAc and not other sugars.

TABLE III

Inhibition of GalNAc-T3 activities with EA2 acceptor substrate

| Donor Substrate | Activity (nmol/min/ml) in the presence of inhibitors (230 mM) | | | | |
|---|---|---|---|---|---|
| | None | GalNAc | GlcNAc | Gal | Fuc |
| UDP-GalNAc | 34 | 35 | 32 | 33 | 34 |
| UDP-Gal | 6.3 | 2.5 | 7 | 7.3 | 6.5 |

The lectin domain of GalNAc-T3 resemble that of GalNAc-T2 in binding to peptide sequences although the sequence motif must be different and partly contained in the EA2 sequence.

Materials and Methods.

The following subsections describe the materials and methods used in Examples 1-6.

Enzyme Reaction Conditions and Substrates

Standard reaction mixtures (50 µl final volume) contained 25 mM cocadylate (pH 7.4), 10 mM $MnCl_2$, 0.25% Triton X-100, 200 µM UDP-[$^{14}$C]-GalNAc (2,000 cpm/nmol) (Amersham), 200-500 µM acceptor peptides. Products were quantified by scintillation counting after chromatography on Dowex-1, octadecyl silica cartridges (Bakerbond), or HPLC (PC3.2/3 or mRPC C2/C18 SC2.1/10 Pharmacia, Smart System). Acceptor peptides included five variants of TAP25 (TAPPAHGV(T/V)SAPDTRPAPG(S/V)(T/V)APPA) (SEQ ID NO: 9) and TAP24 (TAPPAHGVTSAPDTRPAPG-STAPP) (SEQ ID NO: 2) derived from the human MUC1 tandem repeat (31); MUC2 (PTTTPISTTTMVTPTPTPTC) (SEQ ID NO: 10) derived from human intestinal mucin MUC2 (32); MUC5AC (Ac-SAPTTSTTSAPT) (SEQ ID NO: 11) derived from human respiratory gland mucin MUC5AC (33); MUC7 (Ac-CPPTPSATTPAPPSSSAPPET-TAA) (SEQ ID NO: 12) derived from human salivary gland mucin MUC7 (34); EA2 (PTTDSTTPAPTTK) (SEQ ID NO: 13) derived from rat submandibular gland mucin (30); VTHPGY (Ac-PFVTHPGY) (SEQ ID NO: 14)derived from human fibronectin (35); Zonadhesin (PTERTTTPT-KRTTTPTIR) (SEQ ID NO: 15) derived from human zonadhesin (36); OSM fragment (LSESTTQLPGGGPGCA) (SEQ ID NO: 16) derived from ovine submaxillary mucin (37); hCG-β (PRFQDSSSSKAPPPLPSPSRLPG) (SEQ ID NO: 17) derived from human chorionic gonadotropin β-subunit (38); MUC1b (RPAPGSTAPPA) (SEQ ID NO: 18) derived from MUC1 and PSGL-1b (Ac-QATEYEYLDYDFL-PETEPPEM) (SEQ ID NO: 19) derived from the N-terminus of P-selectin ligand-1 (39). GalNAc-glycopeptides of MUC2, MUC5AC and MUC7 were produced using cold UDP-GalNAc and purified human recombinant GalNAc-T1 and -T2 (28). Different GalNAc-glycoforms of EA2 were produced by limiting the ratio of UDP-GalNAc to 2 moles, 3 moles, 4 moles or 5 moles per mole of acceptor peptide. Glycopeptides were purified on Supelclean LC-18 columns (1 ml, Supelco), and the number of GalNAc residues incorporated evaluated by MALDI-TOF mass spectrometry. The enzyme sources used were semipurified as previously described by successive sequential ion-exchange chromatographies on Amberlite (IRA95, Sigma) or DEAE Sephacel (Pharmacia), S-Sepharose Fast Flow (Pharmacia), and Mini-S™ (PC 3.2/3, Pharmacia) using the Smart System (Pharmacia) (28). Secreted GalNAc-T4 was obtained from a stably transfected CHO line (CHO/GalNA-T4/21A) (8) grown in roller bottles in HAMS F12 supplemented with 10% Fetal Bovine Serum. The experiments illustrated in FIG. 1 was performed with recombinant secreted GalNAc-T4 obtained from a stably transfected CHO line (8). Experiments illustrated in FIGS. 2 and 3 were performed with secreted GalNAc-T4 expressed in High Five cells grown in serum-free medium (8). Structural analysis of glycopeptides were performed by a combination of PFPA (pentafluoropropionic acid) hydrolysis and MALDI-TOF mass spectrometry as previously described (40). Secreted GalNAc-T7 was obtained from infected High Five™ cells grown in serum-free medium (Invitrogen) in upright roller bottles shaken 140 rpm in waterbaths at 27° C. GalNAc-T7 was not purified by Mini-S as the yields from cationic chromatography were low due to its low pI (6.4).

Reaction Kinetics Monitored by Capillary Electrophoresis.

Reaction mixtures were modified to include 1.7 mM cold UDP-GalNAc, 25 µg acceptor peptides, and purified GalNAc-transferases in a final volume of 100 µl. The amount of GalNAc-transferase added was adjusted so that the reaction with the appropriate peptide was near completion in six hours. Reactions were incubated in the sample carousel of an Applied Biosystem model HT270 at 30° C. as described previously (28). Electrophoretograms were produced every 60 min, and after six hours the reaction mixtures were separated by reverse phase HPLC for structural determination. HPLC was performed on a Brawnlee ODS column (2.1 mm×30 mm, 5 µm particle size) (Applied Biosystems, Inc.) using a linear gradient (0-30%, 0.1% TFA/ 0.08% TFA, 90% acetonitrile, 30 min) delivered by an ABI 130A micro-bore HPLC system (Perkin Elmer Inc).

Structural Analysis of Reaction Products

Glycopeptides were purified by HPLC and analysed by a combination of PFPA (pentafluoropropionic acid, Sigma) hydrolysis and MALDI-TOF mass spectrometry. Glycopeptides (50 pmol) were lyophilized in 500 µl Eppendorf vials and placed in a 22 ml glass vial with a mininert valve (Pierce, Rockford, Ill.). A solution of 100 µl 20% PFPA (aqueous) containing 500 µg DTT was added to the bottom of the glass vial, which was then flushed with argon. The vial was evacuated to 1 mbar, and placed in an oven at 90° C. for 60 min. The hydrolyzed samples were centrifuged in a vacuum centrifuge for 15 min to remove remaining traces of acid. Lyophilized samples were reconstituted in 0.1% TFA to a concentration of 1 pmol/µl. Mass spectra were acquired on either Voyager-DE or Voyager-Elite mass spectrometers equipped with delayed extraction (Perseptive Biosystem Inc.). The matrix used was 2,5-dihydroxybenzoic acid (10 mg/ml, Hewlett-Packard) dissolved in a 2:1 mixture of 0.1% trifluoroacetic acid in 30% aqueous acetonitrile (Rathburn Ltd.). Samples dissolved in 0.1% trifluoroacetic acid to a concentration of approximately 80 fmol to 1 pmol/ml were prepared for analysis by placing 1 µl of sample solution on a probe tip followed by 1 µl of matrix. The hydrolyzed samples were prepared for MALDI analysis using nanoscale reversed-phase columns (Poros R3, PerSeptive Biosystem), according to previously described procedure (41). Samples were prepared by mixing 0.8 µl of total fraction volume 2 pmol of hydrolyzed glycopeptides and 0.4 µl of matrix solution. Mass spectra were acquired in reflector mode on a Voyager-Elite Biospectrometry Workstation (PerSeptive Biosystems Inc., Framingham, Mass., USA) equipped with delayed ion extraction technology. Data processing was performed using software packages Perseptive- Grams (Galactic Industries Corp.) and protein analysis software GPMAW (htpp://www.welcome.to/gpmaw; Lighthouse data, Odense, Denmark)

Reaction Kinetics Monitored by Mass Spectrometry

MALDI-TOF time-course in terminal reactions were performed in reactions of 25 µl containing 2.5 nmol acceptor (glyco)peptide, 40 nmol UDP-GalNAc, and 0.4 µg GalNAc-T4. Sampling of reactions (1 µl) were purified by nano-scale reversed-phase chromatography (Poros R3, PerSeptive Biosystem) and applied directly to the probe with matrix (41). The amount of GalNAc-transferase added was adjusted so that the reaction with the appropriate peptide was near completion in six hours. Reactions were incubated at 37° C. in a shaker bath. At times 0, 2 hours, and 16 hours a 1 µl aliquot was taken and purified. Mass spectra were acquired on either Voyager-DE mass spectrometer equipped with delayed extraction (Perseptive Biosystem Inc.). The matrix used was 2,5-dihydroxybenzoic acid (10 mg/ml, Hewlett-Packard) dissolved in a 2:1 mixture of 0.1% trifluoroacetic acid in 30% aqueous acetonitrile (Rathburn Ltd.).

Construction, Expression, Purification, and Analysis of a Lectin Domain Mutant of GalNAc T4

The mutant GalNAc-T4$^{459H}$ was prepared by multiplex PCR using the GalNAc-T4-sol construct that encodes residues 32-578 inserted into pT7T3U19 (8). Primers EBHC332 (5'-GTAGAGGGATCTCGTCTGAATGTTTACATTATA-3' (SEQ ID NO: 20) (mutation underlined in bold)) and T7 (5'-TAATACGACTCACTATAGGG-3) (SEQ ID NO: 21) were used in a standard reaction under the following cycling conditions; 95° C. 45 s, 51° C. 5 s, 72° C. 1 min. For 18 cycles using a Tc 2400 thermocycler (PE Biosystems, USA). The PCR product was digested with BstYI gel purified. 5 ng hereof was mixed with 10 ng pAcGP67-GalNAc-T4sol (8), and the mixture used to prime a "shuffle PCR" reaction using primers T7/EBHC201 (5'AAGCGGGCACCATATGCTCG-3') (SEQ ID NO: 22), using standard conditions and the following cycling conditions 95° C. 45 s, 51° C. 5 s, 72° C. 1 min (5 cycles without primers, after which primers were added and the reactions was cycled for an additional 17 cycles). The generated PCR product was digested with HindIII and inserted into HindIII digested GalNAc-T4 pT7T3U19 construct described above. The mutated T4-construct was fully sequenced and the BamHI insert subcloned into pAcGP67.[43].

Wild-type and mutant constructs expressed in insect cells were secreted in comparable yields, and the purified proteins migrated by SDS-PAGE identically. Quantification of purified proteins was done by Coomassie stained SDS-PAGE and titration of immunoreactivity with the monoclonal antibody, UH6(4G2) (8). GalNAc-T4$^{459D}$ and -T4$^{459H}$ were purified to 0.04 µg/µl and 0.1 µg/µl with specific activities of 0.197 U/mg and 0.24 U/mg with a MUC7 tandem repeat derived peptide (7), respectively. Wild-type GalNAc-T4 and mutant GalNAc-T4, GalNAc-T4$^{459H}$, were analysed with unglycosylated peptides (represented by PSGL-1) or GalNAc glycosylated glycopeptides (represented by GalNAc3TAP25V21) in reactions of 25 µl containing 2.5 nmol acceptor (glyco)peptide, 40 nmol UDP-GalNAc, and 0.4 µg GalNAc-T4. Time-course assays were motioned by MALDI-TOF. Sampling of reactions (1 µl) were purified by nano-scale reversed-phase chromatography (Poros R3, PerSeptive Biosystem) and applied directly to the probe with matrix. Evaluation of inhibition of the glycopeptide specificity of wild-type GalNAc-T4 with free sugars was performed to establish if the lectin domain recognized carbohydrate. Analysis was performed as above with 0.23 M free GalNAc, Gal, GlcNAc, or Fuc, and the reaction was monitored by MALDI-TOF. Further, analysis was performed with 10 mM α-D-GalNAc-1-benzyl, αGlcNAc-benzyl, and fully occupied GalNAc-glycopeptide, GalNAc6TAP25, at 5 mM.

Inhibition of the GalNAc-glycopeptide Activity of GalNAc-T7

GalNAc-T7 activity was analysed with GalNAc glycosylated glycopeptides (represented by GalNAc2-3EA2 (7)) in reactions of 25 µl containing 2.5 nmol acceptor (glyco)peptide, 40 nmol UDP-GalNAc, and purified GalNAc-T7. Assays were performed with 0.23 M free GalNAc, Gal, GlcNAc, or Fuc, and the reaction product quantified by Dowex-1 chromatography and scintillation counting. Further, analysis was performed with 10 mM α-D-GalNAc-1-benzyl, αGlcNAc-benzyl, and fully occupied GalNAc-glycopeptide, GalNAc6TAP25, at 5 mM.

Inhibition of Lectin Domains of GalNAc-transferases, GalNAc-T2 and -T3, that do not Exhibit Glycopeptide Specificies GalNAc-T2 exhibits activity with UDP-Gal in the presence of the acceptor substrate Muc2 (28). Galactosyl transferring activities of GalNAc-T1, -T2, and -T3, were assayed with a panel of acceptor peptides in standard reaction mixtures containing 100 µM UDP-Gal instead of UDP-GalNAc. GalNAc-T2 showed activity with Muc2 as well as low activity with Muc7 and very low activity with EA2 acceptor substrates. GalNAc-T3 showed activity with EA2 and lower activity with Muc7, but no activity with other peptides tested. Since the activities with UDP-Gal do not correlate with the general acceptor substrate specificities of these GalNAc-transferase isoforms found with the UDP-GalNAc donor substrate, it was tested if the lectin domains were involved. This was done by analysing if free sugars could selectively inhibit the activities with UDP-Gal and not UDP-GalNAc. Assays were performed with 0.23 M free GalNAc, Gal, GlcNAc, or Fuc, and the reaction product quantified by Dowex-1 chromatography and scintillation counting. Further, analysis was performed with 10 mM α-D-GalNAc-1-benzyl, αGlcNAc-benzyl, and fully occupied GalNAc-glycopeptide, GalNAC6TAP25, at 5 mM.

Example 7

Cloning, Expression, and Purification of Soluble GalNAc-Transferase Proteins and Soluble GalNAc-Transferase Lectins Polypeptide GalNAc-transferases are highly conserved throughout evolution. Orthologous relationships can be defined from man to *Drosophila*,[61] and ortholgous members of all human polypetide GalNAc-transferase isoforms are clearly identifiable in mouse and rats, and likely all mammals.

Polypeptide GalNAc-transferases are predicted to be type II transmembrane Golgi-resident proteins with a domain structure depicted in FIG. 2A. The N-terminal cytoplasmic tail, the hydrophic transmembrane signal sequence, and the stem region may be involved in directing Golgi-localization[60]. The catalytic unit of the enzymes is approximately 300-350 amino acid residues and highly conserved in primary sequence among isoforms and also throughout evolution of the gene family[43,61]. The C-terminal region of approximately 130 amino acids exhibits similarity with the galactose binding lectin, ricin. This region show little sequence similarity among isoforms and is poorly conserved in evolution[43].

Soluble, secreted expression constructs of human GalNAc-transferases GalNAc-T1, -T2, -T3, -T4, -T6, -T7, and -T11 for baculo-virus mediated expression in insect cells have been described in detail previously [7, 8, 26, 27, 43, 48]. His-tagged soluble expression constructs for all human ppGalNAc-transferases, including novel genes designated GalNAc-T12, -T13, -T14, -T15, and -T16, were prepared using PCR primers as listed in Table IV below.

encoding 6×His, a thrombin cleavage site, and a T7 antibody site. pBKS-Histag-I was modified with the sequence 5'-GCGGCCGCTCTAGAACTAGTGGATCCAG-CAGCCATCATCATCATCATCACAGCAGCGGCCTG GTGCCGCGCGGCAGCCATATGGCTAG-CATGACTGGTGGACAGCAAATGGGTCGCGGAATTC CGATATCAAGCTTATCGATACCGTCGACCTCGAG-3'. (SEQ ID NO: 55)

TABLE IV

Primers used for PCR of soluble secreted GalNAc-transferase expression constructs.

```
GalNAc-T1:
EBHC121H:   5'-GCGGGATCCAGGACTTCCTGCTGGAGATG-3'        (SEQ ID NO: 23)
EBHC107B:   5'-GCGGATCCTCAGAATATTTCTGGAAGGG-3'         (SEQ ID NO: 24)
GalNAc-T2:
EBHC75D:    5'-GCGGAATTCTTAAAAAGAAAGACCTTCATCACAGC-3'  (SEQ ID NO: 25)
EBHC68:     5'-GCGGAATTCCTACTGCTGCAGGTTGAGC-3'         (SEQ ID NO: 26)
GalNAc-T3:
EBHC219H:   5'-GCGGGATCCAACGATGGAAAGGAACATG-3'         (SEQ ID NO: 27)
EBHC215:    5'-AGCGGATCCAGGAACACTTAATCATTTTGGC-3'      (SEQ ID NO: 28)
GalNAc-T4:
EBHC318:    5'-GCGGGATCCTTTTCATGCCTCCGCAGGAGCC-3'      (SEQ ID NO: 29)
EBHC307:    5'-GCGGGATCCGACGAAAGTGCTGTTGTGCTC-3'       (SEQ ID NO: 30)
GalNAc-T5:
EBHC909:    5'-GCGGGATCCTGCTTTAACTGGAGGGCTAGAGC-3'     (SEQ ID NO: 31)
EBHC907:    5'-GCGGGATCCATCAGTTACACTTCAGGCTTC-3'       (SEQ ID NO: 32)
GalNAc-T6:
EBHC514H:   5'-GCGGGATCCCCTGGACCTCATGCTGGAGGCCATG-3'   (SEQ ID NO: 33)
EBHC511N:   5'-AGCGGATCCTGGGGATGATCTGGGTCCTAGAC-3'     (SEQ ID NO: 34)
GalNAc-T7:
EBHC1122H:  5'-GCGAAGCTTCAGGATGAGGGAAGACAGAGATG        (SEQ ID NO: 35)
EBHC1116H:  5'-GCGAAGCTTCTCTCTAAACACTATGGATCTTATTC-3'  (SEQ ID NO: 36)
GalNAc-T8:
EBHC1820:   5'-GCGGGATCCTCTGAAAGAAAGTATGAAATTAGC-3'    (SEQ ID NO: 37)
EBHC1821:   5'-GCGGGATCCTCACTGGCTGTTGGTCTGACC          (SEQ ID NO: 38)
GalNAc-T9:
EBHC1320:   5'-GCGGGATCCCTGCCGCCTGCAGGGCCGCTCCCAG-3'   (SEQ ID NO: 39)
EBHC1321:   5'-GCGGGATCCTCAGTGCCGTCGGTGTTTGATCC-3'     (SEQ ID NO: 40)
GalNAc-T10:
EBHC2520:   5'-GCGGGATCCCCGCGAGCGGCAGCCCGACGGC-3'      (SEQ ID NO: 41)
EBHC2521:   5'-GCGGGATCCTCAGTTCCTATTCAATTTTTC-3'       (SEQ ID NO: 42)
GalNAc-T11:
EBHC629:    5'-GCGAATTCGTGAAGTGACTCAGCCACTTAAG-3'      (SEQ ID NO: 43)
EBHC614:    5'-GCGAATTCGTCTCTGTCAGACACGTGTC-3'         (SEQ ID NO: 44)
GalNAc-T12:
EBHC1051:   5'-GCGGGATCCGGCTCGGTGCTGCGGGCGCAGCG-3'     (SEQ ID NO: 45)
EBHC1032:   5'-GCGGGATCCTCATAACATGCGCTCTTTGAAGAACC-3'  (SEQ ID NO: 46)
GalNAc-T13:
EBHC2000:   5'-GCGGGATCCGATGTTGCACVVTCCCCACCACACC-3'   (SEQ ID NO: 47)
EBHC2002:   5'-GCGGGATCCTCATCGTTCATCCACAGCATTC-3'      (SEQ ID NO: 48)
GalNAc-T14:
EBHC1720:   5'-GCGGGATCCTCTGCTGCCTGCATTGAGGGCTG-3'     (SEQ ID NO: 49)
EBH21721:   5'-GCGGGATCCTCATGTGCCCAAGGTCATGTTCC-3'     (SEQ ID NO: 50)
GalNAc-T15:
EBHC412:    5'-GCGGGATCCCAAGAGGAAGTTGGAGGTGCCG-3'      (SEQ ID NO: 51)
EBHC438:    5'-GCGGGATCCAGGGGTCCTCAAGAGCTCACC-3'       (SEQ ID NO: 52)
GalNAc-T16:
EBHC1913:   5'-GCGGGATCCCTACTACTTATGGCAGGACAACCG-3'    (SEQ ID NO: 53)
EBHC1912:   5'-GCGTCATGTGTGTGGCAACAGCTGCCACTG-3'       (SEQ ID NO: 54)
```

Expression constructs were amplified by PCR using 20 ng plasmid DNA as template.

Expand High Fidelity-kit (Roche) was used as recommended by the manufacturer using an ABI2700 thermocycler (Applied Biosystems). Products were digested with EcoRI (GalNAc-T2, -T11, -T12 and -T16), BamHI (GalNAc-T1, -T3, -T4, -T5, -T6, -T8, -T9, -T10, -T13, -T14 and -T15) and HindIII (GalNAc-T7), and sub-cloned into the EcoRI or HindIII site of pBKS-HistagI or the BamHI site of pBKS-HistagII. PBKS-Histag-I and -II vectors were generated from pBluescrip (Stratagene), by inserting a fragment pBKS-Histag-II was modified with the sequence: 5'-GAATTCGCGGCCGCAGCAGCCATCAT-CATCATCATCACAGCAGCGGCCTGGTGC-CGCGCGGC AGCCATATGGCTAGCATGACTGGTG-GACAGCAAATGGATCCACTAGTTCTAGAGCGGC CGC-3'. (SEQ ID NO: 56)

All construct were fully sequenced. His-tagged GalNAc-transferase pBKS-HIS-tag-I constructs were excised with NotI and XhoI (blunt-ended) or as for GalNAc-T11, with NotI and HindIII (blunt-ended) and sub-cloned into the NotI/BglII (blunt-ended) site of the pAcGP67A Baculo expression vector (Pharmingen). His-tagged GalNAc-transferase pBKS-HIS-tag-II constructs were excised with NotI and inserted into the NotI site of pAcGP67A Baculo expression vector.

The coding region for human polypeptide GalNAc-T12 has been submitted to GenBank/EBI Data Bank and assigned accession number AJ132365:

Human GalNAc-T12 DNA sequence:

(SEQ ID NO: 57)
ATGTGGGGCGCACGGCGCGGCGGCGCTGCCCGCGGGAACTGCGGCGCGG
CCGGGAGGCGCTGTTGGTGCTCCTGGCGCTACTGGCGTTGGCCGGGCTGG
GCTCGGTGCTGCGGGCGCAGCGTGGGGCCGGGGCCGGGGCTGCCGAGCCG
GGACCCCCGCGCACCCCGCGCCCCGGGCGGCGCGAGCCGGTCATGCCGCG
GCCGCCGGTGCCGGCGAACGCGCTGGGCGCGCGGGGCGAGGCGGTGCGGC
TGCAGCTGCAGGGCGAGGAGCTGCGGCTGCAGGAGGAGAGCGTGCGGCTG
CACCAGATTAACATCTACCTCAGCGACCGCATCTCACTGCACCGCCGCCT
GCCCGAGCGCTGGAACCCGCTGTGCAAAGAGAAGAAATATGATTATGATA
ATTTGCCCAGGACATCTGTTATCATAGCATTTTATAATGAAGCCTGGTCA
ACTCTCCTTCGGACAGTTTACAGTGTCCTTGAGACATCCCCGGATATCCT
GCTAGAAGAAGTGATCCTTGTAGATGACTACAGTGATAGAGAGCACCTGA
AGGAGCGCTTGGCCAATGAGCTTTCGGGACTGCCCAAGGTGCGCCTGATC
CGCGCCAACAAGAGAGAGGGCCTGGTGCGAGCCCGGCTGCTGGGGGCGTC
TGCGGCGAGGGGCGATGTTCTGACCTTCCTGGACTGTCACTGTGAATGCC
ACGAAGGGTGGCTGGAGCCGCTGCTGCAGAGGATCCATGAAGAGGAGTCG
GCAGTGGTGTGCCCGGTGATTGATGTGATCGACTGGAACACCTTCGAATA
CCTGGGGAACTCCGGGGAGCCCCAGATCGGCGGTTTCGACTGGAGGCTGG
TGTTCACGTGGCACACAGTTCCTGAGAGGGAGAGGATACGGATGCAATCC
CCCGTCGATGTCATCAGGTCTCCAACAATGGCTGGTGGGCTGTTTGCTGT
GAGTAAGAAATATTTTGAATATCTGGGGTCTTATGATACAGGAATGGAAG
TTTGGGGAGGAGAAAACCTCGAATTTTCCTTTAGGATCTGGCAGTGTGGT
GGGGTTCTGGAAACACACCCATGTTCCCATGTTGGCCATGTTTTCCCCAA
GCAAGCTCCCTACTCCCGCAACAAGGCTCTGGCCAACAGTGTTCGTGCAG
CTGAAGTATGGATGGATGAATTTAAAGAGCTCTACTACCATCGCAACCCC
CGTGCCCGCTTGGAACCTTTTGGGGATGTGACAGAGAGGAAGCAGCTCCG
GGACAAGCTCCAGTGTAAAGACTTCAAGTGGTTCTTGGAGACTGTGTATC
CAGAACTGCATGTGCCTGAGGACAGGCCTGGCTTCTTCGGGATGCTCCAG
AACAAAGGACTAACAGACTACTGCTTTGACTATAACCCTCCCGATGAAAA
CCAGATTGTGGGACACCAGGTCATTCTGTACCTCTGTCATGGGATGGGCC
AGAATCAGTTTTTCGAGTACACGTCCCAGAAAGAAATACGCTATAACACC
CACCAGCCTGAGGGCTGCATTGCTGTGGAAGCAGGAATGGATACCCTTAT
CATGCATCTCTGCGAAGAAACTGCCCCAGAGAATCAGAAGTTCATCTTGC
AGGAGGATGGATCTTTATTTCACGAACAGTCCAAGAAATGTGTCCAGGCT
GCGAGGAAGGAGTCGAGTGACAGTTTCGTTCCACTCTTACGAGACTGCAC
CAACTCGGATCATCAGAAATGGTTCTTCAAAGAGCGCATGTTATGA

Human GalNAc-T12 amino acid sequence:

(SEQ ID NO: 58)
MWGRTARRRCPRELRRGREALLVLLALLALAGLGSVLRAQRGAGAGAAEP
GPPRTPRPGRREPVMPRPPVPANALGARGEAVRLQLQGEELRLQEESVRL
HQINIYLSDRISLHRRLPERWNPLCKEKKYDYDNLPRTSVIIAFYNEAWS
TLLRTVYSVLETSPDILLEEVILVDDYSDREHLKERLANELSGLPKVRLI
RANKKKGLVRARLLGASAARGDVLTFLDCHCECHEGWLEPLLQRIHEEES
AVVCPVIDVIDWNTFEYLGNSGEPQIGGFDWRLVFTWHTVPERERIRMQS
PVDVIRSPTMAGGLFAVSKKYFEYLGSYDTGMEVWGGENLEFSFRIWQCG
GVLETHPCSHVGHFSPSKLPTPRNKALANSVRAAEVWMDEFKELYYHRNP
RARLEPFGDVTERKQLRDKLQCKDFKWFLETVYPELHVPEDRPGFFGMLQ
NKGLTDYCFDYNPPDENQIVGHQVILYLCHGMGQNQFFEYTSQKEIRYNT
HQPEGCIAVEAGMDTLIMHLCEETAPENQKFILQEDGSLFHEQSKKCVQA
ARKESSDSFVPLLRDCTNSDHQKWFFKERML

The coding region for human polypeptide GalNAc-T13 has been submitted to GenBank/EBI Data Bank and assigned accession number AR153422.

Human GalNAc-T13 DNA sequence:

(SEQ ID NO: 59)
ATGCTCCTAAGGAAGCGATACAGGCACAGACCATGCAGACTCCAGTTCCT
CCTGCTGCTCCTGATGCTGGGATGCGTCCTGATGATGGTGGCGATGTTGC
ACCCTCCCCACCACACCCTGCACCAGACTGTCACAGCCCAAGCCAGCAAG
CACAGCCCTGAAGCCAGGTACCGCCTGGACTTTGGGGAATCCCAGGATTG
GGTACTGGAAGCTGAGGATGAGGGTGAAGAGTACAGCCCTCTGGAGGGCC
TGCCACCCTTTATCTCACTGCGGGAGGATCAGCTGCTGGTGGCCGTGGCC
TTACCCCAGGCCAGAAGGAACCAGAGCCAGGGCAGGAGAGGTGGGAGCTA
CCGCCTCATCAAGCAGCCAAGGAGGCAGGATAAGGAAGCCCCAAAGAGGG
ACTGGGGGGCTGATGAGGACGGGGAGGTGTCTGAAGAAGAGGAGTTGACC
CCGTTCAGCCTGGACCCACGTGGCCTCCAGGAGGCACTCAGTGCCCGCAT
CCCCCTCCAGAGGGCTCTGCCCGAGGTGCGGCACCCACTGTGTCTGCAGC
AGCACCCTCAGGACAGCCTGCCCACAGCCAGCGTCATCCTCTGTTTCCAT
GATGAGGCCTGGTCCACTCTCCTGCGGACTGTACACAGCATCCTCGACAC
AGTGCCCAGGGCCTTCCTGAAGGAGATCATCCTCGTGGACGACCTCAGCC
AGCAAGGACAACTCAAGTCTGCTCTCAGCGAATATGTGGCCAGGCTGGAG
GGGGTGAAGTTACTCAGGAGCAACAAGAGGCTGGGTGCCATCAGGGCCCG
GATGCTGGGGCCACCAGAGCCACCGGGGATGTGCTCGTCTTCATGGATG
CCCACTGCGAGTGCCACCCAGGCTGGCTGGAGCCCTCCTCAGCAGAATA
GCTGGTGACAGGAGCCGAGTGGTATCTCCGGTGATAGATGTGATTGACTG
GAAGACTTTCCAGTATTACCCCTCAAAGGACCTGCAGCGTGGGGTGTTGG
ACTGGAAGCTGGATTTCCACTGGGAACCTTTGCCAGAGCATGTGAGGAAG
GCCCTCCAGTCCCCATAAGCCCCATCAGGAGCCCTGTGGTGCCCGGAGA
GGTGGTGGCCATGGACAGACATTACTTCCAAAACACTGGAGCGTATGACT

-continued

```
CTCTTATGTCGCTGCGAGGTGGTGAAAACCTCGAACTGTCTTTCAAGGCC
TGGCTCTGTGGTGGCTCTGTTGAAATCCTTCCCTGCTCTCGGGTAGGACA
CATCTACCAAAATCAGGATTCCCATTCCCCCCTCGACCAGGAGGCCACCC
TGAGGAACAGGGTTCGCATTGCTGAGACCTGGCTGGGGTCATTCAAAGAA
ACCTTCTACAAGCATAGCCCAGAGGCCTTCTCCTTGAGCAAGGCTGAGAA
GCCAGACTGCATGGAACGCTTGCAGCTGCAAAGGAGACTGGGTTGTCGGA
CATTCCACTGGTTTCTGGCTAATGTCTACCCTGAGCTGTACCCATCTGAA
CCCAGGCCCAGTTTCTCTGGAAAGCTCCACAACACTGGACTTGGGCTCTG
TGCAGACTGCCAGGCAGAAGGGGACATCCTGGGCTGTCCCATGGTGTTGG
CTCCTTGCAGTGACAGCCGGCAGCAACAGTACCTGCAGCACACCAGCAGG
AAGGAGATTCACTTTGGCAGCCCACAGCACCTGTGCTTTGCTGTCAGGCA
GGAGCAGGTGATTCTTCAGAACTGCACGGAGGAAGGCCTGGCCATCCACC
AGCAGCACTGGGACTTCCAGGAGAATGGGATGATTGTCCACATTCTTTCT
GGGAAATGCATGGAAGCTGTGGTGCAAGAAAACAATAAAGATTTGTACCT
GCGTCCGTGTGATGGAAAAGCCCGCCAGCAGTGGCGTTTTGACCAGATCA
ATGCTGTGGATGAACGATGA.
```

Human GalNAc-T13 amino acid sequence:

(SEQ ID NO: 60)
MLLRKRYRHRPCRLQFLLLLLMLGCVLMMVAMLHPPHHTLHQTVTAQASK
HSPEARYRLDFGESQDWVLEAEDEGEEYSPLEGLPPFISLREDQLLVAVA
LPQARRNQSQGRRGGSYRLIKQPRRQDKEAPKRDWGADEDGEVSEEEELT
PFSLDPRGLQEALSARIPLQRALPEVRHPLCLQQHPQDSLPTASVILCFH
DEAWSTLLRTVHSILDTVPRAFLKEIILVDDLSQQGQLKSALSEYVARLE
GVKLLRSNKRLGAIRARMLGATRATGDVLVFMDAHCECHPGWLEPLLSRI
AGDRSRVVSPVIDVIDWKTFQYYPSKDLQRGVLDWKLDFHWEPLPEHVRK
ALQSPISPIRSPVVPGEVVAMDRIIYFQNTGAYDSLMSLRGGENLELSFK
AWLCGGSVEILPCSRVGHIYQNQDSHSPLDQEATLRNRVRIAETWLGSFK
ETFYKHSPEAFSLSKAEKPDCMERLQLQRRLGCRTFHWFLANVYPELYPS
EPRPSFSGKLHNTGLGLCADCQAEGDILGCPMVLAPCSDSRQQQYLQHTS
RKEIHFGSPQHLCFAVRQEQVILQNCTEEGLAIHQQHWDFQENGMIVHIL
SGKCMEAVVQENNKDLYLRPCDGKARQQWRFDQINAVDER

The coding region for human polypeptide GalNAc-T14 has been submitted to GenBank/EBI Data Bank and assigned accession number AJ505991.

Human GalNAc-T14 DNA sequence:

(SEQ ID NO: 61)
```
ATGAGGAGATTTGTCTACTGCAAGGTGGTTCTAGCCACTTCGCTGATGTG
GGTTCTTGTTGATGTCTTCTTACTGCTGTACTTCAGTGAATGTAACAAAT
GTGATGACAAGAAGGAGAGATCTCTGCTGCCTGCATTGAGGGCTGTTATT
TCAAGAAACCAAGAAGGGCCAGGAGAAATGGGAAAAGCTGTGTTGATTCC
TAAAGATGACCAGGAGAAAATGAAAGAGCTGTTTAAAATCAATCAGTTTA
ACCTTATGGCCAGTGATTTGATTGCCCTTAATAGAAGTCTGCCAGATGTA
AGATTAGAAGGATGTAAGACAAAAGTCTACCCTGATGAACTTCCAAACAC
AAGTGTAGTCATTGTGTTTCATAATGAAGCTTGGAGCACTCTCCTTAGAA
CTGTTTACAGTGTGATAAATCGTTCCCCACACTATCTACTCTCAGAGGTC
ATCTTGGTAGATGATGCCAGTGAAAGAGATTTTCTCAAGTTGACATTAGA
GAATTACGTGAAAAATTTAGAAGTGCCAGTAAAAATTATTAGGATGGAAG
AACGCTCTGGGTTAATACGTGCCCGTCTTCGAGGAGCAGCTGCTTCAAAA
GGGCAGGTCATAACTTTTCTTGATGCACACTGTGAATGCACGTTAGGATG
GCTGGAGCCTTTGCTGGCAAGAATAAAGGAAGACAGGAAAACGGTTGTCT
GCCCTATCATTGATGTGATTAGTGATGATACTTTTGAATATATGGCTGGG
TCAGACATGACTTATGGGGGTTTTAACTGGAAACTGAATTTCCGCTGGTA
TCCTGTTCCCCAAAGAGAAATGGACAGGAGGAAAGGAGACAGAACATTAC
CTGTCAGGACCCCTACTATGGCTGGTGGCCTATTTTCTATTGACAGAAAC
TACTTTGAAGAGATAGGAACTTACGATGCAGGAATGGATATCTGGGGTGG
AGAGAATCTTGAAATGTCTTTTAGGATTTGGCAATGTGGAGGCTCCTTGG
AGATTGTTACTTGCTCCCATGTTGGTCATGTTTTCGGAAGGCAACTCCA
TACACTTTTCCTGGTGGCACTGGTCATGTCATCAACAAGAACAACAGGAG
ACTGGCAGAAGTTTGGATGGATGAATTTAAAGATTTCTTCTACATCATAT
CCCCAGGTGTTGTCAAAGTGGATTATGGAGATGTGTCAGTCAGAAAAACA
CTAAGAGAAATCTGAAGTGTAAGCCCTTTTCTTGGTACCTAGAAAACAT
CTATCCGGACTCCCAGATCCCAAGACGTTATTACTCACTTGGTGAGATAA
GAAATGTTGAAACCAATCAGTGTTTAGACAACATGGGCCGCAAGGAAAAT
GAAAAAGTGGGTATATTCAACTGTCATGGTATGGGAGGAAATCAGGTATT
TTCTTACACTGCTGACAAAGAAATCCGAACCGATGACTTGTGCTTGGATG
TTTCTAGACTCAATGGACCTGTAATCATGTTAAAATGCCACCATATGAGA
GGAAATCAGTTATGGGAATATGATGCTGAGAGACTCACGTTGCGACATGT
TAACAGTAACCAATGTCTCGATGAACCTTCTGAAGAAGACAAAATGGTGC
CTACAATGCAGGACTGTAGTGGAAGCAGATCCCAACAGTGGCTGCTAAGG
AACATGACCTTGGGCACATGA
```

Human GalNAc-T14 amino acid sequence:

(SEQ ID NO: 62)
MRRFVYCKVVLATSLMWVLVDVFLLLYFSECNKCDDKKERSLLPALRAVI
SRNQEGPGEMGKAVLIPKDDQEKMKELFKINQFNLMASDLIALNRSLPDV
RLEGCKTKVYPDELPNTSVVIVFHNEAWSTLLRTVYSVINRSPHYLLSEV
ILVDDASERDFLKLTLENYVKNLEVPVKIIRMEERSGLIRARLRGAAASK
GQVITFLDAHCECTLGWLEPLLARIKEDRKTVVCPIIDVISDDTFEYMAG
SDMTYGGFNWKLNFRWYPVPQREMDRRKGDRTLPVRTPTMAGGLFSIDRN
YFEEIGTYDAGMDIWGGENLEMSFRIWQCGGSLEIVTCSHVGHVFRKATP
YTFPGGTGHVINKNNRRLAEVWMDEFKDFFYIISPGVVKVDYGDVSVRKT

-continued

LRENLKCKPFSWYLENIYPDSQIPRRYYSLGEIRNVETNQCLDNMGRKEN

EKVGIFNCHGMGGNQVFSYTADKEIRTDDLCLDVSRLNGPVIMLKCHHMR

GNQLWEYDAERLTLRHVNSNQCLDEPSEEDKMVPTMQDCSGSRSQQWLLR

NMTLGT

The coding region for human polypeptide GalNAc-T15 has been submitted to GenBank/EBI Data Bank and assigned accession number Y09324.

Human GalNAc-T15 DNA sequence:

(SEQ ID NO: 63)
ATGCGGCGCCTGACTCGTCGGCTGGTTCTGCCAGTCTTCGGGGTGCTCTG

GATCACGGTGCTGCTGTTCTTCTGGGTAACCAAGAGGAAGTTGGAGGTGC

CGACGGGACCTGAAGTGCAGACCCCTAAGCCTTCGGACGCTGACTGGGAC

GACCTGTGGGACCAGTTTGATGAGCGGCGGTATCTGAATGCCAAAAAGTG

GCGCGTTGGTGACGACCCCTATAAGCTGTATGCTTTCAACCAGCGGGAGA

GTGAGCGGATCTCCAGCAATCGGGCCATCCCGGACACTCGCCATCTGAGA

TGCACACTGCTGGTGTATTGCACGGACCTTCCACCCACTAGCATCATCAT

CACCTTCCACAACGAAGCCCGCTCCACGCTGCTCAGGACCATCCGCAGTG

TATTAAACCGCACCCCTACGCATCTGATCCGGGAAATCATATTAGTGGAT

GACTTCAGCAATGACCCTGATGACTGTAAACAGCTCATCAAATTGCCCAA

GGTGAAATGCTTGCGCAATAATGAACGGCAAGGTCTGGTCCGGTCCCGGA

TTCGGGGCGCTGACATCGCCCAGGGCACCACTCTGACTTTCCTCGACAGC

CACTGTGAGGTGAACAGGGACTGGCTCCAGCCTCTGTTGCACAGGGTCAA

AGAAGACTACACGCGGGTGGTGTGCCCTGTGATCGATATCATTAACCTGG

ACACCTTCACCTACATCGAGTCTGCCTCGGAGCTCAGAGGGGGGTTTGAC

TGGAGCCTCCACTTCCAGTGGGAGCAGCTCTCCCCAGAGCAGAAGCTCGG

CGCCTGGACCCCACGGAAGCCCATCAGGACTCCTATCATAGCTGGAGGGC

TCTTCGTGATCGACAAAGCTTGGTTTGATTACCTGGGGAAATATGATATG

GACATGGACATCTGGGGTGGGGAGAACTTTGAAATCTCCTTCCGAGTGTG

GATGTGCGGGGGCAGCCTAGAGATCGTCCCCTGCAGCCGAGTGGGGCACG

TCTTCCGGAAGAAGCACCCCTACGTTTTCCCTGATGGAAATGCCAACACG

TATATAAAGAACACCAAGCGGACAGCTGAAGTGTGGATGGATGAATACAA

GCAATACTATTACGCTGCCCGGCCATTCGCCCTGGAGAGGCCCTTCGGGA

ATGTTGAGAGCAGATTGGACCTGAGGAAGAATCTGCGCTGCCAGAGCTTC

AAGTGGTACCTGGAGAATATCTACCCTGAACTCAGCATCCCCAAGGAGTC

CTCCATCCAGAAGGGCAATATCCGACAGAGACAGAAGTGCCTGGAATCTC

AAAGGCAGAACAACCAAGAAACCCCAAACCTAAAGTTGAGCCCCTGTGCC

AAGGTCAAAGGCGAAGATGCAAAGTCCCAGGTATGGGCCTTCACATACAC

CCAGCAGATCCTCCAGGAGGAGCTGTGCCTGTCAGTCATCACCTTGTTCC

CTGGCGCCCCAGTGGTTCTTGTCCTTTGCAAGAATGGAGATGACCGACAG

CAATGGACCAAAACTGGTTCCCACATCGAGCACATAGCATCCCACCTCTG

CCTCGATACAGATATGTTCGGTGATGGCACCGAGAACGGCAAGGAAATCG

TCGTCAACCCATGTGAGTCCTCACTCATGAGCCAGCACTGGGACATGGTG

AGCTCTTGAGGACCCCTGCCAGAAGCAGCAAGGGCCATGGGGTGGTGCTT

CCCTGGACCAGAACAGACTGGAAACTGGGCAGCAAGCAGCCTGCAACCAC

CTCAGACATCCTGGACTGGGAGGTGGAGGCAGAGCCCCCCAGGACAGGAG

CAACTGTCTCAGGGAGGACAGAGGAAAACATCACAAGCCAATGGGCTCA

AAGACAAATCCCACATGTTCTCAAGGCCGTTAAGTTCCAGTCCTGGCCAG

TCATTCCCTGA

Human GalNAc-T15 amino acid sequence:

(SEQ ID NO: 64)
MRRLTRRLVLPVFGVLWITVLLFFWVTKRKLEVPTGPEVQTPKPSDADWD

DLWDQFDERRYLNAKKWRVGDDPYKLYAFNQRESERISSNRAIPDTRHLR

CTLLVYCTDLPPTSIIITFHNEARSTLLRTIRSVLNRTPTHLIREIILVD

DFSNDPDDCKQLIKLPKVKCLRNNERQGLVRSRIRGADIAQGTTLTFLDS

HCEVNRDWLQPLLHRVKEDYTRVVCPVIDIINLDTFTYIESASELRGGFD

WSLHFQWEQLSPEQKLGAWTPRKPIRTPIIAGGLFVIDKAWFDYLGKYDM

DMDIWGGENFEISFRVWMCGGSLEIVPCSRVGHVFRKKHPYVFPDGNANT

YIKNTKRTAEVWMDEYKQYYYAARPFALERPFGNVESRLDLRKNLRCQSF

KWYLENIYPELSIPKESSIQKGNIRQRQKCLESQRQNNQETPNLKLSPCA

KVKGEDAKSQVWAFTYTQQILQEELCLSVITLFPGAPVVLVLCKNGDDRQ

QWTKTGSHLEHIASHLCLDTDMFGDGTENGKEIVVNPCESSLMSQHWDMV

SS

The coding region for human polypeptide GalNAc-T16 has been submitted to GenBank/EBI Data Bank and assigned accession number AJ505951.

Human GalNAc-T16 DNA sequence:

(SEQ ID NO: 65)
ATGAGGAAGATCCGCGCCAATGCCATCGCCATCCTGACCGTAGCCTGGAT

CCTGGGCACTTTCTACTACTTATGGCAGGACAACCGAGCCCACGCAGCAT

CCTCCGGCGGCCGGGCGCGCAGAGGGCAGGCAGGAGGTCGGAGCAGCTC

CGCGAGGACCGCACCATCCCGCTCATTGTGACAGGAACTCCCTCGAAAGG

CTTTGATGAGAAGGCCTACCTGTCGGCCAAGCAGCTGAAGGCTGGAGAGG

ACCCCTACAGACAGCACGCCTTCAACCAGCTGGAGAGTGACAAGCTGAGC

CCAGACCGGCCCATCCGGGACACCCGCCATTACAGCTGCCCATCTGTGTC

CTACTCCTCGGACCTGCCAGCCACCAGCGTCATCATCACCTTCCACAATG

AGGCCCGTTCCACCCTGCTGCGCACAGTGAAGAGTGTCCTGAACCGAACT

CCTGCCAACTTGATCCAGGAGATCATTTTAGTGGATGACTTCAGCTCAGA

TCCGGAAGACTGTCTACTCCTGACCAGGATCCCCAAGGTCAAGTGCCTGC

GCAATGATCGGCGGGAAGGGCTGATCCGGTCCCGAGTGCGTGGGGCGGAC

GTGGCTGCAGCTACCGTTCTCACCTTTCTGGATAGCCACTGCGAAGTGAA

CACCGAGTGGCTGCCGCCCATGCTGCAGCGGGTGAAGGAGGACCACACCC

-continued

```
GCGTGGTGAGTCCCATCATTGATGTCATCAGTCTGGATAATTTTGCCTAC

CTTGCAGCATCTGCTGACCTTCGTGGAGGGTTCGACTGGAGCCTGCATTT

CAAGTGGGAGCAGATCCCTCTTGAGCAGAAGATGACCCGGACAGACCCCA

CCAGGCCCATAAGGACGCCTGTCATAGCTGGAGGAATCTTCGTGATCGAC

AAGTCCTGGTTTAACCACTTGGGAAAGTATGATGCCCAGATGGACATCTG

GGGGGGAGAGAATTTTGAGCTCTCCTTCAGGGTGTGGATGTGTGGTGGCA

GTCTGGAGATCGTCCCCTGCAGCCGGGTGGGCCATGTCTTCAGGAAACGG

CACCCCTACAACTTCCCTGAGGGTAATGCCCTCACCTACATCAGGAATAC

TAAGCGCACTGCAGAAGTGTGGATGGATGAATACAAGCAATACTACTATG

AGGCCCGGCCCTCGGCCATCGGGAAGGCCTTCGGCAGTGTGGCTACGCGG

ATAGAGCAGAGGAAGAAGATGAACTGCAAGTCCTTCCGCTGGTACCTGGA

GAACGTCTACCCAGAGCTCACGGTCCCCGTGAAGGAAGCACTCCCCGGCA

TCATTAAGCAGGGGGTGAACTGCTTAGAATCTCAGGGCCAGAACACAGCT

GGTGACTTCCTGCTTGGAATGGGGATCTGCAGAGGGTCTGCCAAGAACCC

GCAGCCCGCCCAGGCATGGCTGTTCAGTGACCACCTCATCCAGCAGCAGG

GGAAGTGCCTGGCTGCCACCTCCACCTTAATGTCCTCCCCTGGATCCCCA

GTCATACTGCAGATGTGCAACCCTAGAGAAGGCAAGCAGAAATGGAGGAG

AAAAGGATCTTTCATCCAGCATTCAGTCAGTGGCCTCTGCCTGGAGACAA

AGCCTGCCCAGCTGGTGACCAGCAAGTGTCAGGCTGACGCCCAGGCCCAG

CAGTGGCAGCTGTTGCCACACACATGA
```

Human GalNAc-T16 amino acid sequence:

(SEQ ID NO: 66)
MRKIRANAIAILTVAWILGTFYYLWQDNRAHAASSGGRGAQRAGRRSEQL

REDRTIPLIVTGTPSKGFDEKAYLSAKQLKAGEDPYRQHAFNQLESDKLS

PDRPIRDTRHYSCPSVSYSSDLPATSVIITFHNEARSTLLRTVKSVLNRT

PANLIQEIILVDDFSSDPEDCLLLTRIPKVKCLRNDRREGLIRSRVRGAD

VAAATVLTFLDSHCEVNTEWLPPMLQRVKEDIITRVVSPIIDVISLDNFA

YLAASADLRGGFDWSLHFKWEQIPLEQKMTRTDPTRPIRTPVIAGGIFVI

DKSWFNIILGKYDAQMDIWGGENFELSFRVWMCGGSLEIVPCSRVGHVFR

KRHPYNFPEGNALTYIRNTKRTAEVWMDEYKQYYYEARPSAIGKAFGSVA

TRIEQRKKMNCKSFRWYLENVYPELTVPVKEALPGIIKQGVNCLESQGQN

TAGDFLLGMGICRGSAKNPQPAQAWLFSDHLIQQQGKCLAATSTLMSSPG

SPVILQMCNPREGKQKWRRKGSFIQHSVSGLCLETKPAQLVTSKCQADAQ

AQQWQLLPHT

Additional homologous polypeptide GalNAc-transferase genes have been identified and cloning and expression are in progress, and it follows from the descriptions that similar methods as outlined above will yield soluble secreted proteins for study. Expression constructs may have immunoaffinity tags or purification tags at the N-terminal and/or C-terminal region. These may include myc, FLAG, HIS, GST, and other (Stratagene, Qiagen, Amersham Biosciences).

Soluble secreted expression constructs of GalNAc-transferase lectin domains were prepared from the GalNAc-transferase expression constructs described above by PCR using primer pairs as listed Table V below.

TABLE V

Primers used for amplification of GalNac-transferase lectin domains

```
GalNAc-T1 lectin domain:
T1LECFOR:  5'-CAAAGGAAGCTTATGGAGATATATCGTCAAGAG-3'           (SEQ ID NO: 67)
T1LECREV:  5'-GCAAGCTCGAGGCGGCCGCTCAGAATATTTCTGGAAGGGTGAC-3'  (SEQ ID NO: 68)
GalNAc-T2 lectin domain:
T2LECFOR:  5'-CAAGGAAGCTTCTTATGGAAATATTCAGAGCAGATTG-3'        (SEQ ID NO: 69)
T2LECREV:  5'-GCAAGCTCGAGGCGGCCGCCTACTGCTGCAGGTTGAGC-3'       (SEQ ID NO: 70)
GalNAc-T3 lectin domain:
T3LECFOR:  5'-CAAGGAAGCTTCATTTGGTGATCTTTCAAAAGATTT-3'         (SEQ ID NO: 71)
T3LECREV:  5'-GCAAGCTCGAGGCGGCCGCAGGAACACTTAATCATTTTGG-3'     (SEQ ID NO: 72)
GalNAc-T4 lectin domain:
T4LECFOR:  5'-AGAAAAGAAGCTTATGGTGATATTTCTG-3'                 (SEQ ID NO: 73)
E4HC307:   5'-AGCGGATCCGACGAAGTGCTGTTGTGCT-3'                 (SEQ ID NO: 74)
GalNAc-T5 lectin domain:
T5LECFOR:  5'-CAAGGAAGCTTTAGATGTTGGCAACCTCACCCAGC-3'          (SEQ ID NO: 75)
T5LECREV:  5'-GCAAGCTCGAGGCGGCCGCAAGCATCAGTTACACTTCAGGCTTC-3' (SEQ ID NO: 76)
GalNAc-T6 lectin domain:
T6LECFOR:  5'-CAAGGAAGCTTCCTTCGGTGACATTTCGGAACG-3'            (SEQ ID NO: 77)
T6LECREV:  5'-GCAAGCTCGAGGCGGCCGCTGGGTCCTAGACAAAGAGCC-3'      (SEQ ID NO: 78)
GalNAc-T7 lectin domain:
T7LECFOR:  5'-AGAAAAGAAGCTTATGGGGATATATCGGAGCTG-3'            (SEQ ID NO: 79)
T7LECREV:  5'-GCAAGCTCGAGGCGGCCGCTCTCTAAACACTATGGATGTTATTC-3' (SEQ ID NO: 80)
GalNAc-T8 lectin domain:
T8LECFOR:  5'-CAAGGAAGCTTTTGGAGACGTTTCTTCCAGAATG-3'           (SEQ ID NO: 81)
T8LECREV:  5'-GCAAGCTCGAGGCGGCCGCTCACTGCCTGTTGCTCTGACCCC-3'   (SEQ ID NO: 82)
GalNAc-T9 lectm domain:
T9LECFOR:  5'-CAAGGAAGCTTTCCGGGACGTGTCTCAGAGACTG-3'           (SEQ ID NO: 83)
T9LECREV:  5'-GCAAGCTCGAGGCGGCCGCTCAGTGCCGTGCGTGTTTGATTCC-3'  (SEQ ID NO: 84)
GalNAc-T10 lectin domain:
```

TABLE V-continued

Primers used for amplification of GalNac-transferase lectin domains

```
T10LECFOR:  5'-CAAGGAAGCTTCCGCTGGGGATGTCGCAGTCCAG-3'            (SEQ ID NO: 85)
T10LECREV:  5'-GCAAGCTCGAGGCGCCCCCTCAGTTCCTATTGAATTTTTCC-3'     (SEQ ID NO: 86)
GalNAc-T11 lectin domain:
T11LECFOR:  5'-CAACCAAGCTTGCAATATCAGTGAGCGTGTGG-3'              (SEQ ID NO: 87)
T11LECREV:  5'-GCAAGCTCGAGGCGGCCGCCCACCTTAACCTTCCAAATGC-3'      (SEQ ID NO: 88)
GalNAc-T12 lectin domain:
T12LECFOR:  5'-CAAGGAAGCTTGGGATGTGACAGAGAGGAAG-3'               (SEQ ID NO: 89)
T12LECREV:  5'-GCAAGCTCGAGGCGGCCGCTCATAACATCCCCTCTTTGAAGAACC-3' (SEQ ID NO: 90)
GalNAc-T13 lectin domain:
T13LECFOR:  5'-CAAGGAAGCTTCTGAGAAGCCAGACTGCATGG-3'              (SEQ ID NO: 91)
T13LECREV:  5'-GCAAGCTCCAGGCCCCCGCTCATCGTTCATCCACACCATTC-3'     (SEQ ID NO: 92)
GalNAc-T14 lectin domain:
T14LECFOR:  5'-CAAGGAAGCTTATGCAGATGTGTCAGTCAGAAAAAC-3'          (SEQ ID NO: 93)
T14LECREV:  5'-GCAAGCTCGAGGCGGCCGCTCATGTGCCCAAGGTCATGTTCC-3'    (SEQ ID NO: 94)
GalNAc-T15 lectin domain:
T15LECFOR:  5'-CAACGAACCTTTCCGCAATGTTGAGAGCAGATTG-3'            (SEQ ID NO: 95)
T15LECREV:  5'-GCAAGCTCCAGCCGGCCGCTCAAGAACTCACCATCTCCCAGTG-3'   (SEQ ID NO: 96)
GalNAc-T16 lectin domain:
T16LECFOR:  5'-CAAGGAAGCTTGCAGTGTGGCTACGCGGATAGAGCAGAGG-3'      (SEQ ID NO: 97)
T16LECREV:  5'-GCAAGCTCGAGGCCGCCGCTCATGTGTGTGGCAACAGCTCCC-3'    (SEQ ID NO: 98)
```

PCR amplifications were performed with 10 ng GalNAc-transferase plasmid DNA as template and High Fidelity PCR kit (Roche) with conditions recommended by the manufacturer. Amplified products were digested with HindIII and XhoI and inserted into the HindIII/XhoI site of pBKS-HistagI. All constructs were fully sequenced. Tagged lectin domain constructs were excised with NotI and sub-cloned into the NotI site of pAcGP67-A Baculo expression vector.

The exact borders of the lectin domains and the catalytic units have not been defined, but multiple sequence alignment analysis (FIG. 4) was used to predict the most likely borders and these were used for design of PCR primers as listed in Table V. DNA and amino acid sequences of preferred constructs of GalNAc-transferase lectin domains and their construct design include the following (Table VI):

Table VI: DNA and Amino Acid Sequences of GalNAc-transferase Lectin Domains.

GalNAc-T1 Lectin Domain:

The lectin domain polypeptide sequence comprises amino acid residues 393-559 of GALNT1 (GALNT1 nucleotide sequence accession number is AJ505952)

T1 LECTIN DNA Sequence:

(SEQ ID NO: 99)
AAAGAAGCTTATGGAGATATATCGTCAAGAGTTGGTCTAAGACACAAACT

ACAATGCAAACCTTTTTCCTGGTACCTAGAGAATATATATCCTGATTCTC

AAATTCCACGTCACTATTTCTCATTGGGAGAGATACGAAATGTGGAAACG

AATCAGTGTCTAGATAACATGGCTAGAAAAGAGAATGAAAAAGTTGGAAT

TTTTAATTGCCATGGTATGGGGGGTAATCAGGTTTTCTCTTATACTGCCA

ACAAAGAAATTAGAACAGATGACCTTTGCTTGGATGTTTCCAAACTTAAT

GGCCCAGTTACAATGCTCAAATGCCACCACCTAAAAGGCAACCAACTCTG

GGAGTATGACCCAGTGAAATTAACCCTGCAGCATGTGAACAGTAATCAGT

GCCTGGATAAAGCCACAGAAGAGGATAGCCAGGTGCCCAGCATTAGAGAC

TGCAATGGAAGTCGGTCCCAGCAGTGGCTTCTTCGAAACGTCACCCTTCC

AGAAATATTCTGA-stop

T1 LECTIN Amino Acid Sequence:

(SEQ ID NO: 100)
YGDISSRVGLRTIKLQCKPFSWYLENIYPDSQIPRHYFSLGEIRNVETNQ

CLDNMARKENEKVGIFNCHGMGGNQVFSYTANKEIRTDDLCLDVSKLNGP

VTMLKCHHLKGNQLWEYDPVKLTLQHVNSNQCLDKATEEDSQVPSIRDCN

GSRSQQWLLRNVTLPEIF*

GalNAc-T2 Lectin Domain:

The lectin domain polypeptide sequence comprises amino acid residues 408-571 of GALNT2 (GALNT2 nucleotide sequence accession number is X85019).

T2 LECTIN DNA Sequence:

(SEQ ID NO: 101)
TATCCAGAGTTAAGGGTTCCAGACCATCAGGATATAGCTTTTGGGGCCTT

GCAGCAGGGAACTAACTGCCTCGACACTTTGGGACACTTTGCTGATGGTG

TGGTTGGAGTTTATGAATGTCACAATGCTGGGGGAAACCAGGAATGGGCC

TTGACGAAGGAGAAGTCGGTGAAGCACATGGATTTGTGCCTTACTGTGGT

GGACCGGGCACCGGGCTCTCTTATAAAGCTGCAGGGCTGCCGAGAAAATG

ACAGCAGACAGAAATGGGAACAGATCGAGGGCAACTCCAAGCTGAGGCAC

GTGGGCAGGAACCTGTGCCTGGACAGTCGCACGGCCAAGAGCGGGGGCCT

AAGCGTGGAGGTGTGTGGCCCGGCCCTTTCGCAGCAGTGGAAGTTCACGC

TCAACCTGCAGCAGTAG-Stop

T2 LECTIN Amino Acid Sequence:

(SEQ ID NO: 102)
YPELRVPDHQDIAFGALQQGTNCLDTLGHFADGVVGVYECHNAGGNQEWA

LTKEKSVKHMDLCLTVVDRAPGSLIKLQGCRENDSRQKWEQIEGNSKLRH

VGSNLCLDSRTAKSGGLSVEVCGPALSQQWKFTLNLQQ*

GalNAc-T3 Lectin Domain:

The lectin domain polypeptide sequence comprises amino acid residues 467-633 of GALNT3 (GALNT3 nucleotide sequence accession number is AJ505954).

T3 LECTIN DNA Sequence:

(SEQ ID NO: 103)
TCATTTGGTGATCTTTCAAAAAGATTTGAAATAAAACACCGTCTTCGGTG

TAAAAATTTTACATGGTATCTGAACAACATTTATCCAGAGGTGTATGTGC

CAGACCTTAATCCTGTTATATCTGGATACATTAAAAGCGTTGGTCAGCCT

CTATGTCTGGATGTTGGAGAAAACAATCAAGGAGGCAAACCATTAATTAT

GTATACATGTCATGGACTTGGGGGAAACCAGTACTTTGAATACTCTGCTC

AACATGAAATTCGGCACAACATCCAGAAGGAATTATGTCTTCATGCTGCT

CAAGGTCTCGTTCAGCTGAAGGCATGTACCTACAAAGGTCACAAGACAGT

TGTCACTGGAGAGCAGATATGGGAGATCCAGAAGGATCAACTTCTATACA

ATCCATTCTTAAAAATGTGCCTTTCAGCAAATGGAGAGCATCCAAGTTTA

GTGTCATGCAACCCATCAGATCCACTCCAAAAATGGATACTTAGCCAAAA

TGATTAA-stop

T3 LECTIN Amino Acid Sequence:

(SEQ ID NO: 104)
FGDLSKRFEIKHRLRCKNFTWYLNNIYPEVYVPDLNPVISGYIKSVGQPL

CLDVGENNQGGKPLIMYTCHGLGGNQYFEYSAQHEIRHNIQKELCLHAAQ

GLVQLKACTYKGHKTVVTGEQIWEIQKDQLLYNPFLKMCLSANGEIIPSL

VSCNPSDPLQKWILSQND*

GalNAc-T4 Lectin Domain:

The lectin domain polypeptide sequence comprises amino acid residues 405-578 of GALNT4 (GALNT4 nucleotide sequence accession number is YO8564).

T4 LECTIN DNA Sequence:

(SEQ ID NO: 105)
GAGGATAGACCAGGCTGGCATGGGGCTATTCGCAGTAGAGGGATCTCGTC

TGAATGTTTAGATTATAATTCTCCTGACAACAACCCCACAGGTGCTAACC

TTTCACTGTTTGGATGCCATGGTCAAGGAGGCAATCAATTCTTTGAATAT

ACTTCAAACAAAGAAATAAGGTTTAATTCTGTGACAGAGTTATGTGCAGA

GGTACCTGAGCAAAAAATTATGTGGGAATGCAAAATTGTCCCAAAGATG

GGTTCCCTGTACCAGCAAACATTATTTGGCATTTTAAAGAAGATGGAACT

ATTTTTCACCCACACTCAGGACTGTGTCTTAGTGCTTATCGGACACCGGA

GGGCCGACCTGATGTACAAATGAGAACTTGTGATGCTCTAGATAAAAATC

AAATTTGGAGTTTTGAGAAATAG-stop

T4 LECTIN Amino Acid Sequence (SEQ ID NO: 106)
AYGDISERKLLRERLRCKSFDWYLKNVFPNLHVPEDRPGWHGAIRSRGIS

SECLDYNSPDNNPTGANLSLFGCHGQGGNQFFEYTSNKEIRFNSVTELCA

EVPEQKNYVGMQNCPKDGFPVPANIIWHFKEDGTIFHPHSGLCLSAYRTP

EGRPDVQMRTCDALDKNQIWSFEK*

GalNAc-T5 Lectin Domain:

The lectin domain polypeptide sequence comprises amino acid residues 486-653 of GALTN5 (GALTN5 nucleotide sequence accession number is AJ505956).

T5 LECTIN DNA Sequence (SEQ ID NO: 107)
TTAGATGTTGGCAACCTCACCCAGCAAAGGGAGCTGCGAAAGAAACTGAA

GTGCAAAAGTTTCAAATGGTACTTGGAGAATGTCTTTCCTGACTTAAGGG

CTCCCATTGTGAGAGCTAGTGGTGTGCTTATTAATGTGGCTTTGGGTAAA

TGCATTTCCATTGAAAACACTACAGTCATTCTGGAAGACTGCGATGGGAG

CAAAGAGCTTCAACAATTTAATTACACCTGGTTAAGACTTATTAAATGTG

GAGAATGGTGTATAGCCCCCATCCCTGATAAAGGAGCCGTAAGGCTGCAC

CCTTGTGATAACAGAAACAAAGGGCTAAAATGGCTGCATAAATCAACATC

AGTCTTTCATCCAGAACTGGTGAATCACATTGTTTTTGAAAACAATCAGC

AATTATTATGCTTGGAAGGAAATTTTTCTCAAAAGATCCTGAAAGTAGCT

GCCTGTGACCCAGTGAAGCCATATCAAAAGTGGAAATTTGAAAAATATTA

TGAAGCCTGA-stop

T5 LECTIN Amino Acid Sequence (SEQ ID NO: 108)
DVGNLTQQRELRKKLKCKSFKWYLENVFPDLRAPIVRASGVLINVALGKC

ISIENTTVILEDCDGSKELQQFNYTWLRLIKCGEWCIAPIPDKGAVRLHP

CDNRNKGLKWLHKSTSVFHPELVNHIVFENNQQLLCLEGNFSQKILKVAA

CDPVKPYQKWKFEKYYEA*

GalNAc-T6 Lectin Domain:

The lectin polypeptide sequence comprises amino acid residues 458-622 of GALNT6 (GALNT6 nucleotide sequence accession number is AJ133523).

T6 LECTIN DNA Sequence:

(SEQ ID NO: 109)
TCCTTCGGTGACATTTCGGAACGACTGCAGCTGAGGGAACAACTGCACTG

TCACAACTTTTCCTGGTACCTGCACAATGTCTACCCAGAGATGTTTGTTC

CTGACCTGACGCCCACCTTCTATGGTGCCATCAAGAACCTCGGCACCAAC

CAATGCCTGGATGTGGGTGAGAACAACCGCGGGGGGAAGCCCCTCATCAT

GTACTCCTGCCACGGCCTTGGCGGCAACCAGTACTTTGAGTACACAACTC

AGAGGGACCTTCGCCACAACATCGCAAAGCAGCTGTGTCTACATGTCAGC

AAGGGTGCTCTGGGCCTTGGGAGCTGTCACTTCACTGGCAAGAATAGCCA

-continued

```
GGTCCCCAAGGACGAGGAATGGGAATTGGCCCAGGATCAGCTCATCAGGA

ACTCAGGATCTGGTACCTGCCTGACATCCCAGGACAAAAAGCCAGCCATG

GCCCCCTGCAATCCCAGTGACCCCCATCAGTTGTGGCTCTTTGTCTAG- stop
```

T6 LECTIN Amino Acid Sequence:

(SEQ ID NO: 110)
```
SFGDISERLQLREQLHCHNFSWYLHNVYPEMFVPDLTPTEYGAIKNLGTN

QCLDVGENNRGGKPLIMYSCHGLGGNQYFEYTTQRDLRHNIAKQLCLHVS

KGALGLGSCHFTGKNSQVPKDEEWELAQDQLIRNSGSGTCLTSQDKKPAM

APCNPSDPHQLWLFV*
```

GalNAc-T7 Lectin Domain:

The lectin domain polypeptide sequence comprises amino acid residues 492-657 of GALNT7 (GALNT7 nucleotide sequence accession number is AJ505958).

T7 LECTIN DNA Sequence:

(SEQ ID NO: 111)
```
TATGGGGATATATCGGAGCTGAAAAAATTTCGAGAAGATCACAACTGCCA

AAGTTTTAAGTGGTTCATGGAAGAAATAGCTTATGATATCACCTCACACT

ACCCTTTGCCACCCAAAAATGTTGACTGGGAGAAATCAGAGGCTTCGAA

ACTGCTTACTGCATTGATAGCATGGGAAAAACAAATGGAGGCTTTGTTGA

ACTAGGACCCTGCCACAGGATGGGAGGGAATCAGCTTTTCAGAATCAATG

AAGCAAATCAACTCATGCAGTATGACCAGTGTTTGACAAAGGGAGCTGAT

GGATCAAAAGTTATGATTACACACTGTAATCTAAATGAATTTAAGGAATG

GCAGTACTTCAAGAACCTGCACAGATTTACTCATATTCCTTCAGGAAAGT

GTTTAGATCGCTCAGAGGTCCTGCATCAAGTATTCATCTCCAATTGTGAC

TCCAGTAAAACGACTCAAAAATGGGAAATGAATAACATCCATAGTGTT

TAG-stop
```

T7 LECTIN Amino Acid Sequence:

(SEQ ID NO: 112)
```
YGDISELKKFREDHNCQSFKWFMEEIAYDITSHYPLPPKNVDWGEIRGFE

TAYCIDSMGKTNGGFVELGPCHRMGGNQLFRINEANQLMQYDQCLTKGAD

GSKVMITHCNLNEFKEWQYFKNLHRFTHIPSGKCLDRSEVLHQVFISNCD

SSKTTQKWEMNNIHSV*
```

GalNAc-T8 Lectin Domain:

The lectin domain polypeptide sequence comprises amino acid residues 459-637 of GALNT8 (GALNT8 nucleotide sequence accession number is AJ505959).

T8 LECTIN DNA Sequence:

(SEQ ID NO: 113)
```
GACGTTTCTTCCAGAATGGCACTCCGGGAAAAACTGAAATGTAAAACTTT

TGACTGGTACCTGAAAAATGTTTATCCACTCTTGAAGCCACTCCACACCA

TCGTGGGCTATGGAAGAATGAAAAACCTATTGGATGAAAATGTCTGCTTG

GATCAGGGACCCGTTCCAGGCAACACCCCCATCATGTATTACTGCCATGA

ATTCAGCTCACAGAATGTCTACTATCACCTAACTGGGGAGCTCTATGTGG

GACAACTGATTGCAGAGGCCAGTGCTAGTGATCGCTGCCTGACAGACCCT

GGCAAGGCGGAGAAGCCCACCTTAGAACCATGCTCCAAGGCAGCTAAGAA

TAGACTGCATATATATTGGGATTTTAAACCGGGAGGAGCTGTCATAAACA

GAGATACCAAGCGGTGTCTGGAGATGAAGAAGGATCTTTTGGGTAGCCAC

GTGCTTGTGCTCCAGACCTGTAGCACGCAAGTGTGGGAAATCCAGCACAC

TGTCAGAGACTGGGGTCAGACCAACAGCCAGTGA
```

T8 LECTIN Amino Acid Sequence:

(SEQ ID NO: 114)
```
FGDVSSRMALREKLKCKTFDWYLKNVYPLLKPLHTIVGYGRMKNLLDENV

CLDQGPVPGNTPIMYYCHEFSSQNVYYHLTGELYVGQLIAEASASDRCLT

DPGKAEKPTLEPCSKAAKNRLHIYWDFKPGGAVINRDTKRCLEMKKDLLG

SHVLVLQTCSTQVWEIQHTVRDWGQTNSQ
```

GalNAc-T9 Lectin Domain:

The lectin domain polypeptide sequence comprises amino acid residues 427-603 of GALNT9 (GALNT9 nucleotide sequence accession number is AJ505960).

T9 LECTIN DNA Sequence:

(SEQ ID NO: 115)
```
TTCGGGGACGTGTCTGAGAGGCTGGCCCTGCGTCAGAGGCTGAAGTGTCG

CAGCTTCAAGTGGTACCTGGAGAACGTGTACCCGGAGATGAGGGTCTACA

ACAACACCCTCACGTACGGAGAGGTGAGAAACAGCAAAGCCAGTGCCTAC

TGTCTGGACCAGGGAGCGGAGGACGGCGACCGGGCGATCCTCTACCCCTG

CCACGGGATGTCCTCCCAGCTGGTGCGGTACAGCGCTGACGGCCTGCTGC

AGCTGGGGCCTCTGGGCTCCACAGCCTTCTTGCCTGACTCCAAGTGTCTG

GTGGATGACGGCACGGGCCGCATGCCCACCCTGAAGAGGTGTGAGGATGT

GGCGCGGCCAACACAGCGGCTGTGGGACTTCACCCAGAGTGGCCCCATTG

TGAGCCGGGCCACGGGCCGCTGCCTGGAGGTGGAGATGTCCAAAGATGCC

AACTTTGGGCTCCGGCTGGTGGTACAGAGGTGCTCGGGGCAGAAGTGGAT

GATCAGAAACTGGATCAAACACGCACGGCAC**TGA-stop**
```

T9 LECTIN Amino Acid Sequence:

(SEQ ID NO: 116)
```
FGDVSERLALRQRLKCRSFKWYLENVYPEMRVYNNTLTYGEVRNSKASAY

CLDQGAEDGDRAILYPCHGMSSQLVRYSADGLLQLGPLGSTAFLPDSKCL
```

-continued
VDDGTGRMPTLKRCEDVARPTQRLWDFTQSGPIVSRATGRCLEVEMSKDA

NFGLRLVVQRCSGQKWMIRNWIKHARH*

GalNAc-T10 Lectin Domain:
The lectin domain polypeptide sequence comprises amino acid residues 417-603 of GALNT10 (GALNT10 nucleotide sequence accession number is AJ505950).

T10 LECTIN DNA Sequence:

(SEQ ID NO: 117)
GCTGGGGATGTCGCAGTCCAGAAAAAGCTCCGCAGCTCCCTTAACTGCAA

GAGTTTCAAGTGGTTTATGACGAAGATAGCCTGGGACCTGCCCAAATTCT

ACCCACCCGTGGAGCCCCCGGCTGCAGCTTGGGGGGAGATCCGAAATGTG

GGCACAGGGCTGTGTGCAGACACAAAGCACGGGGCCTTGGGCTCCCCACT

AAGGCTAGAGGGCTGCGTCCGAGGCCGTGGGGAGGCTGCCTGGAACAACA

TGCAGGTATTCACCTTCACCTGGAGAGAGGACATCCGGCCTGGAGACCCC

CAGCACACCAAGAAGTTCTGCTTTGATGCCATTTCCCACACCAGCCCTGT

CACGCTGTACGACTGCCACAGCATGAAGGGCAACCAGCTGTGGAAATACC

GCAAAGACAAGACCCTGTACCACCCTGTCAGTGGCAGCTGCATGGACTGC

AGTGAAAGTGACCATAGGATCTTCATGAACACCTGCAACCCATCCTCTCT

CACCCAGCAGTGGCTGTTTGAACACACCAACTCAACAGTCTTGGAAAAAT

TCAATAGGAACTGA

T10 LECTIN Amino Acid Sequence:

(SEQ ID NO: 118)
AGDVAVQKKLRSSLNCKSFKWFMTKJAWDLPKFYPPVEPPAAAWGEIRNV

GTGLCADTKHGALGSPLRLEGCVRGRGEAAWNNMQVFTFTWREDIRPGDP

QHTKKFCFDAISHTSPVTLYDCITSMKGNQLWKYRKDKTLYHPVSGSCMD

CSESDHRIFMNTCNPSSLTQQWLFEHTNSTVLEKFNRN*

GalNAc-T11 Lectin Domain:
The lectin domain polypeptide sequence comprises amino acid residues 492-608 of GALNT11 (GALNT11 nucleotide sequence accession number is Y12434).

T11 LECTIN DNA Sequence:

(SEQ ID NO: 119)
TGCAATATCAGTGAGCGTGTGGAACTGAGAAAGAAGTTGGGCTGTAAATC

ATTTAAATGGTATTTGGATAATGTATACCCAGAGATGCAGATATCTGGGT

CCCACGCCAAACCCCAACAACCCATTTTTGTCAATAGAGGGCCAAAACGA

CCCAAAGTCCTTCAACGTGGAAGGCTCTATCACCTCCAGACCAACAAATG

CCTGGTGGCCCAGGGCCGCCCAAGTCAGAAGGGAGGTCTCGTGGTGCTTA

AGGCCTGTGACTACAGTGACCCAAATCAGATCTGGATCTATAATGAAGAG

CATGAATTGGTTTTAAATAGTCTCCTTTGTCTAGATATGTCAGAGACTCG

CTCATCAGACCCGCCACGGCTCATGAAATGCCACGGGTCAGGAGGATCCC

AGCAGTGGACCTTTGGGAAAAACAATCGGCTATACCAGGTGTCGGTTGGA

CAGTGCCTGAGAGCAGTGGATCCCCTGGGTCAGAAGGGCTCTGTCGCCAT

GGCGATCTGCGATGGCTCCTCTTCACAGCAGTGGCATTTGGAAGGTTAA

T11 LECTIN Amino Acid Sequence:

(SEQ ID NO: 120)
NISERVELRKKLGCKSFKWYLDNVYPEMQISGSHAKPQQPIFVNRGPKRP

KVLQRGRLYHLQTNKCLVAQGRPSQKGGLVVLKACDYSDPNQIWIYNEEH

ELVLNSLLCLDMSETRSSDPPRLMKCHGSGGSQQWTFGKNNRLYQVSVGQ

CLRAVDPLGQKGSVAMAICDGSSSQQWHLEG*

GalNAc-T12 Lectin Domain:
The lectin domain polypeptide sequence comprises amino acid residues 428-581 of GALNT12 (GALNT12 nucleotide sequence accession number is AJ505963).

T12 LECTIN DNA Sequence:

(SEQ ID NO: 121)
TGGGATGTGACAGAGAGGAAGCAGCTCCGGGACAAGCTCCAGTGTAAAGA

CTTCAAGTGGTTCTTGGAGACTGTGTATCCAGAACTGCATGTGCCTGAGG

ACAGGCCTGGCTTCTTCGGGATGCTCCAGAACAAAGGACTAACAGACTAC

TGCTTTGACTATAACCCTCCCGATGAAAACCAGATTGTGGGACACCAGGT

CATTCTGTACCTCTGTCATGGGATGGGCCAGAATCAGTTTTTCGAGTACA

CGTCCCAGAAAGAAATACGCTATAACACCCACCAGCCTGAGGGCTGCATT

GCTGTGGAAGCAGGAATGGATACCCTTATCATGCATCTCTGCGAAGAAAC

TGCCCCAGAGAATCAGAAGTTCATCTTGCAGGAGGATGGATCTTTATTTC

ACGAACAGTCCAAGAAATGTGTCCAGGCTGCGAGGAAGGAGTCGAGTGAC

AGTTTCGTTCCACTCTTACGAGACTGCACCAACTCGGATCATCAGAAATG

GTTCTTCAAAGAGCGCATGTTATGA

T12 LECTIN Amino Acid Sequence:

(SEQ ID NO: 122)
DVTERKQLRDKLQCKDFKWFLETVYPELHVPEDRPGFFGMLQNKGLTDYC

FDYNPPDENQIVGHQVILYLCHGMGQNQFFEYTSQKELRYNTHQPEGCIA

VEAGMDTLIMHLCEETAPENQKFILQEDGSLFHEQSKKCVQAARKESSDS

FVPLLRDCTNSDHQKWFFKERML*

GalNAc-T13 Lectin Domain:
The lectin domain polypeptide sequence comprises amino acid residues 466-639 of GALNT13 (GALNT13 nucleotide sequence accession number is AJ505964).

T13 LECTIN DNA Sequence:

(SEQ ID NO: 123)
TCTGAGAAGCCAGACTGCATGGAACGCTTGCAGCTGCAAAGGAGACTGGG

TTGTCGGACATTCCACTGGTTTCTGGCTAATGTCTACCCTGAGCTGTACC

CATCTGAACCCAGGCCCAGTTTCTCTGGAAAGCTCCACAACACTGGACTT

-continued

```
GGGCTCTGTGCAGACTGCCAGGCAGAAGGGGACATCCTGGGCTGTCCCAT
GGTGTTGGCTCCTTGCAGTGACAGCCGGCAGCAACAGTACCTGCAGCACA
CCAGCAGGAAGGAGATTCACTTTGGCAGCCCACAGCACCTGTGCTTTGCT
GTCAGGCAGGAGCAGGTGATTCTTCAGAACTGCACGGAGGAAGGCCTGGC
CATCCACCAGCAGCACTGGGACTTCCAGGAGAATGGGATGATTTTTGTAC
CTGCGTCCGTGTGATGGAAAAGCCCGCCAGCAGTGGCGTTTTGACCAGAT
CAATGCTGTGGATGAACGATGA
```

T13 LECTIN Amino Acid Sequence:

(SEQ ID NO: 124)
```
EKPDCMERLQLQRRLGCRTFHWFLANVYPELYPSEPRPSFSGKLHNTGLG
LCADCQAEGDILGCPMVLAPCSDSRQQQYLQHTSRKEIHFGSPQHLCFAV
RQEQVILQNCTEEGLAIHQQHWDFQENGMIVHILSGKCMEAVVQENNKDL
YLRPCDGKARQQWRFDQINAVDER*
```

GalNAc-T14 Lectin Domain:
  The lectin domain polypeptide sequence comprises amino acid residues 352-516 of GALNT14 (GALNT14 nucleotide sequence accession number is AJ505991).

T14 LECTIN DNA Sequence:

(SEQ ID NO: 125)
```
TATGGAGATGTGTCAGTCAGAAAAACACTAAGAGAAAATCTGAAGTGTAA
GCCCTTTTCTTGGTACCTAGAAAACATCTATCCGGACTCCCAGATCCCAA
GACGTTATTACTCACTTGGTGAGATAAGAAATGTTGAAACCAATCAGTGT
TTAGACAACATGGGCCGCAAGGAAAATGAAAAAGTGGGTATATTCAACTG
TCATGGTATGGGAGGAAATCAGGTATTTTCTTACACTGCTGACAAAGAAA
TCCGAACCGATGACTTGTGCTTGGATGTTTCTAGACTCAATGGACCTGTA
ATCATGTTAAAATGCCACCATATGAGAGGAAATCAGTTATGGGAATATGA
TGCTGAGAGACTCACGTTGCGACATGTTAACAGTAACCAATGTCTCGATG
AACCTTCTGAAGAAGACAAAATGGTGCCTACAATGCAGGACTGTAGTGGA
AGCAGATCCCAACAGTGGCTGCTAAGGAACATGACCTTGGGCACATGA
```

T14 LECTIN Amino Acid Sequence:

(SEQ ID NO: 126)
```
YGDVSVRKTLRENLKCKPFSWYLENIYPDSQIPRRYYSLGEIRNVETNQC
LDNMGRKENEKVGIFNCHGMGGNQVFSYTADKEIRTDDLCLDVSRLNGPV
IMLKCHHMRGNQLWEYDAERLTLRHVNSNQCLDEPSEEDKMVPTMQDCSG
SRSQQWLLRNMTLGT*
```

GalNAc-T15 Lectin Domain:
  The lectin domain polypeptide sequence comprises amino acid residues 382-552 of GALNT15 (GALNT15 nucleotide sequence accession number is AJ505966).

T15 LECTIN DNA Sequence:

(SEQ ID NO: 127)
```
TCGGGAATGTTGAGAGCAGATTGGACCTGAGGAAGAATCTGCGCTGCCAG
AGCTTCAAGTGGTACCTGGAGAATATCTACCCTGAACTCAGCATCCCCAA
GGAGTCCTCCATCCAGAAGGGCAATATCCGACAGAGACAGAAGTGCCTGG
AATCTCAAAGGCAGAACAACCAAGAAACCCCAAACCTAAAGTTGAGCCCC
TGTGCCAAGGTCAAAGGCGAAGATGCAAAGTCCCAGGTATGGGCCTTCAC
ATACACCCAGAAGATCCTCCAGGAGGAGCTGTGCCTGTCAGTCATCACCT
TGTTCCCTGGCGCCCCAGTGGTTCTTGTCCTTTGCAAGAATGGAGATGAC
CGACAGCAATGGACCAAAACTGGTTCCCACATCGAGCACATAGCATCCCA
CCTCTGCCTCGATACAGATATGTTCGGTGATGGCACCGAGAACGGCAAGG
AAATCGGCGTCAACCCATGTGAGTCCTCACTCATGAGCCAGCACTGGGAC
ATGGTGAGTTCTTGAG
```

T15 LECTIN Amino Acid Sequence:

(SEQ ID NO: 128)
```
FGNVESRLDLRKNLRCQSFKWYLENIYPELSIPKESSLQKGNIRQRQKCL
ESQRQNNQETPNLKLSPCAKVKGEDAKSQVWAFTYTQKILQEELCLSVIT
LFPGAPVVLVLCKNGDDRQQWTKTGSHIEHIASHLCLDTDMFGDGTENGK
EIGVNPCESSLMSQHWDMVSS*
```

GalNAc-T16 Lectin Domain:
  The lectin domain polypeptide sequence comprises amino acid residues 396-558 of GALNT16 (GALNT16 nucleotide sequence accession number is AJ505951).

T16 LECTIN DNA Sequence:

(SEQ ID NO: 129)
```
AGTGTGGCTACGCGGATAGAGCAGAGGAAGAAGATGAACTGCAAGTCCTT
CCGCTGGTACCTGGAGAACGTCTACCCAGAGCTCACGGTCCCCGTGAAGG
AAGCACTCCCCGGCATCATTAAGCAGGGGGTGAACTGCTTAGAATCTCAG
GGCCAGAACACAGCTGGTGACTTCCTGCTTGGAATGGGGATCTGCAGAGG
GTCTGCCAAGAACCCGCAGCCCGCCCAGGCATGGCTGTTCAGTGACCACC
TCATCCAGCAGCAGGGGAAGTGCCTGGCTGCCACCTCCACCTTAATGTCC
TCCCCTGGATCCCCAGTCATACTGCAGATGTGCAACCCTAGAGAAGGCAA
GCAGAAATGGAGGAGAAAAGGATCTTTCATCCAGCATTCAGTCAGTGGCC
TCTGCCTGGAGACAAAGCCTGCCCAGCTGGTGACCAGCAAGTGTCAGGCT
GACGCCCAGGCCCAGCAGTGGCAGCTGTTGCCACACACATGA
```

T16 LECTIN Amino Acid Sequence:

(SEQ ID NO: 130)
```
SVATRIEQRKKMNCKSFRWYLENVYPELTVPVKEALPGIIKQGVNCLESQ
GQNTAGDFLLGMGICRGSAKNPQPAQAWLFSDHLIQQQGKCLAATSTLMS
```

-continued

SPGSPVILQMCNPREGKQKWRRKGSFIQHSVSGLCLETKPAQLVTSKCQA
DAQAQQWQLLPHT*

In this Example we have defined minimal sequences of functional lectin domains based on multiple sequence alignments. It is clear that changes in the length of sequences used may not affect functionality of the lectins. Such changes could constitute, for example, plus or minus 10-20 amino acid residues of the GalNAc-transferase sequence at their amino or carboxy termini. For example, the GalNAc-T1 lectin domain may comprise 10-20 fewer amino acid residues at its carboxy and/or amino termini than shown in Table VI's T1 lectin domain sequence; i.e. the T1 lectin domain could, for example, stretch from amino acids 403-549 of the GALNT1 sequence, or, for example, from amino acids 413-539 of the GALNT1 sequence. Additionally, the GalNAc-T1 lectin domain may comprise 10-20 more amino acid residues at its carboxy and/or amino termini than shown in Table VI's T1 lecton domain sequence; i.e. the T1 lectin domain could, for example, stretch from amino acids 383-569 of the GALNT1 sequence, or, for example, from amino acids 373-579 of the GALNT1 sequence.

Sf9 cells were co-transfected with pACGP67-GalNAc-transferase soluble expression constructs and Baculo-Gold™ DNA (Pharmingen) as previously described[27]. Briefly, 0.4 µg DNA was mixed with 0.1 µg Baculo-Gold DNA and co-transfected in Sf9 cells in 24-well plates. Ninety-six hours post-transfection recombinant virus was amplified in 6-well plates at dilutions of 1:10 and 1:50. Titer of amplified virus was estimated by titration in 24-well plates. For large scale production and purification of recombinant secreted enzymes and lectins the amplified vira were used to infect High Five™ cells grown in serum free medium (Invitrogen) in upright roller bottles shaking at 140 rpm in 27° C. waterbaths. Recombinant proteins were purified by nickel NiTA chromatography using nickel agarose (Qiagen) as recommended by the manufacturer or by consecutive chromatographies on Amberlite, S-sepharose and Mono-S as previously described[28].

Example 8

Direct Binding Assay for Determination of Carbohydrate Specificity of Polypeptide GalNAc-tranferase Lectins Using Soluble GalNAc-transferase Enzymes GalNAc-transferase lectins were previously shown to direct GalNAc-glycopeptide substrate specificities of some GalNAc-transferase[42]. The mechanism by which the lectin domains mediate this specificity is unknown but the finding that the monosaccharide GalNAc selectively inhibits GalNAc-glycopeptide specificity of some isoforms suggested that the lectin domains were involved in an interaction with the substrate at least partly through the GalNAc-residue. Nevertheless, it has not been possible in the past despite many different attempts to demonstrate direct binding of the enzyme protein or fragments hereof to glycopeptides or saccharides[42]. In this Example a binding assay using HIS-tagged affinity purified and biotinylated secreted enzyme was developed. HIS-tagged secreted human GalNAc-T2 and -T4 were prepared from pAC-GP67-T2-sol and pAC-GP67-T4-sol cDNA[8, 26] by PCR as described in Example 7.

Secreted GalNAc-T2 and -T4 and variant proteins were obtained from infected High Five™ cells crown in serum-free medium (Invitrogen) in upright roller bottles shaken 140 rpm in waterbaths at 27° C. Purification of the recombinant proteins were performed by iminodiacetic acid metal affinity chromatography (IMAC) $Ni^{2+}$-charged (QIAGEN). Elution was achieved with 250 mM imidazole in 50 mM sodium phosphate (pH 8.0) and 500 mM NaCl. In some cases, recombinant proteins were purified by consecutive ionexchange chromatographies as developed and described previously[28], before final purification by $Ni^{2+}$-chromatography. Proteins eluted were dialyzed three times against PBS (10 mM sodium phosphate (pH 7.4) 150 mM NaCl) and concentrated by centrifugal filter device (Millipore; 10,000 kDa cut off). Purity was analyzed by SDS-PAGE under reducing conditions, and stained for proteins with Coomassie Blue R 250.

Protein biotinylation was made as previously reported[62]. The pH of 1 ml purified protein (0.3 mg/ml) in PBS was adjusted to pH 9 with 1 M NaOH and 40 µl N-hydroxy-succinimidobiotin (Sigma) dissolved in DMF (10 mg/ml) was added. The solution was mixed end-over-end for 2 hours at room temperature, and dialyzed three times against PBS and an equal volume of glycerol was added. The biotinylated proteins were stored at −20° C. in 50% glycerol until use.

Glycosylation of MUC1 peptides (0.1 mM) was made in 20 mM cacodylate buffer (pH 8.0), 10 mM $MnCl_2$, 10 mM UDP-GalNAc, and 20 µg purified polypeptide GalNAc-T1 or -T2 with or without subsequent glycosylation with GalNAc-T4 at 37° C. during overnight. Glycopeptides were purified by C-18 reverse phase HPLC. Peptides were custom synthesized by Neosystems (Strasbourg). Biotinylated Helix Pomatia lectin (HPA) was from KemEnTec (Denmark). Anti-MUC1 HMFG2 monoclonal antibody was a generous gift from Joyce Taylor-Papadimitriou. Anti-MUC1 SE5 monoclonal antibody was developed by immunizing Balb/c mice with 60-mer MUC1 tandem repeat peptide glycosylated with 5 moles GalNAc per repeat. Monoclonal antibodies to the lectin domains of human GalNAc-T2 and -T4 were developed as previously described[8, 63].

Direct binding ELISA assay was developed as follows: Polystyrene microtiter plates (Maxisorb, Nunc, Denmark) were coated with peptides or enzymatically glycosylated glycopeptides in PBS overnight at 4° C. Plates were washed and blocked with 0.1% Tween20 and 0.2% BSA in PBS for 1 h at room temperature, followed by incubation with biotinylated proteins in PBS with 0.05% Tween20 for 2 h at room temperature. After four washes with PBS, plates were incubated with 1:2,000 dilution streptavidin-HRP (Sigma) in PBS for 30 min at room temperature and washed four times with PBS. Development was performed with 0.5 mg/ml o-phenylenediamine and 0.02% $H_2O_2$ at room temperature for 15 min, and reaction stopped by adding 100 µl/well of 0.5 N $H_2SO_4$. Competitive inhibition assays were done at end-point titers of GalNAc-transferase proteins with one hour preincubations with inhibitor.

In initial binding experiments it was determined that secreted GalNAc-T2 and -T4 could bind their peptides substrates in the presence of 5 mM UDP and $Mn^{++}$ (may be substituted with other divalent cation), whereas no binding was observed in the absence or when 10 mM EDTA was included. This correlates with our findings that GalNAc-T2 can be purified on an acceptor substrate peptide in the presence of UDP and $Mn^{++}$, and can be eluted by removing UDP in EDTA[26]. This binding is mediated by the catalytic unit of the enzyme, which exposes the acceptor-binding pocket only in the presence of UDP and Mn++, predicted by the ordered catalytic reaction.

In order to selectively evaluate the binding characteristics of the lectin domain, assays were carried out in the absence of UDP and Mn++. Significant binding to GalNAc-peptides was found for both GalNAc-T2 and -T4 (FIG. 6).

We have shown that GalNAc-T4 with a single amino acid change in the lectin domain selectively impairs the GalNAc-glycopeptide substrate specificity of this enzyme[42]. In agreement with this the lectin mutated enzyme protein did not bind GalNAc-glycopeptides. The binding to GalNAc-glycopeptides were unaffected by Ca++ and EDTA further confirming that the catalytic units of the enzyme proteins are not involve in binding.

We have shown that GalNAc and GalNAcα-benzyl inhibit the GalNAc-glycopeptide substrate specificity of GalNAc-T4[42]. Lectins and antibodies to carbohydrates usually recognize the anomeric configuration of the sugar structures they bind. However, surprisingly, both GalNAc-T2 and -T4 exhibit equal inhibition with GalNAcα-benzyl (Sigma) and GalNAcβ-benzyl (NuRx, Alberta Research Council (FIG. 7)[70, 71]. Similar results were obtained with other aryl derivatives.

The methods described in this Example utilize recombinant polypeptide GalNAc-transferases in binding assays and excludes potential binding activity through the catalytic unit. It is clear that recombinant polypeptide GalNAc-transferases with mutations that inactivates the binding activity of the catalytic unit can be used, as well as any truncation of the enzyme protein that eliminate the binding activity of the catalytic unit.

While this binding assay establishes a method for screening for inhibitors of lection mediated binding mediated through the lectins of human GalNAc-T2 and GalNAc-T4, it is clear that the same method with modifications can be applied to all animal and mammalian polypeptide GalNAc-transferases with a functional lectin domain. The ligand target used in this Example is a GalNAc-MUC1 glycopeptide produced enzymatically from synthetic peptides. It is clear that GalNAc-glycopeptides based on any number of peptides with GalNAc attached can be used as target for the binding assay. It is also clear that the assay developed can be modified to accommodate high throughput screening by any assay method available in the prior art that can detect and quantify binding between the polypeptide GalNAc-transferase mediated through its lectin domain and a suitable ligand.

Example 9

Direct Binding Assay for Determination of Carbohydrate Specificity of Polypeptide GalNAc-tranferase Lectins Using Truncated GalNAc-transferase Lectin Domains In Example 8 it was established that secreted soluble enzymatically active proteins of GalNAc-T2 and -T4 bind GalNAc-MUC1 glycopeptides, and that GalNAc could inhibit the binding. The catalytic unit of polypeptide GalNAc-transferase can interact and bind acceptor substrate peptides and possible glycopeptides[52], however, binding studies without donor substrates (UDP), and in the presence of EDTA to chelate $Mn^{2+}$, suggested that the binding was not mediated through the catalytic unit. In this Example direct binding to GalNAc-glycopeptides through the lectin domains of polypeptide GalNAc-transferases GalNAc-T2 and -T4 was established. Attempts to express C-terminal truncated GalNAc-transferase proteins failed due to low secretion rate presumable related to folding problems and intracellular degradation. Similar phenomenon has recently been reported for GalNAc-T1[45]. Numerous attempts to express isolated lectin domains in insect cells and *P. pastoris* have failed due to low expression and apparent degradation. As described in Example 8 successful expression was finally achieved with constructs truncated as described in Table V using an expression vector with a N-terminal HIS tag and thrombin cleavage site as well as a T7 tag. HIS-tagged truncated GalNAc-T2 and -T4 lectins were expressed and purified. Lectins were used in binding studies directly or after biotinylation as described in Example 8. In binding studies using lectins without biotinylation antibodies to the HIS-tag and the T7-tag, or in some experiments antibodies raised to GalNAc-T2 and -T4 enzymes were used to detect binding.

Inhibition experiments were used to further define the binding specificity of GalNAc-T2 and -T4 secreted soluble enzymes as well as lectin domains compared to Helix Pomatia lectin (Table VII). GalNAcα- and GalNAcβ-aryl structures inhibited binding of both enzymes and isolated lectins at comparable levels. In contrast, Helix Pomatia showed strong preference for GalNAcα-derivatives. Gal and other sugars had no inhibitory effect. Interestingly, UDP-GalNAc was not a significant inhibitor of the GalNAc-transferase lectin binding, but a strong inhibitor of Helix Pomatia binding. structures.

| Carbohydrates | T2ld | sT2 | T4ld | sT4 | HPA |
|---|---|---|---|---|---|
| Glc | >100[a] | >100 | >100 | >100 | >100 |
| GlcNAc | >100 | >100 | >100 | >100 | 8 |
| BzlαGlcNAc | >100 | >100 | >100 | >100 | 2 |
| BzlβGlcNAc | >100 | >100 | >100 | >100 | >20 |
| Gal | >100 | >100 | >100 | 50 | >100 |
| MeαGal | >100 | >100 | >100 | 50 | >100 |
| MeβGal | >100 | >100 | >100 | 40 | >100 |
| GalNAc | 37 | 15 | 5 | 1 | 2 |
| BzlαGalNAc | 20 | 15 | 5 | 1 | 0.5 |
| PhlαGalNAc | 15 | 5 | 5 | 1 | 1 |
| oNPαGalNAc | 12 | 7 | 5 | 0.5 | 1.5 |
| oNPβGalNAc | >12 | 10 | 8 | 1 | >20 |
| pNPαGalNAc | >10 | >10 | 10 | 1 | 2 |
| pNPβGalNAc | >10 | >10 | 8 | 0.8 | >20 |
| UDPαGalNAc | >100 | 65 | 50 | 30 | 2 |
| UDP | >100 | >100 | >100 | >100 | >100 |
| Lactose | >100 | >100 | >100 | >100 | ND |
| EDTA | >10 | >10 | >10 | >10 | >10 |

[a]Concentration (mM) required for 50% inhibition (IC50).
ND, not determined.

While this binding assay establishes a method for screening for inhibitors of isolated human GalNAc-T2 and GalNAc-T4 lections, it is clear that the same method with modifications can be applied to all animal and mammalian polypeptide GalNAc-transferase lectins. The ligand target used in this Example is a GalNAc-MUC1 glycopeptide produced enzymatically from synthetic peptides. It is clear that GalNAc-glycopeptides based on any number of peptides with GalNAc attached can be used as target for the binding assay. It is also clear that the assay developed can be modified to accommodate high through put screening by any assay method available in the prior art that can detect and quantify binding between the isolated lectin and a suitable ligand.

The methods described in this Example utilize recombinant GalNAc-transferase lectins in binding assays which excludes potential binding activity through the catalytic unit.

It is clear that recombinant polypeptide GalNAc-transferases with mutations that inactivates the binding activity of the catalytic unit can be used, as well as any truncation of the enzyme protein that eliminate the binding activity of the catalytic unit.

Example 10

Establishment of Cell Line Model Systems for Cell Surface Expression of Mucin and Secreted Mucin—Stably Transfected CHO and CHO ldlD Cells Cell lines and expression constructs: Wild type Chinese Hamster Ovary cells (CHO) and the glycosylation deficient mutant cell line CHO ldlD[53] were stably transfected with a full coding MUC1 construct (MUC1F, supplied by M. A. Hollingsworth, Neb., USA) containing 32 tandem repeats using the pCDNA3 vector (Invitrogen). A secreted MUC1 construct (MUC1-IgGHIS) was generate by insertion of mouse IgGγ2a domain fused to 6×histidine tag at the BsU36I site downstream of the tandem repeat region of MUC1F[64]. Cells were generally grown in Hams F12 containing 10% Fetal Bovine Serum at 37° C. at 5% $CO_2$, and plated 12-24 hours prior to transfection in 6 well plates and grown to approximately 50% confluency. One hour before transfection cells were washed in serum free medium Optimem (Invitrogen) and cells were transfected with 1-2 µg DNA using the Lipofectamine plus reagent (Invitrogen) in a total volume of 1 mL as recommended by the supplier. Three hours after the transfection one mL of Hams F12 containing 10% Fetal Bovine Serum was added and cells grown 24-48 hours before medium was replaced with 2 mL Hams F12 containing 10% Fetal Bovine Serum. Two to three days after transfection cells were trypzinized and plated in 75 mL T-flasks or in 24/96 well microtiter plates in the same medium containing the appropriate selection agent (1 mg/mL G418 or 0.4 mg/mL Zeocin). Selection medium was changed twice weekly until clones appeared. The medium used for CHO ldlD cells included 1 mM GalNAc and 0.1 mM Gal. Transfectant clones were selected by immunocytology with anti-MUC1 antibodies and SDS-PAGE western blot analysis to demonstrate cell surface expression and secretion of MUC1.

Immunocytology: Two different procedures were applied: i) For general screening purposes, cells grown in plates or flasks were trypzinized, washed in saline, and airdried on multiwell coverslides. Slides were fixed in ice-cold acetone and stained with monoclonal antibodies and FITC-conjugated rabbit anti-mouse Ig as previously described[50]. ii) For analysis of cell surface expression, cells were seeded in 6 well plates and grown for 6 hours in Hams F12 medium with serum until approximately 30-50% subconfluent. Medium was hereafter replaced with Optimem supplemented with 1.0 mM GalNAc and 0.1 mM Gal and cells grown for 18 to 42 hours. Cells were washed once in PBS (phosphate buffered saline without Calcium and Magnesium) and subsequently fixed in 2 ml 3% paraformaldehyde at 25° C. for 20 min followed by three washes with PBS. Free aldehyde groups were quenched by incubating in 2 mL 50 mM Ammonium Chloride in PBS for 10 min, followed by three washes with PBS and three washes with 5 min incubations each with PBS containing 0.2% Fish Skin Gelatin (Sigma). Immunostaining of cells was performed by incubation with monoclonal antibodies for 40 min at 25° C., followed by three washes with PBS and three washes of 5 min each with PBS containing 0.2% Fish Skin Gelatin. Subsequently, cells were incubated with FITC-conjugated rabbit anti-mouse Ig (Dako, F261) diluted 1:150 in PBS containing 0.2% Fish Skin Gelatin) for 20 min at 25° C., followed by the same washing procedure, after which wells were cut out of plates and mounted with glycerol as for glass slides.

Characterization of wild type and MUC1 stable transfectant CHO cells: Several representative clones expressing the full coding or secreted MUC1 construct were selected and characterized for expression of MUC1 as well as O-glycosylation. Wild type CHO/MUC1F-clone1 expressed MUC1 at the cell surface as detected by anti-MUC1 monoclonal antibodies on non-permeabilized cells, while wild type CHO/MUC1sol-cloneC4 only was labeled weakly at the surface. Staining with a panel of anti-MUC1 antibodies of permeabilized cells showed intracellular accumulation of MUC1 detected by HMFG2 (general anti-MUC1 reactive,[65]), SM3 (reactive with cancer-associated MUC1,[65]), VU-4H5 (reactive with low density O-glycosylated MUC1,[66]), VU-2G7 (reactive with high density O-glycosylated MUC1,[66]), and a novel antibody 5E5 reactive exclusively with STn/Tn-glycosylated MUC1 glycoforms. In contrast, staining of non-permeabilized cells were only reactive with the anti-MUC1 antibodies HMFG2, SM3 and weakly VU-2G7. Analysis of O-glycosylation using a panel of anti-carbohydrate monoclonal antibodies revealed that wild type CHO cells label very weakly with anti-T antibodies (HH8, 3C9,[68]) at the surface after neuraminidase treatment, while untreated cells are negative indicating that wild type CHO cells express very little O-glycoproteins and the glycosylation is mainly of sialylated core 1 structure (ST) (FIG. 8). Antibodies to Tn (1E3, 5F4,[68]) were weakly reactive without and with neuraminidase treatment and antibodies to STn (TKH2, 3F1,[68]) were negative. Staining with the lectins PNA (T), HPA (Tn), SNA (α2,6sialic acid) and MAA (α2,3sialic acid) were in agreement except the finding of weak reactivity with SNA indicating some presence of α2,6 linked sialic acids which may be derived from N-linked or O-linked glycans. These results demonstrate that the main form of O-glycosylation found on MUC1 expressed in wild type CHO is the sialyl-T structure as found for other recombinant glycoproteins[69].

Staining of permeabilized wild type CHO/MUC1sol-clone-C4 with anti-MUC1 antibodies revealed strong intracellular expression of MUC1 with HMFG2, SM3, vu-4H5, and vu-2G7 (FIG. 8) Staining with anti-carbohydrate antibodies revealed strong intracellular staining with anti-T after neuraminidase only, while anti-Tn only labeled weakly. These results indicate that the main glycosylation of MUC1 in CHO wild type is ST similar to untransfected cells.

In order to characterize the secreted MUC1 product SDS-PAGE western blot analysis of harvested culture medium of confluent cultures were performed. Ten to twenty µL culture supernatant was analysed directly or treated with 0.1 U/mL neuraminidase (C. Perfringes VI, Sigma) for 30-60 min at 37° C. Samples were mixed with SDS sample buffer, reduced with DTT, and run on precast 4-20% gels (Biorad). As shown in FIG. 9 anti-MUC1 antibodies detected two forms of MUC1 in the medium; a low molecular weight form migrating as 130-140 kd corresponding to unglycosylated product, and a high molecular weight form migrating above 250 kd. The high molecular weight form was sensitive to neuraminidase treatment as evidenced by a marked shift and retardation in migration. It is known that sialylated glyoproteins migrate aberrantly and often desialylation results in slower migration by SDS-PAGE analysis regardless of the mass. Interestingly, the antibody VU-4H5 reacted mainly with the unglycosylated form and only a very weak band was found in the high molecular weight forms after neuraminidase treatment. This result indicates that the PDTR region is O-glycosylated as the VU-4H5 antibody was previously found to tolerate O-glycosylation most positions in the tandem repeat except the PDTR region[66]. In agreement with this the antibody VU-2G7 raised against a MUC1 GalNAc-glycopeptide with only one GalNAc per repeat attached in the PDTR region reacted strongly with the secreted MUC1. Furthermore, reactivity with the anti-T antibody after neuraminidase treatment showed that the main type of O-glycosylation on secreted MUC1 was sialylated-T. Anti-Tn and STn produced no staining.

Characterization of mutant and MUC1 stable transfectant CHO ldlD cells: CHO ldlD cells stably transfected with full coding MUC1, e.g. CHOldlD/MUC1F-clone2, expressed MUC1 at the cell surface as detected by anti-MUC1 antibodies when cells were grown in GalNAc and Gal (FIG. 10). Cells were seeded at approximately 30-50% confluency (approx. $0.2 \times 10^6$ per 6 well plate) in Hams F12 medium supplemented with 10% Fetal Bovine serum and grown for 6 hours. Medium was replaced with Optimem with or without 1.0 mM GalNAc and/or 0.1 mM Gal, and cells grown for 18-36 hours after which cells were trypsinised and washed in saline and processed as described for immunocytology. CHOldlD/MUC1F-clone2 cells grown in the absence of sugars and analysed after permeabilization produced very little MUC1 detectable by HMFG2 but not by 5E5. In contrast, cells grown in the presence of only GalNAc strongly expressed MUC1 as evaluated by HMFG2 and 5E5, specifically reactive with GalNAc-MUC1. In agreement with reactivity with 5E5 these cells also labeled strongly with anti-Tn antibodies, 5F4 and 1E3, while anti-T antibodies, HH8 and 3C9, did not label the cells. Very weak or no staining with anti-STn antibodies (3F1 and TKH2) indicates that α2,6 sialylation to form STn does not occur in CHO ldlD cells. CHOldlD/MUC1F-clone2 cells grown in the presence of both GalNAc and Gal show reactivity at the surface with anti-T antibodies (HH8 and 3C9) only after neuraminidase pretreatment, confirming results that the predominant glycoform in CHO cells is sialyl-T (FIG. 10). No staining with anti-Tn or STn antibodies was detected with cells grown in both Gal and GalNAc. CHOldlD/MUC1F-clone2 cells grown in the absence of GalNAc and Gal or in the presence of GalNAc alone showed no reactivity with anti-Tn and T antibodies or lectins (DBA, HPA, VVA, PNA, not shown) were detected indicating complete lack of O-glycosylation (FIG. 10). Cell surface expression of MUC1 was detected in CHOldlD/MUC1F-clone2 cells grown in the presence of GalNAc, while cells grown without GalNAc showed no or only weak expression of MUC1 at the surface (FIG. 10). Surface expression of MUC1 was detected with HMFG2 in cells grown in GalNAc as well as cells grown in both Gal and GalNAc, however, expression analysed with the Tn/STn-MUC1 glycoform specific antibody 5E5 revealed surface expression only with cells grown in the presence of GalNAc (FIG. 10). This latter finding is in agreement with the O-glycosylation pattern determined above in these cells.

Figure 11:
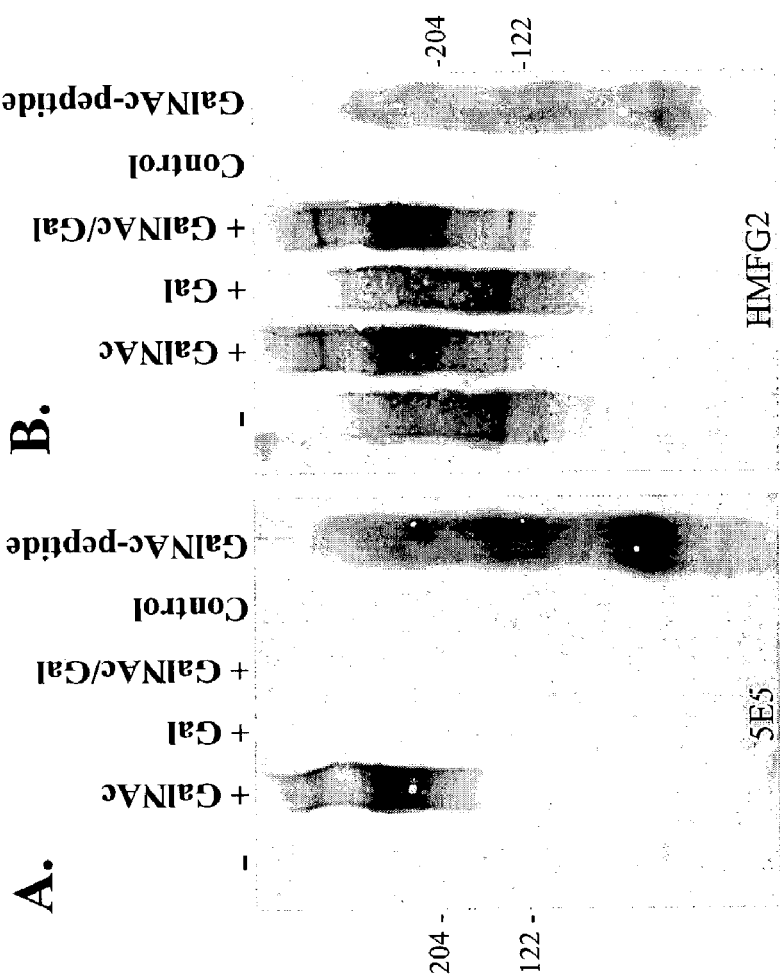
Figure 12:
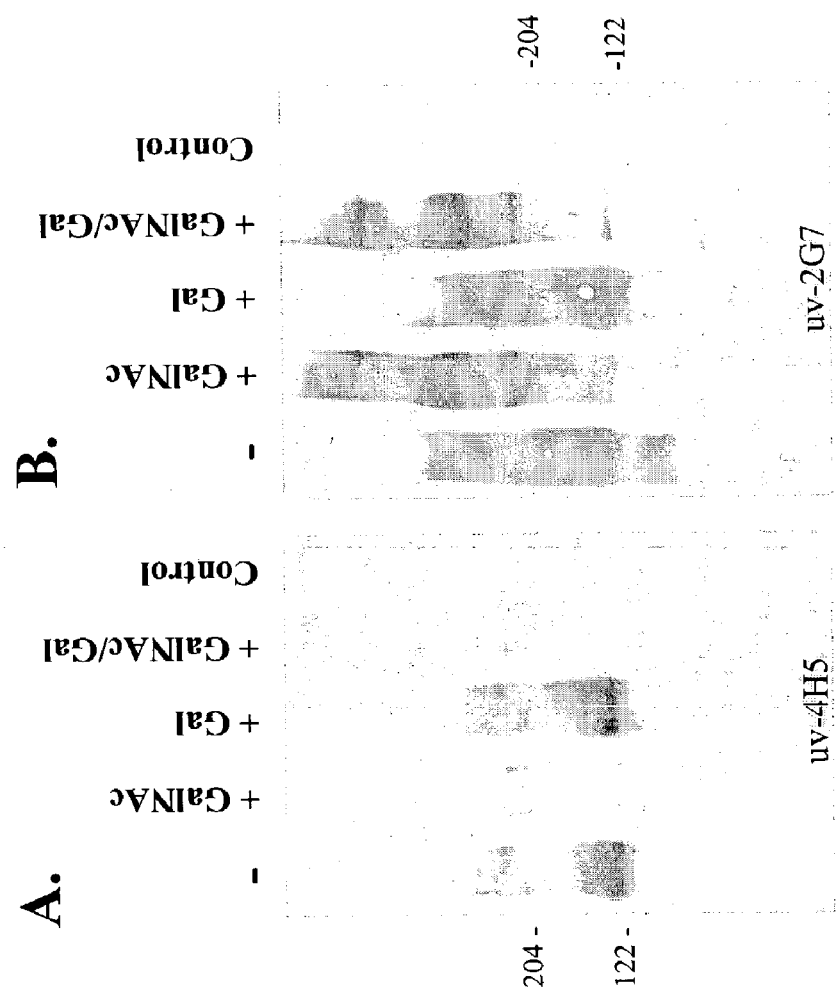

CHOldlD/MUCsol-cloneD5 secretes MUC1 to the culture medium, and permeabilized cells immunostain with antibodies to MUC1 in the cytoplasm. Cells were grown in Hams F12 medium supplemented with 10% Fetal Bovine serum and seeded at a density of $0.2 \times 10^6$ in 6 well plates. Following growth for 6 hours, the medium was replaced with Optimem supplemented with 1 mM GalNAc, 0.1 mM Gal, or 1 mM GalNAc and 0.1 mM Gal, and cells grown for 18-72 hours. Secretion of MUC1 was monitored by immunochemical assays of culture supernatants at differing time points. SDS-PAGE western blot analysis was performed with 5 µl culture supernatant mixed with 5 µl of 2×SDS sample buffer containing 1 mM DTT. Samples were heated to 100° C. for 2 min and loaded on a precast 4-20% gradient gel and run at 125 V for 75 min. Transfer to nitrocellulose membrane was performed by elecroblotting using Biorad Mini Trans Blot apparatus at 350 mA for 1 hour. Membranes were blocked with 15% skimmed milk prepared in $dH_2O$ for 2 hours and stained with anti-MUC1 and anti-carbohydrate monoclonal antibodies for 18 hours at 4° C., followed by washing with Tris buffered saline (TBS) (10 mM Tris pH 8.0 with 8.5% NaCl) 5 times for 5 min, and incubation with with biotinylated rabbit anti-mouse IgG subclass specific antibodies (1:1000 dilution in TBS) for 1 hour at 25° C. Following 5 washes for 5 min each in TBS, membranes were incubated in HRP conjugated Streptavidin (1:3000 dilution in TBS) for 30 min at 25° C. After 5 washings of 5 min each in TBS the blot was developed in 0.04% 4-Chloro-1-Naphthol prepared in 50 mM Tris-HCl (pH 7.4) containing 0.025% $H_2O_2$. Similar to the findings with full coding MUC1 expressed at the cell surface of CHO ldlD cells, glycosylation of the secreted MUC1 was dependent on Gal and GalNAc sugars in culture medium. Cells grown without sugars produced and secreted low amounts of a low molecular weight MUC1 molecule of apparent mw of 120-130 kd without glycosylation detectable by HMFG2 but not 5E5 or anti-Tn and anti-T antibodies (FIG. 11). In contrast, cells grown in 1 mM GalNAc secreted MUC1 glycosylated with GalNAc (Tn) as evidenced by reactivity with both HMFG2 and 5E5 as well as anti-Tn antibodies (FIG. 11). The apparent molecular weight of secreted Tn-MUC1 was 250-300 kd and no significant shift in migration was observed with pretreatment with neuraminidase (0.1 U/ml for 30 min at 37° C.), suggesting lack of α2,6sialylation (STn). This was confirmed by lack of staining with anti-STn antibodies. Cells grown in both 0.1 mM Gal and 1 mM GalNAc produced and secreted MUC1 with sialylated core 1 (T) glycoforms reactive with HMFG2 but not 5E5 (FIG. 11). Pretreatment with neuraminidase resulted in a significant shift in migration and reactivity with anti-T antibodies as well as the lectin PNA. Two novel anti-MUC1 antibodies described recently have been suggested to react with the MUC1 tandem repeat sequence without (Mab VU-4H5) or with (Mab VU-2G7) O-glycans attached in the central immunodominant epitope -PDTR-. Analysis of secreted MUC1 produced in CHO ldlD cells grown without GalNAc show reactivity with unglycosylated MUC1 migrating at mw 120-130 kd with VU-4H5, while no or only weak reactivity was observed when grown in GalNAc with or without Gal (FIG. 12). In contrast, the Mab VU-2G7 reacted strongly with MUC1 migrating at 250-300 kd secreted from cells grown in GalNAc with or without Gal (FIG. 12). Although, Mab VU-2G7 reacted weakly with unglycosylated MUC1 the combined results suggest that MUC1 produced in CHO ldlD cells carry O-glycans on all five sites of the tandem repeat.

Example 11

The Inhibitor GalNAcα-benzyl Inhibits MUC1 Expression Independently of O-glycan Processing As shown in Example 10 CHOldlD/MUC1F-clone2 cells grown in the presence of GalNAc but not Gal have limited O-glycosylation capacity, only produce the Tn glycoform of MUC1, but expresses comparable levels of MUC1 at the cell surface as in wild type CHO cells or in CHO ldlD cells grown in both GalNAc and Gal. This suggested that cell surface expression was not related to O-glycosylation and particular glycoforms as previously proposed (for a review see Huet). We therefore investigated the effect of treatment with GalNAcα-benzyl of CHOldlD/MUC1F-clone2 cells grown in the presence of GalNAc. CHOldlD/MUC1F-clone2 cells were seeded in 6 well plates at a density of $0.2 \times 10^6$ per well and were grown for 6 hours in Hams F12 medium with serum until approximately 30% subconfluent. Medium was hereafter replaced with Optimem supplemented with 1.0 mM GalNAc or 1.0 mM GalNAc and 0.1 mM Gal with or without the inhibitors GalNAcα-benzyl, GalNAcβ-benzyl or the control GlcNAcα-benzyl. After 18 hours, the medium was replaced with fresh Optimem containing the sugars and benzyl derivatives as above and grown for 12-48 hours. Initially we analyzed surface expression of MUC1 by immunocytology. Cells were washed once in PBS-CMF (phosphate buffered saline Calcium and Magnesium free) after carefully removing the medium from the wells and subsequently fixed in 2 ml 3% paraformaldehyde at 25° C. for 20 min followed by three washes with PBS-CMF 3 times. Free aldehyde groups were quenched by incubating in 2 mL 50 mM Ammonium Chloride in PBS-CMF for 10 min, followed by three washes with PBS-CMF and three washes with 5 min incubations each with PBS-CMF containing 0.2% Fish Skin Gelatin (Sigma). Immunostaining of cells was performed by incubation with monoclonal antibodies for 40 min at 25° C., followed by three washes with PBS-CMF and three washes of 5 min each with PBS-CMF containing 0.2% Fish Skin Gelatin. Subsequently, cells were incubated with FITC-conjugated rabbit anti-mouse Ig (Dako F261) diluted 1:150 in PBS-CMF containing 0.2% Fish Skin Gelatin) for 20 min at 25° C., followed by the same washing procedure, after which wells were cut out of plates and mounted with glycerol as for glass slides. FIG. 13 shows that treatment with 1 mM GalNAcα-benzyl, produced strong inhibition of cell surface expression of MUC1, while treatment with a similar control benzyl derivative showed no inhibition. GlcNAcα-benzyl was chosen as a control because this sugar does not serve as a substrate for mammalian glycosyltransferases and hence was not expected to interfere with O-glycosylation in CHO cells. Most anti-MUC1 antibodies reacted with cells grown in GalNAc including VU-2G7 and 5E5, and only VU-4H5 did not react. Reactivity with VU-2G7 indicates that the -PDTR-region is O-glycosylated, while reactivity with 5E5 confirms that the glycoforms of surface MUC1 is mainly or exclusively Tn.

We next analysed the expression of MUC1 produced by CHOldlD/MUC1F-clone2 cells by SDS-PAGE western analysis. Cells were grown for 24 hours or 48 hours in the presence of 1 mM GalNAc or 1 mM GalNAc and 0.1 mM Gal to limit core O-glycosylation to GalNAcα1-O-Ser/Thr and Galβ1-3GalNAcα1-O-Ser/Thr, respectively. Cells were further treated with 2 mM GalNAcα-benzyl, GlcNAcα-benzyl or no inhibitor. Cells were washed and lysed at 24 or 48 hours and the lysates subjected to immunoprecipitation with monoclonal antibody HMFG2, which broadly recognize MUC1 glycoforms. Immunoprecipitates were analysed by SDS-PAGE and western blot using HMFG2 antibody to detect MUC1 expression. As shown in FIG. 14 the MUC1 glycoforms at 24 hours expressed by cells grown in GalNAc or Gal and GalNAc migrated similarly with only little high molecular weight forms in both, indicating that synthesis of sialylated core 1 O-glycans were time limited. At 48 hours, MUC1 glycoforms migrating as higher molecular weight species were expressed more pronounced and selectively by cells grown in Gal and GalNAc. Treatment with GlcNAcα-benzyl produced the same glycoforms at similar intensity as cells without treatment. In striking contrast, treatment with GalNAcα-benzyl had significant effect after 48 hours. A significant reduction in MUC1 expression was found in cells grown in GalNAc as well as in Gal and GalNAc. In the latter case a significant shift in migration into two bands further confirmed that GalNAcα-benzyl also serves as an inhibitor of O-glycan extension and reduces O-glycosylation to GalNAcα1-O-Ser/Thr. Analysis of the same blots with the anti-MUC1 antibody 5E5 (FIG. 15) produced essentially the same results except that the antibody only labeled the lower migrating band of the two bands labeled by HMFG2 in cells grown in Gal and GalNAc and treated with GalNAcα-benzyl. This indicates some heterogeneity in glycosylation.

These results show for the first time that the effect of GalNAcα-benzyl on mucin transport and surface expression is independent of its effects on O-glycosylation in striking contrast to the prevailing hypothesis[46]. Because cells grown in the presence of GalNAc do not produce core 1 (Galβ1-3GalNAcα1-O-Ser/Thr) O-glycosylation, GalNAcα-benzyl cannot serve as a competitive substrate for the core 1 β3galactosyltransferase and subsequently for sialyltransferases. GalNAcα-benzyl must therefore exert its function on mucin transport by another unknown mechanism.

The in vivo cell line model system developed is one example of a method to screen for inhibitors effects of one or more compounds on transport of mucins and O-linked glycoproteins in cells. The Example utilizes MUC1 but any mucin or O-linked glycoprotein could be used with appropriate expression constructs, antibodies and reagents. The developed cell model and modifications hereof can be used for high throughput screens of inhibitors in combination with or as a second screen after the binding assays disclosed in Examples 8 and 9.

Example 12

Identification of a Novel Selective Inhibitor, GalNAcβ-benzyl, of Polypeptide GalNAc-transferase Lectins that Inhibits MUC1 Expression Without Affecting O-glycosylation As shown in Examples 8 and 9, polypeptide GalNAc-transferases contain lectin domains with binding properties for GalNAc-peptides including GalNAc-MUC1 peptides. Since GalNAcα-benzyl was found to inhibit the binding properties of GalNAc-transferase lectins, we tested the possibility that the independent effect on mucin expression this O-glycosylation inhibitor has, could be related to an inhibitory effect on GalNAc-transferase lectins. In Examples 8 and 9 we found surprisingly that the lectin domains of several GalNAc-transferases in addition to GalNAcα-benzyl, which mimics the GalNAc-glycopeptide targets of the lectins, also were inhibited by βGalNAc derivatives. Initial tests with commercially available GalNAcβ and GalNAcα derivatives, p-nitrophenyl and umbrelliferyl did not produce significant effects in our model system. GalNAcβ-benzyl, the β-anomeric configuration of GalNAc-benzyl (there is a β linkage between the N-acetylgalactosamine and the benzyl ring), was custom synthesized by Alberta Research Council (Canada), and its structure was confirmed by mass spectrometry and $^1$H-NMR. CHOldlD/MUC1F-clone2 cells were grown for 12 hours in the presence of 1 mM GalNAc or 1 mM GalNAc and 0.1 mM Gal to limit core O-glycosylation to GalNAcα-O-Ser/Thr and Galβ1-3GalNAcα1-O-

Figure 18:
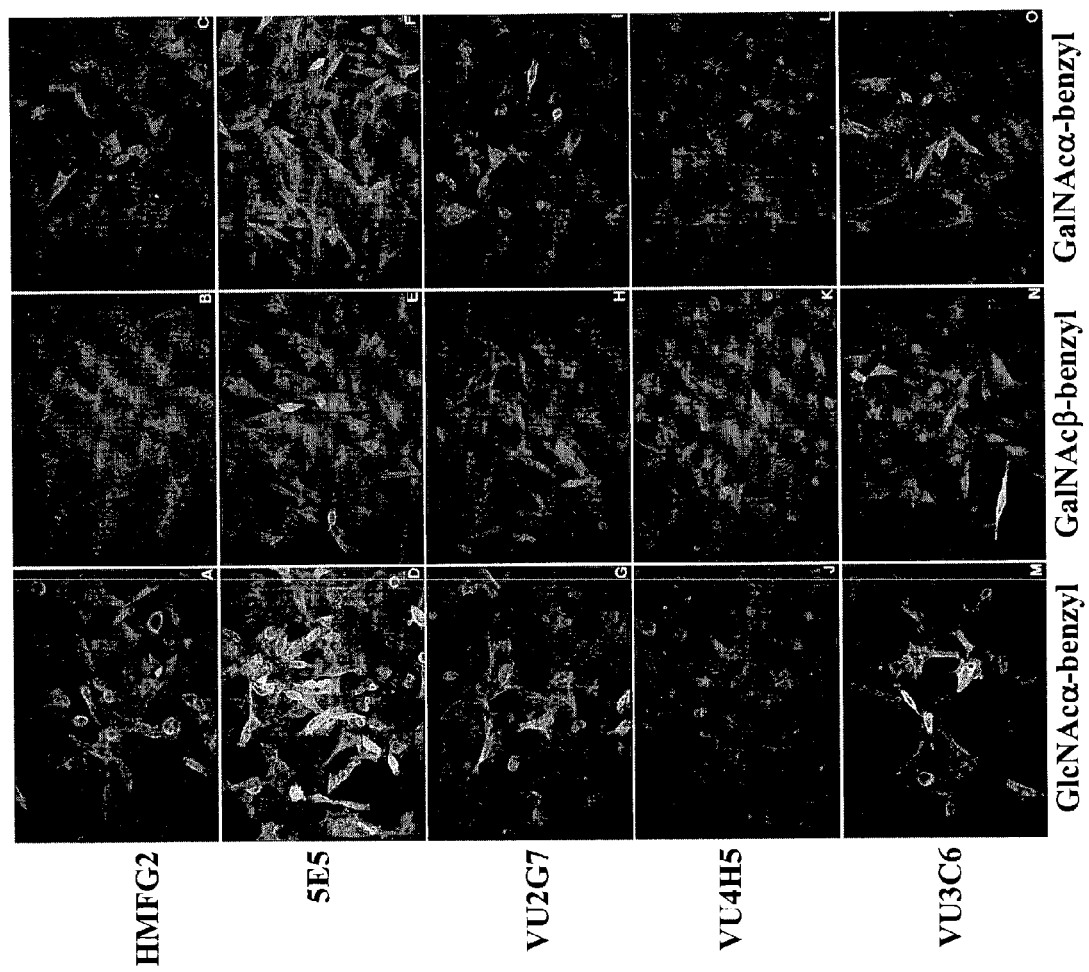

Ser/Thr, respectively. Cells were then treated with 2 mM GalNAcα-benzyl, GalNAcβ-benzyl, or GlcNAcα-benzyl as control (GlcNAcα-benzyl was shown in Example 10 to have no effect). Cells were washed and lysed as described above after 36 hours and the lysates subjected to immunoprecipitation with anti-MUC1 monoclonal antibodies HMFG2 or 5E5. FIG. 16 illustrates that treatment with GalNAcβ-benzyl produced the same or better reduction in MUC1 expression as treatment with GalNAcα-benzyl in cells grown in GalNAc as well as in Gal and GalNAc. In cells grown in Gal and GalNAc MUC1 expression was reduced with GalNAcβ-benzyl treatment, but in contrast to cells treated with GalNAcα-benzyl, GalNAcβ-benzyl produced no change in the migration of MUC1 demonstrating that this inhibitor does not affect the O-glycan processing. The lack of immunoprecipitation of MUC1 by antibody 5E5 in cells grown in Gal and GalNAc indicates that MUC1, is glycosylated with more complex structures than GalNAcα1-O-Ser/Thr as recognized by this antibody. As shown in FIG. 18 the main O-glycan phenotype of CHO ldlD cells grown in Gal and GalNAc is sialylated-T, and 5E5 does not react with MUC1, with T or sialylated T glycoforms of MUC1. FIG. 17 illustrates the same experiments as in FIG. 16 except that the detection antibody is 5E5 and only Tn and STn MUC1 glycoforms are visualised. This experiment confirms the strong inhibition of MUC1 expression in GalNAcα-benzyl and GalNAcβ-benzyl treated cells.

The finding that GalNAcα-benzyl and GalNAcβ-benzyl exhibit the same inhibitory effect on GalNAc-transferase lectin binding, and that they have similar effects on inhibition of MUC1 expression, clearly indicate that the effects these compounds have on mucin expression and secretion are directed through interaction with the lectin domains of polypeptide GalNAc-transferases. The effect GalNAcα-benzyl has on O-glycan processing is a separate phenomenon directed by its ability to serve as a competitive substrate for the core 1 β1,3galactosyltransferase.

GalNAcβ-benzyl is the first identified selective inhibitor of polypeptide GalNAc-transferase lectins and their roles in transport and secretion, which does not modulate O-glycosylation in cells (i.e. does not serve a substrate for mainly core 1 β3galactosyltransferase activities, α2,6sialyltransferase activities, and core 3 β3GlcNAc-transferase activities). Inhibitors structurally related to GalNAcβ-benzyl with the same properties, as identifiable by the binding assays disclosed in Examples 9 and 10, may be designed and syntesized to obtain higher affinity binders. Such inhibitors may be based on carbohydrates such as the monosaccharide GalNAc or modifications thereof, inhibitors may be based on structural and functional mimetics such as polypeptides, glycopeptides, DNA, RNA, antibodies, and antibody fragments including phage antibodies, and inhibitors may be natural or synthetic organic or inorganic compounds. One common feature for such preferred inhibitors is the ability to inhibit the binding of one or more polypeptide GalNAc-transferase lectins to its binding ligand, such as GalNAc-glycopeptides and mucins as exemplified in Examples 8 and 9. Another feature of the novel inhibitor GalNAcβ-benzyl is its ability to enter living cells and reach the Golgi apparatus for in vivo binding to polypeptide GalNAc-transferase. The hydrophic benzyl aglycone is one example of an aryl compound suitable for the β-anomeric configuration of GalNac-R, but other aryl substituents include, without limitation, p-nitrophenyl umbrelliferyl, and naphtalenmethanol. Any pharmaceutical carrier known in the art may be used to achieve the same effect. The appropriate carrier will be evident to those skilled in the art and will depend in large part upon the route of administration.

Example 13

Inhibition of Secretion of Mucins

Because GalNAcα-benzyl exerts separate effects on O-glycan processing and mucin expression, the use of the novel selective inhibitor of mucin expression, GalNAcβ-benzyl, allow analysis of mucin expression and secretion in different cell line models. Examples of human cell lines (available from ATCC, USA) expressing and secreting mucins are without limitations LS174T, HT29, Colo205, CALU, MCF7, T47D, NCI-H292, and A549. Most human adenocarcinoma cell lines express and secret mucins and analysis with antibodies to detect protein expression or probes to detect mRNA can reveal the types and quantities of mucins. The human colon carcinoma cell line LS174T was previously shown to exhibit reduced secretion of mucin following treatment with GalNAcα-benzyl[20]. This and other cell lines can be used to treat with 2 mM GalNAcβ-benzyl. In this Example we used wild type CHO/MUC1sol-cloneC4 and western blot analysis of medium of cells treated with 1-2 mM GalNAcα-benzyl, GalNAcβ-benzyl, or the control GlcNAcα-benzyl. Treatment with both GalNAcα-benzyl and GalNAcβ-benzyl showed inhibition of secreted MUC1 compared to control treated or non-treated cells. The inhibitory effect on mucin secretion can be quantified by a number of assays known to the skilled in the art including western blot, ELISA, gelfiltration, immunocapture, and other assays.

The in vivo cell line model system developed is one example of a method to screen for inhibitors effects of one or more compounds on secretion of mucins and O-linked glycoproteins in cells. The Example utilizes MUC1 but any mucin or O-linked glycoprotein could be used with appropriate expression constructs, antibodies and reagents. The developed cell model and modifications hereof can be used for high throughput screens of inhibitors in combination with or as a second screen after the binding assays disclosed in Examples 8 and 9.

Example 14

Synthesis of Benzyl-2-acetamido-2-deoxy-β-D-galactopyranoside Galactosamine (GalNAcβ-benzyl)

The synthesis of benzyl-2-acetamido-2-deoxy-β-D-galactopyranoside galactosamine (GalNAcβ-benzyl) was carried out by using Galactosamine-hydrochloride as starting material. Treatment of this compound with Troc reagent provided the N-Troc derivative. The reaction was carried out in aqueous sodium hydrogen carbonate solution for 15 hours at ambient temperature. After evaporation and co-evaporation of the mixture with toluene, the crude mass was subjected to acetylation with acetic anhydride and pyridine to obtain the peracetylated derivative of the N-Troc-galactosamine. The acetylated product was converted into its thiobenzyl glycoside by using boronrifluoride ethereate solution as a catalyst. The N-Troc derivative was converted into its corresponding azido compound by reacting the compound with a triflic azide and copper sulfate. The 2-azido-2-deoxy-3,4,6-tri-O-acetyl-β-D-thiogalactoside was then transformed into bromide derivative by treatment with N-bromosuccinamide in dichlorormethane. The reaction of glycosyl benzyl alcohol in the presence of bromide with silver carbonate and silver trifluoromethane sulfonate in dichlorormethane provided quantitative yield of β-benzyl glycoside. After purification on a silica gel column, this product was deactylated with sodium methoxide and methanol. Azido group of the compound was reduced with H2S in the presence of triethylamine-pyridine and water solution to provide 2-amino galactoside, which was N-acetylated with acetic anhydride and methanol solution containing sodium hydrogen carbonate. The β-O-benzyl-2-deoxyl-2-acetamido-galactopyranoside compound was finally purified to homogeneity by chromatography on silica gel.

REFERENCES

1. Paulson, J. C. and Colley, K. J. Glycosyltransferases. Structure, localization, and control of cell type-specific glycosylation. J. Biol. Chem., 264: 17615-17618, 1989.
2. Hassan, H., Bennett, E. P., Mandel, U., Hollingsworth, M. A., and Clausen, H. Control of Mucin-Type O-Glycosylation: O-Glycan Occupancy is Directed by Substrate Specificities of Polypeptide GalNAc-Transferases. In: G. W. Hart and M. Fukuda (eds.), pp. 273-292, New York: Wiley-VCH. 2000.
3. Hagen, F. K., Hazes, B., Raffo, R., deSa, D., and Tabak, L. A. Structure-Function Analysis of the UDP-N-acetyl-D-galactosamine:Polypeptide N-acetylgalactosaminyl-transferase. Essential residues lie in a predicted active site cleft resembling a lactose repressor fold. J. Biol. Chem., 274: 6797-6803, 1999.
4. Hazes, B. The (QxW)3 domain: a flexible lectin scaffold. Protein Science, 5: 1490-1501, 1996.
5. Imberty A., Piller V., Piller F., and Breton C. Fold recognition and molecular modeling of a lectin-like domain in UDP-GalNac: polypeptide N-acetylgalactosaminyltransferases. Protein Eng., 10: 1353-1356, 1997.
6. Breton, C. and Imberty, A. Structure/function studies of glycosyltransferases. Curr. Opin. Struct. Biol, 9: 563-571, 1999.
7. Bennett, E. P., Hassan, H., Hollingsworth, M. A., and Clausen, H. A novel human UDP-N-acetyl-D-Galactosamine:polypeptide N-acetylgalactosaminyltransferase, GalNAc-T7, with specificity for partial GalNAc-glycosylated acceptor substrates. FEBS Letters, 460: 226-230, 1999.
8. Bennett, E. P., Hassan, H., Mandel, U., Mirgorodskaya, E., Roepstorff, P., Burchell, J., Taylor-Papadamitriou, J., Hollingsworth, M. A., Merkx, G., Geurts van Kessel, A., Eiberg, H., Steffensen, R., and Clausen, H. Cloning of a human UDP-N-acetyl-α-D-galactosamine: polypeptide N-acetylgalactosaminyltransferase that complements other GalNAc-transferases in complete O-glycosylation of the MUC1 tandem repeat. J. Biol. Chem., 273: 30472-30481, 1998.
9. Ten Hagen, K. G., Tetaert, D., Hagen, F. K., Richet, C., Beres, T. M., Gagnon, J., Balys, M. M., VanWuyckhuyse, B., Bedi, G. S., Degand, P., and Tabak, L. A. Characterization of a UDP-GalNAc:polypeptide N-acetylgalactosaminyltransferase that displays glycopeptide N-acetylgalactosaminyltransferase activity. J. Biol. Chem., 274: 27867-27874, 1999.
10. Muller, S., Alving, K., Peter-Katalinic, J., Zachara, N., Gooley, A. A., and Hanisch, F. G. High density O-glycosylation on tandem repeat peptide from secretory MUC1 of T47D breast cancer cells. J. Biol. Chem., 274, 1999.
11. Muller, S., Goletz, S., Packer, N., Gooley, A. A., Lawson, A. M., and Hanisch, F. G. Localization of O-glycosylation sites on glycopeptide fragments from lactation-associated MUC1. J. Biol. Chem., 272: 24780-24793, 1997.
12. Jentoft, N. Why are proteins O-glycosylated?. Trends Biochem. Sci., 15: 291-294, 1990
13. Tabak, L. A. In defense of the oral cavity: structure, biosynthesis, and function of salivary mucins. Annual Review of Physiology, 57: 547-564, 1995.
14. Van den Steen, P., Rudd, P. M., Dwek, R. A., and Opdenakker, G. Concepts and principles of O-linked glycosylation. Crit. Rev. Biochem Mol. Biol., 33: 151-208, 1998.
15. Taylor-Papadimitriou, J. and Epenetos, A. A. Exploiting altered glycosylation patterns in cancer: progress and challenges in diagnosis and therapy. Trends In Biotechnology, 12: 227-233, 1994.
16. Taylor-Papadimitriou, J. and Finn, O. J. Biology, biochemistry and immunology of carcinoma-associated mucins. Immunology Today, 18: 105-107, 1997.
17. Scharfman, A., Lamblin, G., and Roussel, P. Interactions between human respiratory mucins and pathogens. Biochemical Society Transactions, 23: 836-839, 1995.
18. Rose, M. C. Mucins: structure, function, and role in pulmonary diseases. Am. J. Physiol. 1992. Oct., 263: L413-L429
19. Thomsson, K. A., Carlstedt, I., Karlsson, N. G., Karlsson, H., and Hansson, G. C. Different O-glycosylation of respiratory mucin glycopeptides from a patient with cystic fibrosis. Glycoconj. J., 15: 823-833, 1998
20. Kuan, S. F., Byrd, J. C., Basbaum, C., and Kim, Y. S. Inhibition of mucin glycosylation by aryl-N-acetyl-alpha-galactosaminides in human colon cancer cells. J. Biol. Chem., 264: 19271-19277, 1989
21. Huet, G., Hennebicq-Reig, S., de Bolos, C., Ulloa, F., Lesuffleur, T., Barbat, A., Carriere, V., Kim, I., Real, F. X., Delannoy, P., and Zweibaum, A. GalNAc-alpha-O-benzyl inhibits NeuAcalpha2-3 glycosylation and blocks the intracellular transport of apical glycoproteins and mucus in differentiated HT-29 cells. J. Cell Biol., 141: 1311-1322, 1998.
22. Byrd, J. C., Dahiya, R., Huang, J., and Kim, Y. S. Inhibition of mucin synthesis by benzyl-alpha-GalNAc in KATO III gastric cancer and Caco-2 colon cancer cells. Eur. J. Cancer, 31A: 1498-1505, 1995.
23. Alfalah, M., Jacob, R., Preuss, U., Zimmer, K. P., Naim, H., and Naim, H. Y. O-linked glycans mediate apical sorting of human intestinal sucrase-isomaltase through association with lipid rafts. Curr. Biol, 9: 593-596, 1999.
24. Yeaman, C., Le Gall, A. H., Baldwin, A. N., Monlauzeur, L., Le Bivic, A., and Rodriguez-Boulan, E. The O-glycosylated stalk domain is required for apical sorting of neurotrophin receptors in polarized MDCK cells. J. Cell Biol., 139: 929-940, 1997.
25. Ulloa, F., Franci, C., and Real, F. X. GalNAc-a-O-Benzyl inhibits sialylation of de novo synthesized apical, but not basolateral, sialoglycoproteins and blocks lysosomal enzyme processing in a post-TGN compartment. J. Biol. Chem. 2000. Prepublished Apr. 5.
26. White, T., Bennett, E. P., Takio, K., Sorensen, T., Bonding, N., and Clausen, H. Purification and cDNA cloning of a human UDP-N-acetyl-alpha-D-galactosamine:polypeptide N-acetylgalactosaminyltransferase. J. Biol. Chem., 270: 24156-24165, 1995.
27. Bennett, E. P., Hassan, H., and Clausen, H. cDNA cloning and expression of a novel human UDP-N-acetyl-alpha-D-galactosamine. Polypeptide N-acetylgalactosaminyltransferase, GalNAc-t3. J. Biol. Chem., 271: 17006-17012, 1996.

28. Wandall, H. H., Hassan, H., Mirgorodskaya, E., Kristensen, A. K., Roepstorff, P., Bennett, E. P., Nielsen, P. A., Hollingsworth, M. A., Burchell, J., Taylor-Papadimitriou, J., and Clausen, H. Substrate specificities of three members of the human UDP-N-acetyl-alpha-D-galactosamine: Polypeptide N-acetylgalactosaminyltransferase family, GalNAc-T1, -T2, and -T3. J. Biol. Chem., 272: 23503-23514, 1997.

29. Day, P. J., Ernst, S. R., Frankel, A. E., Monzingo, A. F., Pascal, J. M., Molina-Svinth, M. C., and Robertus, J. D. Structure and activity of an active site substitution of ricin A chain. Biochemistry, 35: 11098-11103, 1996.

30. Albone, E. F., Hagen, F. K., VanWuyckhuyse, B. C., and Tabak, L. A. Molecular cloning of a rat submandibular gland apomucin. J. Biol. Chem. 269: 16845-16852, 1994.

31. Gendler, S. J., Spicer, A. P., Lalani, E. N., Duhig, T., Peat, N., Burchell, J., Pemberton, L., Boshell, M., and Taylor-Papadimitriou, J. Structure and biology of a carcinoma-associated mucin, MUC1. American Review of Respiratory Disease 144: S42-7, 1991.

32. Gum, J. R., Byrd, J. C., Hicks, J. W., Toribara, N. W., Lamport, D. T., and Kim, Y. S. Molecular cloning of human intestinal mucin cDNAs. Sequence analysis and evidence for genetic polymorphism. J. Biol. Chem. 264: 6480-6487, 1989.

33. Guyonnet, D. V., Audie, J. P., Debailleul, V., Laine, A., Buisine, M. P., Galiegue-Zouitina, S., Pigny, P., Degand, P., Aubert, J. P., and Porchet, N. Characterization of the human mucin gene MUC5AC: a consensus cysteine-rich domain for 11 p15 mucin genes? Biochem. J., 305: 211-219, 1995

34. Bobek, L. A., Tsai, H., Biesbrock, A. R., and Levine, M. J. Molecular cloning, sequence, and specificity of expression of the gene encoding the low molecular weight human salivary mucin (MUC7). J. Biol. Chem. 268: 20563-20569, 1993.

35. Matsuura, H., Greene, T., and Hakomori, S. An alpha-N-acetylgalactosaminylation at the threonine residue of a defined peptide sequence creates the oncofetal peptide epitope in human fibronectin. J. Biol. Chem. 264: 10472-10476, 1989.

36. Hardy, D. M. and Garbers, D. L. A sperm membrane protein that binds in a species-specific manner to the egg extracellular matrix is homologous to von Willebrand factor. J. Biol. Chem. 270: 26025-26028, 1995.

37. Hill, H. D. J., Schwyzer, M., Steinman, H. M., and Hill, R. L. Ovine submaxillary mucin. Primary structure and peptide substrates of UDP-N-acetylgalactosamine:mucin transferase. J. Biol. Chem. 252: 3799-3804, 1977

38. Birken, S. and Canfield, R. E. Isolation and amino acid sequence of COOH-terminal fragments from the beta subunit of human choriogonadotropin. J. Biol. Chem. 252: 5386-5392, 1977

39. Sako, D., Comess, K. M., Barone, K. M., Camphausen, R. T., Cumming, D. A., and Shaw, G. D. A sulfated peptide segment at the amino terminus of PSGL-1 is critical for P-selectin binding. Cell 83 : 323-331, 1995.

40. Mirgorodskaya, E., Hassan, H., Wandall, H. H., Clausen, H., and Roepstorff, P. Partial Vapor-Phase Hydrolysis of Peptide Bonds: A Method for Mass Spectrometric Determination of O-Glycosylated Sites in Glycopeptides. Anal. Biochem. 269: 54-65, 1999.

41. Gobom, J., Nordhoff, E., Mirgorodskaya, E., Ekman, R., and Roepstorff, P. Sample purification and preparation technique based on nano-scale reversed-phase columns for the sensitive analysis of complex peptide mixtures by matrix-assisted laser desorption/ionization mass spectrometry. J. Mass Spectrom. 34: 105-116, 1999.

42. Hassan, H., Reis, C. A., Bennett, E. P., Mirgorodskaya, E., Roepstorff, P., Hollingsworth, M. A., Burchell, J., Taylor-Papadimitriou, J., and Clausen, H. The lectin domain of UDP-N-acetyl-D-galactosamine: polypeptide N-acetylgalactosaminyltransferase-T4 directs its glycopeptide specificities. J Biol Chem, 275: 38197-38205, 2000.

43. Schwientek, T., Bennett, E. P., Flores, C., Thacker, J., Hollmann, M., Reis, C. A., Behrens, J., Mandel, U., Keck, B., Schafer, M. A., Haselmann, K., Zubarev, R., Roepstorff, P., Burchell, J. M., Taylor-Papadimitriou, J., Hollingsworth, M. A., and Clausen, H. Functional conservation of subfamilies of putative UDP-N-acetylgalactosamine:polypeptide N-acetylgalactosaminyltransferases in Drosophila, Caenorhabditis elegans, and mammals. One subfamily composed of 1(2)35Aa is essentail in Drosophila. J. Biol. Chem., 277: 22623-22638, 2002.

44. Ten Hagen, K. G., Bedi, G. S., Tetaert, D., Kingsley, P. D., Hagen, F., BALYS, M. M., BERES, T. M., Degand, P., and Tabak, L. A. Cloning and Characterization of a Ninth Member of the UDP-GalNAc:Polypeptide N-Acetylgalactosaminyltransferase Family, ppGaNTase-T9. J Biol Chem, 276: 17395-17404, 2001.

45. Tenno, M., Saeki, A., Kezdy, F. J., Elhammer, A. P., and Kurosaka, A. The lectin domain of UDP-GalNAc: Polypeptide N-acetylgalactosaminyltransferase 1 (GalNAc-T1) is involved in O-glycosylation of a polypeptide with multiple acceptor sites. J. Biol. Chem., 2002.

46. Gouyer, V., Leteurtre, E., Zanetta, J. P., Lesuffleur, T., Delannoy, P., and Huet, G. Inhibition of the glycosylation and alteration in the intracellular trafficking of mucins and other glycoproteins by GalNAcalpha-O-bn in mucosal cell lines: an effect mediated through the intracellular synthesis of complex GalNAcalpha-O-bn oligosaccharides. Front Biosci., 6: D1235-D1244, 2001.

47. Muller, S. and Hanisch, F. G. Recombinant MUC1 probe authentically reflects cell-specific O-glycosylation profiles of endogenous breast cancer mucin: High-density and prevalent core2-based glycosylation. J. Biol. Chem., 2002.

48. Bennett, E. P., Hassan, H., Mandel, U., Hollingsworth, M. A., Akisawa, N., Ikematsu, Y., Merkx, G., Geurts van Kessel, A., Olofsson, S., and Clausen, H. Cloning and Characterization of a Close Homologue of Human UDP-N-acetyl-α-D-galactosamine: Polypeptide N-Acetylgalactosaminyltransferase T3, designated GalNAc-T6: Evidence for Genetic but not Functional Redundancy. J. Biol. Chem., 274: 25362-25370, 1999.

49. White, K. E., Lorenz, B., Evans, W. E., Meitinger, T., Strom, T. M., and Econs, M. J. Molecular cloning of a novel human UDP-GalNAc:polypeptide N-acetylgalactosaminyltransferase, GalNAc-T8, and analysis as a candidate autosomal dominant hypophosphatemic rickets (ADHR) gene. Gene, 246: 347-356, 2000.

50. Toba, S., Tenno, M., Konishi, M., Mikami, T., Itoh, N., and Kurosaka, A. Brain-specific expression of a novel human UDP-GalNAc:polypeptide N-acetylgalactosaminyltransferase (GalNAc-T9). Biochim. Biophys. Acta, 1493: 264-268, 2000.

51. Homa, F. L., Hollander, T., Lehman, D. J., Thomsen, D. R., and Elhammer, A. P. Isolation and expression of a cDNA clone encoding a bovine UDP-GalNAc:polypeptide N-acetylgalactosaminyltransferase. J. Biol. Chem., 268: 12609-12616, 1993.

52. Sorensen, T., White, T., Wandall, H. H., Kristensen, A. K., Roepstorff, P., and Clausen, H. UDP-N-acetyl-alpha-D-galactosamine:polypeptide N-acetylgalactosaminyltransferase. Identification and separation of two distinct transferase activities. J. Biol. Chem., 270: 24166-24173, 1995.
53. Kingsley, D. M., Kozarsky, K. F., Segal, M., and Krieger, M. Three types of low density lipoprotein receptor-deficient mutant have pleiotropic defects in the synthesis of N-linked, O-linked, and lipid-linked carbohydrate chains. J. Cell Biol., 102: 1576-1585, 1986.
54. Altschuler, Y., Kinlough, C. L., Poland, P. A., Bruns, J. B., Apodaca, G., Weisz, O. A., and Hughey, R. P. Clathrin-mediated endocytosis of MUC1 is modulated by its glycosylation state. Mol. Biol. Cell, 11: 819-831, 2000.
55. Zanetta, J. P., Gouyer, V., Maes, E., Pons, A., Hemon, B., Zweibaum, A., Delannoy, P., and Huet, G. Massive in vitro synthesis of tagged oligosaccharides in 1-benzyl-2-acetamido-2-deoxy-alpha-D-galactopyranoside treated HT-29 cells. Glycobiology, 10: 565-575, 2000.
56. Trombetta, E. S. and Helenius, A. Lectins as chaperones in glycoprotein folding. Curr. Opin. Struct. Biol, 8: 587-592, 1998.
57. Amado, M., Almeida, R., Carneiro, F., Levery, S. B., Holmes, E. H., Nomoto, M., Hollingsworth, M. A., Hassan, H., Schwientek, T., Nielsen, P. A., Bennett, E. P., and Clausen, H. A family of human beta3-galactosyltransferases. Characterization of four members of a UDP-galactose:beta-N-acetyl-glucosamine/beta-nacetyl-galactosamine beta-1,3-galactosyltransferase family. J. Biol. Chem., 273: 12770-12778, 1998.
58. Amado, M., Almeida, R., Schwientek, T., and Clausen, H. Identification and characterization of large galactosyltransferase gene families: galactosyltransferases for all functions. Biochim. Biophys. Acta, 1473: 35-53, 1999.
59. Dohi, T., Yuyama, Y., Natori, Y., SMITH, P. L., Lowe, J. B., and Oshima, M. Detection of N-acetylgalactosaminyltransferase mRNA which determines expression of Sda blood group carbohydrate structure in human gastrointestinal mucosa and cancer. Int. J. Cancer, 67: 626-631, 1996.
60. Colley, K. J. Golgi localization of glycosyltransferases: more questions than answers. Glycobiology, 7: 1-13, 1997.
61. Schwientek, T. J., Bennett, E. P., Flores, C., Thacker, J., Hollman, M., Reis, C. A., Behrens, J., Mandel, U., Keck, B., Schafer, M. A., Hazelmann, K., Zubarev, R., Roepstorff, P., Hollingsworth, M. A., and Clausen, H. Functional conservation of subfamilies of putative UDP-N-acetylgalactosamine: Polypeptide N-acetylgalactosaminyltransferases in *drosophila, C. elegans* and mammals: One subfamily comprised of 1(2)35Aa is essential in *drosophila*. J. Biol. Chem., 2002.
62. Jorgensen, C. S., Heegaard, N. H., Holm, A., Hojrup, P., and Houen, G. Polypeptide binding properties of the chaperone calreticulin. Eur. J. Biochem., 267: 2945-2954, 2000.
63. Mandel, U., Hassan, H., Therkildsen, M. H., Rygaard, J., Jacobsen, M., Juhl, B. R., Dabelsteen, E., and Clausen, H. Expression of polypeptide GalNAc-transferases in stratified epithelia and squamous cell carcinomas: immunohistological evaluation using monoclonal antibodies to three members of the GalNAc-transferase family. Glycobiology, 9: 43-52, 1999.
64. Burdick, M. D., Harris, A., Reid, C. J., Iwamura, T., and Hollingsworth, M. A. Oligosaccharides expressed on MUC1 produced by pancreatic and colon tumor cell lines. J. Biol. Chem., 272: 24198-24202, 1997.
65. Girling, A., Bartkova, J., Burchell, J., Gendler, S., Gillett, C., and Taylor-Papadimitriou, J. A core protein epitope of the polymorphic epithelial mucin detected by the monoclonal antibody SM-3 is selectively exposed in a range of primary carcinomas. International Journal of Cancer, 43: 1072-1076, 1989.
66. Reis, C. A., Hassan, H., Bennett, E. P., and Clausen, H. Characterization of a panel of monoclonal antibodies using GalNAc glycosylated peptides and recombinant MUC1. Tumour Biology, 19 Suppl 1: 127-133, 1998.
67. Ryuko, K., Schol, D. J., Snijdewint, F. G., Mensdorff-Pouilly, S., Poort-Keesom, R. J., Karuntu-Wanamarta, Y. A., Verstraeten, R. A., Miyazaki, K., Kenemans, P., and Hilgers, J. Characterization of a new MUC1 monoclonal antibody (VU-2-G7) directed to the glycosylated PDTR sequence of MUC1. Tumour. Biol., 21: 197-210, 2000.
68. Mandel, U., Petersen, O. W., Sorensen, H., Vedtofte, P., Hakomori, S., Clausen, H., and Dabelsteen, E. Simple mucin-type carbohydrates in oral stratified squamous and salivary gland epithelia. Journal of Investigative Dermatology, 97: 713-721, 1991.
69. Sasaki, H., Bothner, B., Dell, A., and Fukuda, M. Carbohydrate structure of erythropoietin expressed in Chinese hamster ovary cells by a human erythropoietin cDNA. J. Biol. Chem., 262: 12059-12076, 1987.
70. Ramakrishnan, B., Balaji, P. V., and Qasba, P. K. Crystal Structure of β-1,4-Galactosyltransferase Complex with UDP-Gal Reveals an Oligosaccharide Acceptor Binding Site. J. Mol Biol., 318:491-502, 2002.
71. Ramakrishnan, B., and Qasba, P. K. Structure-based Design of β4Gal-T1 with Equally Efficient N-Acetylgalactosaminyltransferase Activity. J. Bio. Chem., 277, 23, 20833-20839, 2002.

We claim:

1. An inhibitor of polypeptide GalNAc-transferase lectin-mediated functions that selectively binds to the lectin domain of said transferase and does not serve as an acceptor substrate for core 1 β3-galactosyltransferase or other glycosyltransferases functioning in O-glycosylation, wherein said inhibitor is from the group consisting of GalNAcβ1-R, a carbohydrate portion of GalNAcβ1-R, or a glycoconjugate that includes a carbohydrate portion of GalNAcβ1-R, wherein R is aglycone or aryl.

2. An inhibitor according to claim 1 wherein R represents an aryl group.

3. An inhibitor according to claim 1 wherein R is selected from the group consisting of benzyl, phenyl, p-nitrophenyl, umbrelliferyl, and naphtalenmethanol.

* * * * *